US008067022B2

(12) United States Patent
Kunz et al.

(10) Patent No.: US 8,067,022 B2
(45) **Date of Patent: *Nov. 29, 2011**

(54) THERAPEUTIC INHIBITOR OF VASCULAR SMOOTH MUSCLE CELLS

(75) Inventors: Lawrence L. Kunz, Sammamish, WA (US); Peter G. Anderson, Birmingham, AL (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 342 days.

This patent is subject to a terminal disclaimer.

(21) Appl. No.: 09/910,388

(22) Filed: Jul. 20, 2001

(65) Prior Publication Data

US 2002/0013275 A1 Jan. 31, 2002

Related U.S. Application Data

(63) Continuation of application No. 09/470,662, filed on Dec. 22, 1999, now Pat. No. 6,268,390, which is a continuation of application No. 09/113,733, filed on Jul. 10, 1998, now Pat. No. 6,074,659, which is a continuation of application No. 08/450,793, filed on May 25, 1995, now Pat. No. 5,811,447, which is a continuation of application No. 08/062,451, filed on May 13, 1993, now abandoned, which is a continuation-in-part of application No. 08/011,669, filed on Jan. 28, 1993, now abandoned, which is a continuation-in-part of application No. PCT/US92/08220, filed on Sep. 25, 1992.

(51) Int. Cl.
*A61F 2/00* (2006.01)
*A61K 31/00* (2006.01)

(52) U.S. Cl. ........................................... 424/423; 514/1

(58) Field of Classification Search .............. 514/2, 429, 514/411, 449, 319, 441; 424/423, 424, 425; 435/7.1

See application file for complete search history.

(56) References Cited

U.S. PATENT DOCUMENTS

| | | | | |
|---|---|---|---|---|
| 2,914,563 | A | 11/1959 | Allen et al. | |
| 3,010,965 | A | 11/1961 | Elpern | |
| 3,168,565 | A | 2/1965 | Palopoli et al. | |
| 3,279,996 | A | 10/1966 | Long et al. | |
| 3,288,806 | A | 11/1966 | Dewald et al. | |
| 3,445,473 | A | 5/1969 | Ruschig et al. | |
| 3,526,005 | A | 9/1970 | Bokros et al. | |
| 3,634,517 | A | 1/1972 | Palopoli et al. | |
| 3,738,365 | A | 6/1973 | Schulte | |
| 3,879,516 | A | 4/1975 | Wolvek | |
| 3,932,627 | A | 1/1976 | Margraf | |
| 3,940,422 | A | 2/1976 | Harita et al. | 260/340 |
| 3,952,334 | A | 4/1976 | Bokros et al. | |
| 4,070,484 | A | 1/1978 | Harita et al. | 424/319 |
| 4,093,709 | A | 6/1978 | Choi et al. | 424/19 |
| 4,133,814 | A | 1/1979 | Jones et al. | |
| 4,205,685 | A | 6/1980 | Yoshida et al. | |
| 4,219,520 | A | 8/1980 | Kline | |
| 4,219,656 | A | 8/1980 | Press et al. | |
| 4,221,785 | A | 9/1980 | Sorenson | |
| 4,230,862 | A | 10/1980 | Suarez et al. | |
| 4,233,968 | A * | 11/1980 | Shaw, Jr. | 128/833 |
| 4,235,988 | A | 11/1980 | Fildes et al. | 528/79 |
| 4,239,778 | A | 12/1980 | Venton et al. | |
| 4,282,246 | A | 8/1981 | Holland | |
| 4,287,190 | A | 9/1981 | Boettcher et al. | |
| 4,292,965 | A | 10/1981 | Nash et al. | |
| 4,300,244 | A | 11/1981 | Bokros | |
| 4,307,111 | A | 12/1981 | Crawley | |
| 4,310,523 | A | 1/1982 | Neumann | |
| 4,315,028 | A | 2/1982 | Scheinberg | |
| 4,317,915 | A | 3/1982 | Confalone et al. | |
| 4,323,707 | A | 4/1982 | Suarez et al. | |
| 4,332,791 | A | 6/1982 | Raaf et al. | |
| 4,339,429 | A | 7/1982 | Raaf et al. | |
| 4,380,635 | A | 4/1983 | Peters | |
| 4,382,143 | A | 5/1983 | Shepherd | |
| 4,389,330 | A | 6/1983 | Tice et al. | 427/213.36 |
| 4,389,393 | A | 6/1983 | Schor et al. | |
| 4,391,797 | A | 7/1983 | Folkman et al. | |
| 4,418,068 | A | 11/1983 | Jones | |
| 4,428,963 | A | 1/1984 | Confalone et al. | |
| 4,440,754 | A | 4/1984 | Sorenson | |

(Continued)

FOREIGN PATENT DOCUMENTS

| | | |
|---|---|---|
| AU | 31079/93 | 7/1993 |
| CA | 2086642 | 7/1993 |
| CA | 2079205 | 3/1994 |
| CA | 2207659 | 6/1996 |
| CA | 2231727 | 9/2004 |
| DE | A 3 918 736 | 12/1990 |
| DE | A 40 22 956 | 2/1992 |
| DE | 4401554 | 8/1994 |
| DE | 4320896 | 1/1995 |
| DE | 4320898 | 1/1995 |

(Continued)

OTHER PUBLICATIONS

Sollott et al., The Journal of Clinical Investigation, vol. 95, Apr. 1995, pp. 1869-1876.*

(Continued)

*Primary Examiner* — Tracy Vivlemore
(74) *Attorney, Agent, or Firm* — Fish & Richardson P.C.

(57) ABSTRACT

Methods are provided for inhibiting stenosis following vascular trauma or disease in a mammalian host, comprising administering to the host a therapeutically effective dosage of a therapeutic conjugate containing a vascular smooth muscle binding protein that associates in a specific manner with a cell surface of the vascular smooth muscle cell, coupled to a therapeutic agent dosage form that inhibits a cellular activity of the muscle cell. Methods are also provided for the direct and/or targeted delivery of therapeutic agents to vascular smooth muscle cells that cause a dilation and fixation of the vascular lumen by inhibiting smooth muscle cell contraction, thereby constituting a biological stent. Also discussed are mechanisms for in vivo vascular smooth muscle cell proliferation modulation, agents that impact those mechanisms and protocols for the use of those agents.

9 Claims, 21 Drawing Sheets

U.S. PATENT DOCUMENTS 4,442,119 A 4/1984 Magarian et al. ............ 424/274
4,485,096 A 11/1984 Bell ............ 424/95
4,485,097 A 11/1984 Bell ............ 424/95
4,487,780 A 12/1984 Scheinberg
4,491,574 A 1/1985 Seifter et al.
4,512,762 A 4/1985 Spears ............ 604/21
4,536,516 A 8/1985 Harper et al.
4,555,402 A 11/1985 Matsuda et al. ............ 424/122
4,577,636 A 3/1986 Spears ............ 128/654
4,605,644 A 8/1986 Foker
4,613,665 A 9/1986 Larm
4,629,694 A 12/1986 Harpel
4,655,771 A 4/1987 Wallsten
4,656,083 A 4/1987 Hoffman et al.
4,657,928 A 4/1987 Sorenson
4,664,097 A 5/1987 McGrath et al.
4,670,428 A 6/1987 Sorenson
4,675,189 A 6/1987 Kent et al. ............ 424/490
4,678,466 A 7/1987 Rosenwald
4,687,482 A 8/1987 Hanson
4,689,046 A 8/1987 Bokros
4,696,949 A 9/1987 Toivola et al.
4,705,647 A 11/1987 Yamaguchi et al.
4,732,763 A 3/1988 Beck et al. ............ 424/433
4,733,665 A 3/1988 Palmaz
4,739,762 A 4/1988 Palmaz
4,744,981 A 5/1988 Pavanasasivam ............ 424/85
4,748,982 A 6/1988 Horzewski et al.
4,753,652 A 6/1988 Langer et al.
4,757,059 A 7/1988 Sorenson
4,758,554 A 7/1988 Sorenson et al.
4,758,555 A 7/1988 Sorenson
4,760,051 A 7/1988 Pickart
4,762,129 A 8/1988 Bonzel
4,767,758 A 8/1988 Breccia et al.
4,768,507 A 9/1988 Fischell et al.
4,776,337 A 10/1988 Palmaz
4,784,659 A 11/1988 Fleckenstein et al.
4,786,500 A 11/1988 Wong
4,793,348 A 12/1988 Palmaz
4,824,436 A 4/1989 Wolinsky ............ 604/53
4,824,661 A 4/1989 Wagner
4,826,672 A 5/1989 Milius et al. ............ 424/1
4,835,002 A 5/1989 Wolf et al. ............ 426/590
RE32,944 E 6/1989 Harita et al. ............ 562/455
4,839,155 A 6/1989 McCague ............ 424/1
4,840,939 A 6/1989 Leveen et al.
4,853,377 A 8/1989 Pollack
4,859,585 A 8/1989 Sonnenschein et al. ........ 435/29
4,867,973 A 9/1989 Goers et al. ............ 530/387
4,872,867 A 10/1989 Joh et al.
4,879,225 A 11/1989 Morgan, Jr. et al. ............ 435/68
4,879,315 A 11/1989 Magarian et al. ............ 514/754
4,886,062 A 12/1989 Wiktor
4,897,255 A 1/1990 Fritzberg et al. ............ 424/1
4,900,561 A 2/1990 Abdel-Monem et al.
4,906,452 A 3/1990 Sivam ............ 424/10
4,916,193 A 4/1990 Tang et al.
4,919,939 A * 4/1990 Baker ............ 424/493
4,922,905 A 5/1990 Strecker
4,929,602 A 5/1990 Harker et al. ............ 514/18
4,935,415 A 6/1990 Nakano et al. ............ 514/211
4,942,184 A * 7/1990 Haugwitz et al. ............ 514/449
4,952,607 A 8/1990 Sorenson
4,954,126 A 9/1990 Wallsten
4,956,188 A 9/1990 Anderson
4,959,355 A 9/1990 Fischbarg et al.
RE33,403 E 10/1990 Stolle et al. ............ 424/87
4,962,091 A 10/1990 Eppstein et al. ............ 514/2
4,968,350 A 11/1990 Bindschaedler et al. ..... 106/170
4,973,601 A 11/1990 Dowd et al.
4,973,755 A 11/1990 Grafe et al.
4,984,594 A 1/1991 Vinegar et al.
4,990,158 A 2/1991 Kaplan et al.
4,990,538 A 2/1991 Harris et al. ............ 514/648
4,994,033 A 2/1991 Shockey et al. ............ 604/101
4,994,071 A 2/1991 McGregor
4,994,384 A 2/1991 Prather et al.
4,996,194 A 2/1991 Cohen et al.
4,996,225 A 2/1991 Toivola et al.
4,997,652 A 3/1991 Wong ............ 424/428
4,999,347 A 3/1991 Sorenson
5,002,531 A 3/1991 Bonzel
5,008,279 A 4/1991 Franckowiak et al.
5,009,659 A 4/1991 Hamlin et al. ............ 606/159
5,015,578 A 5/1991 Schroeder et al. ............ 435/119
5,015,666 A 5/1991 Magarian et al. ............ 514/754
5,019,096 A 5/1991 Fox, Jr. et al.
5,019,504 A 5/1991 Christen et al.
5,023,237 A 6/1991 Pickart et al.
5,026,537 A 6/1991 Daddona et al. ............ 424/1.1
5,030,637 A 7/1991 Einzig et al.
5,032,679 A 7/1991 Brandley et al. ............ 536/21
5,034,265 A 7/1991 Hoffman et al.
5,037,641 A 8/1991 Juhos et al.
5,040,548 A 8/1991 Yock
5,043,335 A 8/1991 Kleinschroth et al. ........ 514/211
5,047,431 A 9/1991 Schickaneder et al. ....... 514/648
5,049,132 A 9/1991 Shaffer et al. ............ 604/101
5,053,033 A 10/1991 Clarke et al. ............ 606/3
5,053,048 A 10/1991 Pinchuk et al.
5,059,166 A 10/1991 Fischell et al. ............ 600/3
5,061,273 A 10/1991 Yock
5,061,275 A 10/1991 Wallsten et al.
5,064,435 A 11/1991 Porter
5,066,789 A 11/1991 Srinivasan et al. ............ 530/388
5,073,633 A 12/1991 Schroeder et al. ............ 540/545
5,075,321 A 12/1991 Schreiber
5,082,834 A 1/1992 Sorensen
5,092,877 A 3/1992 Pinchuk
5,093,330 A 3/1992 Caravatti et al. ............ 514/211
5,098,903 A 3/1992 Magarian et al. ............ 514/255
5,099,504 A 3/1992 Pettit
5,100,885 A 3/1992 Abrams et al.
5,102,402 A 4/1992 Dror et al. ............ 604/265
5,102,417 A 4/1992 Palmaz
5,108,989 A 4/1992 Amento et al.
5,112,305 A 5/1992 Barath et al. ............ 704/96
5,114,719 A 5/1992 Sabel et al. ............ 424/422
5,114,847 A 5/1992 Jungfer et al.
5,116,864 A 5/1992 March et al. ............ 514/455
5,118,791 A 6/1992 Burnier et al.
5,120,535 A 6/1992 Marquardt et al. .......... 424/85.5
5,126,348 A 6/1992 McMurray
5,140,012 A 8/1992 McGovern et al. ............ 514/19
5,145,684 A 9/1992 Liversidge et al.
5,145,838 A 9/1992 Pickart
5,147,332 A 9/1992 Moorehead
5,163,952 A 11/1992 Froix
5,166,143 A 11/1992 Ondetti et al. ............ 514/89
5,166,191 A 11/1992 Cronin et al.
5,167,960 A 12/1992 Ito et al.
5,171,217 A * 12/1992 March et al. ............ 604/507
5,175,235 A 12/1992 Domb et al. ............ 528/271
5,176,617 A 1/1993 Fischell et al. ............ 600/3
5,180,366 A 1/1993 Woods ............ 604/96
5,180,376 A 1/1993 Fischell
5,182,317 A 1/1993 Winters et al.
5,185,260 A 2/1993 Crissman et al. ............ 435/244
5,185,408 A 2/1993 Tang et al.
5,189,046 A 2/1993 Burch et al. ............ 514/330
5,189,212 A 2/1993 Ruenitz ............ 562/468
5,192,525 A 3/1993 Yang et al. ............ 424/11
5,195,984 A 3/1993 Schatz
5,197,977 A 3/1993 Hoffman, Jr. et al.
5,199,939 A 4/1993 Dake et al. ............ 600/3
5,199,951 A 4/1993 Spears
5,208,019 A 5/1993 Hanson et al. ............ 424/85
5,208,238 A 5/1993 King ............ 514/255
5,211,940 A 5/1993 Ishiguro et al.
5,213,576 A 5/1993 Abiuso et al. ............ 604/96
5,213,580 A 5/1993 Slepian et al. ............ 623/1
5,216,021 A 6/1993 Sorenson
5,216,024 A 6/1993 Markaverich et al. ........ 514/543
5,216,115 A 6/1993 Kohn et al.
5,216,126 A 6/1993 Cox et al. ............ 530/350
5,219,548 A 6/1993 Yang et al. ............ 424/1

5,221,620 A 6/1993 Purchio et al. .................. 435/69
5,222,971 A 6/1993 Willard et al.
5,226,430 A 7/1993 Spears et al. .................. 128/898
5,226,913 A 7/1993 Pinchuk
5,229,495 A 7/1993 Ichijo et al. ................... 530/350
5,232,444 A 8/1993 Just et al. ........................ 604/96
5,232,911 A 8/1993 Vidal .............................. 514/12
5,234,456 A 8/1993 Silvestrini
5,234,957 A 8/1993 Mantelle
5,238,714 A 8/1993 Wallace et al. ............... 427/213
5,238,950 A 8/1993 Clader et al. .................. 514/360
5,240,913 A 8/1993 Maraganore et al.
5,242,397 A 9/1993 Barath et al. .................... 604/96
5,248,764 A 9/1993 Flanagan et al. .............. 530/324
5,252,579 A 10/1993 Skotnicki et al. ............. 514/291
5,254,594 A 10/1993 Niikura et al. ................ 514/648
5,258,020 A 11/1993 Froix
5,260,224 A 11/1993 Stossel et al. ................. 436/503
5,262,319 A 11/1993 Iwata et al.
5,262,451 A 11/1993 Winters et al.
5,268,358 A 12/1993 Fretto et al. ..................... 514/12
5,268,455 A 12/1993 Cianciolo ..................... 530/404
5,270,047 A 12/1993 Kauffman et al. ............ 424/422
5,280,016 A 1/1994 Conrad et al. .................. 514/56
5,280,040 A 1/1994 Labroo et al.
5,280,109 A 1/1994 Miyazono et al. ............ 530/399
5,282,785 A 2/1994 Shapland et al. ............... 604/21
5,282,823 A 2/1994 Schwartz et al.
5,283,257 A 2/1994 Gregory et al. ............... 514/458
5,284,763 A 2/1994 Derynk et al. ................ 435/240
5,284,869 A 2/1994 Bisaccia et al. ............... 514/455
5,288,711 A 2/1994 Mitchell et al. ................. 514/56
5,288,735 A 2/1994 Trager et al. .................. 514/363
5,290,271 A 3/1994 Jernberg .................... 604/891.1
5,292,802 A 3/1994 Rhee et al.
5,296,492 A 3/1994 Shiozawa et al. ............. 514/337
5,302,584 A 4/1994 Kao et al. ........................ 514/80
5,304,121 A 4/1994 Sahatjian
5,304,325 A 4/1994 Kaufman et al. ............. 252/312
5,304,541 A 4/1994 Purchio et al. .................. 514/12
5,308,622 A 5/1994 Casscells et al. ............. 424/422
5,308,862 A 5/1994 Ohlstein et al. ............... 514/411
5,308,889 A 5/1994 Rhee et al.
5,314,679 A 5/1994 Lewis et al. ....................... 424/9
5,316,766 A 5/1994 Baldus et al. ................... 424/94
5,318,779 A 6/1994 Hakamatsuka et al.
5,324,736 A 6/1994 Magarian et al. ............. 514/317
5,324,739 A 6/1994 Germick et al.
5,326,757 A 7/1994 Demopoulos ................. 514/167
5,328,471 A 7/1994 Slepian ......................... 604/101
5,332,576 A 7/1994 Mantelle
5,332,584 A 7/1994 Scher et al. ................... 424/408
5,338,770 A 8/1994 Winters et al.
5,340,925 A 8/1994 Lioubin et al. ................ 530/395
5,342,348 A 8/1994 Kaplan
5,342,926 A 8/1994 Hattner
5,344,926 A 9/1994 Murakata et al.
5,346,702 A 9/1994 Na et al. ........................ 424/490
5,346,897 A 9/1994 King ............................ 514/290
5,346,993 A 9/1994 Miyazono et al. ............ 530/399
5,354,562 A 10/1994 Platz et al. .................... 424/489
5,354,774 A 10/1994 Deckelbaum et al. ........ 514/455
5,354,801 A 10/1994 O'toole et al.
5,356,433 A 10/1994 Rowland et al.
5,356,713 A 10/1994 Charmot et al. .............. 428/407
5,358,844 A 10/1994 Stossel et al. ..................... 435/2
5,362,424 A 11/1994 Lee et al. ....................... 264/4.3
5,362,478 A 11/1994 Desai et al. ....................... 424/9
5,362,718 A 11/1994 Skotnicki et al. ............... 514/63
5,364,632 A 11/1994 Benita et al. .................. 424/450
5,364,843 A 11/1994 King ............................... 514/15
5,378,475 A 1/1995 Smith et al.
5,380,299 A 1/1995 Fearnot et al.
5,380,716 A 1/1995 Conrad et al. .................. 514/56
5,383,928 A 1/1995 Scott et al.
5,384,332 A 1/1995 Fontana
5,385,935 A 1/1995 Tamai et al. .................. 514/535
5,387,680 A 2/1995 Nelson .......................... 540/456
5,389,670 A 2/1995 Fontana
5,391,378 A 2/1995 Sanderson
5,391,557 A 2/1995 Cullinan et al.
5,393,763 A 2/1995 Black et al. ................... 514/333
5,393,772 A 2/1995 Yue et al. ...................... 514/410
5,393,785 A 2/1995 Labrie et al.
5,395,610 A 3/1995 King .............................. 424/10
5,395,842 A 3/1995 Labrie et al.
5,399,352 A 3/1995 Hanson
5,401,730 A 3/1995 Sauvage et al.
5,405,919 A 4/1995 Keefer et al.
5,407,609 A 4/1995 Tice et al.
5,407,658 A 4/1995 Hattner
5,411,967 A 5/1995 Kao et al. ...................... 514/291
5,411,988 A 5/1995 Bockow et al.
5,413,797 A * 5/1995 Khan et al. .................... 424/489
5,415,619 A 5/1995 Lee et al.
5,416,205 A 5/1995 della Valle et al. ............. 514/54
5,418,252 A 5/1995 Williams
5,419,760 A 5/1995 Narciso, Jr.
5,420,243 A 5/1995 Ogawa et al.
5,421,955 A 6/1995 Lau et al.
5,422,362 A 6/1995 Vincent et al. ................ 514/410
5,423,885 A 6/1995 Williams .......................... 623/1
5,424,331 A 6/1995 Shlyankevich
5,426,123 A 6/1995 Fontana
5,429,618 A 7/1995 Keogh
5,429,634 A 7/1995 Narciso et al.
5,434,166 A 7/1995 Glasebrook
5,436,243 A 7/1995 Sachs et al.
5,439,689 A 8/1995 Hendrickson et al.
5,439,923 A 8/1995 Cullinan
5,439,931 A 8/1995 Sales
5,441,734 A 8/1995 Reichert et al.
5,441,947 A 8/1995 Dodge et al. .................. 514/179
5,441,964 A 8/1995 Bryant et al.
5,441,965 A 8/1995 Sall et al.
5,441,966 A 8/1995 Dodge
5,441,986 A 8/1995 Thompson
5,443,458 A 8/1995 Eury
5,444,164 A 8/1995 Purchio et al. ............... 536/23.5
5,445,941 A 8/1995 Yang
5,446,053 A 8/1995 Keohane
5,446,070 A 8/1995 Mantelle
5,447,724 A 9/1995 Helmus et al.
5,447,941 A 9/1995 Zuckerman
5,449,382 A 9/1995 Dayton
5,451,233 A 9/1995 Yock
5,451,414 A 9/1995 Steward
5,451,589 A 9/1995 Dodge
5,451,590 A 9/1995 Dodge
5,451,603 A 9/1995 Piggott
5,453,436 A 9/1995 Ohlstein ....................... 514/411
5,453,442 A 9/1995 Bryant et al.
5,453,492 A 9/1995 Butzow et al.
5,455,275 A 10/1995 Fontana
5,457,113 A 10/1995 Cullinan et al.
5,457,116 A 10/1995 Black et al.
5,457,117 A 10/1995 Black et al.
5,458,568 A 10/1995 Racchini et al. ................ 604/19
5,460,807 A 10/1995 Cardin et al. ................... 424/78
5,461,064 A 10/1995 Cullinan
5,461,065 A 10/1995 Black et al.
5,462,925 A 10/1995 Ogawa et al. ................... 514/12
5,462,937 A 10/1995 Cullinan et al.
5,462,949 A 10/1995 Jones et al.
5,462,950 A 10/1995 Fontana
5,462,966 A 10/1995 Sofia ............................ 514/483
5,464,450 A 11/1995 Buscemi et al.
5,464,650 A 11/1995 Berg et al. ...................... 427/2.3
5,466,810 A 11/1995 Godfrey
5,468,746 A 11/1995 Casagrande et al. ....... 514/235.5
5,470,876 A 11/1995 Proctor
5,470,883 A 11/1995 Stromberg
5,472,985 A 12/1995 Grainger et al.
5,474,563 A 12/1995 Myler et al.
5,478,847 A 12/1995 Draper
5,478,860 A 12/1995 Wheeler et al. ............... 514/449
5,480,888 A 1/1996 Kodama et al.
5,480,903 A 1/1996 Piggott et al.

5,480,904 A 1/1996 Bryant et al.
5,482,851 A 1/1996 Derynck et al.
5,482,949 A 1/1996 Black et al.
5,482,950 A 1/1996 Bryant et al.
5,484,795 A 1/1996 Bryant et al.
5,484,796 A 1/1996 Bryant et al.
5,484,797 A 1/1996 Bryant et al.
5,484,798 A 1/1996 Bryant et al.
5,484,808 A 1/1996 Grinnell
5,486,357 A 1/1996 Narayanan
5,489,587 A 2/1996 Fontana
5,491,159 A 2/1996 Malamas
5,491,173 A 2/1996 Toivola et al.
5,492,895 A 2/1996 Vlasuk et al.
5,492,921 A 2/1996 Bryant et al.
5,492,922 A 2/1996 Palkowitz
5,492,926 A 2/1996 Cullinan et al.
5,492,927 A 2/1996 Gitter et al.
5,496,346 A 3/1996 Horzewski et al.
5,496,557 A 3/1996 Feijen et al.
5,496,581 A 3/1996 Yianni et al. ................ 427/2.12
5,496,828 A 3/1996 Cullinan
5,496,851 A 3/1996 Grinnell
5,498,775 A 3/1996 Novak et al.
5,500,013 A 3/1996 Buscemi et al.
5,504,091 A 4/1996 Molnar-Kimber et al. ... 514/291
5,508,292 A 4/1996 Sall et al.
5,510,077 A 4/1996 Dinh et al.
5,510,370 A 4/1996 Hock et al.
5,512,055 A 4/1996 Domb et al.
5,512,268 A 4/1996 Grinstaff et al. ........... 424/9.322
5,514,154 A 5/1996 Lau et al.
5,516,781 A 5/1996 Morris et al. ................ 514/291
5,516,807 A 5/1996 Hupe et al.
5,519,042 A 5/1996 Morris et al. ................ 514/378
5,521,171 A 5/1996 Sorenson
5,521,172 A 5/1996 Bryant et al.
5,521,191 A 5/1996 Greenwald
5,521,198 A 5/1996 Zuckerman
5,523,092 A 6/1996 Hanson et al.
5,525,357 A 6/1996 Keefer et al.
5,525,610 A 6/1996 Caufield et al. ............... 514/291
5,525,624 A 6/1996 Gitter et al.
5,527,337 A 6/1996 Stack et al. ................... 606/198
5,534,527 A 7/1996 Black et al.
5,538,892 A 7/1996 Donahoe et al.
5,541,174 A 7/1996 Sorenson
5,543,155 A 8/1996 Fekete et al.
5,545,208 A 8/1996 Wolff et al.
5,545,409 A 8/1996 Laurencin et al.
5,545,569 A 8/1996 Grainger et al.
5,551,954 A 9/1996 Buscemi et al.
5,552,415 A 9/1996 May
5,552,433 A 9/1996 Bryant et al.
5,554,182 A 9/1996 Dinh et al.
5,556,876 A 9/1996 Bryant et al.
5,562,922 A 10/1996 Lambert
5,563,054 A 10/1996 Briggs et al.
5,563,145 A 10/1996 Failli et al. .................... 514/291
5,563,146 A 10/1996 Morris et al. ................ 514/291
5,567,417 A 10/1996 Sasisekharan et al.
5,567,713 A 10/1996 Cullinan et al.
5,569,463 A 10/1996 Helmus et al.
5,571,166 A 11/1996 Dinh et al.
5,571,714 A 11/1996 Dasch et al.
5,571,808 A 11/1996 Leeds
5,574,047 A 11/1996 Bumol et al.
5,576,345 A 11/1996 Mansson et al.
5,578,075 A 11/1996 Dayton
5,578,703 A 11/1996 Ichijo et al.
5,580,898 A 12/1996 Trojanowski et al.
5,583,153 A 12/1996 Brahn
5,591,224 A 1/1997 Schwartz et al.
5,591,227 A 1/1997 Dinh et al. ........................ 623/1
5,595,722 A 1/1997 Grainger et al.
5,597,578 A 1/1997 Brown et al.
5,599,352 A 2/1997 Dinh et al. ........................ 623/1
5,599,844 A 2/1997 Grainger et al.
5,605,696 A 2/1997 Eury et al.
5,605,700 A 2/1997 DeGregorio et al.
5,607,463 A 3/1997 Schwartz et al.
5,609,629 A 3/1997 Fearnot et al.
5,610,166 A 3/1997 Singh
5,610,168 A 3/1997 Draper
5,616,608 A 4/1997 Kinsella et al. ............... 514/449
5,622,975 A 4/1997 Singh et al.
5,624,411 A 4/1997 Tuch ............................ 604/265
5,626,600 A 5/1997 Horzewski et al.
5,629,077 A 5/1997 Turnlund et al.
5,632,840 A 5/1997 Campbell
5,632,981 A 5/1997 Saavedra et al.
5,635,489 A 6/1997 Haley
5,637,113 A 6/1997 Tartaglia et al.
5,639,274 A 6/1997 Fischell et al.
5,639,738 A 6/1997 Falk et al.
5,641,790 A 6/1997 Draper
5,643,580 A 7/1997 Subramaniam
5,646,160 A 7/1997 Morris et al. ................ 514/291
5,650,447 A 7/1997 Keefer et al.
5,651,627 A 7/1997 Dowzall et al.
5,652,259 A 7/1997 May
5,656,450 A 8/1997 Boyan et al.
5,656,587 A 8/1997 Sporn et al.
5,658,883 A 8/1997 Ogawa et al.
5,658,927 A 8/1997 Magarian et al.
5,658,951 A 8/1997 Magarian et al.
5,660,873 A 8/1997 Nikolaychik et al.
5,662,712 A 9/1997 Pathak et al.
5,665,728 A 9/1997 Morris et al. ................ 514/291
5,667,764 A 9/1997 Kopia et al.
5,677,295 A 10/1997 Failli et al. .................... 514/183
5,679,400 A 10/1997 Tuch
5,681,835 A 10/1997 Willson
5,686,467 A 11/1997 Bumol et al.
5,686,476 A 11/1997 May
5,688,813 A 11/1997 Sall et al.
5,688,855 A 11/1997 Stoy et al.
5,693,607 A 12/1997 Segarini et al.
5,697,967 A 12/1997 Dinh et al.
5,700,559 A 12/1997 Sheu et al.
5,705,477 A 1/1998 Sporn et al.
5,705,609 A 1/1998 Ruoslahti et al.
5,716,981 A 2/1998 Hunter et al. ................ 514/449
5,722,984 A 3/1998 Fischell et al.
5,726,186 A 3/1998 Grese
5,731,144 A 3/1998 Toothman et al.
5,731,200 A 3/1998 Ichijo et al.
5,731,424 A 3/1998 Toothman et al.
5,733,303 A 3/1998 Israel et al.
5,733,925 A * 3/1998 Kunz et al. .................... 514/449
5,735,897 A 4/1998 Buirge
5,747,510 A 5/1998 Draper
5,749,888 A 5/1998 Yock
5,749,915 A 5/1998 Slepian
5,767,079 A 6/1998 Glaser et al.
5,770,609 A 6/1998 Grainger et al.
5,773,479 A 6/1998 Grainger et al.
5,776,184 A 7/1998 Tuch ................................ 623/1
5,779,732 A 7/1998 Amundson
5,797,898 A 8/1998 Santini, Jr. et al.
5,800,507 A 9/1998 Schwartz
5,811,447 A 9/1998 Kunz et al. .................... 514/411
5,821,234 A 10/1998 Dzau
5,824,048 A 10/1998 Tuch ................................ 623/1
5,824,049 A 10/1998 Ragheb et al.
5,824,054 A 10/1998 Khosravi et al.
5,824,647 A 10/1998 Postlethwaite et al.
5,837,008 A 11/1998 Berg et al. ........................ 623/1
5,837,313 A 11/1998 Ding et al.
5,843,120 A 12/1998 Israel et al.
5,847,007 A 12/1998 Grainger et al.
5,849,034 A 12/1998 Schwartz
5,863,285 A 1/1999 Coletti
5,873,904 A 2/1999 Ragheb et al.
5,877,224 A 3/1999 Brocchini et al.
5,900,246 A 5/1999 Lambert
5,902,332 A 5/1999 Schatz
5,945,456 A 8/1999 Grainger et al. .............. 514/651

| | | | | |
|---|---|---|---|---|
| 5,948,639 | A | 9/1999 | Gimeno et al. | |
| 5,972,018 | A | 10/1999 | Israel et al. | |
| 5,980,972 | A | 11/1999 | Ding | |
| 5,981,568 | A * | 11/1999 | Kunz et al. | 514/411 |
| 5,990,095 | A | 11/1999 | Falk et al. | |
| 5,994,388 | A | 11/1999 | Udagawa et al. | |
| 6,001,622 | A | 12/1999 | Dedhar et al. | |
| 6,013,099 | A | 1/2000 | Dinh et al. | |
| 6,022,866 | A | 2/2000 | Falk et al. | |
| 6,036,715 | A | 3/2000 | Yock | |
| 6,042,875 | A | 3/2000 | Ding et al. | |
| 6,066,167 | A | 5/2000 | Lau et al. | |
| 6,074,337 | A | 6/2000 | Tucker et al. | |
| 6,074,659 | A * | 6/2000 | Kunz et al. | 424/423 |
| 6,086,910 | A | 7/2000 | Howard et al. | |
| 6,087,479 | A | 7/2000 | Stamler et al. | 530/363 |
| 6,093,221 | A | 7/2000 | Grull et al. | |
| 6,096,070 | A | 8/2000 | Ragheb et al. | |
| 6,099,499 | A | 8/2000 | Ciamacco et al. | |
| 6,099,562 | A | 8/2000 | Ding et al. | |
| 6,106,454 | A | 8/2000 | Berg et al. | |
| 6,110,483 | A | 8/2000 | Whitbourne et al. | |
| 6,120,536 | A | 9/2000 | Ding et al. | |
| 6,129,757 | A | 10/2000 | Weadock | |
| 6,133,242 | A | 10/2000 | Zalewski et al. | |
| 6,146,358 | A | 11/2000 | Rowe | |
| 6,152,869 | A | 11/2000 | Park et al. | |
| 6,168,619 | B1 | 1/2001 | Dinh et al. | |
| 6,171,609 | B1 | 1/2001 | Kunz | 424/422 |
| 6,187,370 | B1 | 2/2001 | Dinh et al. | |
| 6,198,016 | B1 | 3/2001 | Lucast et al. | |
| 6,200,558 | B1 | 3/2001 | Saavedra et al. | |
| 6,203,536 | B1 | 3/2001 | Berg et al. | |
| 6,210,393 | B1 | 4/2001 | Brisken et al. | |
| 6,241,762 | B1 | 6/2001 | Shanley | |
| 6,251,920 | B1 | 6/2001 | Grainger et al. | |
| 6,268,390 | B1 * | 7/2001 | Kunz | 514/411 |
| 6,306,421 | B1 | 10/2001 | Kunz et al. | 424/423 |
| 6,309,412 | B1 | 10/2001 | Lau et al. | |
| 6,309,414 | B1 | 10/2001 | Rolando et al. | |
| 6,358,989 | B1 | 3/2002 | Kunz et al. | 514/411 |
| 6,379,660 | B1 | 4/2002 | Saavedra et al. | |
| 6,395,326 | B1 | 5/2002 | Castro et al. | |
| 6,403,635 | B1 | 6/2002 | Kinsella et al. | |
| 6,429,232 | B1 | 8/2002 | Kinsella et al. | |
| 6,432,133 | B1 | 8/2002 | Lau et al. | |
| 6,443,982 | B1 | 9/2002 | Israel et al. | |
| 6,461,381 | B2 | 10/2002 | Israel et al. | |
| 6,476,200 | B1 | 11/2002 | Sabatini et al. | |
| 6,485,511 | B2 | 11/2002 | Lau et al. | |
| 6,488,694 | B1 | 12/2002 | Lau et al. | |
| 6,491,617 | B1 | 12/2002 | Ogle et al. | |
| 6,491,938 | B2 | 12/2002 | Kunz et al. | 424/423 |
| 6,492,106 | B1 | 12/2002 | Sabatini et al. | |
| 6,497,647 | B1 | 12/2002 | Tucker | |
| 6,515,009 | B1 | 2/2003 | Kunz et al. | 514/411 |
| 6,527,789 | B1 | 3/2003 | Lau et al. | |
| 6,544,544 | B2 | 4/2003 | Hunter et al. | |
| 6,544,790 | B1 | 4/2003 | Sabatini | |
| 6,555,138 | B1 | 4/2003 | Karlsson | |
| 6,562,065 | B1 | 5/2003 | Shanley | |
| 6,569,441 | B2 | 5/2003 | Kunz et al. | |
| 6,575,993 | B1 | 6/2003 | Yock | |
| 6,596,022 | B2 | 7/2003 | Lau et al. | |
| 6,599,928 | B2 | 7/2003 | Kunz et al. | |
| 6,616,690 | B2 | 9/2003 | Rolando et al. | |
| 6,616,765 | B1 | 9/2003 | Castro et al. | |
| 6,656,162 | B2 | 12/2003 | Santini, Jr. et al. | |
| 6,656,216 | B1 | 12/2003 | Nossainy et al. | |
| 6,663,881 | B2 * | 12/2003 | Kunz et al. | 424/423 |
| 6,689,159 | B2 | 2/2004 | Lau et al. | |
| 6,720,350 | B2 | 4/2004 | Kunz et al. | |
| 6,764,507 | B2 | 7/2004 | Shanley et al. | |
| 6,783,543 | B2 | 8/2004 | Jang | |
| 2002/0013275 | A1 | 1/2002 | Kunz et al. | |
| 2002/0032477 | A1 | 3/2002 | Helmus et al. | |
| 2002/0040064 | A1 | 4/2002 | Kunz et al. | 514/656 |
| 2002/0086896 | A1 | 7/2002 | Kunz et al. | 514/449 |
| 2002/0091433 | A1 | 7/2002 | Ding et al. | |
| 2002/0119115 | A1 | 8/2002 | Keefer et al. | |
| 2003/0039675 | A1 | 2/2003 | Kunz et al. | 424/423 |
| 2004/0236416 | A1 | 11/2004 | Falotico | |

FOREIGN PATENT DOCUMENTS

| | | | |
|---|---|---|---|
| EP | 0 002 341 | | 6/1979 |
| EP | 0 024 096 | | 2/1981 |
| EP | 0 054 168 | A1 | 6/1982 |
| EP | 0 095 875 | A2 | 12/1983 |
| EP | 0 260 066 | | 3/1988 |
| EP | 0 290 012 | | 11/1988 |
| EP | 0 297 946 | | 1/1989 |
| EP | 0 302 034 | | 2/1989 |
| EP | 0 365 863 | | 5/1990 |
| EP | 0 374 044 | | 6/1990 |
| EP | 0 377 526 | B1 | 7/1990 |
| EP | A 0 430 542 | | 11/1990 |
| EP | A 0 435 518 | | 12/1990 |
| EP | 0 405 831 | | 1/1991 |
| EP | 0 411 893 | | 2/1991 |
| EP | 0 470 569 | A1 | 8/1991 |
| EP | 0 470 246 | | 9/1991 |
| EP | 0 451 202 | | 10/1991 |
| EP | 0 524 093 | | 1/1993 |
| EP | 0 577 215 | | 1/1993 |
| EP | 0 526 102 | | 2/1993 |
| EP | 0 701 802 | A1 | 3/1993 |
| EP | 0 567 816 | A1 | 4/1993 |
| EP | 0 568 310 | A1 | 4/1993 |
| EP | 0 542 679 | | 5/1993 |
| EP | 0 543 653 | A1 | 5/1993 |
| EP | 0 551 182 | | 7/1993 |
| EP | 0 566 245 | A1 | 10/1993 |
| EP | 0 578 998 | | 1/1994 |
| EP | 0 588 518 | | 3/1994 |
| EP | 0 623 345 | A1 | 5/1994 |
| EP | 0 604 022 | A1 | 6/1994 |
| EP | 0 606 613 | | 7/1994 |
| EP | 0 619 314 | | 10/1994 |
| EP | 0 622 076 | | 11/1994 |
| EP | 0 623 354 | | 11/1994 |
| EP | 0 623 354 | A1 | 11/1994 |
| EP | 0 629 697 | | 12/1994 |
| EP | 0 635 270 | | 1/1995 |
| EP | 0 639 577 | | 2/1995 |
| EP | 0 659 413 | A2 | 6/1995 |
| EP | 0 659 415 | A2 | 6/1995 |
| EP | 0 659 418 | | 6/1995 |
| EP | 0 659 419 | A1 | 6/1995 |
| EP | 0 659 429 | A1 | 6/1995 |
| EP | 0 664 121 | | 7/1995 |
| EP | 0 664 122 | | 7/1995 |
| EP | 0 664 123 | | 7/1995 |
| EP | 0 664 124 | A1 | 7/1995 |
| EP | 0 664 125 | | 7/1995 |
| EP | 0 664 198 | | 7/1995 |
| EP | 0 665 015 | A2 | 8/1995 |
| EP | 0 668 075 | A2 | 8/1995 |
| EP | 0 670 162 | | 9/1995 |
| EP | 0 673 936 | | 9/1995 |
| EP | 0 674 903 | | 10/1995 |
| EP | 0 675 121 | | 10/1995 |
| EP | 0357003 | | 10/1995 |
| EP | 0 684 259 | A1 | 11/1995 |
| EP | 0 716 836 | A1 | 12/1995 |
| EP | 0 691 130 | | 1/1996 |
| EP | 0 734 721 | A2 | 2/1996 |
| EP | 0 699 673 | | 3/1996 |
| EP | 0 717 041 | B1 | 6/1996 |
| EP | 0717041 | | 6/1996 |
| EP | 0 734 721 | A2 | 10/1996 |
| EP | 0 747 069 | | 12/1996 |

| | | | |
|---|---|---|---|
| EP | 0 706 376 | B1 | 6/1997 |
| EP | 0 975 340 | | 10/1998 |
| EP | 1 181 943 | A1 | 2/2002 |
| EP | 0 623 354 | B1 | 10/2002 |
| EP | 1 360 967 | A1 | 11/2003 |
| EP | 0711158 | | 12/2003 |
| EP | 0 621 015 | A1 | 4/2004 |
| EP | 0809515 | | 4/2004 |
| EP | 1407786 | | 4/2004 |
| EP | 0975340 | | 10/2004 |
| FR | 2255063 | | 7/1975 |
| GB | 1 587 084 | | 5/1981 |
| GB | 2 153 253 | | 1/1985 |
| GB | 2 273 873 | | 6/1994 |
| GB | 1 015 787 | | 1/1996 |
| GB | 1 205 743 | | 7/1996 |
| IT | 1247527 | | 4/1991 |
| JP | 59-042375 | | 3/1984 |
| JP | 01-501476 | | 5/1989 |
| JP | 02-152993 | | 6/1990 |
| JP | 02-152994 | | 6/1990 |
| JP | 03-297469 | | 12/1991 |
| JP | 60-25288 | | 2/1994 |
| JP | 06-121828 | | 6/1994 |
| JP | 06-205838 | | 7/1994 |
| JP | 08-33718 | | 2/1996 |
| JP | 09-255570 | | 3/1996 |
| JP | 08/131180 | | 5/1996 |
| JP | 08-131180 | | 5/1996 |
| JP | 08-506112 | | 7/1996 |
| JP | 09-040567 | | 2/1997 |
| JP | 09-40567 | | 2/1997 |
| WO | WO 85/00107 | | 1/1985 |
| WO | WO 88/10259 | | 12/1988 |
| WO | WO 89/03232 | | 4/1989 |
| WO | WO 90/01969 | | 3/1990 |
| WO | WO 90/07328 | | 7/1990 |
| WO | WO 90/11676 | | 10/1990 |
| WO | WO 90/12597 | | 11/1990 |
| WO | WO 90/13293 | | 11/1990 |
| WO | WO 90/13332 | | 11/1990 |
| WO | WO 91/07154 | | 5/1991 |
| WO | WO 91/08291 | | 6/1991 |
| WO | WO 91/10424 | | 7/1991 |
| WO | WO 91/11193 | | 8/1991 |
| WO | WO 91/12779 | | 9/1991 |
| WO | WO 91/12846 | | 9/1991 |
| WO | WO 91/15219 | | 10/1991 |
| WO | WO 91/15222 | | 10/1991 |
| WO | WO 91/17731 | | 11/1991 |
| WO | WO 91/17789 | A1 | 11/1991 |
| WO | WO 91/18940 | A1 | 12/1991 |
| WO | WO 92/00330 | | 1/1992 |
| WO | WO 92/06068 | | 4/1992 |
| WO | WO 92/08480 | | 5/1992 |
| WO | WO 92/10210 | | 6/1992 |
| WO | WO 92/11872 | | 7/1992 |
| WO | WO 92/11890 | | 7/1992 |
| WO | WO 92/11895 | | 7/1992 |
| WO | WO 92/12717 | | 8/1992 |
| WO | WO 92/13867 | | 8/1992 |
| WO | WO92/15282 | | 9/1992 |
| WO | WO 92/15282 | | 9/1992 |
| WO | WO 92/15286 | | 9/1992 |
| WO | WO 92/18546 | | 10/1992 |
| WO | WO 92/19273 | | 11/1992 |
| WO | WO 92/19612 | | 11/1992 |
| WO | WO 92/21363 | | 12/1992 |
| WO | WO 93/02065 | | 2/1993 |
| WO | WO 93/04191 | | 3/1993 |
| WO | WO 93/06792 | | 4/1993 |
| WO | WO 93/07748 | | 4/1993 |
| WO | WO 93/09228 | | 5/1993 |
| WO | WO 93/09765 | | 5/1993 |
| WO | WO 93/09790 | | 5/1993 |
| WO | WO 93/09800 | | 5/1993 |
| WO | WO 93/09802 | | 5/1993 |
| WO | WO 93/10808 | | 6/1993 |
| WO | WO 93/11120 | | 6/1993 |

| | | |
|---|---|---|
| WO | WO 93/11757 | 6/1993 |
| WO | WO 93/16687 | 9/1993 |
| WO | WO 93/16724 | 9/1993 |
| WO | WO 93/17121 | 9/1993 |
| WO | WO 93/17669 | 9/1993 |
| WO | WO 93/19746 | 10/1993 |
| WO | WO 93/19769 | 10/1993 |
| WO | WO93/24476 | 12/1993 |
| WO | WO 93/24476 | 12/1993 |
| WO | WO 94/01056 | 1/1994 |
| WO | WO 94/02595 | 2/1994 |
| WO | WO 94/03644 | 2/1994 |
| WO | WO 94/04164 | 3/1994 |
| WO | WO 94/04178 | 3/1994 |
| WO | WO 94/07529 | 4/1994 |
| WO | WO 94/08604 | 4/1994 |
| WO | WO 94/08605 | 4/1994 |
| WO | WO 94/09010 | 4/1994 |
| WO | WO 94/09764 | 5/1994 |
| WO | WO 94/09812 | 5/1994 |
| WO | WO 94/10187 | 5/1994 |
| WO | WO 94/13268 | 6/1994 |
| WO | WO 94/13706 | 6/1994 |
| WO | WO 94/15589 | 7/1994 |
| WO | WO 94/15590 | 7/1994 |
| WO | WO 94/15646 | 7/1994 |
| WO | WO 9415583 | 7/1994 |
| WO | WO 94/16706 | 8/1994 |
| WO | WO 94/17786 | 8/1994 |
| WO | WO 94/18345 | 8/1994 |
| WO | WO 94/18954 | 9/1994 |
| WO | WO 94/18967 | 9/1994 |
| WO | WO 94/18968 | 9/1994 |
| WO | WO 94/19000 | 9/1994 |
| WO | WO 94/19001 | 9/1994 |
| WO | WO 94/19003 | 9/1994 |
| WO | WO 94/20096 | 9/1994 |
| WO | WO 94/20097 | 9/1994 |
| WO | WO 94/20098 | 9/1994 |
| WO | WO 94/20099 | 9/1994 |
| WO | WO 94/20116 | 9/1994 |
| WO | WO 94/20117 | 9/1994 |
| WO | WO 94/20126 | 9/1994 |
| WO | WO 94/20127 | 9/1994 |
| WO | WO 94/21308 | 9/1994 |
| WO | WO 94/21309 | 9/1994 |
| WO | WO 94/21679 | 9/1994 |
| WO | WO 94/22436 | 10/1994 |
| WO | WO 94/23068 | 10/1994 |
| WO | WO 94/23699 | 10/1994 |
| WO | WO 94/24961 | 11/1994 |
| WO | WO 94/25020 | 11/1994 |
| WO | WO 94/25053 | 11/1994 |
| WO | WO 94/25588 | 11/1994 |
| WO | WO 94/26291 | 11/1994 |
| WO | WO 94/26303 | 11/1994 |
| WO | WO 94/26888 | 11/1994 |
| WO | 94/28721 | 12/1994 |
| WO | WO 94/27612 | 12/1994 |
| WO | WO 94/28721 | 12/1994 |
| WO | 95/03075 | 2/1995 |
| WO | WO 95/03036 | 2/1995 |
| WO | WO 95/03795 | 2/1995 |
| WO | WO 95/04544 | 2/1995 |
| WO | WO 95/05191 | 2/1995 |
| WO | WO 95/10611 | 4/1995 |
| WO | WO 95/17095 | 6/1995 |
| WO | WO 95/19987 | 7/1995 |
| WO | WO 95/20582 | 8/1995 |
| WO | WO 95/30900 | 11/1995 |
| WO | WO 95/33736 | 12/1995 |
| WO | WO 96/01102 | 1/1996 |
| WO | WO 96/03092 | 2/1996 |
| WO | WO 96/07402 | 3/1996 |
| WO | WO 96/15224 | 5/1996 |
| WO | WO 96/20698 | 7/1996 |
| WO | WO 96/21442 | 7/1996 |
| WO | WO 96/21443 | 7/1996 |
| WO | WO96/21576 | 7/1996 |

| | | |
|---|---|---|
| WO | WO 96/24356 | 8/1996 |
| WO | WO 96/25176 | 8/1996 |
| WO | WO 96/32907 | 10/1996 |
| WO | WO 96/36349 | 11/1996 |
| WO | WO 96/40098 | 12/1996 |
| WO | WO 97/10011 | 3/1997 |
| WO | WO 97/10334 | 3/1997 |
| WO | WO 97/15319 | 5/1997 |
| WO | WO 97/21455 | 6/1997 |
| WO | WO 97/22697 | 6/1997 |
| WO | WO 97/33552 | 9/1997 |
| WO | WO 97/45105 | 12/1997 |
| WO | WO 00/00238 | 1/2000 |
| WO | WO 0047197 | 8/2000 |

OTHER PUBLICATIONS

Bissery et al. (Cancer Research, 1991, vol. 51, pp. 4845-4852.*

Ringel et al. (JNCI, 1991, vol. 83 (4), pp. 288-291.*

Pastan et al. Annual Review of Biochemistry 1992, vol. 61, pp. 331-354.*

Akselband et al., "Rapamycin Inhibits Spontaneous and Fibroblast Growth Factor Beta-Stimulated Proliferation of Endothelial Cells and Fibroblasts", *Transplantation Proceedings*, 23, 2833-2836 (1991).

Graham et al., "Dexamethasone Inhibits Growth and Na:H Exchange in Vascular Smooth Muscle Cells", *Journal of Endocrinology*, 129 (Suppl.), Abstract 180, 10th Joint Meeting of British Endocrine Societies, Brighton, England, UK, Apr. 15-18, 1991.

Gregory et al., "Rapamycin Inhibits Arterial Intimal Thickening Caused by Both Alloimmune and Mechanical Injury", *Transplantation*, 55, 1409-1418 (1993).

Meiser et al., "Effects of Cyclosporin, FK506, and Rapamycin on Graft-Vessel Disease", *The Lancet*, 338, 1297-1298 (1991).

Morris et al., "Immunosuppressive Effects of the Morpholinoethyl Ester of Mycophenolic Acid (RS-61443) in Rat and Nonhuman Primate Recipients of Heart Allografts", *Transplantation Proceedings*, 23, 19-25 (1991).

Morris, "Rapamycins: Antifungal, Antitumor, Antiproliferative, and Immunosuppressive Macrolides", *Transplantation Reviews*, 6, 39-87 (1992).

Nakano, "Glucocorticoid Inhibits Thrombin-Induced Expression of Platelet-Derived Growth Factor A-chain and Heparin-Binding Epidermal Growth Factor-Like Growth Factor in Human Aortic Smooth Muscle Cells", *The Journal of Biological Chemistry*, 268, 22941-22947 (1993).

Palmaz et al., "Intravascular Stents", *Advances in Vascular Surgery*, 1, 107-135 (1993).

Powell et al., "Suppression of the Vascular Response to Injury: The Role of Angiotensin-Converting Enzyme Inhibitors", *JACC*, 17, 137B-142B (1991).

Schatz, "A View of Vascular Stents", *Circulation*, 79, 445-457 (1989).

Feelisch, M., et al., "Biotransformation of Organic Nitrates to Nitric Oxide by Vascular Smooth Muscle and Endothelial Cells", *Biochemical and Biophysical Research Communications*, 180, 286-293 (1991).

Garg, U.C., et al., "Nitric Oxide-Generating Vasodilators and 8-Bromo-Cyclic Guanosine Monophosphate Inhibit Mitogenesis and Proliferation of Cultured Rat Vascular Smooth Muscle Cells", *Journal of Clinical Investigation*, 83, 1774-1777 (1989).

Gregory et al., "Effects of Treatment with Cyclosporine, FK 506, Rapamycin, Mycophenolic Acid, or Deoxyspergualin on Vascular Muscle Proliferation In Vivo", *Transplantation Proceedings*, 25, 770-771 (1993).

More et al., "A Targeted Antithrobotic Conjugate with Antiplatelet and Fibrinolytic Properties which Reduces in vivo Thrombus Formation", *Cardiovascular Research*, 27, 2200-2204 (1993).

Nunes et al., "Vitamins C and E Improve the Response to Coronary Balloon Injury in the Pig: Effect of Vascular Remodeling", *Circulation*, 88, Abstract No. 1994, I-372 (1993).

Speir et al., "Potential Role of Human Cytomegalovirus and p53 Interaction in Coronary Restenosis", *Science*, 265, 391-394 (1994).

Barnhart, et al., "Accelerated arteriosclerosis in cardiac transplant recipients," Transplantation Rev., 1, 31-46 (1987).

Kirschenlohr et al., "Adult Human Aortic Smooth Muscle Cells in Culture Produce Active TFG-Beta", Amer. J. Physiol., 265, C571-C576 (1993).

Kreuzer et al., "Lipoprotein (a) Displays Increased Accumulation Compared with Low-Density Lipoprotein in the Murine Arterial Wall," Chemistry and Physics of Lipids, 67/68, 175-190 (1990).

Palmaz et at, "Balloon Expandable Intraluminal Grafting of Normal and Abnormal Renal Arteries: Experimental Study," Radiology, 161(P), 40-41 Abstract 85 (Nov. 1986).

Reiner, et al., "Antiestrogen Tamoxifen Reduces Lipoprotein(a)," Abstracts, The Second International Conference on Lipoprotein(a), New Orleans, LA, 124, (Nov. 12-14, 1992).

Sunkara, et al., "Cytochalasin B inhibits polyamine biosynthesis in Hela cell", Abstract of European Journal of Cell Biology, vol. 26. No. 1, pp. 154-157 (Dec. 1981).

Takagi. et al., "Nitric oxide blocks the cell cycle of mouse macrophage-like cells in the early G2+M phase", FEBS Letters, vol. 340, No. 3. pp. 159-162 (Mar. 7, 1994).

Vrudhula, et al.. "Selective Synethic Transformations with Roridin A," Abstracts, 199th American Chemical Society National Meeting, Abstract No. 50, Boston, MA (Apr. 22-27, 1990).

U.S. Appl. No. 07/767,254, filed Sep. 27, 1991, Kunz, et al.

U.S. Appl. No. 08/526,273, filed Sep. 11, 1995, Ding.

Merkel et al. Protein kinase C and vascular smooth muscle contractility: effects of inhibitors and down-regulation.J Pharmacol Exp Ther. Apr. 1991;257(1):134-40.

Sasaki et al., Concanavalin A- and fetal-calf-serum-induced rounding and myosin light chain phosphorylation in cultured smooth muscle cells.J Cell Physiol. Aug. 1990;144(2):183-9.

Sjölund and Thyberg, Suramin inhibits binding and degradation of platelet-derived growth factor in arterial smooth muscle cells but does not interfere with autocrine stimulation of DNA synthesis.Cell Tissue Res. Apr. 1989;256(1):35-43.

Non-Final Office Action for U.S. Appl. No. 11/703,191, Aug. 31, 2007.

Final Office Action for U.S. Appl. No. 11/703,191, Jun. 4, 2008.

Restriction Requirement for U.S. Appl. No. 11/679,650, Oct. 3, 2007.

Non-Final Office Action for U.S. Appl. No. 11/679,650, Jan. 25, 2008.

Final Office Action for U.S. Appl. No. 11/679,650, Jul. 29, 2008.

"Breast Cancer Prevention Trial Should Resume, ODAC Says", *The Breast Cancer Letter*, 20, 4-5, (Jun. 17, 1994).

"Churchill's Medical Dictionary", *definition of "cytostatic*". 473, (1989).

"Coronary Artery Disease: Restenosis and Reocclusion After Surgical and Nonsurgical Interventions, Part I", Durg and Market Development, 5, 121-129 (Sep. 26, 1994).

"Glaxo Wellcome Preclinical Data: Preclinical studies conducted with GW 5638, a selective estrogen receptor modulator developed by Glaxo Wellcome, indicate that the compound acts both as an agonist and antagonist at estrogen receptor within specific . . . ", R & D Focus Drug News, (Sep. 8. 1997).

"Growth Factor Via Gene Therapy Abates Sore Rheumatoid Joints", BioWorld Today: The Daily Biotechnology Newspaper, 9(115), Leff, David N., Editor, 1, (Jun. 17, 1998).

"Health Report—The Good News", Time, 23, (Apr. 1, 1996).

"Heparin", In: Modern Pharmacology, Craig, C.R., et al., (eds.), Little, Brown and Company, Boston, MA, p. 399, (1982).

"ICI United States, Inc., Tamoxifen citrate, Summary For Basis of Approval", (Dec. 30, 1977).

"Johnson & Johnson receives FDA approval to market Palmaz Balloon-expandable Stent for iliac arteries," Business Wire, Oct. 2, 1991.

"Micellar and Lyotropic Liquid Crystalline Phases Containing Nonionic Active Substances". In: Lyotropic Liquid Crystals and the Structure of Biomembranes, S. Fribert, (ed.), Advances in Chemistry Series. No. 152, American Chemical Society, 28-42, (1976).

"Muscle-Binding Gene Sees Two-Track Payoff: Human Therapies, Animal Meat". BioWorld Today: The Daily Biotechnology Newspaper, 8(85), Leff, David N., Editor, 1-3, (May 2, 1997).

"Prevention of Coronary Heart Disease", In: Avery's Drug Treatment—Principles and Practice of Clinical Pharmocology and Therapeutics, Speight, T. M., (ed.), Williams and Wilkins, Baltimore, 594-595, (1987).
"Quantikine Human TGF-betal Immunoassay", Product Brochure, Catalog No. DB100, R&D Systems, Inc., pp. 1-19 (Mar. 1996).
"Schering/Orion Fareston Anti-Estrogen for Treatment of Metastatic Breast Cancer 'Similar' to Tamoxifen, FDA Oncologic Committee Says in Approval Vote", F-D-C Reports, 15-16, (Oct. 23, 1995).
Shiga Medical Center for Adult Diseases, "The Impact of Tranilast on Restenosis Following Coronary Angioplasty: The Tranilast Restenosis Following Angioplasty Trial (TREAT)", Circulation, 90, 1-82, Abstract No. 0, (Oct. 1988).
"Tamoxifen therapy found safe for survivors of breast cancer", Fred Hutchinson Cancer Research Center Newsletter, 1(21), (Oct. 1995).
"Toprol XLTM Tablets", In: Physician's Desk Reference., 658-660, (Probably 1992).
Agarwal, A.K., et al., "Estrogen Receptor-Binding Affinity of Tamoxifen Analogs with Various Side Chains and their Biologic Profile in Immature Rat Uterus", Steroids, 56, 486-489, (1991).
AinMelk, Y., et al., "Tamoxifen Citrate Therapy in Male Fertility", Fertility and Sterility, 48, 113-117, (Jul. 1987).
Alberts, B. et al., "Molecular Biology of the Cell" 2nd edition 1989, p. 653.
Alberts, B., et al., "Actin Filaments are Continually Formed and Broken Down in Cells", In: Molecular Biology of the Cell, Garland Publishing, London, 571, (1983).
Alderson, T. 1990.. "New targets for cancer chemotherapy—poly(ADP-ribosylation) processing and polyisoprenc metabolism," Biol. Rev. 65:623-641.
Aldridge, D.C., et al., "The Structures of Cytochalasins A and B", J. Chem. Soc., 17, 1667-1676, ( 1967).
Alich, A.A., et al., "Comparison of Aspirin and Copper Aspirinate with Respect to Gastric Mucosal Damage in the Rat", Journal of Pharmaceutical Sciences, 72, 1457-1461, (Dec. 1983).
Alich, A.A., et al., "Gastric Mucosal Damage Due to Aspirin and Copper Aspirinate Assessed by Gastric Mucosal Potential Difference Changes", Journal of Pharmacological and Toxicological Methods, 27, 245-250, (Jul. 1992).
Alich, A.A., et al:, "Response to: 'The Ulcerogenic Potential of Copper Aspirinate Seems to be More Imaginary than Real'", Journal of Pharmaceutical Sciences, 73, Open Forum, 1876-1877, (Dec. 1984).
Allemann, et al., "Distribution, Kinetics, and Elimination of Radioactivity after Intravenous and Intramuscular Injection of 14C-Savoxepoine Loaded Poly (D,L-lactic acid) Nanospheres to Rats", J. Controlled Release, 29, 97-104, (1994).
Allen, K.E., et al., "Evidence for the Metabolic Activation of Non-Steroidal Antioestrogens: A Study of Structure-Activity Relationships", Br.J. Pharmac., 71, 83-91, (1980).
Allen, R.E. & Boxhor, L.K. "Inhibition of skeletal muscle satellite cell differentiation by transforming growth factor-beta," J Cell. Physiol. 133:567-572.(1987).
Allgemeine und spezielle Pharmakologie und Toxikolgie, by W. Forth et al. 1984, pp. 524-531 and 627-633.
Alvarado, et al. "Evaluation of Polymer-Coated Balloon Expandable Stents in Bile Ducts," Radiology 165 (suppl.):33 1 (1987).
Anderson et al., "Restenosis after coronary angioplasty," J. Interv. Cardiol., 6(3)187-202 (1993).
Ando et al., "Chimeric DNA-RNA hammerhead ribozyme targeting transforming growth factor-beta 1 mRNA inhibits neointima formation in rat carotid artery after balloon injury", Eur. J. Phamacol., 438:207-14 (2004).
Anker, et at., "Plasma Levels of the Atherogenic Amino Acid Homocysteine in Post-Menopausal Women with Breast Cancer Treated with Tamoxifen", Int. J. Cancer, 60, 365-368, (1995).
Arao, Y., et al., "A synthetic oestrogen antagonist, tamoxifen, inhibits oestrogen-induced transcriptional, but not post-transcriptional, regulation of gene expression", Biochem, J., 313, 269-274, (1996).
Askelband et al., "Rapamycin Inhibits Spontaneous and Fibroblast Growth Factor Beta-Stimulated Prolifereation of Endothelial Cells and Fibroblasts," Transplantantion Proceedings, 23 2833-2836 (1991).
Assoian et al., "Transforming growth factor-beta in human platelets: identification of a major storage site, purification, .and characterization", J. Biol. Chem. 258:7155-7160 (t983).
Assoian, R.K., et al., "Cellular Transformation by Coordinated Action of Three Peptide Growth Factors from Human Platelets", Nature, 309, 804-806, (Jun. 28, 1984).
Babaev, et al.,"Heterogeneity of smooth muscle cells in atheromatous plaques of human aorta," Am J. Pathol. 136:1031-1042. (1990).
Bailey et al., "Polymer Coating of Palmaz-Schatz Stent Attenuates Vascular Spasm after stent placement." Circulation 82:111-541 (1990).
Baim, D.S., et al., "Nonatherosclerotic Coronary Heart Disease", In: The Heart: Arteries and Veins, Sixth Edition, Logue, R.B., et al., (eds.), McGraw-Hill Book Company, New York, 1016-1025, (1986).
Bang, H.O., et al., "The Composition of the Eskimo Food in North Western Greenland", Am. J. Clin. Nutr., 33, 2657-2661, (1980).
Baquial, J.G., et al., Down-Regulation of NADPH-Diaphorase (Nitric Oxide Synthase) May Account for the Pharmacological Activities of Cu(II)sub2(3,5-Diisopropylsalicylate)sub4., J. Inorganic Biochem., 60, 133-148, (1995).
Baral, E., et al., "Modulation of Lymphokine-Activated Killer Cell-Mediated Cytotoxicity by Estradiol and Tamoxifen", Int. J. Cancer, 66, 214-218, (1996).
Barbucci, et al., Coating of Commercially available materials with a new heparinizable material, 1991, pp. 1259-1274.
Baringa. "Gene Therapy for Clogged Arteries Passes Test in Pigs", Science, 265, 738 (Aug. 5, 1994).
Barnard, et al., "Regulation of intestinal epithelial cell growth by transforming growth factor-beta." Proc. Natl Acad. Sci. USA 86:1518-1582.(1989).
Bassing et al., "FKBP12 is not required for the modulation of transforming growth factor beta receptor I signaling activity in embryonic fibroblasts and thymocytes". Cell Growth Differ., 9(3):223-8 (1998).
Battegay et al., "TGF-beta induces bimodal proliferation of connective tissue cells via complex control of an autocrine PDGF loop", Cell, 63:5t5-524 (1990).
"Duraflo Biocompatible Treatment", Baxter Healthcare Corp., 1995.
Beck, L., et al., "Vascular Development: Cellular and Molecular Regulation", The FASEB Journal, II, 365-373, (1997).
Benita et al., "Submicron Emulsions as Colloidal Drug Carries for Intravenous Administration: Comprehensive Physicochemical Characterization", Journal of Pharmaceutical Sciences, 82, (Nov. 1993).
Bergstrom, Reduction of fibrinogen adsorption on PEG-coated polystyrene surfaces, 1992, p. 779-790, Baxter Healthccare Corp. Duraflo Biocompatible Treatment.
Bernhardt et al., "Acetylsalicylic acid, at high concentrations, inhibits vascular smooth muscle cell proliferation", J. Cardiovasc. Pharmacol., 21(6):973-6 (1993).
Berven. L.A., et al., "Cellular Function of p70S6K: A Role in Regulating Cell Motility", Immunology and Cell Biology, 78, 447-451, (2000).
Bier et al., "Arterial Remodeling: Importance in Primary Versus Restenoic Lesions", JACC, p. 139A, Abstract No. 875-96 (Feb. 1994).
Billmeyer, F., Textbook of Polymer Science (2d ed.) John Wiley & Sons, Inc. (1971).
Binmoeller, el al., "Silicone-Covered Expandable Metallic Stents in the Esophagus: An Experimental Study" Endoscopy 1992;24:416-20.
Bittiner, S.B., et al., "A Double-Blind, Randomised, Placebo-Controlled Trial of Fish Oil in Psoriasis", The Lancet, 1, 378-380, (Feb. 20, 1988).
Bjorkerud, "Effects of transforming growth factor-betal on human arterial smooth muscle cells in vitro", Arterioscler. Thromb., 11(4):892-902 (1991).
Block, P.C. "Coronary-artery stents and other endoluminal devices," New Engl.J.Med. 1991; 324-52-3.
Bluming, "Hormone Replacement Therapy: Benefits and Risks for the General Postmenopausal Female Population and for Women with a History of Previously Treated Breast Cancer", Seminars in Oncology, 20, 662-674, (Dec. 1993).

Bohmova et al., "Effect of sirolimus on ischemia/reperfusion injury in transgenic hypertensive rat", Transplant Proc., 34(8):3051-3052 (2002).
Border, W.A., et al., "Targeting TGF-Beta for Treatment of Disease". Nature Medicine, 1(10), 1000-1001, (Oct. 1995).
Boscoboinik et al., "Alpha-tocopherol (vitamin E) regulates vascular smooth muscle cell proliferation and protein kinase C activity", Arch. Biochem. Biophys., 286(1):264-9 (1991).
Boyle, "Macrophage activation in atherosclerosis: pathogenesis and pharmacology of plaque rupture", Curr. Vasc. Pharmacol., 3(1):63-8 (2005).
Brand, C., et al., "Transforming Growth Factor Betal Decreases Cholesterol Supply to Mitochondria via Repression of Steroidogenic Acute Regulatory Protein Expression", The Journal of Biochemistry, 273(11), 6410-6416, (1998).
Braun-Dullaeus et al., "Cell cycle protein expression in vascular smooth muscle cells in vitro and in vivo is regulated through phosphatidylinositol 3-kinase and mammalian target of rapamycin", Arterioscler Thromb Vasc Biol. 21(7):1152-58 (2001).
Brem et al., "Polymers as Controlled Drug Delivery Devices for the Treatment of Malignant Brain Tumours." European Journal of Pharmaceuticals and Biopharmaceutics, 1993, vol. 39, No. 1, pp. 2-7.
Brody, J.E., "Study Finds New Estrogen Offers Benefit Without Risk", The New York Times, A32, (Dec. 4, 1997).
Brott et al., "Vessel Remodeling After Angioplasty: Comparative Anatomic Studies", JACC, p. 138A, Abstract No. 875-43 (Feb. 1994).
Burr, M.L., et al., "Effects of Changes in Fat, Fish and ibre Intakes on Death and Myocardial Reinfarction: Diat and Reinfarction Trial (DART)", The Lancet, 757-761, (Sep. 30, 1989).
Burton, T.M., "Lilly Osteoporosis Treatment Shows Promise", The Wall Street Journal, p. A3, A6, (Jun. 6. 1997).
C. Chamsangavej et al., A New Expandable Metallic Stent for Dilation of Stenotic Tubular Structures: Experimental and Clinical Evaluation, Houston Medical Journal 1987;2:41-51.
C. T. Dotter, "Transluminally Placed Coil Spring Endarterial Tube Grafts Long Term Patency in Canine Popliteal Arteries," Investigative Radiology 1969;4:329-332.
Calver et al. "Intracoronary Multi-link stents: experience in 218 patients using aspirin alone," Heart 1998;80:499-504.
Camenzind, et al., "Use of Locally Delivered Conventional Drug Therapies", Semin. Intervent. Cardiol., 1, 67-76, (1996).
Cannon, M., et al., "Competition Between Trichodermin and Several Other Sesquiterpene Antibiotics for Binding to their Receptor Site(s) on Eukaryotic Ribosomes", Biochem. J., 160, 137-145, (1976).
Castellot et al., "Cultured endothelial cells produce a heparinlike inhibitor of smooth muscle cell growth", J. Cell Biol., 90:372-379 (1981).
Castellot et al., "Effect of heparin on vascular smooth muscle cells. I. Cell metabolism", J. Cell. Physiol., 124:21-28 (1985).
Castellot et al., Heparin selectively inhibits a protein kinase c-dependent mechanism of cell cycle progression in calf aortic smooth muscle cells, J Cell Biol.., 109:3147-3155 (1989).
Chamberlain, Transforming growth factor-beta: a promising target for anti-stenosis therapy, Cardiovasc. Drug Rev.., 19(4):329-344 (2001).
Chamley-Camphell and Campbell, "What controls smooth muscle phenotype?", Atherosclerosis, 40:347-357 (1981 ).
Chamsangavej et al., "Endovascular Stent for Vena Caval Stenosis: Laboratory Experiment and Potential Clinical Applications," Radiology Nov. 1985;157(P):66 Abs. 129.
Chandrasekar, B., et al., "Dietary Omega-3 Lipids Delay the Onset and Progression of Autoimmune Lupus Nephritis by Inhibiting Transforming Growth Factor Beta mRNA and Protein Expression", Journal of Autoimmunity, 8, 381-393, (1995).
Chandy, T., et al., "Chitosan Matrix for Oral Sustained Delivery of Ampicillin", Biomaterials, 14, 939-944, (1993).
Chang, M.P., et al., "Comparison of the Intoxication Pathways of Tumor Necrosis Factor and Diphtheria Toxin", Infection and Immunity, 58, 2644-2650, (Aug. 1990).
Charles Dotter et al., "Transluminal Treatment of Arteriosclerotic Obstruction Description of a New Technique and a Preliminary Report of its Application," Circulation 1964;30:654-669.
Charlier, C., et al., "Tamoxifen and Its Active Metabolite Inhibit Growth of Estrogen Receptor-Negative MDA-MB-435 cells", Biochemical Pharmacology, 49(3), 351-358, (Jan. 1995).
Charlier, et al., "Tamoxifen in the Treatment of Breast Cancer", J. Gynecol. Obstet Biol. Reprod., 23, 751-756, (1994).
Charnsangavej, et al., "Stenosis of the Vena Cava: Preliminary Assessment of Treatment with Expandable Metallic Stents," Radiology Nov. 1986;161:295.
Chauhan et al., "Activation of Transforming Growth Factor-B is Inversely Correlated with Three Major Risk Factors for Coronary Artery Disease: Lipoprotein(a), LDL-Cholesterol and Plasminogen Activator Inhibitor-1", Circulation, 90 I-623, Abstract No. 3354 (Oct. 1994).
Cheitlin, M.D., et al., "Myocardial Infarction without Atherosclerosis", JAMA, 231, 951-959, (1975).
Chen et al., "Transforming growth factor type beta specifically stimulates synthesis of proteoglycan in human adult arterial smooth muscle cells", Proc. Natl. Acad. Sci., 84:5287-5291 (1987).
Clark, D.A., et al., "Coronary Artery Spasm: Medical Management, Surgical Denegration, and Autotransplantation", The Journal of Thoracic and Cardiovascular Surgery, 73, 332-339, (1977).
Clarke, S.C., et al., "Tolerance and Responses To Tamoxifen and Toremifene in Male Patients with Coronary Artery Disease.", Abstract for ACC Meeting, Mar. 1999.
Clinton, S.K., et al., "Induction in vivo of Interleukin-1 (IL-1) Gene Expression in Rabbit Aortic Tissue", Abstracts of the 61st Scientific Sessions of the Americna Heart Association, Washington, D.C., Nov. 14-17, 1988, Circulation, 78 (4 Part 2): p. 1165 (1988).
Clowes and Kamowsky, "Suppression by heparin of smooth muscle cell proliferation in injured arteries", Nature, 265:625-626 (1977).
Clowes et al., "Heparin and cilazapril together inhibit injury-induced intimal hyperplasia", Hypertension, 18:11-65-11-69 (1991).
Colletta, A.A. et al., "Anti-oestrogens induce the secretion of active transforming growth factor beta from human fetal fibroblasts", Br. J. Cancer, 62, 405-409, (1990).
Columbo et al., "A Novel Strategy for Stent Deployment in the Treatment of Acute or Threatened Closure Complicating Balloon Coronary Angioplasty," JACC Dec. 1993;22(7):1887-91.
Comezoglu, F.T. et al., "Serum Stability and Cytotoxicity of the Macrocyclic Trichothecenes Roridin A, Verrucarin A and Their Monoclonal Antibody Conjugates", Proceedings of the American Association for Cancer Research, 31, Abstract No. 1723, p. 291, (Mar. 1990).
Coombes, R.C., et al., "Idoxifene: Report of a Phase I Study in Patients with Metastatic Breast Cancer", Cancer Research, 55, 1070-1074, (Mar. 1, 1995).
Corcos, et al., "Failure of diltiazem to prevent restenosis after percutaneous transluminal coronary angioplasty", Am. Heart J., 109(5):926-931 (1985).
Cotton, P., "Restenosis Trials Suggest Role for Remodeling", JAMA, 271, 1302-1305, (May 4, 1994).
Craig et al., "Anticoagulant Drugs" in Modern Pharmacology; Little, Brown & Co.: Boston; p. 399 (1982).
Csernok, E., et al., "Transforming Growth Factor-beta (TGF-beta) Expression and Interaction with Proteinase 3 (PR3) in Anti-Neutrophil Cytoplasmic Antibody (ANCA)-associated Vasculitis", Clin. Exp. Immunol., 105, 104-111, (1996).
Cunningham, A., et al., "A Study of the Structural Basis of the Carcinogenicity of Tamoxifen, Toremifene and their Metabolites", Mutation Research, 349, 85-94, (1996).
Currier et al., "Low molecular weight heparin (enoxaparin) reduces restenosis after iliac angioplasty in the hypercholesterolemic rabbit", J. Am. Coll. Cardiol., 17(6):118B-125B (1991).
Currier, "Restenosis After Percutaneous Transluminal Coronary Angioplasty: Have We Been Aiming at the Wrong Target?", JACC, 25 516-520 (Feb. 1995).
Dangas, G., et al., "Management of Restenosis after Coronary Intervention", American Heart Journal, 132, 428-436, (1996).
Davies, A.M., et al., "Peroxidase Activation of Tamoxifen and Toremifene Resulting in DNA Damage and Covalently Bound Protein Adducts", Carcinogenesis, 16, 539-545, (1995).

deAlvare, L.R., et al., "Mechanism of Superoxide Anion Scavenging Reaction by Bis-(Salicylato)-Copper(II) Complex", Biochemical and Biophysical Research Communications, 69, 687-694, (1976).
Dehmer, G.J., et al., "Reduction in the Rate of Early Restenosis After Coronary Angioplasty by a Diet Supplemented with n-3 Fatty Acids", N. Engl. J. Med., 319, 733-740, (1988).
Del Vecchio et al., "Inhibition of human scleral fibroblast proliferation with heparin, Invest".. Ophthalmol. Vis. Sci., 29:1272-1276 (1988).
Delmas, P.D., "Effects of Raloxifene on Bone Mineral Density, Serum Cholesterol Concentrations, and Uterine Endometrium in Postmenopausal Women", The New England Journal of Medicine, 337(23), (1997).
Chenoweth, D. E., "Complement Activation in Extracorporeal Circuits" Annals of the New York Academy of Sciences vol. 516 pp. 306-313 (1987).
DiGiacomo, R.A., et al., "Fish-Oil Dietary Supplementation in Patients with Raynaud's Phenomenon: A Double-Blind, Controlled, Prospective Study", Am. J. Med., 86, 158-164, (Feb. 1989).
DiLuccio, R.C., et al., "Sustained-Release Oral Delivery of Theophylline by Use of Polyvinyl Alcohol and Polyvinyl Alcohol-Methyl Acrylate Polymers", Journal of Pharmaceutical Sciences, 83, 104-106, (Jan. 1994).
DiMario, "Is the Mechanism of Restenosis Device-Independent? Serial Assessment with Intracoronary Ultrasound", Circulation, 90, 1-24, Abstract 115 (Oct. 1994).
Donnelly, J., et al., "Protective Efficacy of Intramuscular Immunization with Naked DNA; DNA Vaccines: A New Era in Vaccinology, Margaret A. Liu et al., eds.", Annals of the New York Academy of Sciences, 772, 40-44, (1995).
Dotter, "Intraventional Radiology—Review of an Emerging Field," Seminars In Roentgenology 1982;16(1 ):7-8.
Dove, C.R., et al., "Effect of Vitamin E and Copper on the Vitamin E Status and Performance of Growing Pigs", J. Anim. Sci., 69, 2516-2523, (1991).
Dowsett, M., "New Developments in the Hormonal Treatment of Breast Cancer", In: The Treatment of Cancer: Beyond Chemotherapy, Conference Documentation, The Glouster Hotel, London, 7 p., (Mar. 13-14, 1995).
Dragan, Y.P., et al., "Comparison of the Effects of Tamoxifen and Toremifene on Liver and Kidney Tumor Promotion in Female Rats", Carcinogenesis, 16, 2733-2741, (1995).
Draper, M.W., et al., "Antiestrogenic Properties of Raloxifene", Pharmacology, 50, 209-217, (Apr. 1995).
Dyerberg, J., "Platelet—Vessel Wall Interaction: Influence of Diet", Phil. Trans. R. Soc. Lond., B 294, 372-381, (1981).
Dyerberg, J., et al., "The Effect of Arachidonic- and Eicosapentaenoic Acid on the Synthesis of Prostacyclin-like Material in Human Umbilical Vasculature", Artery, 8, 12-17, (1980).
Edelman, E.R., et al., "Effect of Controlled Adventitial Heparin Delivery on Smooth Muscle Cell Proliferation Following Endothelial Injury", Proc. Natl. Acad. Sci. USA, 87, 3773-3777, (May 1990).
Ellis et al., "Effect of 18- to 24-hour heparin administration for prevention of restenosis after uncomplicated coronary angioplasty", Am, Heart J., 117(4):777-782 (1989).
Ellis, S.G., et al., "In-Hospital Cost of Percutaneous Coronary Revascularization: Critical Determinants and Implications", Circulation, 92, 741-747, (1995).
Endres, S., et al., "The Effect of Dietary Supplementation with n-3 polyunsaturated Fatty Acids on the Synthesis of Interleukin-1 and Tumor Necrosis Factor by Mononuclear Cells", N. Engl. J. Med., 320, 265-271, 1989).
Esnouf, M.P., et al., "The Inhibition of the Vitamin K-Dependent Carboxylation of Glutamyl Residues in Prothombin by Some Copper Complexes", FEBS Letters, 107, 146-150, (1979).
Espinosa, E., et al.. "17-Estradiol and Smooth Muscle Cell Proliferation in Aortic Cells of Male and Female Rats", Biochemical and Biophysical Research Communication, 221, 8-14, (1996).
Evans, G.L., et al., "Tissue-Selective Actions of Estrogen Analogs", Bone, 17, 181S-190S, (Oct. 1995).
Faxon et al., "Enozaprain, a low molecular weight heparin, in the prevention of restenosis after angioplasty: results of a double blind randomized trial", JACC 19:258A, Abstract 783-3 (1992).
Ferrari, R.P., et al., "Changes of Serum Iron Transferrin and Copper Ceruloplasmin in Rats Given Cu(II) sub2 (Acetylsalicyate) sub4 During Acute Inflammation", Anticancer Res., 9, 771-774, (1989).
Fett-Neto, A.G., et al., "Effect of White Light on Taxol and Baccatin III Accumulation in Cell Cultures of *Taxus cuspidata* Sieb and Zucc.", J. Plant Physiol., 146, 584-590, (1995).
Fischell , et al., "Low-Dose, beta-Particle Emission From 'Stent' Wire Results in Complete, Localize Inhibition of Smooth Muscle Cell Proliferation", Circulation, 90 2956-2963 (Dec. 1994).
Fischman, et al., A Randomized Comparison of Coronary-Stent Placement and Balloon Angioplasty in the Treatment of Coronary Artery Disease:, The New England Journal of Medicine, 331, 496-501 (Aug. 1994).
Fisher, M., et al., "Dietary n-3 Fatty Acid Supplementation Reduces Superoxide Production and Chemiluminescence in a Monocyte-Enriched Preparation of Leukocytes", Am. J. Clin. Nutr., 51, 804-808, (1990).
Flanders, K.C., et al., "Altered Expression of Transforming Growth Factor-B in Alzheimer's Disease", Neurology, 45, 1561-1569, (Aug. 1995).
Flanders, K.C., et al., "Transforming Growth Factor-B1: Histochemical Localization With Antibodies to Different Epitopes", Journal of Cell Biology, 108, 653-660, (Feb. 1989).
Foekens, J.A., et al., "Urokinase-Type Plasminogen Activator and Its Inhibitor PAI-1 : Predictors of Poor Response to Tamoxifen Therapy in Recurrent Breast Cancer", Journal of the National Cancer Institute, 87(10), 751-756, (May 1995).
Forney-Prescott et al., "Angiotensin-converting enzyme inhibito' versus angiotensin II, ATI receptor antagonist: effects on smooth muscle cell migration and proliferation after balloon catheter injury", Am J Pathol, 139:1291-1296 (1991).
Fox and DiCorleto, "Fish oils inhibit endothelial cell production of platelet-derived growth factor-like protein", Science, 241 (4864):453-456 (1988).
Frautschy, S.A., et al., "Rodent Models of Alzheimer's Disease: Rat A Infusion Approaches to Amyloid Deposits", Neurobiology of Aging, 17, 311-321, (1996).
Frazier-Jessen, et al., "Estrogen Modulation of JE/Monocytte Chemoattractant Protein-1 mRNA Expression in Murine Macrophages", J. Immunol., 1828-1845.
Frye, L.L., et al., "Oxolanosterol Oximes: Dual-Action Inhibitors of Cholesterol Biosynthesis", Journal of Lipid Research, 35, 11333-1344,(1994).
Fukaura, H., et al., "Induction of Circulating Myelin Basic Protein and Proteolipid Protein-Specific Transforming Growth Factor-B1-secreting Th3 T Cells by Oral Administration of Myelin in Multiple Sclerosis Patients", J. Clin. Invest., 98, 70-77, (1996).
Fukuda, et al., "Distinct Expression of Transforming Growth Factor-B Receptor Subtypes on Vascular Smooth Muscle Cells from Spontaneously Hypertensive Rats and Wistar-Kyoto Rats", Clin. Exp. Pharmacol. Physiol. Supply., 1, S120, 1995.
Furr, B.J., et al., "The Pharmacology and Clinical Uses of Tamoxifen", Pharmac. Ther., 25, 127-205, (1984).
Gebhardt, R., et al., "Differential Inhibitory Effects of Garlic-Derived Organosulfur Compounds on Cholesterol Biosynthesis in Primary Rat Hepatocyte Cultures", Lipids, 31, 1269-1276, (1996).
Gebhardt, R., et al., "Inhibition of Cholesterol Biosynthesis by Allicin and Ajoene in Rat Hepatocytes and HepG2 Cells", Biochimica et Biophysica Acta, 1213, 57-62, (1994).
Gertz et al., "Geometric Remodeling Is Not the Principal Pathogenic Process in Restoenosis After Balloon Angioplasty", Circulation, 90, 3001-3008 (Dec. 1994).
Giachelli, et al., "Osteopontin is Elevated During Neointima Formation in Rat Arteries and is a Novel Component of Human Atherosclerosis Plaques", J. Clin. Invest., 92, 1686-1696, (Oct. 1993).
Gibbons et al., "The emerging concept of vascular remodeling", New Engl. J. of Medicine, 330 1431-1437 (1994).
Gibson, D.M., et al., "Initiation and Growth of Cell Lines of *Taxus brevifolia* (Pacific Yew)", Plant Cell Reports, 12, 479-482, (1993).
Glagov, S., "Intimal Hyperplasia, Vascular Modeling, and the Restenosis Problem", Circulation, 89, 2888-2891, (1994).
Gradishar, W.J., et al., "Clinical Potential of New Antiestrogens", Journal of Clinical Oncology, 15, 840-852, (1997).

Graham et al., "Dexamethasone Inhibits Grown and Na:H Exchange in Vascular Smooth Muscle Cells" Journal of Endocrinology, 129 (Suppl.) Abstract 180, $10^{th}$ Joint Metting of British Endocdrine Societies, Brighton, England, UK, Apr. 15-18, 1991.
Grainger and Metcalfe, "Transforming growth factor-β and cardiovascular protection, draft"(NeoRx 019151-019213).
Grainger and Metcalfe, TGF-beta: implications for human vascular disease. J Hum Hypertens., 9(8):679 (1995).
Grainger and Mosedale, "TGF-β and the cardiovascular system, TGF-β and Related Cytokines in Inflammation," Breit, SN and Wahl, SM (ed.), Birkhauser Verlag, 91-146 (2001) (DJG 006134-006190).
Grainger et al., "Dietary fat and reduced levels of TGFbeta 1 act synergistically to promote activation of the vascular endothelium and formation of lipid lesions", J. Cell Sci., 113:2355-2361(2000).
Grainger et al., "Red wine, but not white wine, elevates circulating TGF-β levels—possible role of a salicylate complex".
Grainger et al., "Transforming growth factor-beta dynamically regulates vascular smooth muscele cell differentiation in vivo", J. Cell Sci., 111:2977-2988 (1998).
Grainger, D.J., "Transforming growth factor beta and atherosclerosis: so far, so good for the protective cytokine hypothesis", Arterioscler. Thromb. Vasc. Biol., 24:399-404 (2004) (DJG 006208-006213).
Grainger, D.J., ct al., "A Pivotal Role for TGF-Beta in Atherogenesis?", Biol. Rev., 70, 571-596, (1995).
Grainger, D.J., et al., "Activation of Transforming Growth Factor-beta is Inhibited by Apolipoprotein (a) in vivo", Circulation, 90, $67^{th}$ Scientific Session, Abstract No. 3353, p. 1-623, (Oct. 1994).
Grainger, D.J., et al., "Activation of Transforming Growth Factor-beta is Inhibited in Transgenic Apolipoprotein (a) Mice", Nature, 370 460-462, (Aug. 11, 1994).
Grainger, D.J., et al., "Active and Acid-Activatable TGF-beta in Human Sera, Platelets and Plasma", Clinica Chemica Acta., 235, 11-31, (Feb. 1995).
Grainger, DJ., et al., "Active TGF-beta is Depressed Five-fold in Triple Vessel Disease Patients Compared with Syndrome X Patients", Journal of Cellular Biochemistry, 18A, Abstract No. E111, p. 267, (1994).
Grainger, D.J., et al., "Active Transforming Growth Factor-beta is Depressed in Patients with Three Vessel Coronary Artery Disease", Circulation, 90, $67^{th}$ Scientific Sessions, Abstract No. 2754, p. 1-512, (Oct. 1994).
Grainger, D.J., et al., "Mitogens for Adult Rat Aortic Vascular Smooth Muscle Cells in Serum-Free Primary Culture", Cardiovascular Research, 28, 1238-1242, (1994).
Grainger, D.J., et al., "Proliferation of Human Smooth Muscle Cells Promoted by Lipoprotein(a)", Science, 260, 1655-1658, (Jun. 11, 1993).
Grainger, D.J., et al., "Release and Activation of Platelet Latent TFG-Beta in Blood Clots During Dissolution with Plasmin", Nature Medicine, 1, 932-937, (1995).
Grainger, D.J., et al., "Tamoxifen Elevates Transforming Growth Factor-beta and Suppresses Diet-Induced Formation of Lipid Lesions in Mouse Aorta", Nature Medicine, 1, 1067-1073, (Oct. 1995).
Grainger, D.J., et al., "Tamoxifen: Teaching an Old Drug New Tricks?", Nature Medicine, 2, 381-385, (Apr. 1996).
Grainger, D.J., et al., "The Serum Concentration of Active Transforming Growth Factor-beta is Severely Depressed in Advanced Atherosclerosis". Nature Medicine, 1, 74-80, (Jan. 1995).
Grainger, D.J., et al., "Transforming Growth Factor beta Decreases the Rate of Proliferation of Rat Vascular Smooth Muscle Cells by Extending the G2 Phase of the Cell Cycle and Delays the Rise in Cyclic AMP Before Entry into M Phase", Biochemical Journal, 299, 227-235, (1994).
Grainger, D.J., et al., "Transforming Growth Factor-beta and Cardiovascular Protection", In: TheEendothelium in Clinical Practice, Rubanyi, G.M., et al., (eds.), Marcel Dekker, Inc., New York, 203-243, (1997).
Grainger, D.J., et al., "Transforming Growth Factor-beta is Sequestered into an Inactive Pool by Lipoproteins", Journal of Lipid Research, 38, 117-125, (1997).
Grainger, D.J., et al., "Transforming Growth Factor-beta: The Key to Understanding Lipoprotein(a)?", Current Opinion In Lipidology, 6, 81-85, (1995).
Grainger, D.J., University of Cambridge Ph.D. Thesis, Control of the proliferation and differentiation of vascular smooth muscle cells, DJG 005911-006102 (1992) and all references therein.
Gravlee,G.P. MD, Heparin-Coated Cardiopulmonary Bypass Circuits, Journal of Cardiothoracic and Vascular Anesthesia, vol. 8, No. 2, Apr. 1994, pp. 213-222.
Gref, et al., "Biodegradable Long-Circulating Polymeric Nanoshoeres", Science, 263, 1600-1603, (Mar. 18, 1994).
Gregory et al., Rapamycin Inhibits Arterial Intimal Thickening Caused by Both Alloimmune and Mechanical Injury:, Transplantation, 55 1409-1418 (1993).
Gregory et al., "Treatment with rapamycin blocks arterial intimal thickening following mechanical and alloimmune injury", Transplant. Proc., 25:120-21 (1993).
Grese, T.A., et al., "Structure-Activity Relationships of Selective Estrogen Receptor Modulators: Modification to the 2-Arylbenzothiophene Core of Raloxifene", J. Med. Chem.. 40, 146-167, (1997).
Grey, A.B., et al., "The Effect of the Anti-Estrogen Tamoxifen on Cardiovascular Risk Factors in Normal Postmenopausal Women", J. Clinical Endocrinology and Metabolism, 80, 3191-3195, (1995).
Grigg, L.E., et al., "Determinants of Restenosis and Lack of Effect of Dietary Supplementation with Eicosapentaenoic Acid on the Incidence of Coronary Artery Restenosis After Angioplasty", JACC, 13, 655-672, (1989).
Gruntzig, et al., "Nonoperative Dilatation of Coronary-Artery Stenosis," New England J. Med.. Jul 12, 1979;301(2):61-68.
Guba et al., "Rapamycin inhibits primary and metastatic tumor growth by antiangiogenesis: involvement of vascular endothelial growth factor", Nat. Med., 8(2):128-35 (2002).
Guetta, V., et al., "Effects of the Antiestrogen Tamoxifen on Low-Density Lipoprotein Concentrations and Oxidation in Postmenopausal Women", The American Journal of Cardiology, 76, 1072-1073, (Nov. 15, 1995).
Gulino, A., et al., Heterogeneity of Binding Sites for Tamoxifen and Tamoxifen Derivatives in Estrogen Target and Nontarget Fetal Organs of Guinea Pig, Cancer Research 42, 1913-1921, (May 1982).
Guyton et al., "Inhibition of rat arterial smooth muscle cell proliferation by heparin: in vivo studies with anticoagulant and noncoagulant heparin", Circ. Res., 4615):625-634 (1980).
Gylling, H., et al., "Tamoxifen and Toremifene Lower Serum Cholesterol by Inhibition of Delta8-Cholesterol Conversion to Lathosterol in Women with Breast Cancer", Journal of Clinical Oncology, 13, 2900-2905, (1995).
Gylling, H.. et al., "Tamoxifen Decreases Serum Cholesterol by Inhibiting Cholesterol Synthesis", Atherosclerosis, 96, 245-247, (1992).
Hafzi et al., "Differential effects of rapamycin, cyclosporine A, and FK506 on human coronary artery smooth muscle cell proliferation and signalling", Vascul. Pharmacol., 41:167-76 (2004).
Hahn, L., et al., "The Influence of Acetylsalicylic Acid and Paracetamol on Menstrual Blood Loss in Woman With and Without an Intrauterine Contraceptive Device", Am. J. Obstet. Gnecol., 135, 393-396, (1979).
Hall, I.H., et al., "Hypolipidemic Activity of Tetrakis-mu-(trimethylamine-boranecarboxylato)-bis (trimethylamine-carboxyborane)-dicopper (II) in Rodents and Its Effect on Lipid Metabolism", J. Pharmaceut. Sci., 73, 973-977, (1984).
Hanson, el al.,"In vivo evaluation of artificial surfaces with a nonhuman primate model of arterial thrombosis,"J. Lab. Clin. Med. 95:289-304; 1980.
Hanson, et al., "Testing of Blood—Materials Interactions," Biomaterials Scicnce (B.D. Ratner, Ed.), Academic Press, 222-238 (1996).
Hanson, S., "Device Thrombosis and Thromboembolism," Cardiovasc Pathol. 2(3) (Suppl.): 157S-I65S (Jul.-Sep. 1993).
Harpel, et al., "Lp(a) Inhibitor of Plasminogen," Proc. Natl. Acad. Sci. USA, 86, 3847 (1989).

Harrison, D.C., "Nonatherosclerotic Coronary Artery Disease", In.: Atherosclerosis and Coronary Artery Disease. V. Fuster, et al., (eds.), Lippencott-Raven Publishers, pp. 757-772, (1996).
Hayden, L.J., "Inhibitors of Gastric Lesion in the Rat", J. Pharm. Pharmac., 30, 244-246, (1978).
Hayes, D.F., et al., "Randomized Comparison of Tamoxifen and Two Separate Doses of Toremifene in Postmenopausal Patients with Metastatic Breast Cancer", Journal of Clinical Oncology, 13, 2556-2566, (Oct. 1995).
Hehrlein, C., et al., "Low-Dose Radiactive Endovascular Stents Prevent Smooth Muscle Cell Proliferation and Neointimal Hyperplasia in Rabbits", Circulation, 92, 1570-1575, (1995).
Hehrlein, C., et al., "Pure Beta-particle-emitting Stents Inhibit Neointima Formation in Rabbits", Circulation, 93, 641-645,(1996).
Hermann and Hirshfeld, Jr., "Clinical Use of the Palmaz-Schatz Intracoronary Stent," Futura Publishing Co. (1993).
Hoffman, A., "Modification of Material Surfaces to Affect How They Interact with Blood, Blood in Contact with Natural and Artificial Surfaces," Leonard, E. et al., (eds), Annals of the New York Academy of Sciences, 516:96-100 (1987).
Holmes, et al., "Analysis of 1-year clinical outcomes in the SIRIUS trial: a randomized trial of a sirolimus-eluting stent versus a standard stent in patients at high risk for coronary restenosis",Circulation, 109:634-640 (2004).
Holmes, Jr., D.R., "Remodeling Versus Smooth Muscle Cell Hyperpasia", Restenosis Summit VI, The Cleveland Clinic Foundation, 222-223, (1994).
Hoover, et al., "Inhibition of rat arterial smooth muscle cell proliferation by heparin:II. In vitro studies", Circ. Res., 47(4):578-83 (1980).
Hopfenberg, H., "Transport Through Polymers, 7 Encyclopedia of Materials Science and Engineering," (Michael B. Bever, (ed.); The MIT Press, 5141-5145 (1986).
Howell, A., et al., "New Endocrine Therapies for Breast Cancer", European Journal of Cancer, 32A, 576-588, (1996).
Hsu, Li-Chien "Principles of Heparin-Coating Techniques", Perfusion 6: 209-219 (1991).
Huang, et al., "Rapamycins: mechanism of action and cellular resistance." Cancer Biol. Ther., 2(3):222-32 (2003).
Huang, S.S., et al., "Transforming Growth Factor Beta peptide Antagonists and Their Conversion to Partial Agonists", The Journal of Biological Chemistry, 272(43), 27155-57159, 1997.
Huehns, et al., "Adventitia as a Trarget for Intravascular Local Drug Delivery", Heart, 75, 437-438 (1996).
Hughes, D.E., et al., "Estrogen Promotes Apoptosis of Murine Osteoclasts Mediated by TFG-beta", Nature Medicine, 2. 1132-1136, (1996).
Ishihara, et al., "Synthesis of phospholipid polymers having a urethane bond in the side chain as coating material on segmented polyurethane and their platelet adhesion-resistant properties,"Biomaterials, 1995 16(11): 873-879.
Isner, "Vascular Remodeling: Honey, I Think I Shrunk the Artery", Circulation, 89 2937-2841 (Jun. 1994).
Jacinto and Hall, "Tor signalling in bugs, brain and brawn", Nature Rev. Mol. Cell Biol., 4:117-126 (2003).
Jande et al., "Effects of cytochalasin B and dihydrocytochalasin B on calcium transport by intestinal absorptive cells", Calcif. Tissue Int. 33, 143-151 (1981); Chem. Abs. 94 Abstract No. 189223e (1981).
Hubbell, J.A., "Pharmacologic Modification of Materials", Cardiovasc Pathol., vol. 2, No. 3 (Suppl.), Jul.-Sep. 1993, pp. 121S-127S.
Jeng, et al., "Regulation of the levels of three transforming growth factor beta mRNAs by estrogen and their effects on the proliferation of human breast cancer cells", Mol. Cell Endocrinol., 92:115-123 (1993).
Jenkins et al., Local Delivery of Taxol Inhibits Neointimal Regrowth Following Balloon Injury of the Rat Carotid Artery: , Circulation, 90, p. 1-297, Abrstract No. 1596 (Oct. 1994).
Johnston, S.R.. et al., "Changes in Estrogen Receptor, Progesterone Receptor, and ps2 Expression in Tamoxifen-resistant Human Breast Cancer", Cancer Research, 55, 3331-3338, (Aug. 1995).
Jones, R.H., et al., "Increased Susceptibility to Metal Catalysed Oxidation of Diabetic Lens beta subL Crystallin: Possible Protection by Dietary Supplementation with Acetylsalicylic Acid", Exp. Eye Res., 57, 783-790, (1993).
Jordan, A. et al., "Tubulin as a Target for Anticancer Drugs: Agents which Interact with the Mitotic Spindle", Medicinal Research Reviews, 18.259-296, (1998).
Jordan, V.C., et al., "A Mutant Receptor as a Mechanism of Drug Resistance to Tamoxifen Treatment", Annals New York Academy of Science, 761, 138-147, (1995).
Jordan, V.C., et al., "Structural Requirements for the Pharmacological Activity of Nonsteroidal Antiestrogens in Vitro", Molecular Pharmacology, 26, 272-278, (1984).
Jordan, V.C., et al., "Tamoxifen: Toxicities and Drug Resistance During the Treatment and Prevention of Breast Cancer", Annu. Rev. Pharmacol. Toxicol., 35, 195-211, (1995).
Joswig, B.C., et al., "Transmural Myocardial Infarction in the Absence of Coronary Arterial Luminal Narrowing in a Young Man with Single Coronary Arterial Anomaly", Catheterization and Cardiovascular Diagnosis, 4, 297-304, (1978).
Kakuta, T., et al.. "Differences in Compensatory Vessel Enlargement, Not Intimal Formation, Account for Restenosis After Angioplasty in the Hypercholesterolemic Rabbit Model", Circulation, 89, 2809-2815, (1994).
Kakuta, T., et al., "The Impact of Arterial Remodeling on the Chronic Lumen Size After Angioplasty in the Atherosclerotic Rabbit", JACC, Abstract No. 875-95, p. I38A, (Feb. 1994).
Kanzaki, et al., "In vivo effect of TGF-beta1 : enhanced intimal thickening by administration of TGF-beta1 in rabbit arteries injured with a balloon catheter", Arterioscler. Thromb. Vasc. Biol., 15(11):1951-57 (1995).
Kardami et al.. "Heparin Inhibits Skeletal Muscle Growth in Vitro", Dev. Biol.., 126:19-28 (1988).
Kariya et al., "Antiproliferative action of cyclic GMP-elevating vasodilators in cultured rabbit aortic smooth muscle cells". Atherosclerosis, 80:143-147 (1989).
Kaski, J.C., et al., "Local Coronary Supersensitivity to Diverse Vasoconstrictive Stimuli in Patients with Variant Angina", Circulation, 74, 1255-1265, (1996).
Kastrati et al., "Restenosis after coronary placement of various stent types," Am. J. Cardiol., 87:34-49 (2001).
Ke, H.Z., et al., "Comparative Effects of Droloxifene, Tamoxifen, and Estrogen on Bone, Serum Cholesterol, and Uterine Histology in the Ovariectomized Rat Model", Bone, 20, 31-39, (1997).
Keen, C.L., et al., "Hypertension Induced Alterations in Copper and Zinc Metabolism: A Link to Vascular Disease?", In: Biology of Copper Complexes, Sorenson, J.R.J., (ed.), Humana Press, Clifton, New Jersey, 141-153, (1987).
Kellen, J.A., '"Tamaoxifen Beyond the Antiestrogen", BirkhΣuser, 392 pages, (1996).
Kellen, J.A., et al., "The Effect of Toremifene on the Expression of Genes in a Rat Mammary Adenocarcinoma", In Vivo, 10, 511-514, (1996).
Kemp, P.R., et al., "Cloning and Analysis of the Promoter Region of the Rat SMI 1-Alpha Gene". Biochem. J., 310, 11043, (1995).
Kemp, P.R., et al., "Inhibition of PDGF BB Stimulated DNA Synthesis in Rat Aortic Vascular Smooth Muscle Cells by the Expression of a Truncated PDGF Receptor", FEBS Letters, 336, 119-123, (Dec. 1993).
Kemp, P.R., et. al., "ID—A Dominant Negative Regulator of Skeletal Muscle Differentiation—is Not Involved in Maturation or Differentiation of Vascular Smooth Muscle Cells", FEBS Letters, 368, 81-86, (1995).
Kim, et al., "Suppression of Vascular Transforming Growth Factor-B1 and Extracellular Matrix Gene Expressions by Cilazapril and Nifedipine in Hypertensive Rats", Clin. Exp. Pharmacaol. Physiol. Suppl., 1, S355, (1995).
Kim, J. et al., "Production of Taxol and Related Taxanes in *Taxus brevifolia* Cell Cultures: Effect of Sugar", Biotechnology Letters, 17, 101-106, (Jan. 1995).
Kingston, D.G., et al., "Synthesis and Structure-Activity Relationships of Taxol Derivatives As Anticancer Agents", In: New Trends in Natural Products Chemistry. Atta-ur-Rahman, et al., (eds.), Studies in Organic Chemistry, vol. 26, Elsevier Science Publishers B.V., Amsterdam, 219-235, (1986).
Kirk-Othmer, Encyclopedia of Chemical Technology, $33^{rd}$ edition, vol. 17, 1982, John Wiley & Sons, pp. 281-310.
Kirschenlohr, H.L., et al., "Cultures of Proliferating Vascular Smooth Muscle Cells from Adult Human Aorta", In: Human Cell Culture, Jones, G.E., (Ed.), Humana Press, Inc., 24 p. (1996).
Kirschenolohr, H.L., et al., "Proliferation of Human Aortic Vascular Smooth Muscle Cells in Culture is Modulated by Active TGF-Beta", Cardiovascular Research, 29, 848-855, (1995).
Klebe et al., "Regulation of cell motility, morphology, and growth by sulfated glycosaminoglycans", Cell Motil. Cytoskel., 6:273-281 (1986).
Klein, H.O. et al., "Experimental Investigations on a Sequential Combination Chemotherapy Protocol" J. Cancer Res. Clin. Oncol vol. 96 No. 2 Jan. 1980 p. 65-78.
Kleinman, N.S., et al., "Prinzmetal's Angina during 5-Fluorouracil Chemotherapy", The American Journal of Medicine, 82, 566-568, (1987).
Knabbe, C.. et al., "Induction of Transforming Grown Factor-B by the Antiestrogens Droloxifene, Tamaoxifen, and Toremifene in MCF-7 Cells", Am. J. Clin. Oncol. 14, S15-S20, (1991).
Kopp, A., et al., "Transforming Growth Factor Beta2 (TGF-Beta2) Levels in Plasma of Patients with Metastatic Breast Cancer Treated with Tamoxifen", Cancer Research, 55. 4512-4515, (Oct. 15, 1995).
Kost, J. Langer R, "Controlled Release of Bioactive Agents," Trends in Biotechnology, vol. 2, No. 2, 1984, pp. 47-51.
Kotoulas, I.G., et al., "Tamoxifen Treatment in Male Infertility. I. Effect on Spermatozoa". Fertility and Sterility, 61, 911-914, (May 1994).
Koyama, N., et al., "Regulation of Smooth Muscle Cells Migration by a New Autocrine Migration Factor and TGF-beta", Circulation, 84, Abstract No. 1829, II-459, (1991).
Kremer, J.M.. et al., "Fish-Oil Fatty Acid Supplementation in Active Rheumatoid Arthritis", Annals of Internal Medicine, 106, 497-502, (1987).
Kunert, et al., Paclitaxel Inhibits Developpment of Restenosis Following Experimental Balloon Angioplasty in the Rabbit Carotid Artery:, European Heart Journal, 17, Abstract No. P1998, p. 368 (1996).
Kunz et al., "Defining Coronary Restenosis Newer Clinical and Angiographic Paradigms". Circulation. 88 1310-1323 (Sep. 1993).
Kunz et al., "Sustained Dilation and Inhibition of Restenosis in a Pig Femoral Atery Injury Model". Circulation, 90, p. 1-297, Abstract No. 1598 (Oct. 1994).
Kunz et al., "Inhibition of Microfilament Reorganization Following Balloon Angioplasty Decreases Extent of Geometric Remodeling in Restenosis,"J. of Amer. Coll. of Cardiology, AMerican College of Geometric Cardiology $44^{th}$ Annual Scientific Session, Abstract No. 122292. (Mar. 19-22, 1995).
Kunz, L.L., et al., "Efficacy of Cytochalasin B in Inhibiting Coronary Restenosis Caused by Chronic Remodeling After Balloon Trauma in Swine", Journal of the American College of Cardiology, Supplement A., Abstract No. 984-23, p. 302, (Mar. 1995).
Kuramochi, H., "Conformational Studies and Electronic Structures of Tamoxifen and Toremifene and Their Allylic Carbocations Proposed as Reactive Intermediates Leading to DNA Adduct Formation", J. Med. Chem., 39, 2877-2886. (1996).
Kuzana, S., et al., "Effects of Some Anti-Rheumatic Agents on Copper-Catalyzed Thermal Aggregation of Gamma Globulin", Agents and Actions, 9 375-380, (1979).
L C.. Palmaz et. al., Expandable Intraluminal Grail: A Preliminary Study, Radiology 1985; 1:73-77.
Labhsetwar et al., "Nanoparticles for site specific delivery of U-86983 in restenosis on pig coronary arteries," Proc. Intern. Symp. Control. Rel. Bioact. Mater. 22, 182-183 (1995).
Laird, J., et al., "Inhibition of Neointimal Proliferation with Low-dose Irradiation from a Beta-particle-emitting Stent", Circulation, 93, 529-536, (1996).
Langbein, W., "Too Many Drugs, Too Little Value in CV Conditions", In Vivo, 14-20, (Jun. 1995).
Lange, R.A., et al., "Cocaine-Induced Coronary-Artery Vasoconstriction", The New England Journal of Medicine, 321, 1557-1562, (1989).
Lange, R.L., et al., "Nonatheromatous Ischemic Heart Disease following Withdrawal from Chronic Industrial Nitroglycerin Exposure", Circulation, 46, 666-678, (1972).
Langer, R. et al., "Polymeric Delivery Systems for Macromolecules—Approaches for Studying In Vivo Release Kinetics and Designing Constant Rate Systems", in: *Biological Activities of Polymers*, Carraher, Jr. and Gebelein (eds), American Chemical Society Symposium Series 186, pp. 95-105 (1982).
Langer, R. et al., "Polymers for the Sustained Release of Proteins and Other Macromolecules", Nature 263:797-799 (1976).
Langer, R., "New Methods of Drug Delivery". Science, vol. 249, Sep. 28, 1990, pp. 1527-1533.
Langer, R., "Polymeric Delivery Systems for Controlled Drug Release", Chem. Eng. Communi. 6:1-48 (1980).
Law et al., "Rapamycin potentiates transforming growth factor beta-induced growth arrest in nontransformed, oncogene-transformed, and human cancer cells", Mol.. Cell. Biol., 22:8184-8198 (2002).
Lawn, R.M.. et al., "Feedback Mechanism of Focal Vascular Lesion Formation in Transgenic Apolipoprotein(a) Mice", The Journal of Biological Chemistry, 271, 31367-31371, (1996).
Lazier, C.B., et al., "Comparison of the Effects of Tamoxifen and of a Tamoxifen Analogue that Does Not Bind the Estrogen Receptor on Serum Lipid Profiles in the Cockerel", Biochem. Cell Biol., 68, 210-217, (1990).
LC. Palmaz et al., Expandable Intraluminal Vascular Graft: A Feasibility Study, Surgery Feb. 1986; 199(2): 199-205.
Lehmann, K. et al., "Effect of cilazapril on the proliferative response after vascular damage", J. of Cardiovascular Pharmacology, 22 (Suppl. 4), S19-24, (1993).
Lehmann-Bruinsma, et al., "Transforming Growth Factor B2 (TGF-B) Suppression of Smooth Muscle Cell (SMC) Proliferation After Balloon Angioplasty of Rat Carotid Arteries", Clin. Res. 42, Abstract No. 4A, (Feb. 9-12, 1994).
Leroux, J.C., et al., "Internalization of poly(d L-lactic acid) nanoparticles by isolated human leukocytes and analysis of plasma proteins absorbed onto the particles", J. Biomed. Mater. Res, 28, 471-481, (1994).
Leroux, et al., "New Approach for the Preparation of Nanoparticles by an Emulsification-Diffusion Method", Eur. J. Pharm. Biopharm, 41, 14-18, (1995).
Levy, et al., "Strategies for Treating Arterial Restenosis Using Polymeric Controlled Release Implants," Chemical Abstracts, 121, 580: Abstract No. 263625g (1994).
Levy, R.J., et al., "Strategies for Treating Arterial Restonosis Using Polymeric Controlled Release Implants", In: Biotechnology and Bioactive Polymers, Proceedings of an American Chemical Society Symposium, Gebelein, C.G., (ed.), Plenum Press, New York, 259-268, (1994).
Liau and Chan, "Regulation of extracellular matrix RNA levels in cultured smooth muscle cells: relationship to cellular quiescence", J. Cell Biol., 264:10315-10320 (1989).
Lichtlen et al.. "Retardation of angiographic progression of coronary artery disease by nifedipine", Lancet, 335:1109-1113 (1990).
Lincoff et al., "Local Drug Delivery for the Prevention of Restenosis" Circulation, 90 2070-2084 (Oct. 1994).
Lindkaer-Jensen, S., et al., "Inhibition of Salicylate and Lithium Absorption in the Human Intestine by Copper Sulfate", Arch. Toxicol., 35, 175-179, (1976).
Lindner, "Vascular repair processes mediated by transforming growth factor-beta, Z Kardiol", 90 Suppl 3:17-22 (2001).
Lipold, B.C., "Retardarzneiformen" in E. Numberg, Hagers Handbuch der pharmazeutischen Praxis, vol. 2, Springer-Verlag Berlin Heidelberg New York, $5^{th}$ edition, 1991 pp. 832-840.
Lippman and Mathews, "Heparins: varying effects on cell proliferation in vitro and lack of correlation with anticoagulant activity", Fed. Proc., 36:55-59 (1977).
Liu et al., "Trapidil in preventing restenosis after balloon angioplasty in the atherosclerotic rabbit", Circulation, 81(3): 1089-1093 (1990).

Lopez-Anaya, A., et al., "Pharmacokinetics and Pharmacodynamics in Copper Deficiency I", Biological Trace Element Research, 40, 161-176, (1994).
Lopez-Casillas, et al., "Beta-glycan Presents Ligand to the TGFBeta Signaling Receptor", Cell, 73, 1435-1444, (Jul. 2, 1993).
Loser, R., et al., "In Vivo and in Vitro Antiestrogenic Action of 3-Hydroxytamoxifen, Tamoxifen and 4-Hydroxytamoxifen", Eur. J. Cancer Clin. Oncol., 21, 985-990, (1985).
Lowe, et al., "Coronary In-Stent Restenosis: Current Status and Future Strategies", Journal of the American College of Cardiology, 1992, vol. 39 No. 2, pp. 183-193.
Luan et al., "Rapamycin is an effective inhibitor of human renal cancer metastasis", Kidney Int., 63:917-926 (2003).
Lucas, C., et al., "The Authocrine Production of Transforming Growth Factor-B1 During Lymphocyte Activation", The Journal of Immunology, 145(5), 1415-1422, (1990).
Ludwig K. von Segesser, MD., Heparin-Bonded Surfaces in Extracorporeal Membrane Oxygenation for Cardiac Support:, The Society of THoracic Surgeons, (1996).
Luo, H. et al., "Chronic Vessel Constriction is an Important Mechanism of Restenosis After Balloon Angioplasty: An Intravascular Ultrasound Analysis", Circulation, 90, 67 Scientific Sessions, Abstract No. 0318, p. 1-61, (1994).
Luostarinen, R., et al., "Effect of Dietary Fish Oil Supplemented with Different Doses of Vitamin E on Neutrophil Chemotaxis in Healthy Volunteers", Nutrition Research, 12, 1419-1430, (1992).
Lutgens et al., "Transforming growth factor-beta mediates balance between inflammation and fibrosis during plaque progression", Arterioscler. Thromb. Vasc. Biol., 22:975-982 (2002).
Lyons et al., "Mechanism of activation of latent recombinant transforming growth factor betal by plasmin", J. Cell. Biol., 110:1361-1367 (1990).
Macander et al., "Balloon Angioplasty for Treatment of In-Stent Restenosis: Feasibility, Safety, and Efficacy", Catheterization and Cardiovascular Diagnosis, 32 125-131 (1994).
Madri et al., "Endothelial cell behavior after denudation injury is modulated by transforming growth factor-beta1 and fibronectin", Lab. Invest., 60:755-764 (1989).
Magarian, "The Medicinal Chemistry of Nonsteroidal Antiestrogens: A Review", Current Medicinal Chemistry, 1, 61-104, (1994).
Majack, "Beta-type transforming growth factor specifies organizational behavior in vascular smooth muscle cell cultures", J. Cell Biol., 105:465-471 (1987).
Majack, R.A., et al., "Role of PDGF-A Expression in the Control of Vascular Smooth Muscle Cell Growth by Transforming Growth Factor-B", The Journal of Cell Biology, 111, 239-247, (1990).
Majesky, M.W., et al., "Production of Transforming Growth Factor beta1 During Repair of Arterial Injury", J. Clin. Invest., 88, 904-910, (1991).
Mambetisaeva, E.T., et al. "Effect of New Synthetic Cholesterol Derivatives on Cholesterol Metabolism in Cultured Rabbit Hepatocytes", Biokhimiya (Russia), 58, Translation, Plenum Publishing Corporation, 1126-1132, (1993).
Amiji, M., et al., "Surface Modification of Polymeric Materials with Poly (ethylene oxide), Albumin, and Heparin for Reduced Thrombogenicity," J. Biomater. Sci. Plymer Edn., vol. 4, No. 3, pp. 217-234 (1993).
Manucci, P.M., et al., "Effect of Tamoxifen on Measurements of Hemostatis in Healthy Women", Arch. Intern. Med., 156, 1806-1810, (1996).
Marx and Marks, "Bench to Bedside: The development of rapamycin and its application to stent restenosis", Circulation 104:852-55 (2001).
Marx, "CMV-p.53 Interaction May Help Explain Clogged Arteries", Science, 265, 320, (Jul. 1994).
Marzocchi, A., et al., "Restenosis after Coronary Angioplasty: It's Pathogenesis and Prevention," Cardiologia, 36, 309-320 (Dec. 1991) English Abstract only, reported in Medline, Accession No. 93046311.
Massague and Wotton, "Transcriptional control by the TGF-beta/Smad signaling system", EMBO J., 19(8):1745-54 (2000).
Massague et al., "Type beta transforming growth factor is an inhibitor of myogenic differentiation", Proc,. Natl. Acad. Sci., 83:8206-8210 (1986).
Massague,"Subunit structure of a high-affinity receptor for type beta-transforming growth factor: evidence for a disulfide-linked glycosylated receptor complex", J. Biol. Chem., 260(11):7059-7066 (1985).
McAuslan, B.R., et al., "Cellular and Molecular Mechanisms in Angiogenesis", Trans. Ophthal. Soc. U.K., 100, 354-358, (1980).
McCaffrey et al, "Genomic instability in the type II TGF-b1 receptor gene in atherosclerotic and restenotic vascular cells," J Clin Invest, 100:2182-2188 (1997).
McCaffrey et al., "Aging and arteriosclerosis: the increased proliferation of arterial smooth muscle cells isolated from old rats is associated with increased platelet-derived growth factor-like activity," J. Exp. Med., 167:163-174 (1988).
McCaffrey et al., "Decreased type II/type I TGF-beta receptor ratio in cells derived from human atherosclerotic lesions. Conversion from an antiproliferative to profibrotic response to TGF-beta I", J. Clin. Invest., 96:2667-2675 (1995).
McCaffrey, "TGF-betas and TGF-beta receptors in atherosclerosis," Cytokine and Growth Factor Rev., 11:103-114 (2000).
McCaffrey, T.A., et al., "Fucoidan is a Non-Anticoagulant Inhibitor of Intimal Hyperplasia", Biochemical and Biophysical Research Communications, 184, 773-781, (1992).
McCague, R., et al., "An Efficient, Large Scale Synthesis of Idoxifene ((E)-1(4-(2-(N-pyrrolidino) ethoxyl)-1-(4-iodophenyl)-2-phenyl-1-butene)", Organic Preparations and Proc. Int., 26, 343-346, (1994).
McCague, R., et al., "Synthesis of 4-Stannylated Tamoxifen Analogues: Useful Precursors to Radiolabelled Idoxifene and Axiridinyl 4-lodotamoxifen.", J. Labelled Compounds and Pharmaceuticals, 34, 297-302, (1994).
McClean, et al., "cDNA sequence of human apolipoprotein (a) is homologous to plasminogen", Nature, 330, 132-137 (1987), 132-137, (1987).
McDonald, C.C., et al., "Cardiac and vascular morbidity in women receiving adjvant tamoxifen for breast cancer in a randomised trial", BMJ, 311, 977-980, (Oct. 14, 1995).
McDonnell, D.P., et al., "Analysis of Estrogen Receptor Function in Vitro Reveals Three Distinct Classes of Anti estrogens", Molecular Endocrinology, 9, 65-669, (Jun. 1995).
McLaughlin, C.S., et al., "Inhibition of Protein Synthesis by Trichothecenes", In: Mycotoxins in Human and Animal Health, Pathotox Publishers, Inc., 263-273, (1977).
McMurray et at., "A standardised method of culturing aortic explants, suitable for the study of factors affecting the phenotypic modulation, migration and proliferation of aortic smooth muscle cells," Atherosclerosis, 86:227-237 (1991).
Merck Index, Eleventh Edition 2796, Cytochalasins, p. 438 (1989).
Merck Index, (Susan Budavari et al, ed.) 1989, p. 1435.
Merrilees and Scott, "Antisense S-oligonucleotide against transforming growth factor-beta 1 inhibits proteoglycan synthesis in arterial wall," L Vase. Res. 31:322-329 (1994).
Merrilees et al., "Effect of TGF-beta(1) antisense S-oligonucleotide on synthesis and accumulation of matrix proteoglycans in balloon catheter-injured neointima of rabbit carotid arteries, 3". Vasc. Res. 37:50-60 (2000).
Metcalfe et al., "Calcium and cell proliferation," Br. Med.. Bull., 42(4):405-4t2 (1986).
Metcalfe, et al., "Protein Markers of Lesion Development in the Vessels of Transgenic Apo(a) Mice" Inflammation, Growth Regulatory Molecules & Atherosclerosis, J. Cellular Biochem., Supplement 18A, p. 208, Abstract No. E212 (1994).
Metcalfe, et al., "Transforming Growth Factor-beta and the Protection From Cardiovascular Injury Hypothesis", Biochem. Soc. Trans., May 1995; 23(2): pp. 403-406.
Meyer, S.C., "Functionalized Cytochalasins for Potential Biotechnology Transfer", Ph. D. Thesis (Selected Pages), Syracuse University, New York, 13 p., (May 1994).
Michael N. Helmus, "Materials Selection, Chapter 2." Encyclopedic Handbook of Biomaterials and Bioengineering, Part A: Materials, vol. 1 (1995).

Michael N. Helmus, Materials Selection, Chapter 6, Cardiovsc. Pathol. 2(3)(Suppl.):53s-71s (Jul.-Sep. 1993).
Michael N. Helmus, "Materials Selecton for Medical Devices," Spectrum, 1-21, (Jul. 30, 1993).
Michael N. Helmus, "Medical Device Design—A Systems Approach: Central Venous Catheters", (1990).
Michael N. Helmus, "Opportunities for Biomaterials," DH Reports, (Feb. 1995).
Michael N. Helmus, "Technological Advances in Thromboresistant Materials," Spectrum, 1-13 (Jun. 19, 1990).
Michael N. Helmus, "Thromboresistant Biomaterials: Technical Developments and Applications," Spectrum, (Sep. 12, 1990).
Middlebrook, J.L., et al., "Binding of T-2 Toxin to Eukaryotic Cell Ribosomes", Biochemical Pharmacology, 38 33110, (1989).
Milner, M.R., et al., "Usefulness of Fish Oil Supplements in Preventing Clinical Evidence of Restenosis After Percutaneous Transluminal Coronary Angioplasty", Am. J. Cardiol., 64, 294-299 (1989).
Mintz, G.S., et al., "Chronic Compensatory Arterial Dilation Following Coronary Angioplasty: An Intravascular Ultrasound Study", JACC, Abstract No. 875-97, p. 138A, (Feb. 1994).
Mintz, G.S., et al., "Geometric Remodeling is the Predominant Mechanism of Clinical Restenosis After Coronary Angioplasty", JACC, Abstract No. 875-42, p. 138A, (Feb. 1994).
Mintz, G.S., et al., "Mechanisms of Late Arterial Response to Transcatheter Therapy: A Serial Quantitative Angiographic and Intravascular Ultrasound Study", Circulation, 90, Abstract No. 117, p. 1-24, (Oct. 1994).
Mirjalili, N. et al., "Methyl Jasmonate Induced Production of Taxol in Suspension Cultures of *Taxus cuspidata*: Ethylene Interaction and Induction Models", Biotechnol. Prog., 12, 110-118, (1996).
Mirjalili, N., et al., "Gas Phase Composition Effects on Suspension Cultures of *Taxus cuspidata*", Biotechnology and Bioengineering, 48, 123-132, (1995).
Mitchell, L.L., et al., "Copper Deficiency Depresses Rat Aortae Superoxide Dismutase Activity and Prostacyclin Synthesis", Prostaglandins, 35, 977-986, (1988).
Moiling, K., "Naked DNA for Vaccine or Therapy", J. Mol. Med., 75, 242-246, (1997).
Moorthy, B., et al., "Tamoxifen Metabolic Activation: Comparison of DNA Abducts Formed by Microsomal and Chemical Activation of Tamoxifen and 4-Hydroxytamoxifen with DNA Abducts Formed in Vivo", Cancer Research, 56, 53-57, (Jan. 1, 1996).
More, R.S., et al., "A targeted antithrombotic conjugate with antiplatelet and fibrinolytic properties which reduces in vivo thrombus formation", Chemical Abstracts, vol. 120, No. 22, (May 30, 1994).
Morris et al., "Rapamycin (sirolimus) inhibits vascular smooth muscle DNA synthesis in vitro and suppresses narrowing in arterial allografts and in balloon-injured carotid arteries: evidence that rapamycin antagonizes growth factor action on immune and nonimmune cells," Transplant Proc, 27:430-31 (1995).
Morris, R.E., "Rapamycins: Antifungal, Antitumor, Antiproliferative, and Immunosuppressive Macrolides", Transplantation Reviews, 6, 39-87, (1992).
Morris, R.E., et al., "Immunosuppressive Effects of the Morpholinoethyl Ester of Mycophenolic Acid (RS-61443) in Rat and Nonhuman Primate Recipients of Heart Allografts", Transplantation Proceedings, 23, 19-25, (1991).
Mosedale and Grainger, "An antibody present in normal human serum inhibits the binding of cytokines to their receptors in an in vitro system," Biochem J., 343:125-133 (1999).
Mosedale, D.E. University of Cambridge Ph.D. Thesis, Differentiated state of smooth muscle and its relationship to TGF-β in vivo, DJG 005652-005910 (1998) and all references therein.
Mosedale. D.E., et al., "Transforming Growth Factor-beta is Correlated with Smooth Muscle Cell Differentiation in Vivo", Circulation, 90, $67^{th}$ Scientific Session, Abstract No. 1590. p. 1-296, (Oct. 1994).
Mueller, B.M., et al., "Antibody Conjugates with Morpholinodoxorubicin and Acid-Cleavable Linkers", Bioconjugate Chem. 1, 325-330, (1990).
Murphy, C.S., et al., "Structural Components Necessary for the Antiestrogenic Activity of Tamoxifen", J. Steroid Biochem, 34, 1-6 (1989).
Murphy, C.S., et al., "Structure-Activity Relationships of Nonisomerizable Derivatives of Tamoxifen: Importance of Hydroxyl Group and Side Chain Positioning for Biological Activity", Molecular Pharmacology, 39, 421-428, (1991).
Murphy, L.C., et al., "Differential Effects of Tamoxifen and Analogs with Nonbasic Side Chains on Cell Proliferation in Vitro", Endocrinology, 116, 1071-1078, (1985).
Myer, R.O, et al., "Performance and Carcass Characteristics of Swine When Fed Diets Containing Canola Oil and Added Copper to Alter the Unsaturated:Saturated Ration of Pork Fat", J. Anim. Sci., 70, 1417-1423, (1992).
Nabel, E.G., et al., "Direct Transfer of Transforming Growth Factor Beta 1 Group Into Arteries Stimulates Fibrocellular Hyperplasia", Proc. Natl. Acad. Sci. USA, 90, 10759-10763, (1993).
Nagakawa, Y., et al., "Effect of Eicosapentaenoic Acid on the Platelet Aggregation and Composition of Fatty Acid in Man", Atherosclerosis, 47, 71-75, (1983).
Nakagawa, et al., "A Case of Acute Myocardinal Infarction Intracoronary Arteries Due to Hormone Therapy.", Angiology, 45, 333-338, (May 1994).
Nakano, Glucocorticoid Inhibits Thromin-Induced Expression of Platelet-Derived Growth Factor A-chain and Heparin-Binding Epidermal Growth Factor-Like Growth Factor in Human Aortic Smooth Muscle Cells:, The Journal of Biological Ch emistry, 268, 22941-22947 (1993).
Navarro, S.E., et al., "Notes from Transcatheter Cardiovascular Therapeutics 1995 Conference", USB Securities, Equity Research—Medical Technology, 10 p., (Mar. 3, 1995).
Nayfield, S.G., et al., "Tamoxifen-Associated Eye Disease: A Review", Journal of Clinical Oncology, 14(3), 1018-1026, (1996).
Nikol et al., "Persistently increased expression of the transforming growth-factor-131 gene in human vascular restenosis: Analysis of 62 patients with one or more episode of restenosis," Cardiovasc. Pathol., 3:57-64 (1994).
O'Leary, V.J., et al., "The Resistance of Low Density Lipoprotein to Oxidation Promoted by Copper and Its Used as an Index of Antioxidant Therapy", Atherosclerosis, 119, 169-179, (1996).
Ohno, et al., "Gene Therapy for Vascular Smooth Muscle Proliferation After Afterial Injury", Science, 265, 781-784, (Aug. 5, 1994).
Okuyyama, S., et al., "Copper Complexes of Non-Steroidal Anti-inflammatory Agents: Analgesic Activity and Possible Opoid Receptor Activation", Agents and Actions, 21, 130-144, (1987).
Opherk, D.. et al., "Four-Year Follow-up Study in Patients With Angina Pectoris and Normal Coronary Arteriograms ("Syndrome X")", Circulation, 80, 1610-1616, (1989).
Orlov, S.N., et al., "Altered beta-Adrenergic Regulation of Na-K-Cl Cotransport in Cultured Smooth Muscle Cells Form the Aorta of Spontaneously Hypertensive Rats", American Journal of Hypertension, 8, 739-747, (1995).
Osborne, M.R., et al., "Identification of the Major Tamoxifen-Deoxyguanosine Adduct Formed in the Liver DNA of Rats Treated with Tamoxifen", Cancer Research, 56, 66-71, (1996).
Owens, G.K., et al., "Transforming Growth Factor-B-induced Growth Inhibition and Cellular Hypertrophy in Cultured Vascular Smooth Muscle Cells", The Journal of Cell Biology, 107. 771-780, (1988).
Ozer, et al., "New Roles of low density lipoproteins and vitamin E in the pathogenesis of atherosclerosis", Biochem Mol. Biol. Intern, 35, 117-124, (1995).
Palmaz et al., "Expandable Intrahepatic Portacaval Shunt Stents in Dogs with Chronic Portal Hypertension," A JR 1986 Dee; 147:1251-54.
Palmaz et al., "Expandable Intrahepatic Portacaval Shunt Stents: Early Experience in the Dog." 145 Am. J. Roentgenol. 1985;145:821-825.
Palmaz et al., "Expandable Intraluminal Grafting in Atherosclerotic Rabbit Aortas," Radiology Nov. 1985; 157(P):66 Abs 130.
Palmaz et al.. "Normal and Stenotic Renal Arteries: Experimental Balloon-expandable Intraluminal Stenting," Radiology Sep. 1987; 164(3):705-708.
Palmaz et al., "Removable Biliary Endoprosthesis," Am, J. Roentgenol. 1983;140(4):812-4.

Palmaz, et al., "Atherosclerotic Rabbit Aortas: Expandable Intraluminal Grafting," Radiology Sep. 1986; 160:723-726.
Palmaz, et al., "Expandable Intrahepatic Portocaval Shunt Stents in Dogs with Chronic Portal Hypertension," American Roentgen Ray Soc'y 1986 Annual Meeting. Washington, D.C., (BT 000079) (Apr. 13-18, 1986).
Palmaz. et al., "Intravascular Stents: Basic Physical and Biological Properties, Endoluminal Treatment: The Different Techniques.". Editors Michel Henry, Max Arnor, Edward B. Diethrich and Barry Katzen. Published by Springer Verlag; 4:149-158 (1997).
Palmaz, J.C. "Balloon-Expandable Intravascular Stent," A JR Jun. 1988; 150:1263-1269.
Palmaz, J.C. "Expandable Intraluminal Graft: A Preliminary Study," Radiology Nov. 1984; 153(P):329 Abs. 993.
Pandey, B.L., et al., "A Study of the Effects of Tamrabhasma, an Indigenous Preparation of Copper on Experimental Gastric Ulcers and Secretion", Indian Journal of Experimental Biology, 21, 258-264, (1983).
Pardoll, D., et al., "Exposing the Immunology of Naked DNA Vaccines", Immunity, 3, 165-169, (1995).
Parthasatathy, S., et al., "A Role for Endothelial Cell Lipoxygenase in the Oxidative Modification of Low Density Lipoprotein", Proc. Nat'l Acad. Sci., USA, 86, 1046-1050, (1989).
Pedron, N. et al., "The Effect of Acetylsalicyclic Acid on Menstrual Blood Loss in Women with IUDs", Contraception, 36, 295-303, (1987).
Peng et al., "The immunosuppressant rapamycin mimics a starvation-like signal distinct from amino acid and glucose deprivation," Mol. Cell.. Biol., 22:5575-84 (2002).
Pennisi, E., "Drug's Link to Genes Reveals Estrogen's Many Sides", Science, 273, 1171, (Aug. 30, 1996).
Peress, N.S., et al., "Differential Expression of TGF-B1, 2 and 3 Isotypes in Alzheimer's Disease : A Comparative Immunohistochemical Study with Cerebral Infarction, Aged Human and Mouse Control Brains", Journal of Neuropathology and Experimental Neurology, 54, 802-811, (Nov. 1995).
Peress, N.S., et al., "Glial Transforming Growth Factor (TGF)-B Isotypes in Multiple Sclerosis: Differential Glial Expression of TGF-B1, 2, and 3 Isotypes in Multiple Sclerosis", Journal of Neuroimmunology, 71, 115-123, (1996).
Perez, J.R., et al., "Regulation of Adhesion and Growth of Fibrosarcoma Cells by NF-kb ReIA Involves Transforming Growth Factor Beta", Molecular and Cellular Biology, 14, 5326-5332, (1994).
Pfister, W.R. et al., "Silicone Based Sustained and Controlled Release Drug Delivery Systems", 1985, 30$^{th}$ National SAMPE Symposium and Exhibition, Anaheim, CA, Mar. 19-21, 1985, pp. 490-498 (1985).
Pinto, H.C., et al., "Tamoxifen-associated Steatohepatitis C Report of Three Cases", Journal of Hepatology, 23, 95-97, (1995).
Polysciences Inc., TDMAC-Heparin Coatings, Nov. 1988, Data Sheet #172.
Post et alk., "The Relative Importance of Arterial Remodeling Compared With Intimal Hyerplasia in Lumen Renarrowing After Balloon ANgioplasty" Circulation 89, 2816-2821 (Jun. 1994).
Potter et al., "A mechanism hypothesis for DNA adduct formation following hepatic oxidative metabolism," Carcinogenesis, 15, 439-442 (1994).
Powell et al., "Inhibitors of angiotensin-converting enzyme prevent myointimal proliferation after vascular injury," Science, 245:186-188 (1989).
Presentation at The Society of CV & Interventional Radiology's Twelfth Annual Course on "Diagnostic Angiography and Interventional Radiology." Includes: "The Current Status of Vascular Prostheses" by Julio Palmaz at 118-120 (Mar. 23-26, 1987).
Program and abstracts of the Seventh International Conference on the Adjuvant Therapy of Cancer, held in Tuscon, Arizona on Mar. 10-13, 1993.
Pupita, G., et al., "Myocardial Ischemia Caused by Distal Coronary-Artery Constriction in Stable Angina Pectoris", The New England Journal of Medicine, 323, 514-520, (1990).
Rainsford, K.D., et al., "Concerning the Merits of Copper Aspirin as a Potential Anti-Inflammatory Drug", J. Pharm. Pharmac., 28, 83-86, (1976).

Rainsford, K.D., ct al., "Gastric Mucus Effusion Elicited by Oral Copper Compounds: Potential Anti-Ulcer Activity", Experientia, 32, 1172-1173, (1976).
Raisz, L.G., "Estrogen and Bone: New Pieces to the Puzzle". Nature Medicine, 2, 1077-1078, (1996).
Raloff, "Tamoxifen Puts Cancer on Starvation Diet", Science News, 146, 292, (Nov. 5, 1994).
Ray, P., et al., "Repression of interleukin-6 gene expression by 17beta-estradiol: Inhibition of the DNA-binding activity of the transcription factors NF-IL6 and NF-6B by the estrogen receptor", FEBS Letters, 409, 79-85, (1997).
Razavi, M., "Unusual Forms of Coronary Artery Disease", Cleveland Clinic Consultations, 7, 25-46, (1975).
Recchia, F., et al., "Interferon-beta, Retinoids, and Tamoxifen in the Treatment of Metastatic Breast Cancer: A Phase II Study", Journal of Interferon and Cytokine Research. 15, 605-610, (1995).
Reckless, J., et al., "Tamoxifen Decreases Cholesterol Sevenfold and Abolishes Lipid Lesion Development in Apolipoprotein E Knockout Mice", Circulation, 95, 1542-1548, (1997).
Reilly et al., "Antiproliferative effects of heparin on vascular smooth muscle cells are reversed by epidermal growth factor," J. Cell Physiol., 131 :t 49-157 (1987).
Reilly, C.F., "Rat Vascular Smooth Muscle Cells Immortalized with SV40 Large T Antigen Possess Defined Smooth Muscle Cell Characteristics Including Growth Inhibition by Heparin", Journal of Cellular Physiology, 142, 342-351, (1990).
Reis, G.J., et al., "Randomized Trial of Fish Oil for Prevention of Restenosis After Coronary Angioplasty", The Lancet, 177-181,(1989).
Ribeiro, G., et al., "Adjuvant Tamoxifen for Male Breast Cancer (MBC)", Br. J. Cancer, 65, 252-254, (1992).
Rieckmann, P., et al., "Tumor Necrosis Factor-a Messenger RNA Expression in Patients with Relapsing-Remitting Multiple Sclerosis is Associated with Disease Activity", Ann. Neurol, 27, 82-88, (1996).
Riessen et al., "Prospects for Site-Specific Delivery of Pharmacologic and Molecular Therapies", J. Amer. Collage of Cardiol., 23 , 1234-1244 (Apr. 1994).
Riessen et al., "Regional Differences in the Distribution of the Proteoglycans Biglycan and Decorin in the Extracellular Matrix of Atherosclerotic and Restenotic Human Coronary Ateries", Amer. J. Path 144, 962-974 (May 1994).
Roberts et al., "Type beta transforming growth factor: a bifunctional regulator of cellular growth," Proc. Natl. Acad. Sci., 82:119-123 (1985).
Robinson, J.R. (ed), "Sustained and Controlled Release Drug Delivery Systems," New York, Marcel Dekker (1978). Chapters 1-2, 4, and 7-9.
Roche Lexikon Medizin, Urban and Schwarzenberg, 1984, p. 69 "Antibiotika", and p. 515 "Fibrin".
Rompp Chemie-Lexikon, 9$^{th}$ ed., 1989-1990, pp. 206-208, & pp. 1350 and 1351.
Rompp, Chemie-Lexikon, 8$^{th}$ ed., 1987, p. 2633 "Mitosehemmer".
Roubin, "Intracoronary Stenting of Canine Coronary Arteries After Percutaneous Coronary Angioplasty (PTCA)," Circulation Oct. 1986;74(Supp. II-458):1825 Abstract.
Rowinsky et al., "Taxol: Twenty years Later, the Story Unfolds," Journal of the National Cancer Institute, 1991, vol. 83 No. 24 pp. 1778-1781.
Rutqvist, L.E., et al., "Cardiac and Thromboembolic Morbidity Among Postmenopausal Women with Early-Stage Breast Cancer in a Randomized Trial of Adjuvant Tamoxifen", Journal of the National Cancer Institute, 85, 1398-1406, (1993).
Rutsch, et al., "Benestent-II Pilot Study: 6 months Follow Up of Phase 1" Abstract, Society of Cardiology, (1995).
Ruygrok and Serruys, "From Bench to Bedside, Intracoronary Stenting, From Concept to Custom," Circulation 1996; 94:882-890.
Ryan et al., "Transforming growth factor-beta-dependent events in vascular remodeling following arterial injury," J.. Vase. Res., 40:37-46 (2003).
Saarto, T., et al., "Antiatherogenic Effects of Adjuvant Antiestrogens: A Randomized Trial Comparing the Effects of Tamoxifen and Toremifene on Plasma Lipid Levels in Postmenopausal Women with Node-Positive Breast Cancer", Journal of Clinical Oncology, 14, 429-433, (Feb. 1996).
Sabatini et al., "RAFT1: a mammalian protein that binds to Fk.BP12 in a rapamycin-dependent fashion and is homologous to yeast TORs", Cell, 78:35-43 (1994).
Saito, H., et al., "Influence of Maternal Drug Metabolism on the Fetal Toxicity Induced by Acetylsalicylic Acid", The Journal of Toxicological Sciences, 7, 177-184, (1982).
Sanchez, et al., "Control of Contact activation on end-point immobilized heparin, The role of antithrombin and the specific antithrombin-binding sequence," *J. Of Biomedical Materials Research*, pp. 655-661 (1995).
Sanderson et al., "Antibody-Coated Microspheres for Drug Delivery to Prevent Restenosis" , Circulation, 90, I 508, Abstract No. 2734 (Oct. 1994).
Sargent, L.M., et al., "Induction of Hepatic Aneuploidy in Vivo by Tamoxifen, Toremifene and Idoxifene in Female Sprague-Dawley Rats", Carcinogenesis, 17, 1051-1056, (1996).
Schatz et al., "Balloon Expandable Intravascular Stents in Diseased Human Cadaver Coronary Arteries," Circulation 1987 Oet;70(4): Abstract 0102.
Schatz et al., "Balloon-expandable Intra-coronary Stents in the Adult Dog," Circulation Aug. 1987; 76(2):450-457.
Schatz, et al., "Balloon Expandable Intracoronary Stents in Dogs," Circulation Oct. 1986;74(Supp. II-458): 1824 Abstract.
Schatz, et al., "Clinical Experience with the Palmaz-Schatz Stent: Initial Results of a Multicenter Study," Circulation Jan. 1991;83(1): 148-161.
Schatz, R.A. Introduction to Intravascular Stents, Cardiology Clinics Aug. 1988;6(3):357-72.
Schlaak, J.F., et al., "Different Cytokine Profiles in the Synovial Fluid of Patients with Osteoarthritis, Rheumatoid Arthritis and Seronegative Spondylarthropathies", Clinical and Experimental Rheumatology, 14, 155-162, (1996).
Schmidt, E.B., et al., "Long-Term Supplementation with n-3 Fatty Acids, II: Effect on Neutrophil and Monocyte Chemotaxis", Scand. J. Clin. Lab. Invest., 52, 229-236, (1992).
Schoenemanne, et al., "The Differential Diagnoses of Spontaneous Pneumothrax and Pulmonary Lymphangioleimyomatosis Clinical Picture Diagnoses and Theory.", Chiraq, 61, 301-303 (1990); reported in Biosis, 90, 432367 (1990), English abstract only.
Schulick et al.., "Overexpression of transforming growth factor beta1 in arterial endothelium causes hyperplasia, apoptosis, and cartilaginous metaplasia," PNAS 95:6983-6988 (1998).
Schwartz, C.J., et al., "The Pathogenesis of Atherosclerosis: An Overview", Clin. Cardiol., 14, 1-1-1-16, (1991).
Schwartz, G.G., et al., "Pathophysiology of Chronic Stable Angina", In: Atherosclerosis and Coronary Artery Disease, V. Fuster, et al., (eds.), Lippencott-Raven Publishers, Philadelphia, pp. 1386-1400, (1996).
Sedlacek, S. "Estrogenic Properties of Tamoxifen on Serum Lipids in Postmenopausal Women with Breast Cancer (BCA)", Breast Cancer Research and Treatment, 14, Abstract No. 82, 153, (1989).
Sehgal et al., "Rapamycin (AY-22,989), a new antifungal antibiotic. II. Fermentation, isolation and characterization." J. Antibiot., 28:727-32 (1975).
Sehgal, "Sirolimus: its discovery, biological properties, and mechanism of action." Transplant. Proc., 35(3 Suppl):7S-148 (2003).
Serruys et al., "The new angiotensin converting enzyme inhibitor cilazapril does not prevent restenosis after coronary angioplasty: the results of the MERCATOR trial," JACC 19:258A, Abstract 783-2 (1992).
Serruys, et al., "A Comparison of Balloon-Expendable-Stent Implantation with Balloon Angioplasty in Patients with Coronary Artery Disease", The New England Journal of Medicine, 331, 489-495 (Aug. 1994).
Serruys, P.W., et al., "Heparin-Coated Palmaz-Schatz Stents in Human Coronary Arteries—Early Outcome of the Benestent-II Pilot Study", Circulation, 93, 412-422, (Feb. 1996).
Shanahan and Weissberg, "Smooth muscle cell heterogeneity: patterns of gene expression in vascular smooth muscle cells in vitro and in vivo," Arterioscler. Thromb. Vasc. Biol., 18(2):333-338 (1998).
Shanahan, C.M., et al., "High Expression of Genes for Calcification-regulating Proteins in Human Atherosclerotic Plaques", Journal of Clinical Investigation, 93, 2393-2402, (Jun. 1994).
Shapiro, L.M., "Echocardographic Features of Impaired Ventricular Function in Diabetes Mellitus", British Heart Journal, 47, 439-444, (1982).
Shemon, et al., "Tamoxifen Decreases Lipoprotein(a) in Patients with Breast Cancer.", Metabolism, 43, 531-532, (May 1994).
Shewmon, et al., "Tamoxifen and Estrogen Lower Circulating Lipoprotein(a) Concentration in Healthy Postmenopausal Women", Arteriosclerosis and Thrombosis, 14, 1589-1593, (1994).
Shimaoka, I., et al., "Purification of a Copper Binding Peptide from the Mushroom *Grifola frondosa* and Its Effect on Copper Absorption", J. Nutr. Biochem., 4, 33-38, (1993).
Shou et al., "Cardiac defects and altered ryanodine receptor function in mice lacking FK-BP 12," Nature, 391 (6666):489-92 (1998).
Siebenlist, U., et al., "Structure, Regulation and Function of NF-kB", Annu. Rev. Cell. Biol., 10, 405-455, (1994).
Sigwart, et al., "Intravascular Stents to Prevent Occlusion and Restenosis After Transluminal Angioplasty," N. Engl. J. Med., Mar. 19, 1987, vol. 316, No. 12, pp. 701-706.
Sigwart, U., Frank, G.I., "Bioabsorbable, Drug-Eluting, Intracoronary Stents: Design and Future Applications," Coroinary Stents. Springer-Verlag (1992).
Sigwart, Ulrich, "The Self Expanding Mesh Stent" Textbook of Interventional Cardiology, (Eric J. Topol, ed) 1990, Chapter 29, pp. 605-622.
Silber, S. "Drug-eluting stents: aktueller Stand", internet article on sigmund-silber.com/deutsch/varia/var-2003/03-09-5-Silber-Chemnitz.pdf of Aug. 6, 2003.
Sismondi, et al., "Metabolic Effects of Tamoxifen in Postmenopause. ", Anticancer Res., 14, 2237-2244, (1994).
Soderberg, L.S., et al., "Copper (II) (3,5-Diisopropylsalicylate) sub2 Accelerates Recovery of B and T Cell Reactivity Following Irradiation", Scand J. Immunol., 26, 495-502, (1987).
Soderberg, L.S., et al., "Copper (II) sub2(3, 5-diisopropylsalicylate) sub4 Stimulates Hemopoiesis in Normal and Irradiated Mice", Exp. Hematol., 18, 577-580, (1988).
Soderberg, L.S., et al., "Postirradiation Treatment with Copper (II) sub2 (3,5-diisopropylsalicylate) sub4 Enhances Radiation Recovery and Hemopoietic Regeneration", Exp. Hematol., 18, 801-805, (1990).
Soderberg, L.S., et al., "Radiation Recovery Agents", DN & P, 3, 600-605, (1990).
Sollott, S.J., et al., "Taxol Inhibits Neointimal Smooth Muscle Cell Accumulation after Angioplasty in the Rat", The Journal of Clinical Investigation, 95, 1869-1876, (Apr. 1995).
Song "Dexamethasone-nanoparticles for intra-arterial localization in restenosis in rats," Prceed. Intern .Symp. Control. Rel. Mater., 22, 444-445 (1995).
Song, J., et al.. "Tamoxifen (Estrogen Antagonist) Inhibits Voltage-Gated Calcium Current and Contractility in Vascular Smooth Muscle from Rats", The Journal of Pharmacology and Experimental Therapeutics, 227, 1444-1453, (1996).
Sorenson, J.R., "Copper Complexes Offer a Physiological Approach to Treatment of Chronic Disease", Progress in Medicinal Chemistry, 26, 437-568, (1989).
Sorenson, J.R., "Essential Metalloelement Metabolism and Radiation Protection and Recovery", Radiation Research, 132, 19-29, (1992).
Sorenson, J.R., "Pharmacological Activities of Copper Compounds", In: Handbook of Metal-Ligand Interactions in Biological Fluids—Bioinorganic Medicince, vol. 2, Berton, G., (ed.), Marcel Dekker, Inc., New York, 1128-1139 (1995).
Sorenson, J.R., "Radiation Protection and Radiation Recovery with Essential Metalloelement Chelate", P.S.E.B.M., 210, 191-204, (1995).
Sorenson, J.R., "The Ulcerogenic Potential of Copper Aspirinate Seems to be More Imaginary than Real", Journal of Pharmaceutical Sciences, 73, Open Forum, 1875-1878, (1984).

Sorenson, J.R., et al.. "Antieoplastic Activities of Some Copper Salicylates", In: Trace Substances in Environmental Health, vol. XVI, Hemphill, D.D., (ed.), University of Missouri, Columbia, 362-369, (1982).
Sorenson. J.R., et al., "Bis (3, 5-diisopropylsalicylato) copper (II), a Potent Radioprotectant with Superoxide Dismutase Mimetic Activity", J. Med. Chem., 27, 1747-1749, (1984).
Sorenson, J.R., et al., "Copper Complexes as 'Radiation Recovery' Agents", Chemistry in Britain, 25, 169-171, (1989).
Sorenson, J.R., et al., "Copper-, Iron-, Manganese- and zinc-3, 5-diisopropylsalicylate Complexes Increase Survival of Gamma-Irradiated Mice", Eur. J. Med. Chem., 28, 221-229, (1993).
Sousa et al., "Sustained suppression of neointimal proliferation by sirolimus-eluting stents: one-year angiographic and intravascular ultrasound follow-up," Circulation, 104:2007-i 1 (2001) (CYP228071-228075).
Sousa et al., "Two-year angiographic and intravascular ultrasound follow-up after implantation of sirolimus-eluting stents in human coronary arteries," Circulation. 107(3 ):381-3 (2003) (BSX 024170-024172).
Sousa, J.E. et al., "New Frontiers in Cardiology Drug-Eluting Stens: Part I", Circulation, 2003, 107:2274-2279.
Southgate and Newby, "Serum-induced proliferation of rabbit aortic smooth muscle cells from the contractile state is inhibited by 8-Br-cAMP but not 8-Br-cGMP," Atherosclerosis, 82:113-123 (1990).
Srivastava, K.C., "Effects of Dietary Fatty Acids, Prostaglandins and Related Compounds on the Role of Platelets in Thrombosis", Biochem. Exp. Biol., 16, 317-338, (1980).
Standley, P.R., et al., "Tamoxifen (an Antiestrogen) Reduces K Positive- and Agonist-Induced Vascular Contractility in Rat Resistance Vessels", Abstract No. 159.
Stevenson, F., et al., "Idiotypic DNA Vaccines against B-cell Lymphoma", Immunological Reviews, 145, 221-228, (1995).
Stork, G., et al., "Total Synthesis of Cytochalasin B", Journal of the American Chemical Society, 100, 7775-7777, (1978).
Stouffer, et al., "TGF beta Has a Biphasic, Concentration Dependant Effect on EFG and PDGR-BB Induced Smooth Muscle Cell Proliferation, Inflammation, Growth Regulatory Molecules and Atherosclerosis.", J. Cellular Biochem, Supplement 18A, Abstract No. A321, 288, (1994).
Strepetti, A.V., et al., "Formation of Myointimal Hyperplasia and Cytokine Production in Experimental Vein Grafts", Surgery, 123(4), 461-469, (1998).
Suckling, "Atherosclerosis Patents: Clues to the Next Drug Generation", Bio/Tech, 12 1379-1380 (Dec. 1994).
Sudo, K., et al., "Antiestrogen-Binding Sites Distinct from the Estrogen Receptor: Subcellular Localization, Ligand Specificity, and Distribution in Tissues of the Rat", Endocrinology, 112, 425-434, (1983).
Swain, "Blazing new paths for product introductions," Medical Device & Diagnostic Industry, Sep. 2003, p. 68-81.
Szekanecz, Z., et al., "Increased Synovial Expression of Transforming Growth Factor (TGF)-B Receptor Endoglin and TGF-B 1 in Rheumatoid Arthritis: Possible Interaction in the Pathogenesis of the Disease", Clinical Immunology and Immunopathology, 76, 187-194, (Aug. 1995).
Tabas et al., "The Actin Cytoskeleton in Important for the Stimulation of Cholesterol Esterification by Atherogenic Lipoprotiens in Macrophages" J. Biol. Chem., 269, 22547-22556 (Sep. 9, 1994).
Takashima, K. et al., "The Hypocholesterolemic Action of TA-7552 and its Effects on Cholesterol Metabolism in the Rat", Atherosclerosis, 107, 247-257, (1994).
Tanaka et al., "Ialpha 25 (OH) 303 Exerts Cytostatic effects on Murine Osteosarcoma Cells and Enhance Cytocidal Effects on Anticancer Drugs" Clinical Orthopaedics and related Research No. 247 1989 pp. 290-296.
Tanaka et al., "Prominent Inhibitory Effects of Tranilast on Migration and Proliferation of and Collagen Synthesis by Vascular Smooth Muscle Cells" Atherosclerosis, 107, 179-185 (1994).
Tanenbaum, S.W., "Microbiological, Preparative and Analytical Aspects of Cytochalasin Production", In: Cytochalasins—Biochemical and Cell Biological Aspects, Tanenbaum, S.W., (ed.), Elsevier/North-Holland Biomedical Press, 2-14, (1978).
Tang et al., "Regression of collagen-induced arthritis with taxol, a microtubule stabilizer". Arthritis and Rheumatism, 36 (9) Suppl. :S45, 1993.
Tawashi, R., "The dissolution rates of crystalline drugs" . J. Mond. Pharm, 4,11,1968, pp. 371-379.
Teirstein (ed.), "Coronary Stents: pros and cons," Coronary Artery Disease, 5:561-600 (1994).
Tessari et al.. "Antiproliferative activity of unfractioned heparin on a human smooth muscle cell line, Pharmacol." Res., 21:145-6 (1989).
Testart, J., et al., "The Action of Anti-Inflammatory Drugs to the Fertility of Female Rats with Intrauterine Contraceptive Devices", J. Reprod. Fert., 63, 257-261. (1981).
Thompson, J.T., et al., "Comparison of Recombinant Transforming Growth Factor-beta-2 and Placebo as an adjunctive Agent for Macular Hole Surgery", Ophthalmology, 15(4), 700-706, (1998).
Thompson, N. L., et al.. "Expression of Transforming Growth Factor-B1 in Specific Cells and Tissue of Adult and Neonatal Mice", Journal of Cell Biology, 108, 661-669, (1989).
Tong et al., Non-Thrombogenic Hemofiltration System for Acute renal failure Treatment: ASAIO Trans. 38: M702-M706 (1992).
Toomasian et al., "Evaluation of Duraflo II Herparin Coating in Prolonged Extracorporeal Membrane Oxygenation", ASAIO Trans 34: 410-14 (1988).
Topol, E. et al., "Frontiers in Interventional Cardiology" Circulation, 1998, 98:1802-1820.
Treasure, C.B., et al., "Hypertension and Left Ventricular Hypertrophy Are Associated With Impaired Endothelium-Mediated Relaxation in Human Coronary Resistance Vessels", Circulation, 87, 86-93, (1993).
Treiber, A., et al., "Chemical and Biological Oxidation of Thiophene: Preparation and Complete Characterization of Tiophene S-Oxide Dimers and Evidence for Thiophene S-Oxide as an Intermediate in Thiophene Metabolism in vivo and In Vitro", J. Am. Chem. Soc., 119, 1565-1571, (1997).
Tucker et al., "Growth inhibitor from BSC-1 cells closely related to platelet type beta transforming growth factor," Science, 226:705-707 (1984).
Ulman, et al., "Drug Permeability of Modified Silicone Polymers," Journal of Controlled Release 1989; 10:276-281.
Ulman, K.L. et al., "Drug Permeability of Modified Silicone Polymers", J. Controlled Release, 10:251-260 (1989).
Van Der Giessen, et al., "Coronary Stenting With Polymer-Coated and Uncoated Self-Expanding Endoprosthesis in Pigs" Coron. Art. Disease 1992; 3:631-40.
Van Der Giessen, et al., "Self-expandable Mesh Stents: an Experimental Study Comparing Polymer Coated and Uncoated Wallstent Stents in the Coronary Circulation of Pigs" Circulation 82:111-542 (1990).
Van Sickle, W.A., et al., "An Alternative Mechanism for the Inhibition of Cholesterol Biosyntesis in HepG2 Cells by N-[(1,5,9)-Trimethyldecyl]-4alpha, 10-dimethyl 8-aza-trans-decal-3beta-ol (MDL 28, 815)", The Journal of Pharmacology and Experimental Therapeutics, 267, 243-1249, (1993).
Vawter, M.P., et al., "TGF B1 and TGF B2 Concentrations are Elevated in Parkinson's Disease in Ventricular Cerebrospinal Fluid", Experimental Neurology, 141, 313-332, (1996).
Vidensek N., et al., "Taxol Content in Bark, Wood, Root, Leaf, Twig, and Seedling from Several *Taxus* Species", Journal of Natural Products, 53, 1609-1610, (Nov./Dec. 1990).
Voigt, R., Lehbuch der pharmazeutischen Technologie, $5^{th}$. edition VEB Verlag Volk and Gesundheit Berlin, 1984, p. 689.
Von Schacky, C., et al., "Long-Term Effects of Dietary Marine omega-3 Fatty Acids upon Plasma and Cellular Lipids, Platelet Function, and Eicosanoid Formation in Humans", J. Clin. Invest., 76, 1626-1631, (1985).
Waksman, R., et al., "Intracoronary Radiation Before Stent Implantation Inhibits Neointima Formation in Stented Porcine Coronary Arteries", Circulation, 92, 1383-1386, (1995).
Wallace, et al., "Tracheobronchial Tree: Expandable Metallic Stents Used in Experimental and Clinical Applications," Radiology Feb. 1986; 158(2):309-12.

Wallace, J.M., et al., "Dietary Fish Oil Supplementation Alter Leukocyte Function and Cytokine Production in Healthy Women", Arteriosclerosis, Thrombosis and Vascular Biology, 15, 185-189, (1995).
Waller et al., "Crackers, Breakers, Stretchers, Drillers, Scrappers, Shavers, Burners, Welders and Melters: The Future Treatment of Atherosclerotic Coronary Artery Disease?A Clinical-Morphologic Assessment," JACC 13:969-87 (1989).
Waller et al., "Differential effects of modem immunosuppressive agents on the development of intimal hyperplasia," Transpl. Int. 17:9-14 (2004).
Waller et al., "Mycophenolate mofetil inhibits intimal hyperplasia and attenuates the expression of genes favouring smooth muscle cell proliferation and migration," Transplant Proc. 37(1): 164-6 (2005).
Waller, B.F. X.L., et al., "Atherosclerotic and Nonatherosclerotic Coronary Artery Factors in Acute Myocardial Infarction", In: Acute Myocardial Infarction, Pepine, C.J., (ed.), F.A. Davis Company, Philadelphia, 29-104 (1989).
Walternberger, "Modulation of growth factor action: implications for the treatment of cardiovascular diseases," Circulation, 96:4083-4094 (1997).
Wang, X.L., et al., "Circulating Transforming Growth Factor Betal and Coronary Artery Disease", Cardiovascular Research, 34, 404-410 (1997).
Ward et al., "Inhibitory effects of tranilast on expression of transforming growth factor-beta isoforms and receptors in injured arteries," Atherosclerosis, 137:267-275 (1998).
Ward et al., "Tranilast prevents activation of transforming growth factor-beta system, leukocyte accumulation, and neointimal growth in porcine coronary arteries after stenting," Arterioscler. Thromb. Vasc. Biol. 22:940-948 (2002).
Watson, et al., "TGF-B1 and 25-Hydroxcholesterol Stimulate Osteoblast-Like Vascular Cells to Calcify", J. Clin. Invest., 93, 2106-2113 (May 1994).
Wei, C.M. et al., "Binding of Trichodermin to Mammalian Ribosomes and Its Inhibition by Other 12, 13-Epoxytrichotheces", Molecular & Cellular Biochemistry, 3, 215-219 (May 30, 1974).
Weissberg, P.L., et al., "Is Vascular Smooth Muscle Cell Proliferation Beneficial?", Lancet, 347, 305-307 (Feb. 3, 1996).
West, G.B., "Comments on 'The Ulcerogenic Potential of Copper Aspirinate Seems to be More Imaginary than Real'", Journal of Pharmaceutical Sciences, 74, Open Forum, 700 (1985).
West, G.B., "Testing for Drugs Inhibiting the Formation of Gastric Ulcers", Journal of Pharmacological Methods, 8, 33-37 (1982).
Wickremesinhe, E.R., et al., "*Taxus* Callus Cultures: Initiation, Growth, Optimization, Characterization and Taxol Production", Plan Cell, Tissue and Organ Culture, 35, 181-193 (1993).
Wickremesinhe, E.R., et al., "*Taxus* Cell Suspension Cultures: Optimizing Growth and Production of Taxol", J. Plant Physiol., 144, 183-188 (1994).
Wilensky, et al., "Regional and Arterial Localization of Radioactive Microparticles after Local Delivery by Unsupported Porous Balloon Catheters", American Heart Jounal, 129, 852-859 (May 1995).
Wilensky, R.L., et al., "A Prospective, Randomized, Double-Blind, Dose-Escalation Study Evaluating the Safety and Tolerability of Cytochalasin B to Reduce Vascular Remodeling Following Percutaneous Transluminal Coronary Angioplasty", Abstract, $46^{th}$ Annual Scientific Session of the American College of Cardiology, 1 p. (1997).
Williams, J.K., et al., "The Estrogen Receptor Agonist/Antagonist Tamoxifen Inhibits Progression of Coronary Artery Atherosclerosis in Monkeys", Circulation, 92, Nov. 1995, AHA Meeting (Oct. 15, 1995).
Willson, T.M., et al., "Dissection of the Molecular Mechanism of Action of GW5638, a Novel Estrogen Receptor Ligand, Provides Insights into the Role of Estrogen Receptor in Bone", Endocrinology, 138(9) (Sep. 1997).
Winokur et al., "Expression of transforming growth factors β 1, 2, and 3 following vascular injury," J. Cell Biochem., Suppl. 15C:G414 (Abstr.) (1991).
Winslow, R., "Going for the Flow", The Wall Street Journal (Oct. 23, 1995).
Winternitz, C.I. et al., "Development of a Polymetric Surgical Paste Formulation for Taxol", Pharmaceutical Research, 13 368-375 (1996).
Wiseman, H., "Tamoxifen as an Antioxidant and Cardioprotectant", Biochem. Soc. Symp., 61, 209-219 (1995).
Wiseman, L.R., et al., "Toremifene—A Review of its Pharmacological Properties and Clinical Efficacy in the Management of Advanced Breast Cancer", Drugs, 54, 141-160 (Jul. 1997).
Witherup, K.M., et al., "*Taxus* Spp. Needles Contain Amounts of Taxol Comparable to the Bark of *Taxus brevifolia*: Analysis and Isolation", Journal of Natural Products, 53, 1249-1255 (Sep./Oct. 1990).
Wolf, Y.G., et al., "Antibodies Against Transforming Growth Factor Beta1 Suppress Intimal Hyperplasia in a Rat Model", J. Clin. Invest., 93, 1172-1178 (Mar. 1994).
Wrana, et al., "Mechanism of Activation of the TGF-B Receptor", Nature, 370 341-347 (Aug. 4, 1994).
Wright et al., "Cytoclasin Inhibition of Slow Tension Increase in Rat Aortic Rings", Am. J. Physion., 267 H1437-H1446 (1994).
Wright et al., "Percutaneous Endovascular Stents: An Experimental Study," Radiology Nov. 1984;153(P):206 Abs 593.
Wright et al., "Percutaneous Endovascular Stents: An Experimental Evaluation," Radiology 1985;1:69-72.
Wu et al., "Comparative immunoregulatory effects of rapamycin, FK 506 and cyclosporine on mitogen-induced cylokine production and lymphoproliferation," Transplant. Porc., 23:238-240 (1991).
Wu et al., "The inhibitory mechanism of YC-1, a benzyl indazole, on smooth muscel cell proliferation: an in vitro and in vivo study," J. Pharmacol. Sci. 94:252-60 (2004).
Wu, et al., "Silicone-covered Seft-expanding Metallic Stents for the Palliation of Malignant Esophageal Obstruction and Esophagorespiratory Fistulas: Experience in 32 Patients and a Review of the Literature," Gastrointest. Endosc. 1994; 40:22-33.
Yamamoto et al., "Ribozyme oligonucleotides against transforming growth facotr-beta inhibited neointimal formation after vascular injury in rat model: potential application of ribozyme strategy to treat cardiovascular disease," Circulation, 102(11):1308-14 (2000).
Yang, N., et al., "Developing Particle-mediated Gene-transfer Technology for Research Into Gene Therapy of Cancer", Molecular Medicine Today, 476-481, (1996).
Yang, N.N., et al., "Estrogen Receptor: One Transcription Factor, Two Genomic Pathways", Calcified Tissue Intl., 54, 342, (1994).
Yang, N.N., et al., "Identification of an Estrogen Response Element Activated by Metabolites of 17Beta-Estradiol and Raloxifene", Science, 273, 1222-1225, (Oct. 30, 1996).
Young H., et al., "Pharmacokinetics and Biodistribution of Radiolabelled Idoxifene: Prospects for the Use of PET in the Evaluation of a Novel Antioestrogen for Cancer Therapy", Nucl. Med. Biol., 22, 405-411, (May 1995).
Zhang, L. et al., "MCF-7 breast carcinoma cells overexpressing FGF-I form vascularized, metastatic tumors in ovariectomized and tamoxifen-treated nude mice", Oncogen, 15, 2093-2108, (1997).
Ziegler, J. "Raloxifene, Retinoids, and Lavender: AMe Too@ Tamoxifen Alternatives Under Study", Journal of the National Cancer Institute, 88, 1100-1102, (1996).
Zohlnhofer et al., "Rapamycin effects transcriptional programs in smooth muscle cells controlling proliferative and inflammatory properties," Mol. Pharmacol. 65:880-889 (2004).
Answering Memorandum in Opposition to Plaintiffs' Motion for a Preliminary Injunction, Civil Action No. 03-283 Dated Apr. 3, 2003. U.S. District Court for the District of Delaware.
Appendix to Answering Memorandum in Opposition to Plaintiffs' Motion for a Preliminary Injunction, vol. 1, Civil Action No. 03-283 Dated Apr. 3, 2003. U.S. District Court for the District of Delaware.
Non-Final Office Action for U.S. Appl. No. 11/679,650, dated Apr. 21, 2009.
Non-Final Office Action for U.S. Appl. No. 09/910,388, dated Jul. 7, 2009.
Non-Final Office Action for U.S. Appl. No. 11/650,059, dated Sep. 11, 2009.
Non-Final Office Action for U.S. Appl. No. 11/703,191, dated May 12, 2009.

Pastan et al., Annual Review of Biochemistry vol. 61:331-354 (1992).
Non-Final Office Action for U.S. Appl. No. 11/650,059, dated May 26, 2010.
Non-Final Office Action for U.S. Appl. No. 11/703,191, dated Jan. 13, 2010.
Non-Final Office Action for U.S. Appl. No. 11/679,650, dated May 26, 2010.
Prosecution History for U.S. Appl. No. 11/650,059, filed Jan. 4, 2007.
Prosecution History for U.S. Appl. No. 11/703,191, filed Feb. 5, 2007.
Prosecution History for U.S. Appl. No. 11/679,650, filed Feb. 27, 2007.
Prosecution History for U.S. Appl. No. 12/418,209, filed Apr. 3, 2009.
"Cytochalasins", In: The Merck Index, Eleventh Edition, Merck & Co., Rahway NJ, 438-439 (1989).
"Nolvadex Tamoxifene Citrate", ICI Pharma, 64033-02, Rev L/07/92.
Allemann, et al., "Drug Loaded Poly(Lactic Acid) Nanoparticles Produced by a Reversible Salting-out Process: Purification of an Injectable Dosage Form," *Eur. J. Pharm. Biopharm.*, vol. 39 (1), pp. 13-18 (1993).
Anderson, et al., "Effects of Acetate Dialysate on Transforming Growth Factor $\beta_1$ Interleukin, and $\beta_2$-Microglobulin Plasma Levels," *Kidney International*, vol. 40, pp. 1110-1117 (1991).
Aschermann, M., "Restenosis After Percutaneous Transluminal Coronary Angioplasty Pathophysiology, New Trends in Prevention and Treatment," *Cor. Vasa.*, 36:211-218 (1994).
Assoian, et al., "Type β Transforming Growth Factor in Human Platelets: Release During Platelet Degranulation and Action on Vascular Smooth Muscle Cells," *The Journal of Cell Biology*, vol. 102, pp. 1217-1223 (1986).
Attwood, et al., "A Light Scattering Study on Oil-in-Water Microemulsions" Int'l J. Pharm, 52 165-171 (1989).
Bagdade, et al., Treatment "Effects of Tamoxifen Treatment on Plasma Lipids and Lipoprotein Lipid Composition," *J. of Clinical Endocrinology and Metabolism*, vol. 70, No. 4, pp. 1132-1135 (1990).
Bamburg, James R., "Biological and Biochemical Actions of Trichothecene Mycotoxins," *Progress in Molecular and Subcellular Biology*, (Hahn F.E., et al., ed.), Springer-Verlag, pp. 41-110) (1983).
Barath, et al., "Low Dose of Antitumor Agents Prevents Smooth Muscle Cell Proliferation After Endothelial Injury," *JACC*, vol. 13, No. 2, p. 252A Abstract (1989).
Barbacid, et al., "Binding of [acetyl-$^{14}$ C] Trichodermin to the Peptidyl Transferase Center of Eukaryotic Ribosomes," *Eur. J. Biochem*. 44, pp. 437-444 (1974).
Bartoli et al. "In vitro and in vivo antitumoral activity of free, and encapsulated taxol". J. Microencapsulation, 7 (2):191-197, 1990.
Beck, et al., "Poly(DL-Lactide-co-glycolide) /Norethisterone Microcapsules: An Injectable Biodegradable Contraceptive," *Biology of Reproduction*, vol. 28, pp. 186-195 (1983).
Bertelli, et al., "Adjuvant Tamoxifen in Primary Breast Cancer: Influence on Plasma Lipids and Antithrombin III Levels," *Breast Cancer Res. and Treatment*, vol. 12, pp. 307-310 (1988).
Bogyo, et al., "Cytochalasin-β-Induced Immunosuppression of Murine Allogeneic Anti-tumor Response and the Effect of Recombinant Human Interleukin-2," *Cancer Immunol. Immunother*, vol. 32, pp. 400-405 (1991).
Bousquet, et al., "Effects of Cytochalasin β in Culture and in Vivo on Murine Madison 109 Lung Carcinoma and on B16 Melanoma," *Cancer Res.*, vol. 50, pp. 1431-1439 (1990).
Bruengger, et al., "Smooth Muscle Cell of the Canine Prostate in Spontaneous Benign Hyperplasia, Steroid Induced Hyperplasia and Estrogen or Tamoxifen Treated Dogs," *J. Urol.* vol. 130, No. 6, pp. 1208-1210 (1983).
Bruning, et al., "Tamoxifen, Serum Lipoproteins and Cardiovascular Risk" , Br. J. Cancer, 58, 497-499 (1988).
Bumol, et al., "Unique Glycoprotein-Proteoglycan Complex Defined by Monoclonal Antibody on Human Melanoma Cells," *PNAS* (USA), vol. 79, pp. 1245-1249 (1982).
Butta, et al., "Unique Glycoprotein-Proteoglycan Complex Defined by Monoclonal Antibody on Human Tamoxifen Treatment," *Cancer Res.* vol. 52, pp. 4261-4264 (1992).
Casscells, W., et al., "Elimination of Smooth Muscle Cells in Experimental Restenosis: Targeting of Fibroblast Growth Factor Receptors", Proc. Natl. Acad. Sci. USA, 89, 7159-7163 (1992).
Chaldakov, et al., "Cyclic AMP- and Cytochalasin B-induced Arborization in Cultured Aortic Smooth Muscle Cells: Its Cytopharmacological Characterization," *Cell Tissue Res.* Vol. 255, pp. 435-442 (1989).
Chander, et al., "Pyrrolidino-4-iodotamoxifen and 4-lodotamoxifen, New Analogues of the Antiestrogen Tamoxifen for the Treatment of Breast Cancer," *Cancer Research*, vol. 51, pp. 5851-5858 (1991).
Chao, et al., "Altered Cytokine Release in Peripheral Blood Mononuclear Cell Cultures from Patients with the Chronic Fatigue Syndrome," *Cytokine*, vol. 3, No. 4, pp. 292-298 (1991).
Chapman, et al., "A Bioabsorbable Stent: Initial Experimental Results," *Supplement III Cir.*, vol. 82, No. 4, p. III-72 (1990).
Clowes et al., "Significance of Quiescent Smooth Muscle Migration in the Injured Rat Carotid Artery," *Cir. Res.* vol. 56, No. 1, pp. 139-145 (1985).
Clowes, et al. "Mechanisms of Stenosis After Arterial Injury", *Laboratory Investigation*, vol. 49, No. 2, pp. 208-215 (1983).
Clowes, et al., "Kinetics of Cellular Proliferation After Arterial Injury—I. Smooth Muscle Growth in the Absence of Endothelium", *Laboratory Investigation*, vol. 49, No. 3, pp. 327-333 (1983).
Clowes, et al:, "Kinetics of Cellular Proliferation After Arterial Injury—III, Endothelial and Smooth Muscle Growth in Chronically Denuded Vessels", *Laboratory Investigation*, vol. 54, No. 3, pp. 295-303 (1986).
Cohen, et al., "Controlled Delivery Systems for Proteins Based on Poly(Lactic/Glycolic Acid) Microspheres," *Pharmaceutical Research*, vol. 8, No. 6, pp. 713-720 (1991).
Cole, R. J. et al., "The Cytochalasins", In: Handbook of Toxic Fungal Metabolics, Academic Press, New York, p. 264-265, 281-282 (1981).
Coomber and Gotlieb "In vitro endothelial wound repair. Interaction of cell migration and proliferation". Ateriosclerosis, 10 (2):215-222, 1990.
Cowsar, et al., "Poly(Lactide-co-glycolide) Microcapsules for Controlled Release of Steroids," *Methods in Enzymology*, vol. 112, pp. 101-117 (1985).
Cox et al., "Effects of local delivery of heparin and methotrexate on neointimal proliferation in stented porcine coronary arteries". Coronary Artery Disease, 3:237-248, 1992.
Cox et al., "Local Delivery of Heperin and methotrexate fails to inhibit in vivo smooth muscle cell proliferation". Circulation Suppl. 84(4):II-71, #0284, 1991.
Crissman, et al., "Transformed Mammalian Cells are Deficient in Kinase-Mediated Control of Progression Through the $G_1$ Phase of the Cell Cycle," *PNAS* (USA), vol. 88, pp. 7580-7584 (1991).
Danielpour, David, "Improved Sandwich Enzyme-Linked Immunosorbent Assays for Transforming Growth Factor," *Journal of Immunological Methods*, vol. 158, pp. 17-25 (1993).
Danielpour, et al., "Evidence for Differential Regulator of TGFβ1 and TGFβ2 Expression in Vivo by Sandwich Enzyme-linked Immunosorbent Assays," *Annals New York Academy of Sciences*, pp. 300-302, 1990.
Danielpour, et a, "Immunodetection and Quantitation of the Two Forms of Transforming Growth Factor-Beta (TGF-1 and TGF-2) Secreted by Cells in Culture," *Journal of Cellular Physiology*, vol. 138, pp. 79-86 (1989).
Dasch, et al., "Capture Immunoassays Specific for TGF1 and TGF2: Use in Pharmacokinetic Studies," *Annals New York Academy of Sciences*, pp. 303-305, 1990.
Detre, et aL, "Percutaneous Transluminal Coronary Angioplasty in 1985-1986 and 1977-1981", *The New England J. of Med.*, vol. 318, No. 5, pp. 265-270 (1988).
Dimond, Patricia F., Ph.D., "TGF-Beta Shows Potential as Therapeutic Agent for Macular Holes," *Genetic Engineering News*, pp. 7 & 19 (1993).
Ebner, et al., "Cloning of a Type 1 TGF-β Receptor and Its Effect on TGF-β Binding to the Type II Receptor," *Science*, vol. 260, pp. 1344-1348 (1993).

Eldridge, et al., "Biodegradable and Biocompatible Poly(DL-Lactide-CO-Glycolide) Microspheres as an Adjuvant for Staphylococcal Enterotoxin B Toxoid which Enhances the Level of Toxin-Neutralizing Antibodies," *Infection and Immunity*, 59(9):2978-2986 (1991).
Epstein, Stephen E., MD., "Cytotoxic Effects of a Recombinant Chimeric Toxin on Rapidly Proliferating Vascular Smooth Muscle Cells," *Cir.* vol. 84, No. 2, pp. 778-787 (1991).
Ettenson and Gotlieb "Centrosomes, Microtubules, and Microfilaments in the Reendothelialization and Remodeling of Double-Sided In Vitro Wounds". Laboratory Investigation, vol. 68, No. 6, pp. 722-733, 1992, United States and Canadian Academy of Pathology, Inc.
Fanelli, et al., "Restenosis Following Coronary Angioplasty", *Amer. Heart J.*, vol. 119, No. 2, Part 1. pp. 357-368 (1990).
Farhat, et al., "In Vitro Effect of Oestradiol on Thymidine Uptake in Pulmonary Vascular Smooth Muscle Cell: Role of the Endothelium," *Br. J. Pharmacol.* vol. 107, pp. 679-683 (1992).
Faxon et al., "Restenosis Following Transluminal Angioplasty in Experimental Atherosclerosis", *Arteriosclerosis*, vol. 4, No. 3, pp. 189-195 (1984).
Fay,et al., "Effects of Gytochalasin B On The Uptake of Ascorbic Acid and Glucose By 3T3 Fibroblasts: Mechanism of Impaired Ascorbate Transport in Diabetes," *Life Sci.*, vol. 46, pp. 619-624 (1990) (USA).
Feelisch, et al., "Biotransformation of Organic Nitrates to Nitric Oxide by Vascular Smooth Muscle and Endothelial Cells," *Biochemical and Biophysical Research Communications*, vol. 180, No. 1, pp. 286-293 (1991).
Fischer, et al., "A Possible Mechanism in Arterial Wall for Mediation of Sex Difference in Atherosclerosis Experimental and Molecular Pathology", Exp. Mol. Pathol., 43 288-296 (1985).
Forrester, J.S., et al., A Paradigm for Restenosis Based on Cell Biology: Clues for the Development of New Preventive Therapies: JACC, 17, 758-769, (1991).
Friberg, et al., "Microemulsions and Solubilization by Nonionic Surfactants", Prog. Colloid and Polymer Sci., 56, 16-20 (1975).
Fulop, et al., "Age-Dependent Variations of Intralysosomal Enzyme Release from Human PMN Leukocytes Under Various Stimuli," *Immunobiol.*, vol. 171, pp. 302-310 (1986).
Garrigues, et aL, "The Melanoma Proteoglycan: Restricted Expression on Microspikes, a Specific Microdomain of the Cell Surface," *J. Cell Biol.* vol. 103, pp. 1699-1710 (1986).
Gasco, et al., "In Vitro Permeation of Azelaic Acid from Viscosized Microemulsions", International Journal of Pharmaceutics, 69, 193-196 (1991).
Gasco, M. R., et al., Long-acting Delivery Systems for Peptides: Reduced Plasma Testosterone Levels in Male Rats after a Single Injection:, Intl. J. of Pharmaceut, 62 119-123 (1990).
Glagov, et al., "Compensatory Enlargement of Human Atherosclerotic Coronary Arteries," *New England J. of Med.*, vol. 316 No. 22, p. 1371-1375 (1987).
Goldman, et al., "Influence of Pressure on Permeability of Normal and Diseased Muscular Arteries to Horseradish Peroxidase," *Atherosclerosis*, vol. 65. pp. 215-225 (1987).
Grainger, et al., "Heparin decreases the rate of proliferation of rat vascular smooth muscle cells by releasing transforming growth factor-like activity from serum," *Cardiovascular Research*, vol. 27, pp. 2238-2247 (1993).
Grainger, et al., "Tamoxifen Decreases the Rate of Proliferation of Rat Vascular Smooth Muscle Cells in Culture by Inducing Production of Transforming Growth Factor β," *Biochem J.* vol. 294, pp. 109-112 (1993).
Grainger, et al., A Large Accumulation of Non-Muscle Myosin Occurs at First Entry into M Phase in Rat Vascular Smooth-Muscle Cells, *Biochem. J.* vol. 277, pp. 145-151 (1991).
Grainger, et al., Hexamethylenebisacetamide Selectively Inhibits the Proliferation of Human and Rat Vascular Smooth Muscle Cells, *Biochem. J.* vol. 283, p. 403-408 (1992).
Gregory, et al. "Effects of Treatment with Cyclosporine, FK 506, Rapamycin, Mycophenolic Acid, or Deoxyspergualin on Vascular Muscle Proliferation in Vivo," *Transplantation Proceedings*, 25:770-771 (1993).
Hanke, et al., Inhibition of Cellular Proliferation After Experimental Balloon Angioplasty by Low-Molecular-Weight Heparin, *Circulation*, vol. 85, No. 4, pp. 1548-1556 (1992).
Harpel, et al., "Plasmin Catalyzes Binding of Lipoprotein (α) to Immobilized Fibrinogen and Fibrin," *Proc. Natl. Acad. Sci. USA*, vol. 86, pp. 3847-3851 (1989).
Heldin, et al., "Demonstration of an Antibody Against Platelet-derived Growth Factor," *Experimental Cell Research*, vol. 136, pp. 255-261 (1981).
Heller, et al., "Preparation of Polyacetals by the Reaction of Divinyl Ethers and Polyols," *J. of Polymer Science: Polymer Letters Edition*, vol. 18, pp. 298-297 (1980).
Henriksson, et al., Hormonal Regulation of Serum Lp (α) Levels; *J. Clin. Invest.* vol. 89, p. 1166-1171 (1992).
Hermans et al., "Prevention of restenosis after percutaneous transluminal coronary angioplasty: the search for a "magic bullet"" American Heart Journal, 122 (1) Part, 1, 171-187, 1991.
Hirata et al., "Inhibition of in vitro vascular endothelial cell proliferation and in vivo neovascularization by low-dose methotrexate". Arthritis and Reumatism, 32(9): 1065-1073, 1989.
Hoff, et al., "Modification of Low Density Lipoprotein with 4-Hydroxynonenal Induces Uptake by Macrophages." *Arteriosclerosis*, vol. 9, No. 4, pp. 538-549 (1989).
Hoffman, et al., "Enhancement of the Antiproliferative Effect of *cis*-Diamminedichloroplatinum(II) and Nitrogen Mustard by Inhibitors of Protein Kinase C," *Int. J. Cancer*, vol. 42, pp. 382-388 (1988).
Holland, et al., "Atherogenic Levels of Low-density Lipoprotein Increase Endocytotic Activity in Cultured Human Endothelial Cells," *Amer. J. of Pathology*, vol. 140, No. 3, pp. 551-558 (1992).
Hwang et al., "Effects of Platelet-Contained Growth Factors (PDGF, EGF, IGF-1 and TGF-B) on DNA Synthesis in Porcine Aortic Smooth Muscle Cells in Culture." Exp. Cell Res., 200, 358-360 (1992).
Jampel et al., "In vitro release of hydrophobic drugs from polyanhydride disks". Ophthal Surg, 23 (11):676-680, 1991.
Jarvis, et al., "Allelopathic Agents from *Parthenium hysterophorus* and *Baccharis megapotamica," Chemistry of Alleopathy*, pp. 149-159 (1985).
Jarvis, et al., "Macrocylic and Other Novel Trichothecenes: Their Structure, Synthesis, and Biological Significance,"*Acc. Chem. Res.* 15 pp. 338-395 (1982).
Johnson, et al., "Coronary Atherectomy: Light Microscopic and Immunochemical Study of Excised Tissues," *Supp. II Circulation*, vol. 78, No. 4, p. II-82 (1988).
Jordan, V. Craig, "Long-Term Tamoxifen Therapy to Control or to Prevent Breast Cancer: Laboratory Concept to Clinical Trials," *Hormones, Cell Biol. and Cancer: Perspectives and Potentials*, pp. 105-123 (1988).
Jung, S.M., et al., "Platelet Cytoskeletal Protein Distributions in Two Triton-Insoluble Fractions and How They are Affected by Stimulants and Reagents that Modify Cytoskeletal Protein Interactions" Thrombosis Research, 50 775-787 (1988).
Kambic, et al., "Biomaterials in Artificial Organs," *Chemical & Engineering News*, pp. 31-48 (1986).
Kemp et al., "The *Id* Gene is Activated by Serum But is Not Required for De-differentiation in Rat Vascular Smooth Muscle Cells," *Biochem. J.* (Great Britain), vol. 277, pp. 285-288 (1991).
Knabbe, C., et al., "Evidence That Transforming Growth Factor beta is a Hormonally Regulated Negative Growth Factor in Human Breast Cancer Cells" Cell, 48 417-428, 1987.
Koff, et al., Negative Regulation of GI in Mammalian Cells: Inhibition of Cyclin E-Dependent Kinase by TGF-β, *Science*, vol. 260, pp. 536-538 (1993).
Kovach. et al., "Serial Intravascular Ultrasound Studies Indicate That Chronic Recoil Is an Important Mechanism of Restenosis Following Transcatheter Therapy," *JACC* vol. 484A, Abstract 835-3 (1993).
LaFont,et al., "Post-angioplasty Restenosis in the Atherosclerotic Rabbit: Proliferative Response or Chronic Constriction?," *Circulation*, vol. 88, I-521, Abstract 2806 (1993).
Lambert et al., "A new method for arterial drug delivery via removable stent". JACC, 21(2):483A, #834-2, 1992.

Lambert, et al., "Local Drug Delivery Catheters: Functional Comparison of Porous and Microporous Designs," *Coronary Artery Disease*, vol. 4, No. 5, pp. 469-475 (1993).
Lefer, Allen M., "Role of Transforming Growth Factor β in Cardioprotection of the Ischemic-Reperfused Myocardium," *Growth Factors and the Cardiovascular System*, Chapter 14 (Cummins, P. ed.), Kluwer Academic Publishers, pp. 249-260 (1993).
Lefer, et al., "Mechanism of the Cardioprotective Effect of Transforming Growth Factor $\beta_1$, in Feline Myocardial Ischemia and Reperfusion," *PNAS* (USA), vol. 90, pp. 1018-1022 (1993).
Lefer, et al., "Mediation of Cardioprotection by Transforming Growth Factor-β," *Science*, vol. 249, pp. 61-64 (1990).
Levy, "Drug Release from Submicronized O/W Emulsion: A New in Vitro Kinetic Evaluation Model", Intl. J. Pharrnaceut. ,66, 29-37 (1990).
Levy, et al., "Strategies for Treating Arterial Restenosis Using Polymeric Controlled Release Implants," *Chemical Abstracts*, 121, 580: Abstract No. 263625g (1994).
Li, et al., "Structure and Dynamics of Microemulsions which Mimic the Lipid Phase of Low-Density Lipoproteins", Biochimica et Biophysica Acta, 1042, 42-50 (1990).
Liaw, et at., "Osteopontin Promotes Vascular Cell Adhesion and Spreading and Is Chemotactic for Smooth Muscle Cells In Vitro," *Cir. Res*. vol. 74, No. 2, pp. 214-224 (1994).
Lin, et al., "Expression Cloning of the TGF-β Type II Receptor, a Functional Transmembrane Serine/Threonine Kinase," *Cell*. vol. 68, pp. 775-785 (1992).
Linn, et al., "Microemulsion for Intradermal Delivery of Cetyl Alcohol and Octyl Dimethyl Paba" , Drug Development and Industrial Pharmacy, 16, 899-920, 1990.
Lipski, et al., "Cytochalasin B: Preparation, Analysis in Tissue Extracts, and Pharmacokinetics After Intraperitoneal Bolus Administration in Mice," *Analytical Biochem*., vol. 161, pp. 332-340 (1987).
Liu, et al., "Restenosis After Coronary Angioplasty—Potential Biologic Determinants and Role of Intimal Hyperplasia," *Circulation*, vol. 79, No. 6, pp. 1374-1387 (1989).
Love, et al., "Effects of Tamoxifen on Cardiovascular Risk Factors in Postmenopausal Women," *Annals of Internal Medicine*, vol. 115, No. 11, pp. 860-864 (1991).
Love, et al., "Effects of Tamoxifen Therapy on Lipid and Lipoprotein Levels in Postmenopausal Patients with Node-Negative Breast Cancer," *J. of the National Cancer Institute*, vol. 82, No. 16, pp. 1327-1332 (1990).
Maione, Theodore E. And Sharpe, Richard J. "Development of angiogenesis inhibitors for clinical applications" TiPS—Nov. 1990 [vol. 11].
Malcolmson, et al., "A Comparison Between Nonionic Micelles and Microemulsions as a Means of Incorporating the Poorly Water Soluble Drug Diazepam", J. Pharm. Pharmacol, 42 6p, (1990).
Manasek, et al., The Sensitivity of Developing Cardiac Myofibrils to Cytochalasin-B, *PNAS* (USA), vol. 69, No. 2, pp. 308-312 (1972).
Mang, Tien-Dung Duc, "Distribution to Normal and Tumor Tissues of Cytochalasin B After Intravenous Administration in Mice," Thesis Submitted for Honors B.S. in Biology, Syracuse University.
Massagué, Joan, "The Transforming Growth Factor-B; Family", *Annu. Rev. Cell Biol*. vol. 6, pp. 597-641 (1990).
McCaffrey, et al., "Transforming Growth Factor, β Activity is Potentiated by Heparin Via Dissociation of the Transforming Growth Fact—Macroglobulin Inactive Complex," *The J. of Cell Biology*, vol. 109, pp. 441-448 (1989).
McCarroll, et al., Preliminary Studies on the Regulation of Secretion of Latent Transforming Growth Factor-β (TGF-β) by Endothelial Cells in Culture*Clin. Chem*. vol. 36, No. 6, pp. 1152 (1990) Abstract No. 0934.
McCormick, et al., "Retinoid-Tamoxifen Interaction in Mammary Cancer Chemoprevention." *Carcinogenesis*, vol. 7, No. 2, pp. 193-196 (1986).
McDonald, et al., "Fatal Myocardial Infarction in the Scottish Adjuvant Tamoxifen Trial," *BMJ*, vol. 303 pp. 435-437 (1991).
McLean, et al., "cDNA Sequence of Human Apolipoprotein(α) is Homologous to Plasminogen," *Nature*, vol. 330, No. 6143, pp. 132-137 (1987).
McQuiggan, James Daniel: "Tissue Distribution of Cytochalasin B After Intraperitoneal Bolus and Microencapsulated Injection in Mice and its Effect on β-N-Acetylglucosaminidase Activity in Cultured B16-BL6 Melanoma Cells," Thesis Submitted in partial fulfillment of the requirements for the degree of Master of Science in Biology in the Graduate School of Syracuse University, published Syracuse University, Biology Dept. (1988).
Merrilees, et al., "Synthesis of TGF-$\beta_1$ by Vascular Endothelial Cells is Correlated with Cell Spreading," *J. Vasc. Res*., vol. 29, pp. 376-384 (1992).
Middlebrook, et al., "Specific Association of T-2 Toxin with Mammalian Cells," *Biochem. Pharmacology*, vol. 38, No. 18, pp. 3093-3102 (1989).
Morisaki, et al., "Effects of Transforming Growth Factor β on Growth of Aortic Smooth Muscle Cells," *Atherosclerosis*, vol. 88, pp. 227-234 (1991).
Moses and Langer "Inhibitors of angiogenesis". Bio/Technology. 9:630-634, 1991.
Nabel, "Recombinant Gene Expression in Vivo Within Endothelial Cells of the Arterial Wall", Science, 244, 1342-1344 (1983).
Naito, et al., "Vascular Endothelial Cell Migration In Vitro Roles of Cyclic Nucleotides, Calcium Ion and Cytoskeletal System," *Artery*, vol. 17(1), pp. 21-31 (1989).
Nakao, et al., "Calcium Dependency of Aortic Smooth Muscle Cell Migration Induced by 12-L-Hydroxy-5,8,10,14-eicosatetraenoic Acid," *Atherosclerosis*, vol. 46, pp. 309-319 (1983).
Nikol, et al., "Expression of Transforming Growth Factor $\beta_1$ is Increased in Human Vascular Restenosis Lesions," *J. Clin. Invest*., vol. 90, pp. 1582-1592 (1992).
Nunes, et al., "Vitamins C and E Improve the Response to Coronary Balloon Injury in the Pig: Effect of Vascular Remodeling," *Circulation*, vol. 88, No. 4, Part 2, p. I-372 (1993).
O'Brien, et al., "Osteopontin mRNA and Protein are Overexpressed in Human Coronary Atherectomy Specimens: Clues to Lesion Calcification," *Cir*. vol. 88, p. I-619, Abstracts from the $66^{th}$ Scientific Sessions (1993).
O'Connor-McCourt, et al., "Latent Transforming Growth Factor β in Serum: A Specific Complex with $_2$-Macroglobulin," *The Journal of biological Chemistry*, vol. 262, No. 29, pp. 14090-14099 (1987).
Ohmi, et al., "Effect of K252a, A Protein Kinase Inhibitor, on the Proliferation of Vascular Smooth Muscle Cells," *Biochemical and Biophysical Research Communications*, vol. 173, No. 3, p. 976-981 (1990).
O-Keefe Jr. et al., "Ineffectiveness of colchicine for the prevention of restenosis after coronary angioplasty". JACC, 19(7): 1597-1600, 1992.
Oliveira, et al., "Isolation and Characterization of Smooth Muscle Cell Membranes," *Biochimica et Biophysica Acta*. vol. 332, pp. 221-232 (1974).
Osborne, et al., "Microemulsions as Topical Drug Delivery Vehicles: In Vitro Trandermal Studies of a Model Hydrophilic Drug", J. Pharm. Pharmacol., 43, 451-454 (1991).
Osipow, "Transparent Emulsion" J. Soc. Cosmetic Chemists, 277-285 (1963).
Palmaz et al., "Intravascular Stents", Advances in Vascular Surgery, 1, 107-135 (1993).
Pardee, et al., "Control of Cell Proliferation," *Cancer*, vol. 39, pp. 2747-2754 (June Supplement 1977).
Pathak, at al., "Enhanced Stability of Physostigmine Salicylate in Submicron o/w Emulsion", International Journal of Pharmaceutics, 65, 1690175 (1990).
Podzimek, et al., "O/W Microemulsions" , J. Dispersion Science and Technology, I, 341-359 (1980).
Popma, et al., "Factors Influencing Restenosis After Coronary Angioplasty", *The Amer. J. of Med*. vol. 88, pp. 1-16N-1-24N (1990).
Post, et aL, "Restenosis Is Partly Due to Intimal Hyperplasia and Partly to Remodeling of the Injured Arterial Wall," *European Heart J*., vol. 14, p. 201, Abstract P1164 (1993).
Post, et al., "Which Part Of The Angiographic Diameter Reduction After Balloon Dilation Is Due To Intimal Hyperplasia?", *JACC*, vol. 21, 36A, Abstract, 851-95 (1993).

Pouton, C.W., "Self-Emulsifying Drug Delivery Systems: Assessment of the Efficiency of Emulsification", International Journal of Pharmaceutics, 27, 335-348, (1985).
Rauterberg, et aL, "Collagens in Atherosclerotic Vessel Wall Lesions," *Current Topics in Pathology*, vol. 87, pp. 163-192 (1993).
Reid, et al., "Fragmentation of DNA in $P388D_1$ Macrophages Exposed to Oxidized Low-density Lipoprotein," *FEBS Letters*, vol. 332, No. 3, pp. 218-220 (1993).
Ross, et al., Chronic Inflammation, PDGF, TGF, and Smooth Muscle Proliferation, Abstracts from the $20^{th}$ Annual Meeting of the Keystone Symposia on Molecular Biology, Session on Molecular Mechanisms of Vascular Disease, *J. Cell Biochem*. S15C, Abstract No. G006, p. 96 (1991).
Ross, Russell, The Pathogenesis of Atherosclerosis: A Perspective for the 1990s, *Nature*, vol. 362, pp. 801-809 (1993).
Sagitani, et al., "Microemulsion Systems with a Nonionic Cosurfant" J. Dispersion Science and Technology, 1 (2), 151-164 (1980).
Sanders, et al., "Controlled Release of a Luteinizing Hormone-Releasing Hormone Analogue from Poly(d,1-lactide-co-glycolide) Microspheres," *Journal of Pharmaceutical Sciences*, vol. 73, No. 9, pp. 1294-1297 (1984).
Schatz. "A View of Vascular Stents". Circulation, 79 445-457 (1989).
Schlingemann, et al., Expression of the High Molecular Weight Melanoma-Associated Antigen by Pericytes During Angiogenesis in Tumors and in Healing Wounds, *Amer. J. Pathology*, vol. 136, No. 6, pp. 1393-1405 (1990).
Schneiderman, et al., "Increased Type I Plasminogen Activator Inhibitor Gene Expression in Atherosclerotic Human Arteries," *PNAS* (USA), vol. 89, pp. 6998-7002 (1992).
Schwartz, et al., "Maintenance of Integrity in Aortic Endothelium," *Fed. Proc*., vol. 39, No. 9, pp. 2618-2625 (1980).
Schwartz, et al., Restenosis After Balloon Angioplasty—A Practical Proliferative Model in Porcine Coronary Arteries, *Circulation*, vol. 82, No. 6, pp. 2190-2200 (1990).
Schwartz, et al., "The Restenosis Paradigm Revisited: An Alternative Proposal for Cellular Mechanisms," *JACC*, vol. 20, No. 5, pp. 1284-1293 (1992).
Shananhan, et al., "Isolation of Gene Markers of Differentiated and Proliferating Vascular Smooth Muscle Cells," *Circulation Research*, vol. 73, No. 1 (1993).
Shewmon, et al., "Tamoxifen Lowers Lp(a) in Males with Heart Disease," *Supplement I Cir*., vol. 86, No. 4, p. 1345 (1992).
Shoji, et al., "Enhancement of Anti-Inflammatory Effects of Biphenylylacetic Acid by its Incorporation into Lipid Microspheres," *J. Pharm. Pharmacol*. 38:118-121 (1985).
Simpson,J.B., et al., "Percutaneous Coronary Atherectomy", Circulation, 78, $61^{st}$ Scientific Session, Abstract No. 0326, p. II-82, (1988).
Singh, et al., "Phylogenetic Analysis of Platelet-derived Growth Factor by Radio-Receptor Assay," *The Journal of Cell Biology*, vol. 95, pp. 667-671 (1982).
Snow, et al., "Heparin Modulates the Composition of the Extracellular Matrix Domain Surrounding Arterial Smooth Muscle Cells," *American J. of Pathology*, vol. 137, No. 2 (1990).
Speir et al., "Potential Role of Human Cytomegalorvirus and p53 Interaction in Coronary Restenosis", Science, 265, 391-394 (1994).
Steele, P.M. et al., "Balloon Angioplasty—Nature History of the Pathophysiological Response to Injury in a Pig Model", Circulation Research, 57 105-112 (1985).
Streuli, et al., "Extracellular Matrix Regulators Expression of the TGF-β1 Gene," *The J. of Cell Biol*. vol. 120, No. 1, pp. 253-260 (1993).
Suckling, Keith E., "Emerging Strategies for the Treatment of Atherosclerosis as Seen from the Patent Literature," *Biochem. Society Transactions*. vol. 21, pp. 660-662 (1993).
Tamm, Ch. Basel, "The Antibiotic Complex of the Verrucarins and Roridins," *Fortschr. Chem. Org. Naturst*., 31:65 117 (1974).
Tice, et al., "Biodegradable controlled-release parental systems" Pharmaceutical Technology, 26-35 (1984).
Topol, Eric J.," The Restenosis Antitheory", *Mayo Clinic Proc*. vol. 68, pp. 88-90 (1993).
Vanhoutte, P.M., "Hypercholesterolemia, Atherosclerosis and Release of Endothelium-Derived Relaxing Factor by Aggregating Platelets," *European Heart J*. vol. 12, Supplement E. pp. 25-32 (1991).
Vargas, et al., "Oestradiol Inhibits Smooth Muscle Cell Proliferation of Pig Coronary Artery," *Br. J. Pharmacol*., vol. 109, pp. 612-617 (1993).
Vijayagopal, et al., "Human Monocyte-Derived Macrophages Bind Low-Density-Lipoprotein-Proteoglycan Complexes by a Receptor Different from the Low-Density-Lipoprotein Receptor," *Biochem. J*., vol. 289, pp. 837-844 (1993) (GB).
Vijayagopal, et al., "Lipoprotein-Proteoglycan Complexes Induce Continued Cholesteryl Ester Accumulation in Foam Cells from Rabbit Atherosclerotic Lesions," *J. Clin. Invest*. vol. 91, pp. 1011-1018 (1993).
Voisard, et al., "The In-Vitro Effect of Antineoplastic Agents on Proliferative Activity and Cytoskeletal Components of Plaque-derived Smooth-muscle Cells from Human Coronary Arteries," *Coronary Artery Disease*, 4:935-942 (1993).
Voisard, R., et al., "Search for new strategies for prevention of restenosis after angioplasty: the effect of cytostatic drugs on cell migration of re-stenosing human plaques cells in vitro". Vasa Suppl. 1992; 35: 132-3 [Article in German].
Wakefield, et al., "Latent Transforming Growth Factor β from Human Platelets: A High Molecular Weight Complex Containing Precursor Sequences," *The Journal of Biological Chemistry*, vol. 263, No. 16, pp. 7646-7654 (1988).
Wakefield, et al., "Recombinant Latent Transforming Growth Factor I Has a Longer Plasma Half-Life in Rats than Active Transforming Growth Factor, I, and a Different Tissue Distribution," *The Journal of Clinical Investigation, Inc*., vol. 86, pp. 1976-1984 (1990).
Weissberg, et al., "Approaches to the development of selective inhibitors of vascular smooth muscle cell proliferation," *Cardiovascular Res*., vol. 27, pp. 1191-1198 (1993).
Weissberg, et al.. "The Endothelin Peptides ET-1, ET-2, ET-3 and Sarafotoxin S6b are Comitogenic with Platelet-Derived Growth Factor for Vascular Smooth Muscle Cells," *Atherosclerosis*, vol. 85, pp. 257-262 (1990).
Weissberg, et al., Effects of TGFB on Vascular Smooth Muscle Cell Growth, *Growth Factors and the Cardiovascular System*, (Cummins, P.ed), Kluwer Academic Publishers, p. 189-205 (1993).
Wight, etal., "Proteoglycans Structure and Function," *Cell Biol. of Extracellular Matrix*, Second Edition, edited by Elizabeth D. Hay, Plenum Press, New York Chapter 2, pp. 45-78 (1991).
Wight, et aL, "The Role of Proteoglycans in Cell Adhesion, Migration and Proliferation," *Current Opinion in Cell Biol*. vol. 4, pp. 793-801 (1992).
Wight, Thomas N., "Cell Biology of Arterial Proteoglycans," *Arteriosclerosis*, vol. 9, No. 1., pp. 1-20 (1989).
Wilensky, et al., "Direct Intraarterial Wall Injection of Microparticles via a Catheter: A Potential Drug Delivery Strategy Following Angioplasty," *American Heart Journal*, vol. 122, No. 4, pp. 1136-1140 (1991).
Wolinsky, et al., Use of a Perforated Balloon Catheter to Deliver Concentrated Heparin Into the Wall of the Normal Canine Artery, *JACC*, vol. 15, No. 2, pp. 475-481 (1990).
Zuckerman, et al., "Cytokine Regulation of Macrophage apo E Secretion: Opposing Effects of GM-CSF and TGF-β," *Atherosclerosis*, vol. 96, pp. 203-214 (1992).
Zukerman, et al., "Exogenous Glucocorticoids Increase Macrophage Secretion of E by Cholesterol-Independent Pathways," *Atherosclerosis*, vol. 103, pp. 43-54 (1993).
Appendix To Answering Memorandum In Opposition To Plaintiffs' Motion For A Preliminary Injunction, vol. 2, Civil Action No. 03-283 Dated Apr. 3, 2003, U.S. District Court for the District of Delaware.
Complaint, Civil Action No. 03-283, Filed Mar. 13, 2003, U.S. District Court for the District of Delaware.
Declaration Of Brian G. Firth, Civil Action No. 03-283 SLR, Dated Mar. 31, 2003, U.S. District Court for the District of Delaware.
Declaration Of Dr. Jeffrey W. Moses, M.D., Civil Action No. 03-283 SLR, Dated Mar. 31, 2003, U.S. District Court for the District of Delaware.

Declaration Of Dr. Martin B. Leon, M.D., Civil Action No. 03-283 SLR, Dated Mar. 31, 2003, U.S. District Court for the District of Delaware.
Declaration Of Dr. Paul S. Teirstein, M.D., F.A.C.C., Civil Action No. 03-283 SLR, Dated Mar. 28, 2003, U.S. District Court for the District of Delaware.
Declaration Of Dr. Peter Fitzgerald, M.D., Ph.D., Civil Action No. 03-283 SLR, Dated Mar. 31, 2003, U.S. District Court for the District of Delaware.
Declaration Of Dr. Richard E. Kuntz, M.D. M.Sc., Civil Action No. 03-283 SLR, Dated Mar. 21, 2003, U.S. District Court for the District of Delaware.
Declaration Of Eric Simso, Civil Action No. 03-0283, Dated Mar. 20, 2003, U.S. District Court for the District of Delaware.
Declaration Of Jermone Segal, M.D., Civil Action No. 03-283 Dated Mar. 20, 2003, U.S. District Court for the District of Delaware.
Declaration Of Kinam Park, Ph.D., Civil Action No. 03-283 Dated Mar. 20, 2003, U.S. District Court for the District of Delaware.
Defendants' Answer, Counterclaim And Demand For Jury Trial, Civil Action No. 03-283, Filed Apr. 7, 2003, U.S. District Court for the District of Delaware.
Opening Expert Report of Robson F. Storey, Ph.D., Civil Action No. 03-283 SLR, Dated May 23, 2003, U.S. District Court for the District of Delaware.
Opening Expert Report of Stephen R. Hanson. Ph.D., Civil Action No. 03-283 SLR. Dated May 23, 2003, U.S. District Court for the District of Delaware.
Plaintiffs' Opening Brief In Support Of Their Motion For Preliminary Injunction, Civil Action No. 03-283 Filed Mar. 20, 2003, U.S. District Court for the District of Delaware.
Plaintiffs' Reply Brief In Support Of their Motion For Preliminary Injunction, Civil Action No. 03-283 SLR. Dated Apr. 10, 2003, U.S. District Court for the District of Delaware.
Plaintiffs' Reply To Defendant's Counterclaim, Civil Action No. 03-283 Filed Apr. 21, 2003, U.S. District Court for the District of Delaware.
Preliminary Injuction Hearing Transcript, vol. A, Civil Action No. 03-27 (SLR), Dated Jul. 21, 2003, U.S. District Court for the District of Delaware.
Preliminary Injunction Hearing Transcript, vol. B, Civil Action No. 03-27 (SLR), Dated Jul. 22, 2003, U.S. District Court for the District of Delaware.
Preliminary Injunction Hearing Transcript, vol. C, Civil Action No. 03-27 (SLR), Dated Jul. 23, 2003, U.S. District Court for the District of Delaware.
Rebuttal Expert Report Of Kiman Park, Ph.D., Civil Action No. 03-283 SLR, Dated Jun. 2, 2003, U.S. District Court for the District of Delaware.
Redacted Public Version: Opening Brief in Support of Cordis' Motion for Summary Judgment Barring BSC from Asserting Equivalents for Certain Limitations of the Ding Patent. Civil Action No. 03-283 SLR U.S. District Court for the District of Delaware.
Second Declaration Of Jerome Segal, M.D., Civil Action No. 03-283 SLR, Dated Apr. 10, 2003, U.S. District Court for the District of Delaware.
Second Declaration Of Kinam Park, Ph.D., Civil Action No. 03-283 SLR, Dated Apr. 10, 2003, U.S. District Court for the District of Delaware.
Goodnight, S.H., "The Effects of n-3 Fatty Acids on Atherosclerosis and the Vascular Response to Injury", Arch. Pathol. Lab. Med., 117, 102-106, (Jan. 1993).
Daniels, "Taxol treatment of experimental proliferative vitreoretinopathy," Graefe's Archive of Clinical and Experimental Ophthalmology, vol. 228, pp. 513-516, (1990).
Definitions of "Cytostatic", (biology-online.org, 1 page, 2008), (MSN Encart.com, 2 pages, 2008), and (thefreedictionary.com, 1 page, 2008).
Ellis et al., "Effect of 18-to 24-hour heparin administration for prevention of restenosis after uncomplicated coronary angioplasty," American Heart Journal, vol. 117, No. 4, pp. 777-782, Apr. 1989.
Geer et al., "A novel role of fibrin in epidermal healing: Plasminogen-Mediated Migration and selective detachment of differentiated keratinocytes," Journal of Investigative Dermatology, vol. 121, pp. 1210-1216, (2003).
Jampel et al., "Glaucoma filtration surgery in nonhuman primates using taxol and etoposide in polyanhydride carriers,"Investigative Ophthalmology & Visual Science, vol. 34, No. 11, pp. 3076-3083, (1993).
Manfredi et al., "Taxol: an antimitotic agent with a new mechanism of action," Pharmacology and Therapeutics, vol. 25, pp. 83-125, Jan. 1, 1984.
Ranjit et al., "A targeted antithrombotic conjugate with antiplatelet and fibrinolytic properties which reduces in vivo thrombus formation," Cardiovascular Research, vol. 27, No. 12, pp. 2200-2204, (1993).
Ruiz, "Inhibition of posterior capsule opacification by 5-flurouracil in rabbits," Ophthalmic Res, vol. 22, pp. 201-208, (1990).
Al-Ghobainy, " Local application of Paclitaxel with the double-balloon method by Schneider following experimental stenting of the coronary arteries of a pig," Justus Liebig University Gieβen, p. 13 of the PhD thesis, 2001.
Bauer et al., Pharmaceutical Technology, 5th ed., p. 208-211, (1997).
Bauriedel, "Pathomechanisms of Restenosis after Angioplasty: Cellular and Molecular Biological Studies on human arteriosclerotic tissue," From Medical Clinic I Of the Ludwig Maximilian University of Munich, ISBN 3-929115-31-X, Summary, pp. 104-106, (1993).
Corvinus, "In-vitro Examinations of the cytostatic/cytotoxic mechanism of action of the Ether lipid-5-Fluorouridine Conjugate BM 92.0700 Na," Heidelberg University, 3 pages, (1998).
Definition of "Taxol", Red List 1995: Drug directory of the BPI and VFA, title page and p. 85/091, Dec. 1994.
Forth et al., General and Special Pharmacology and Toxicology, 7th Edition, pp. 482, 617, 618, 805, 810, (1996).
Mayer, "Radiochemotherapy with Paclitaxel (Taxol)—The role of synchronization effects under special consideration of the p53 status," Ruprecht-Karls-University Heidelberg Faculty for Clinical Medicine Mannheim, Dissertation Abstract, 1 page.
Rompp, Encyclopedia of Chemistry, 10th ed., p. 3379.
Voigt, Pharmaceutical Technology, 8th ed., p. 178-211, (1995).

* cited by examiner

RORIDIN A
1

RORIDIN A HEMISUCCINATE
2

RORIDIN A HEMISUCCINYL SUCCINIMIDATE
(RA-HS-NHS)
3

RORIDIN A
1

4

5

6

RORIDIN A HEMISUCCINATE
7

RORIDIN A HEMISUCCINYL SUCCINIMIDATE (RA-HS-NHS)
8

THERAPEUTIC INHIBITOR OF VASCULAR SMOOTH MUSCLE CELLS

CROSS-REFERENCE TO RELATED APPLICATIONS

This application is a continuation of U.S. application Ser. No. 09/470,662, filed on Dec. 22, 1999, now U.S. Pat. No. 6,268,390 which is a continuation of U.S. application Ser. No. 09/113,733, filed on Jul. 10, 1998, now U.S. Pat. No. 6,074, 659, which is a continuation of U.S. application Ser. No. 08/450,793, filed on May 25, 1995, now U.S. Pat. No. 5,811, 447, which in turn is a continuation of U.S. application Ser. No. 08/062,451, filed on May 13, 1993, now abandoned, which in turn is a continuation-in-part of U.S. application Ser. No. 08/011,669, filed on Jan. 28, 1993, now abandoned, which in turn is a continuation-in-part of PCT Application No. PCT/US92/08220, filed on Sep. 25, 1992, now completed, which applications are incorporated herein by reference.

FIELD OF THE INVENTION

This invention relates generally to therapeutic methods involving surgical or intravenous introduction of binding partners directed to certain target cell populations, such as smooth muscle cells, cancer cells, somatic cells requiring modulation to ameliorate a disease state and effector cells of the immune system, particularly for treating conditions such as stenosis following vascular trauma or disease, cancer, diseases resulting from hyperactivity or hyperplasia of somatic cells and diseases that are mediated by immune system effector cells. Surgical or intravenous introduction of active agents capable of altering the proliferation or migration of smooth muscle cells or contraction of smooth muscle proteins is also described. The invention also relates to the direct or targeted delivery of therapeutic agents to vascular smooth muscle cells that results in dilation and fixation of the vascular lumen (biological stenting effect). Combined administration of a cytocidal conjugate and a sustained release dosage form of a vascular smooth muscle cell inhibitor is also disclosed. Mechanisms for in vivo vascular smooth muscle cell proliferation modulation, agents that impact those mechanisms and protocols for the use of those agents are discussed.

BACKGROUND OF THE INVENTION

Percutaneous transluminal coronary angioplasty (PTCA) is widely used as the primary treatment modality in many patients with coronary artery disease. PTCA can relieve myocardial ischemia in patients with coronary artery disease by reducing lumen obstruction and improving coronary flow. The use of this surgical procedure has grown rapidly, with 39,000 procedures performed in 1983, nearly 150,000 in 1987, 200,000 in 1988, 250,000 in 1989, and over 500,000 PTCAs per year are estimated by 1994 (1, 2, 3). Stenosis following PTCA remains a significant problem, with from 25% to 35% of the patients developing restenosis within 1 to 3 months. Restenosis results in significant morbidity and mortality and frequently necessitates further interventions such as repeat angioplasty or coronary bypass surgery. No surgical intervention or post-surgical treatment (to date) has proven effective in preventing restenosis.

The processes responsible for stenosis after PTCA are not completely understood but may result from a complex interplay among several different biologic agents and pathways. Viewed in histological sections, restenotic lesions may have an overgrowth of smooth muscle cells in the intimal layers of the vessel (3). Several possible mechanisms for smooth muscle cell proliferation after PTCA have been suggested (1, 2, 4, 5).

Compounds that reportedly suppress smooth muscle proliferation in vitro (4, 6, 7) may have undesirable pharmacological side effects when used in vivo. Heparin is an example of one such compound, which reportedly inhibits smooth muscle cell proliferation in vitro but when used in vivo has the potential adverse side effect of inhibiting coagulation. Heparin peptides, while having reduced anti-coagulant activity, have the undesirable pharmacological property of having a short pharmacological half-life. Attempts have been made to solve such problems by using a double balloon catheter, i.e., for regional delivery of the therapeutic agent at the angioplasty site (e.g., 8; U.S. Pat. No. 4,824,436), and by using biodegradable materials impregnated with a drug, i.e., to compensate for problems of short half-life (e.g., 9; U.S. Pat. No. 4,929,602).

Verrucarins and Roridins are trichothecene drugs produced as secondary metabolites by the soil fungi *Myrothecium verrucaria* and *Myrothecium roridium*. Verrucarin is a macrocyclic triester. Roridin is a macrocyclic diester of verrucarol (10). As a group, the trichothecenes are structurally related to sesquiterpenoid mycotoxins produced by several species of fungi and characterized by the 12,13-epoxytrichothec-9-ene basic structure. Their cytotoxic activity to eukaryotic cells is closely correlated with their ability to bind to the cell, to be internalized, and to inhibit protein and macromolecular synthesis in the cell.

At least five considerations would, on their face, appear to preclude use of inhibitory drugs to prevent stenosis resulting from overgrowth of smooth muscle cells. First, inhibitory agents may have systemic toxicity that could create an unacceptable level of risk for patients with cardiovascular disease. Second, inhibitory agents might interfere with vascular wound healing following surgery and that could either delay healing or weaken the structure or elasticity of the newly healed vessel wall. Third, inhibitory agents killing smooth muscle cells could damage surrounding endothelium and/or other medial smooth muscle cells. Dead and dying cells also release mitogenic agents that might stimulate additional smooth muscle cell proliferation and exacerbate stenosis. Fourth, delivery of therapeutically effective levels of an inhibitory agent may be problematic from several standpoints: namely, a) delivery of a large number of molecules into the intercellular spaces between smooth muscle cells may be necessary, i.e., to establish favorable conditions for allowing a therapeutically effective dose of molecules to cross the cell membrane; b) directing an inhibitory drug into the proper intracellular compartment, i.e., where its action is exerted, may be difficult to control; and, c) optimizing the association of the inhibitory drug with its intracellular target, e.g, a ribosome, while minimizing intercellular redistribution of the drug, e.g. to neighboring cells, may be difficult. Fifth, because smooth muscle cell proliferation takes place over several weeks it would appear a priori that the inhibitory drugs should also be administered over several weeks, perhaps continuously, to produce a beneficial effect.

As is apparent from the foregoing, many problems remain to be solved in the use of inhibitory drugs, including cytotoxic agents, to effectively treat smooth muscle cell proliferation. It would be highly advantageous to develop new methods for inhibiting stenosis due to proliferation of vascular smooth muscle cells following traumatic injury to vessels such as occurs during vascular surgery. In addition, delivery of compounds that produce inhibitory effects of extended duration to the vascular smooth muscle cells would be advantageous. Local administration of such sustained release compounds would also be useful in the treatment of other conditions where the target cell population is accessible by such administration.

SUMMARY OF THE INVENTION

In one aspect of the invention, new therapeutic methods and therapeutic conjugates are provided for inhibiting vascular smooth muscle cells in a mammalian host. The therapeutic conjugates contain a vascular smooth muscle binding protein or peptide that binds in a specific manner to the cell membranes of a vascular smooth muscle cell or an interstitial matrix binding protein/peptide that binds in a specific manner to interstitial matrix (e.g., collagen) of the artery wall, coupled to a therapeutic agent that inhibits the activity of the cell. In one embodiment, inhibition of cellular activity results in reducing, delaying, or eliminating stenosis after angioplasty or other vascular surgical procedures. The therapeutic conjugates of the invention achieve these advantageous effects by associating with vascular smooth muscle cells and pericytes, which may transform into smooth muscle cells. The therapeutic conjugate may contain: (1) therapeutic agents that alter cellular metabolism or are inhibitors of protein synthesis, cellular proliferation, or cell migration; (2) microtubule and microfilament inhibitors that affect morphology or increases in cell volume; and/or (3) inhibitors of extracellular matrix synthesis or secretion. In one representative embodiment, the conjugates include a cytotoxic therapeutic agent that is a sesquiterpenoid mycotoxin such as a verrucarin or a roridin. Other embodiments involve cytostatic therapeutic agents that inhibit DNA synthesis and proliferation at doses that have a minimal effect on protein synthesis such as protein kinase inhibitors (e.g., staurosporin), suramin, transforming growth factor-beta (TGF-beta) activators or production stimulators such as trans-2-[4-(1,2-diphenyl-1-butenyl)phenoxy]-N,N-dimethylethylamine (tamoxifen), TGF-beta itself, and nitric oxide releasing compounds (e.g., nitroglycerin) or analogs or functional equivalents thereof. Other moieties that inhibit cell division and are, therefore, useful in the practice of the present invention, include, for example, taxol and analogs thereof such as taxotere. In addition, therapeutic agents that inhibit the contraction or migration of smooth muscle cells and maintain an enlarged luminal area following, for example, angioplasty trauma (e.g., the cytochalasins, such as cytochalasin B, cytochalasin C, cytochalasin D, taxol or analogs thereof such as taxotere or the like) are also contemplated for use in accordance with the present invention. Other aspects of the invention relate to vascular smooth muscle binding proteins that specifically associate with a chondroitin sulfate proteoglycan (CSPG) expressed on the membranes of a vascular smooth muscle cell, and a preferred embodiment this CSPG has a molecular weight of about 250 kDaltons. In preferred embodiments the vascular smooth muscle binding protein binds to a CSPG target on the cell surface with an association constant of at least $10^{-4}$ M. In another preferred embodiment, the vascular smooth muscle binding protein contains a sequence of amino acids found in the Fab, Fv or CDR (complementarity determining regions) of monoclonal antibody NR-AN-01 or functional equivalents thereof.

Other aspects of the invention include methods for inhibiting stenosis, e.g., following angioplasty in a mammalian host, by administering to a human or animal subject in need of such treatment a therapeutically effective dosage of a therapeutic conjugate of the invention. In one representative embodiment, the dosage of therapeutic conjugate may be administered with an infusion catheter, to achieve a $10^{-3}$ M to $10^{-12}$ M concentration of said therapeutic conjugate at the site of administration in a blood vessel.

The present invention also contemplates therapeutic methods and therapeutic dosage forms involving sustained release of therapeutic agent to target cells. Preferably, the target cells are vascular smooth muscle cells, cancer cells, somatic cells requiring modulation to ameliorate a disease state and cells involved in immune system-mediated diseases that are accessible by local administration of the dosage form. Consequently, the methods and dosage forms of this aspect of the present invention are useful for inhibiting vascular smooth muscle cells in a mammalian host, employing a therapeutic agent that inhibits the activity of the cell (e.g., proliferation, contraction, migration or the like) but does not kill the cell and, optionally, a vascular smooth muscle cell binding protein. Also, the methods and dosage forms of this aspect of the present invention are useful for inhibiting target cell proliferation or killing such target cells, employing a therapeutic agent that inhibits proliferation or is cytotoxic to the target cells and, optionally, a target cell binding protein. In addition, the methods and dosage forms of this aspect of the present invention are useful for delivering cytostatic, cytocidal or metabolism modulating therapeutic agents to target cells, such as effector cells of the immune system, that are accessible by local administration of the dosage form, optionally employing a target cell binding protein. Finally, dosage forms of the present invention are useful to reduce or eliminate pathological proliferation or hyperactivity of normal tissue (i.e., somatic cells).

The dosage forms of the present invention are preferably either non-degradable microparticulates or nanoparticulates or biodegradable microparticulates or nanoparticulates. More preferably, the microparticles or nanoparticles are formed of a polymer containing matrix that biodegrades by random, nonenzymatic, hydrolytic scissioning. A particularly preferred structure is formed of a mixture of thermoplastic polyesters (e.g., polylactide or polyglycolide) or a copolymer of lactide and glycolide components. The lactide/glycolide structure has the added advantage that biodegradation thereof forms lactic acid and glycolic acid, both normal metabolic products of mammals.

Preferable therapeutic agents dispersed within the microparticulates or nanoparticulates are those exhibiting inhibition of a therapeutically significant target cell activity without killing the target cell, or target cell killing activity. For treatment of restenosis of vascular smooth muscle cells, useful therapeutic agents inhibit target cell activity (e.g., proliferation or migration) without killing the target cells. Preferred therapeutic moieties for this purpose are protein kinase inhibitors (e.g., staurosporin or the like), TGF-beta production or activation stimulators, such as tamoxifen or TGF-beta itself, taxol or analogs thereof (e.g., taxotere), smooth muscle migration and/or contraction inhibitors (e.g., the cytochalasins, such as cytochalasin B, cytochalasin C, cytochalasin D or the like), suramin, and nitric oxide-releasing compounds, such as nitroglycerin, or analogs or functional equivalents thereof. In cancer therapy, useful therapeutic agents inhibit proliferation or are cytotoxic to the target cells. Preferred therapeutic moieties for this purpose are TGF-beta production or activation stimulators, such as tamoxifen or TGF-beta itself, taxol or analogs thereof (e.g., taxotere), Roridin A and *Pseudomonas* exotoxin, or analogs or functional equivalents thereof. For treatment of immune system-modulated diseases, such as arthritis, useful therapeutic agents deliver cytostatic, cytocidal or metabolism-modulating therapeutic agents to target cells that are accessible by local administration of the dosage form. Preferred therapeutic moieties for this purpose are Roridin A, *Pseudomonas* exotoxin, suramin, TGF-beta production or activation stimulators, such as tamoxifen or TGF-beta itself, taxol or analogs thereof (e.g., taxotere) and protein kinase inhibitors (e.g., staurosporin), sphingosine, or analogs or functional equivalents thereof. For treatment of pathologically proliferating normal tissues (e.g., proliferative vitreoretinopathy, corneal pannus and the like), anti-proliferative agents or antimigration agents are preferred (e.g., cytochalasins, taxol or analogs thereof, somatostatin, somatostatin analogs, N-ethylmaleimide, antisense oligonucleotides, TGF-beta production or activation stimulators, such as tamoxifen or TGF-beta itself and the like).

The dosage forms of the present invention are optionally targeted to a relevant target cell population by a binding protein or peptide. Preferred binding proteins/peptides of the present invention are vascular smooth muscle cell binding protein, tumor cell binding protein and immune system effector cell binding protein. Preferred vascular smooth muscle cell binding proteins specifically associate with a chondroitin sulfate proteoglycan (CSPG) expressed on the membranes of a vascular smooth muscle cell, and in a preferred embodiment this CSPG has a molecular weight of about 250 kDaltons. In preferred embodiments, the vascular smooth muscle binding protein binds to a CSPG target on the cell surface with an association constant of at least $10^{-4}$ M. In other preferred embodiments, the vascular smooth muscle binding protein contains a sequence of amino acids found in the Fab, Fv or CDR (complementarity determining regions) of monoclonal antibody NR-AN-01 or functional equivalents thereof. Other preferred binding peptides useful in this embodiment of the present invention include those that localize to intercellular stroma and matrix located between and among vascular smooth muscle cells. Preferred binding peptides of this type are specifically associated with collagen, reticulum fibers or other intercellular matrix compounds. Preferred tumor cell binding proteins are associated with surface cell markers expressed by the target tumor cell population or cytoplasmic epitopes thereof. Preferred immune system-modulated target cell binding proteins are associated with cell surface markers of the target immune system effector cells or cytoplasmic epitopes thereof. Binding peptides/proteins of the present invention also target pathologically proliferating normal tissues.

The present invention also provides therapeutic methods and therapeutic dosage forms involving administration of free (i.e., non-targeted or non-binding partner associated) therapeutic agent to target cells. Preferably, the target cells are vascular smooth muscle cells and the therapeutic agent is an inhibitor of vascular smooth muscle cell contraction, allowing the normal hydrostatic pressure to dilate the vascular lumen. Such contraction inhibition may be achieved by actin inhibition, which is preferably achievable and sustainable at a lower dose level than that necessary to inhibit protein synthesis. Consequently, the vascular smooth muscle cells synthesize protein required to repair minor cell trauma and secrete interstitial matrix, thereby facilitating the fixation of the vascular lumen in a dilated state near its maximal systolic diameter. This phenomenon constitutes a biological stenting effect that diminishes or prevents the undesirable recoil mechanism that occurs in up to 25% of the angioplasty procedures classified as successful based on an initial post-procedural angiogram. Cytochalasins (which inhibit the polymerization of G- to F-actin which, in turn, inhibits the migration and contraction of vascular smooth muscle cells) are the preferred therapeutic agents for use in this embodiment of the present invention. Free therapeutic agent protocols of this type effect a reduction, a delay, or an elimination of stenosis after angioplasty or other vascular surgical procedures. Preferably, free therapeutic agent is administered directly or substantially directly to vascular smooth muscle tissue. Such administration is preferably effected by an infusion catheter, to achieve a $10^{-3}$ M to $10^{-12}$ M concentration of said therapeutic agent at the site of administration in a blood vessel.

Another embodiment of the present invention incorporates administration of a cytocidal targeted conjugate to destroy proliferating vascular smooth muscle cells involved in vascular stenosis. The mitogenic agents released after this biological arteromyectomy are prevented from stimulating the remaining viable vascular smooth muscle cells to proliferate and restenose the vessel by administration of the anti-contraction anti-migration) or anti-proliferative sustained release agents of the present invention.

TGF-beta, TGF-beta activator and TGF-beta production stimulator sustained release dosage forms of the present invention may be employed in the prevention or treatment of conditions characterized by inappropriate proliferation of smooth muscle cells, such as the prevention or reduction of restenosis following angioplasty or other vascular trauma. TGF-beta or such TGF-beta activators and production stimulators inhibit abnormal proliferation of smooth muscle cells. A preferred TGF-beta activator/production stimulator is trans 2-[4-(1,2-diphenyl-1-butenyl) phenoxy-N,N-dimethylethylamine.

The amount of TGF-beta, TGF-beta activator or TGF-beta production stimulator therapeutic or prophylactic agent administered in sustained release dosage forms is selected to treat vascular trauma of differing severity, with smaller doses being sufficient to treat lesser vascular trauma such as in the prevention of vascular rejection following graft or transplant. Such dosage forms are also amenable to chronic use for prophylactic purposes with respect to disease states involving proliferation of vascular smooth muscle cells over time (e, atherosclerosis, coronary heart disease, thrombosis, myocardial infarction, stroke, smooth muscle neoplasms such as leiomyoma and leiomyosarcoma of the bowel and uterus, uterine fibroid or fibroma and the like). For the prevention/treatment of restenosis, for example, a large dose (optionally, in sustained release form) is administered before or during an angioplasty procedure, followed by a sustained release dosage form designed to release smaller, follow up doses over time to maintain an anti-proliferative effect for a time sufficient to substantially reduce the risk of or prevent restenosis. A preferred therapeutic protocol duration for this purpose is from about 3 to about 26 weeks.

Further provided is a method for upregulating cellular mRNA coding for TGF-beta. Cells (e.g., smooth muscle cells) amenable to such metabolic manipulation are identified in the manner described herein and are exposed to sustained release formulation of an effective amount of a TGF-beta mRNA regulator (i.e., a subset of TGF-beta production stimulators). In this manner, TGF-beta production is stimulated, thereby inhibiting the abnormal proliferation of smooth muscle cells.

Free TGF-beta, TGF-beta production stimulator or TGF-beta activator may be employed in combination protocols to prevent or combat conditions characterized by abnormal proliferation of smooth muscle cells. In one such protocol, systemic TGF-beta or TGF-beta activator or TGF-beta production stimulator is administered prior to a local (e.g., via catheter) administration of a cytotoxic agent (e.g., free cytotoxic agent, a cytotoxic agent-containing conjugate, or a cytotoxic agent-containing sustained release dosage form). The TGF-beta, TGF-beta activator or TGF-beta production stimulator decreases the effect of the proliferative stimulus provided upon cell death caused by the action of the cytotoxic agent. In this manner, proliferating smooth muscle cells can be killed without causing rampant proliferation of the remaining cells. Preferably, systemic TGF-beta or TGF-beta activator or TGF-beta production stimulator administrations occur following cytotoxic agent administration to maintain an anti-proliferative environment. Also, localized TGF-beta, TGF-beta activator or TGF-beta production stimulator administration can optionally be carried out in conjunction with the localized delivery of cytotoxic agent. Similarly, TGF-beta, TGF-beta activator or TGF-beta production stimulator may be administered in combination with one or more cytostatic agents.

DETAILED DESCRIPTION OF THE INVENTION

Figure 1A:
FIG. 1(A-B) is a photomicrograph of vascular smooth muscle cells in an artery of a 24-year-old male patient with vascular smooth muscle binding protein bound to the cell surface and membrane. The patient received the vascular smooth muscle binding protein by i.v. administration 4 days before the arterial tissue was prepared for histology.

As used herein the following terms have the meanings as set forth below:

"Therapeutic conjugate" means a vascular smooth muscle or an interstitial matrix binding protein coupled (e.g., optionally through a linker) to a therapeutic agent.

"Therapeutic agent" includes any moiety capable of exerting a therapeutic or prophylactic effect in the practice of the present invention.

"Target" and "marker" are used interchangeably in describing the conjugate aspects of the present invention to mean a molecule recognized in a specific manner by the matrix or vascular smooth muscle binding protein, e.g., an antigen, polypeptide antigen or cell surface carbohydrate (e.g., a glycolipid, glycoprotein, or proteoglycan) that is expressed on the cell surface membranes of a vascular smooth muscle cell or a matrix structure.

"Epitope" is used to refer to a specific site within the "target" molecule that is bound by the matrix or smooth muscle binding protein, e.g., a sequence of three or more amino acids or saccharides.

"Coupled" is used to mean covalent or non-covalent chemical association (i.e., hydrophobic as through van der Waals forces or charge-charge interactions) of the matrix or vascular smooth muscle binding protein with the therapeutic agent. Due to the nature of the therapeutic agents employed, the binding proteins will normally be associated with the therapeutic agents by means of covalent bonding.

"Linker" means an agent that couples the matrix or smooth muscle binding protein to a therapeutic agent, e.g., an organic chemical coupler.

"Migration" of smooth muscle cells means movement of these cells in vivo from the medial layers of a vessel into the intima, such as may also be studied in vitro by following the motion of a cell from one location to another (e.g., using time-lapse cinematography or a video recorder and manual counting of smooth muscle cell migration out of a defined area in the tissue culture over time).

"Proliferation," i.e., of smooth muscle cells or cancer cells, means increase in cell number, i.e., by mitosis of the cells.

"Abnormal or Pathological or Inappropriate Proliferation" means division, growth or migration of cells occurring more rapidly or to a significantly greater extent than typically occurs in a normally functioning cell of the same type.

"Expressed" means mRNA transcription and translation with resultant synthesis, glycosylation, and/or secretion of a polypeptide by a cell, e.g., CSPG synthesized by a vascular smooth muscle cell or pericyte.

"Macrocyclic trichothecene" is intended to mean any one of the group of structurally related sesquiterpenoid macrocyclic mycotoxins produced by several species of fungi and characterized by the 12,13-epoxytrichothec-9-ene basic structure, e.g., verrucarins and roridins that are the products of secondary metabolism in the soil fungi *Myrothecium verrucaria* and *Myrothecium roridium.*

"Sustained release" means a dosage form designed to release a therapeutic agent therefrom for a time period ranging from about 3 to about 21 days. Release over a longer time period is also contemplated as a "sustained release" dosage form of the present invention.

"Dosage form" means a free (non-targeted or non-binding partner associated) therapeutic agent formulation, as well as sustained release therapeutic formulations, such as those incorporating microparticulate or nanoparticulate, biodegradable or non-biodegradable polymeric material capable of binding to one or more binding proteins or peptides to deliver a therapeutic moiety dispersed therein to a target cell population.

"Staurosporin" includes staurosporin, a protein kinase C inhibitor of the following formula,

I

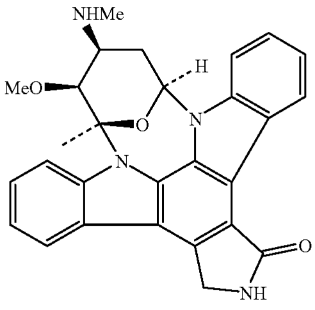

as well as diindoloalkaloids having one of the following general structures:

II

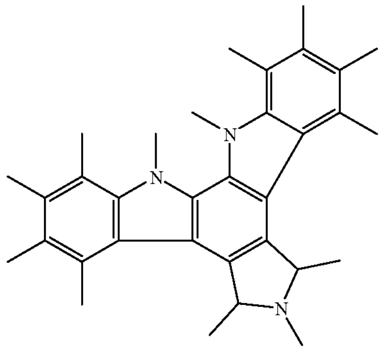

III

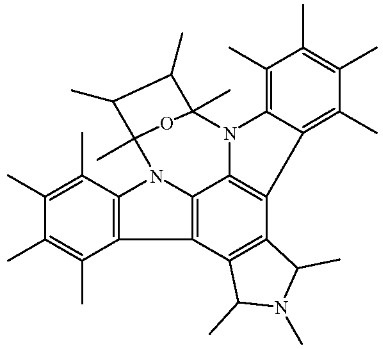

IV

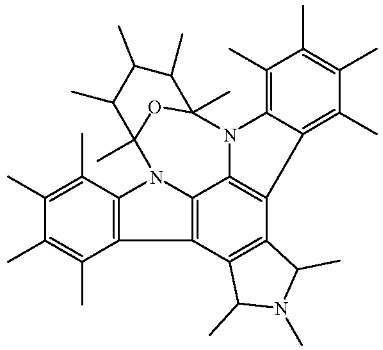

More specifically, the term "staurosporin" includes K-252 (see, for example, Japanese Patent Application No. 62,164,626), BMY-41950 (U.S. Pat. No. 5,015,578), UCN-01 (U.S. Pat. No. 4,935,415), TAN-999 (Japanese Patent Application No. 01,149,791), TAN-1030A (Japanese Patent Application No. 01,246,288), RK-286C (Japanese Patent Application No. 02,258,724) and functional equivalents and derivatives thereof. Derivatives of staurosporin include those discussed in Japanese Patent Application Nos. 03,72,485; 01,143,877; 02,09,819 and 03,220,194, as well as in PCT International Application Nos. WO 89 07,105 and WO 91 09,034 and European Patent Application Nos. EP 410,389 and EP 296,110. Derivatives of K-252, a natural product, are known. See, for example, Japanese Patent Application Nos. 63,295,988; 62,240,689; 61,268,687; 62,155,284; 62,155,285; 62,120,388 and 63,295,589, as well as PCT International Application No. WO 88 07,045 and European Patent Application No. EP 323,171.

"Cytochalasin" includes fungal metabolites exhibiting an inhibitory effect on target cellular metabolism, including prevention of contraction or migration of vascular smooth muscle cells. Preferably, cytochalasins inhibit the polymerization of monomeric actin (G-actin) to polymeric form (F-actin), thereby inhibiting cell functions requiring cytoplasmic microfilaments. Cytochalasins typically are derived from phenylalanine (cytochalasins), tryptophan (chaetoglobosins), or leucine (aspochalasins), resulting in a benzyl, indol-3-yl methyl or isobutyl group, respectively, at position C-3 of a substituted perhydroisoindole-1-one moiety (Formula V or VI).

V

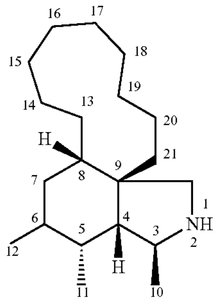

VI

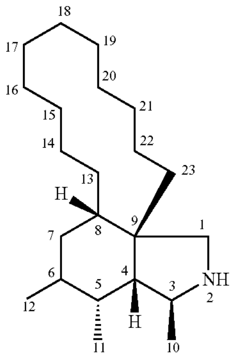

The perhydroisoindole moiety in turn contains an 11-, 13- or 14-atom carbocyclic- or oxygen-containing ring linked to positions C-8 and C-9. All naturally occurring cytochalasins contain a methyl group at C-5; a methyl or methylene group at C-12; and a methyl group at C-14 or C-16. Exemplary molecules include cytochalasin A, cytochalasin B, cytochalasin C, cytochalasin D, cytochalasin E, cytochalasin F, cytochalasin G, cytochalasin H, cytochalasin J, cytochalasin K, cytochalasin L, cytochalasin M, cytochalasin N, cytochalasin O, cytochalasin P, cytochalasin Q, cytochalasin R, cytochalasin S, chaetoglobosin A, chaetoglobosin B, chaetoglobosin C, chaetoglobosin D, chaetoglobosin E, chaetoglobosin F, chaetoglobosin G, chaetoglobosin J, chaetoglobosin K, deoxaphomin, proxiphomin, protophomin, zygosporin D, zygosporin E, zygosporin F, zygosporin G, aspochalasin B, aspochalasin C, aspochalasin D and the like, as well as functional equivalents and derivatives thereof. Certain cytochalasin derivatives are set forth in Japanese Patent Nos. 72 01,925; 72 14,219; 72 08,533; 72 23,394; 72 01924; and 72 04,164. Cytochalasin B is used in this description as a prototypical cytochalasin.

As referred to herein, "tamoxifen" includes trans-2-(4-(1,2-diphenyl-1-butenyl)phenoxy]-N,N-dimethyl-ethylamine which is capable of enhancing the production or activation of TGF-beta. The activated form of TGF-beta, in turn, inhibits vascular smooth muscle cell proliferation. Evidence exists that tamoxifen also acts to stabilize or organize areas of smooth muscle cell trauma. This organization/stabilization may stem from a blockage of smooth muscle cell maturation. Functional equivalents and derivatives of the aforementioned chemical compound are also included within the scope of the term "tamoxifen" for the purposes of this disclosure. Exemplary tamoxifen functional equivalents are plasmin, heparin, compounds capable of reducing the level or inactivating the lipoprotein Lp(a) or the glycoprotein apolipoprotein(a) and derivatives or analogs thereof.

As referred to herein, "TGF-beta" includes transforming growth factor-beta as well as functional equivalents, derivatives and analogs thereof. TGF-beta is a polypeptide produced in a latent propeptide form having, at this time, no identified biological activity. To be rendered active and, therefore, capable of inhibiting vascular smooth muscle cell proliferation, the propeptide form of TGF-beta must be cleaved. Functional equivalents of TGF-beta are, for example, moieties capable of disrupting cyclin-dependent protein kinase (CDK) transformation from a slow migrating form to a rapid migrating form, disrupting CDK-cyclin complex formation or activation or the like.

"TGF-beta activator" includes moieties capable of directly or indirectly activating the latent form of TGF-beta to the active form thereof. Plasmin, plasmin activators, tamoxifen as well as analogs, derivatives or functional equivalents thereof are exemplary TGF-beta activators useful in the practice of the present invention.

"TGF-beta production stimulator" includes moieties capable of directly or indirectly stimulating the production of TGF-beta (generally the latent form thereof). Such TGF-beta production stimulators may be TGF-beta mRNA regulators (i.e., moieties that increase the production of TGF-beta RNA), enhancers of TGF-beta mRNA expression or the like.

"Direct" action implies that a first moiety acts on a second moiety, e.g., a TGF-beta activator acts on the latent form of TGF-beta. Such direct action of TGF-beta production stimulators indicates that cells upon which the production stimulate acts to increase TGF-beta mRNA production or expression of TGF-beta.

"Indirect" action implies that a first moiety acts on one or more intermediate moieties, one of which ultimately acts on the second moiety, e.g., a TGF-beta activator acts on a moiety that itself or through one or more other moieties acts on latent TGF-beta. Such indirect action of TGF-beta production stimulators indicates that the stimulators act on a moiety that itself or through one or more other moieties acts on a population of cells to stimulate the production of TGF-beta mRNA or the expression of TGF-beta.

As referred to herein, "taxol" includes taxol, analogs thereof such as taxotere as well as functional equivalents or derivatives thereof. Taxol is readily taken up into cells and stabilizes such cells against cell division.

As referred to herein, a "cytostatic agent" includes moieties capable of inhibiting one or more pathological activities of target cells for a time sufficient to achieve a therapeutic benefit.

As referred to herein, smooth muscle cells and pericytes include those cells derived from the medial layers of vessels and adventitia vessels which proliferate in intimal hyperplastic vascular sites following injury, such as that caused during PTCA.

Characteristics of smooth muscle cells include a histological morphology (under light microscopic examination) of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus. The majority of the sarcoplasm is occupied by thin, parallel myofilaments that may be, for the most part, oriented to the long axis of the muscle cell. These actin containing myofibrils may be arranged in bundles with mitochondria interspersed among them. Scattered through the contractile substance of the cell may also be oval dense areas, with similar dense areas distributed at intervals along the inner aspects of the plasmalemma.

Characteristics of pericytes include a histological morphology (under light microscopic examination) characterized by an irregular cell shape. Pericytes are found within the basement membrane that surrounds vascular endothelial cells and their identity may be confirmed by positive immuno-staining with antibodies specific for alpha smooth muscle actin (e.g., anti-alpha-sm1, Biomakor, Rehovot, Israel), HMW-MAA, and pericyte ganglioside antigens such as MAb 3G5 (11); and, negative immuno-staining with antibodies to cytokeratins (i.e., epithelial and fibroblast markers) and von Willdebrand factor (i.e., an endothelial marker). Both vascular smooth muscle cells and pericytes are positive by immunostaining with the NR-AN-01 monoclonal antibody.

The therapeutic conjugates and dosage forms of the invention are useful for inhibiting the activity of vascular smooth muscle cells, e.g., for reducing, delaying, or eliminating stenosis following angioplasty. As used herein the term "reducing" means decreasing the intimal thickening that results from stimulation of smooth muscle cell proliferation following angioplasty, either in an animal model or in man. "Delaying" means delaying the time until onset of visible intimal hyperplasia (e.g., observed histologically or by angiographic examination) following angioplasty and may also be accompanied by "reduced" restenosis. "Eliminating" restenosis following angioplasty means completely "reducing" and/or completely "delaying" intimal hyperplasia in a patient to an extent which makes it no longer necessary to surgically intervene, i.e., to re-establish a suitable blood flow through the vessel by repeat angioplasty, atheroectomy, or coronary artery bypass surgery. The effects of reducing, delaying, or eliminating stenosis may be determined by methods routine to those skilled in the art including, but not limited to, angiography, ultrasonic evaluation, fluoroscopic imaging, fiber optic endoscopic examination or biopsy and histology. The therapeutic conjugates of the invention achieve these advantageous effects by specifically binding to the cellular membranes of smooth muscle cells and pericytes.

Therapeutic conjugates of the invention are obtained by coupling a vascular smooth muscle binding protein to a therapeutic agent. In the therapeutic conjugate, the vascular smooth muscle binding protein performs the function of targeting the therapeutic conjugate to vascular smooth muscle cells or pericytes, and the therapeutic agent performs the function of inhibiting the cellular activity of the smooth muscle cell or pericyte.

Therapeutic dosage forms (sustained release-type) of the present invention exhibit the capability to deliver therapeutic agent to target cells over a sustained period of time. Therapeutic dosage forms of this aspect of the present invention may be of any configuration suitable for this purpose. Preferred sustained release therapeutic dosage forms exhibit one or more of the following characteristics:

- microparticulate (e.g., from about 0.5 micrometers to about 100 micrometers in diameter, with from about 0.5 to about 2 micrometers more preferred) or nanoparticulate (e.g., from about 1.0 nanometer to about 1000 nanometers in diameter, with from about 50 to about 250 nanometers more preferred), free flowing powder structure;
- biodegradable structure designed to biodegrade over a period of time between from about 3 to about 180 days, with from about 10 to about 21 days more preferred, or non-biodegradable structure to allow therapeutic agent diffusion to occur over a time period of between from about 3 to about 180 days, with from about 10 to about 21 days preferred;
- biocompatible with target tissue and the local physiological environment into which the dosage form is being administered, including biocompatible biodegradation products;
- facilitate a stable and reproducible dispersion of therapeutic agent therein, preferably to form a therapeutic agent-polymer matrix, with active therapeutic agent release occurring through one or both of the following routes: (1) diffusion of the therapeutic agent through the dosage form (when the therapeutic agent is soluble in the polymer or polymer mixture forming the dosage form); or (2) release of the therapeutic agent as the dosage form biodegrades; and
- capability to bind with one or more cellular and/or interstitial matrix epitopes, with from about 1 to about 10,000 binding protein/peptide-dosage form bonds preferred and with a maximum of about 1 binding peptide-dosage form per 150 square angstroms of particle surface area more preferred. The total number bound depends upon the particle size used. The binding proteins or peptides are capable of coupling to the particulate therapeutic dosage form through covalent ligand sandwich or non-covalent modalities as set forth herein.

Nanoparticulate sustained release therapeutic dosage forms of preferred embodiments of the present invention are biodegradable and bind to the vascular smooth muscle cells and enter such cells primarily by endocytosis. The biodegradation of such nanoparticulates occurs over time (e.g., 10 to 21 days) in prelysosomic vesicles and lysosomes. The preferred larger microparticulate therapeutic dosage forms of the present invention bind to the target cell surface or interstitial matrix, depending on the binding protein or peptide selected, and release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the present invention depends on the morphology, physiology and metabolic processes of those cells.

The size of the targeted sustained release therapeutic particulate dosage forms is also important with respect to the mode of cellular assimilation. For example, the smaller nanoparticles can flow with the interstitial fluid between cells and penetrate the infused tissue until it binds to the normal or neoplastic tissue that the binding protein/peptide is selected to target. This feature is important, for example, because the nanoparticles follow lymphatic drainage channels from infused primary neoplastic foci, targeting metastatic foci along the lymphatic tract. The larger microparticles tend to be more easily trapped interstitially in the infused primary tissue.

Preferable sustained release dosage forms of the present invention are biodegradable microparticulates or nanoparticulates. More preferably, biodegradable microparticles or nanoparticles are formed of a polymer containing matrix that biodegrades by random, nonenzymatic, hydrolytic scissioning to release therapeutic agent, thereby forming pores within the particulate structure.

Polymers derived from the condensation of alpha hydroxycarboxylic acids and related lactones are preferred for use in the present invention. A particularly preferred moiety is formed of a mixture of thermoplastic polyesters (e.g., polylactide or polyglycolide) or a copolymer of lactide and glycolide components, such as poly(lactide-co-glycolide). An exemplary structure, a random poly(DL-lactide-co-glycolide), is shown below, with the values of x and y being manipulable by a practitioner in the art to achieve desirable microparticulate or nanoparticulate properties.

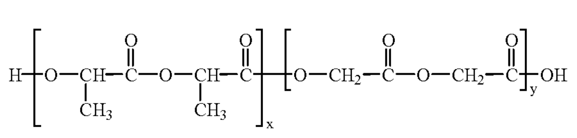

Other agents suitable for forming particulate dosage forms of the present invention include polyorthoesters and polyacetals (*Polymer Letters,* 18:293, 1980) and polyorthocarbonates (U.S. Pat. No. 4,093,709) and the like.

Preferred lactic acid/glycolic acid polymer containing matrix particulates of the present invention are prepared by emulsion-based processes, that constitute modified solvent extraction processes such as those described by Cowsar et al., "Poly(Lactide-Co-Glycolide) Microcapsules for Controlled Release of Steroids," *Methods Enzymology,* 112:101-116, 1985 (steroid entrapment in microparticulates); Eldridge et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies," *Infection and Immunity,* 59:2978-2986, 1991 (toxoid entrapment); Cohen et al., "Controlled Delivery Systems for Proteins Based on Poly(Lactic/Glycolic Acid) Microspheres," *Pharmaceutical Research,* 8(6):713-720, 1991 (enzyme entrapment); and Sanders et al., "Controlled Release of a Luteinizing Hormone-Releasing Hormone Analogue from Poly(D,L-Lactide-Co-Glycolide) Microspheres," *J. Pharmaceutical Science,* 73(9):1294-1297, 1984 (peptide entrapment).

In general, the procedure for forming particulate dosage forms of the present invention involves dissolving the polymer in a halogenated hydrocarbon solvent, dispersing a therapeutic agent solution (preferably aqueous) therein, and adding an Additional agent that acts as a solvent for the halogenated hydrocarbon solvent but not for the polymer. The polymer precipitates out from the polymer-halogenated hydrocarbon solution onto droplets of the therapeutic agent containing solution and entraps the therapeutic agent. Preferably the therapeutic agent is substantially uniformly dispersed within the sustained release dosage form of the present invention. Following particulate formation, they are washed and hardened with an organic solvent. Water washing and aqueous non-ionic surfactant washing steps follow, prior to drying at room temperature under vacuum.

For biocompatibility purposes, particulate dosage forms, characterized by a therapeutic agent dispersed therein in matrix form, are sterilized prior to packaging, storage or administration. Sterilization may be conducted in any convenient manner therefor. For example, the particulates can be irradiated with gamma radiation, provided that exposure to such radiation does not adversely impact the structure or function of the therapeutic agent dispersed in the therapeutic agent-polymer matrix or the binding protein/peptide attached thereto. If the therapeutic agent or binding protein/peptide is so adversely impacted, the particulate dosage forms can be produced under sterile conditions.

Release of the therapeutic agent from the particulate dosage forms of the present invention can occur as a result of both diffusion and particulate matrix erosion. Biodegradation rate directly impacts therapeutic agent release kinetics. The biodegradation rate is regulable by alteration of the composition or structure of the sustained release dosage form. For example, alteration of the lactide/glycolide ratio in preferred dosage forms of the present invention can be conducted, as described by Tice et al., "Biodegradable Controlled-Release Parenteral Systems," *Pharmaceutical Technology, pp.* 26-35, 1984; by inclusion of polymer hydrolysis modifying agents, such as citric acid and sodium carbonate, as described by Kent et al., "Microencapsulation of Water Soluble Active Polypeptides," U.S. Pat. No. 4,675,189; by altering the loading of therapeutic agent in the lactide/glycolide polymer, the degradation rate being inversely proportional to the amount of therapeutic agent contained therein, and by judicious selection of an appropriate analog of a common family of therapeutic agents that exhibit different potencies so as to alter said core loadings; and by variation of particulate size, as described by Beck et al., "Poly(DL-Lactide-Co-Glycolide)/Norethisterone Microcapsules: An Injectable Biodegradable Contraceptive," *Biol. Reprod.,* 28:186-195, 1983, or the like. All of the aforementioned methods of regulating biodegradation rate influence the intrinsic viscosity of the polymer containing matrix, thereby altering the hydration rate thereof.

The preferred lactide/glycolide structure is biocompatible with the mammalian physiological environment. Also, these preferred sustained release_dosage forms have the advantage that biodegradation thereof forms lactic acid and glycolic acid, both normal metabolic products of mammals.

Functional groups required for binding protein/peptide-particulate dosage form bonding to the particles, are optionally included in the particulate structure, along with the non-degradable or biodegradable polymeric units. Functional groups that are exploitable for this purpose include those that are reactive with peptides, such as carboxyl groups, amine groups, sulfhydryl groups and the like. Preferred binding enhancement moieties include the terminal carboxyl groups of the preferred (lactide-glycolide) polymer containing matrix or the like.

Useful vascular smooth muscle binding protein is a polypeptide, peptidic, or mimetic compound (as described below) that is capable of binding to a target or marker on a surface component of an intact or disrupted vascular smooth muscle cell in such a manner that allows for either release of therapeutic agent extracellularly in the immediate interstitial matrix with subsequent diffusion of therapeutic agent into the remaining intact smooth muscle cells and/or internalization by the cell into an intracellular compartment of the entire targeted biodegradable moiety, permitting delivery of the therapeutic agent. Representative examples of useful vascular smooth muscle binding proteins include antibodies (e.g., monoclonal and polyclonal affinity-purified antibodies, $F(ab')_2$, Fab', Fab, and Fv fragments and/or complementarity determining regions (CDR) of antibodies or functional equivalents thereof, (e.g., binding peptides and the like)); growth factors, cytokines, and polypeptide hormones and the like; and macromolecules recognizing extracellular matrix receptors (e.g., integrin and fibronectin receptors and the like).

Other preferred binding peptides useful in targeting the dosage form embodiment of the present invention include those that localize to intercellular stroma and matrix located between and among vascular smooth muscle cells. Such binding peptides deliver the therapeutic agent to the interstitial space between the target cells. The therapeutic agent is released into such interstitial spaces for subsequent uptake by the vascular smooth muscle cells. Preferred binding peptides of this type are associated with epitopes on collagen, extracellular glycoproteins such as tenascin, reticulum and elastic fibers and other intercellular matrix material.

Preferred tumor cell binding peptides are associated with epitopes of myc, ras, bcr/Abl, erbB and like gene products, as well as mucins, cytokine receptors such as IL-6, EGF, TGF and the like, which binding peptides localize to certain lymphomas (myc), carcinomas such as colon cancer (ras), carcinoma (erbB), adenocarcinomas (mucins), breast cancer and hepatoma (IL-6 receptor), and breast cancer (EGF and TGF), respectively. Preferred immune system effector cell-binding peptides are anti-TAC, IL-2 and the like, which localize to activated T cells and macrophages, respectively. Other preferred binding proteins/peptides useful in the practice of the present invention include moieties capable of localizing to pathologically proliferating normal tissues, such as pericytes of the intraocular vasculature implicated in degenerative eye disease.

Therapeutic agents of the invention are selected to inhibit a cellular activity of a vascular smooth muscle cell, e.g., proliferation, migration, increase in cell volume, increase in extracellular matrix synthesis (e.g., collagens, proteoglycans, and the like), or secretion of extracellular matrix materials by the cell. Preferably, the therapeutic agent acts either: a) as a "cytostatic agent" to prevent or delay cell division in proliferating cells by inhibiting replication of DNA (e.g., a drug such as adriamycin, staurosporin, tamoxifen or the like), or by inhibiting spindle fiber formation (e.g., a drug such as colchicine) and the like; or b) as an inhibitor of migration of vascular smooth muscle cells from the medial wall into the intima, e.g., an "anti-migratory agent" such as a cytochalasin; or c) as an inhibitor of the intracellular increase in cell volume (i.e., the tissue volume occupied by a cell; a "cytoskeletal inhibitor" or "metabolic inhibitor"); or d) as an inhibitor that blocks cellular protein synthesis and/or secretion or organization of extracellular matrix (i.e., an "anti-matrix agent" such as tamoxifen).

Representative examples of "cytostatic agents" include, e.g., modified toxins, methotrexate, adriamycin, radionuclides (e.g., such as disclosed in Fritzberg et al., U.S. Pat. No. 4,897,255), protein kinase inhibitors (e.g., staurosporin), stimulators of the production or activation of TGF-beta, including tamoxifen and functional equivalents or derivatives thereof, TGF-beta or functional equivalents, derivatives or analogs thereof, taxol or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like, which when delivered into a cellular compartment at an appropriate dosage will act to impair proliferation of a smooth muscle cell or pericyte without killing the cell. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors, (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents for smooth muscle proliferation include: subfragments of heparin, triazolopyrimidine (Trapidil; a PDGF antagonist), lovastatin, and prostaglandins E1 or I2.

Representative examples of "anti-migratory agents" include inhibitors (i.e., agonists and antagonists, and competitive or non-competitive inhibitors) of chemotactic factors and their receptors (e.g., complement chemotaxins such as C5a, C5a desarg or C4a; extracellular matrix factors, e.g., collagen degradation fragments), or of intracellular cytoskeletal proteins involved in locomotion (e.g., actin, cytoskeletal elements, and phosphatases and kinases involved in locomotion). Representative examples of useful therapeutic agents in this category of anti-migratory agents include: caffeic acid derivatives and nilvadipine (a calcium antagonist), and steroid hormones. Preferred anti-migratory therapeutic agents are the cytochalasins.

Representative examples of "cytoskeletal inhibitors" include colchicine, vinblastin, cytochalasins, taxol and the like that act on microtubule and microfilament networks within a cell.

Representative examples of "metabolic inhibitors" include staurosporin, trichothecenes, and modified diphtheria and ricin toxins, *Pseudomonas* exotoxin and the like. In a preferred embodiment, the therapeutic conjugate is constructed with a therapeutic agent that is a simple trichothecene or a macrocyclic trichothecene, e.g., a verrucarin or roridin. Trichothecenes are drugs produced by soil fungi of the class *Fungi imperfecti* or isolated from *Baccharus megapotamica* (Bamburg, J. R. *Proc. Molec. Subcell. Biol.* 8:41-110, 1983; Jarvis & Mazzola, *Acc. Chem. Res.* 15:338-395, 1982). They appear to be the most toxic molecules that contain only carbon, hydrogen and oxygen (Tamm, C. *Fortschr. Chem. Org. Naturst.* 31:61-117, 1974). They are all reported to act at the level of the ribosome as inhibitors of protein synthesis at the initiation, elongation, or termination phases.

There are two broad classes of trichothecenes: those that have only a central sesquiterpenoid structure and those that have an additional macrocyclic ring (simple and macrocyclic trichothecenes, respectively). The simple trichothecenes may be subdivided into three groups (i.e., Group A, B, and C) as described in U.S. Pat. Nos. 4,744,981 and 4,906,452 (incorporated herein by reference). Representative examples of Group A simple trichothecenes include: Scirpene, Roridin C, dihydrotrichothecene, Scirpen-4,8-diol, Verrucarol, Scirpentriol, T-2 tetraol, pentahydroxyscirpene, 4-deacetylneosolaniol, trichodermin, deacetylcalonectrin, calonectrin, diacetylverrucarol, 4-monoacetoxyscirpenol, 4,15-diacetoxyscirpenol, 7-hydroxydiacetoxyscirpenol, 8-hydroxydiacetoxy-scirpenol (Neosolaniol), 7,8-dihydroxydiacetoxyscirpenol 7-hydroxy-8-acetyldiacetoxyscirpenol, 8-acetylneosolaniol, NT-1, NT-2, HT-2, T-2, and acetyl T-2 toxin.

Representative examples of Group B simple trichothecenes include: Trichothecolone, Trichothecin, deoxynivalenol, 3-acetyldeoxynivalenol, 5-acetyldeoxynivalenol, 3,15-diacetyldeoxynivalenol, Nivalenol, 4-acetylnivalenol (Fusarenon-X), 4,15-idacetylnivalenol, 4,7,15-triacetylnivalenol, and tetra-acetylnivalenol. Representative examples of Group C simple trichothecenes include: Crotocol and Crotocin. Representative macrocyclic trichothecenes include Verrucarin A, Verrucarin B, Verrucarin J (Satratoxin C), Roridin A, Roridin D, Roridin E (Satratoxin D), Roridin H, Satratoxin F, Satratoxin G, Satratoxin H, Vertisporin, Mytoxin A, Mytoxin C, Mytoxin B, Myrotoxin A, Myrotoxin B, Myrotoxin C, Myrotoxin D, Roritoxin A, Roritoxin B, and Roritoxin D. In addition, the general "trichothecene" sesquiterpenoid ring structure is also present in compounds termed "baccharins" isolated from the higher plant *Baccharis megapotamica*, and these are described in the literature, for instance as disclosed by Jarvis et al. (Chemistry of Alleopathy, ACS Symposium Series No. 268: ed. A. C. Thompson, 1984, pp. 149-159).

Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

For the sustained release dosage form embodiments of the present invention, therapeutic agents preferably are those that inhibit vascular smooth muscle cell activity without killing the cells (i.e., cytostatic therapeutic agents). Another way to define a cytostatic agent is a moiety capable of inhibiting one or more pathological activities of the target cells for a time sufficient to achieve a therapeutic benefit. Preferred therapeutic agents for this purpose exhibit one or more of the following capabilities: to inhibit DNA synthesis prior to protein synthesis inhibition or to inhibit migration of vascular smooth muscle cells into the intima. These therapeutic agents do not significantly inhibit protein synthesis (i.e., do not kill the target cells) and, therefore, facilitate cellular repair and matrix production to stabilize the vascular wall lesion caused by angioplasty, by reducing smooth muscle cell proliferation.

Exemplary of such preferred therapeutic agents are protein kinase inhibitors, such as staurosporin (staurosporine is available from Sigma Chemical Co., St. Louis, Mo.) cytochalasins, such as cytochalasin B (Sigma Chemical Co.), and suramin (FBA Pharmaceuticals, West Haven, Conn.), as well as nitroglycerin (DuPont Pharmaceuticals, Inc., Manuti, Puerto Rico) or analogs or functional equivalents thereof. These compounds are cytostatic and have been shown to exert minimal protein synthesis inhibition and cytotoxicity at concentrations where significant DNA synthesis inhibition occurs (see Example 8 and FIGS. 10A-10D). Other exemplary preferred therapeutic agents are TGF-beta activators or production stimulators, such as tamoxifen and functional equivalents or derivatives thereof. TGF-beta and its analogs, derivatives or functional equivalents may also be employed. Taxol and its analogs, derivatives or functional equivalents are also useful in the practice of the present invention. A useful protocol for identifying therapeutic agents useful in sustained release dosage form embodiments of the present invention is set forth in Example 8, for example. A practitioner in the art is capable of designing substantially equivalent experimental protocols for making such an identification for different target cell populations, such as adherent monolayer target cell types.

Other embodiments of the present invention involve agents that are cytotoxic to cancer cells. Preferred agents for these embodiments are Roridin A, *Pseudomonas* exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

Modulation of immune system-mediated disease effector cells can also be accomplished using the sustained release dosage forms of the present invention. Such modulation is preferably conducted with respect to diseases having an effector cell population that is accessible through local sustained release dosage form administration. Therapeutic moieties having the requisite modulating activity, e.g., cytocidal, cytostatic, metabolism modulation or like activity upon lymphorecticular cells in the treatment of arthritis (intra-articular administration), sprue (oral administration), uveitis and endophthalmitis (intra-ocular administration) and keratitis (sub-conjunctival administration), are identifiable using techniques that are known in the art. These agents can also be used to reduce hyperactivity of epithelial glands and endocrine organs that results in multiple disorders. Preferred agents for these embodiments include Roridin A, *Pseudomonas* exotoxin, suramin, protein kinase inhibitors (e.g., staurosporin), TGF-beta and TGF-beta activators or production stimulators such as tamoxifen, taxol and the like, or analogs or functional equivalents thereof.

Other preferred therapeutic agents useful in the practice of the present invention include moieties capable of reducing or eliminating pathological proliferation, migration or hyperactivity of normal tissues. Exemplary of such therapeutic agents are those capable of reducing or eliminating hyperactivity of corneal epithelium and stroma, pathological proliferation or prolonged contraction of smooth muscle cells or pericytes of the intraocular vasculature implicated in degenerative eye disease resulting from hyperplasia or decreased vascular lumen area. Preferred agents for this purpose are TGF-beta and TGF-beta activators or production stimulators such as tamoxifen, taxol and analogs thereof, staurosporin and cytochalasin B as well as functional equivalents or derivatives thereof.

Vascular smooth muscle binding proteins of the invention bind to targets on the surface of vascular smooth muscle cells. It will be recognized that specific targets, e.g., polypeptides or carbohydrates, proteoglycans and the like, that are associated with the cell membranes of vascular smooth muscle cells are useful for selecting (e.g., by cloning) or constructing (e.g., by genetic engineering or chemical synthesis) appropriately specific vascular smooth muscle binding proteins. Particularly useful "targets" are internalized by smooth muscle cells, e.g., as membrane constituent antigen turnover occurs in renewal. Internalization by cells may also be by mechanisms involving phagolysosomes, clathrin-coated pits, receptor-mediated redistribution or endocytosis and the like. In a preferred embodiment, such a "target" is exemplified by chondroitin sulfate proteoglycans (CSPGs) synthesized by vascular smooth muscle cells and pericytes, and a discrete portion (termed an epitope herein) of the CSPG molecule having an apparent molecular weight of about 250 kD is especially preferred. The 250 kD target is an N-linked glycoprotein that is a component of a larger 400 kD proteoglycan complex (14). In one presently preferred embodiment of the invention, a vascular smooth muscle binding protein is provided by NR-AN-01 monoclonal antibody (a subculture of NR-ML-05) that binds to an epitope in a vascular smooth muscle CSPG target molecule. The monoclonal antibody designated NR-ML-05 reportedly binds a 250 kD CSPG synthesized by melanoma cells (Morgan et al., U.S. Pat. No. 4,897,255). Smooth muscle cells and pericytes also reportedly synthesize a 250 kD CSPG as well as other CSPGs (11). NR-ML-05 binding to smooth muscle cells has been disclosed (Fritzberg et al., U.S. Pat. No. 4,879,225). Monoclonal antibody NR-ML-05 and subculture NR-ML-05 No. 85-41-4I-A2, freeze # A2106, have both been deposited with the American Type Culture Collection, Rockville, Md. and granted Accession Nos. HB-5350 and HB-9350, respectively. NR-ML-05 is the parent of, and structurally and functionally equivalent to, subclone NR-AN-01, disclosed herein. It will be recognized that NR-AN-01 is just one example of a vascular smooth muscle binding protein that specifically associates with the 400 kD CSPG target, and that other binding proteins associating with this target and other epitopes in this target (14) are also useful in the therapeutic conjugates and methods of the invention. In the present case, six other murine monoclonal antibodies and two human chimeric monoclonal antibodies have also been selected, as described herein, that specifically target to the 250 kD CSPG of vascular smooth muscle cells. The antibodies also appear to be internalized by the smooth muscle cells following binding to the cell membrane. Immunoreactivity studies have also shown the binding of the murine MAbs to the 250 kD antigen in 45 human normal tissues and 30 different neoplasms and some of these results have been disclosed previously (U.S. Pat. No. 4,879,225). In this disclosure and other human clinical studies, MAbs directed to the CSPG 250 kD antigen localized to vascular smooth muscle cells in vivo. Further, it will be recognized that the amino acid residues involved in the multi-point kinetic association of the NR-AN-01 monoclonal antibody with a CSPG marker antigenic epitope (i.e., the amino acids constituting the complementarity determining regions) are determined by computer-assisted molecular modeling and by the use of mutants having altered antibody binding affinity. The binding-site amino acids and three dimensional model of the NR-AN-01 antigen binding site serve as a molecular model for constructing functional equivalents, e.g., short polypeptides ("minimal polypeptides"), that have binding affinity for a CSPG synthesized by vascular smooth muscle cells and pericytes.

In a presently preferred embodiment for treating stenosis following vascular surgical procedures, e.g., PTCA, selected binding proteins, e.g., antibodies or fragments, for use in the practice of the invention have a binding affinity of $>10^4$ liter/mole for the vascular smooth muscle 250 kD CSPG, and also the ability to be bound to and internalized by smooth muscle cells or pericytes.

Three-dimensional modeling is also useful to construct other functional equivalents that mimic the binding of NR-AN-01 to its antigenic epitope, e.g., "mimetic" chemical compounds that mimic the three-dimensional aspects of NR-AN-01 binding to its epitope in a CSPG target antigen. As used herein, "minimal polypeptide" refers to an amino acid sequence of at least six amino acids in length. As used herein, the term "mimetic" refers to an organic chemical polymer constructed to achieve the proper spacing for binding to the amino acids of, for example, an NR-AN-01 CSPG target synthesized by vascular smooth muscle cells or pericytes.

It will be recognized that the inventors also contemplate the utility of human monoclonal antibodies or "humanized" murine antibody as a vascular smooth muscle binding protein in the therapeutic conjugates of their invention. For example, murine monoclonal antibody may be "chimerized" by genetically recombining the nucleotide sequence encoding the murine Fv region (i.e., containing the antigen binding sites) with the nucleotide sequence encoding a human constant domain region and an Fc region, e.g., in a manner similar to that disclosed in European Patent Application No. 0,411,893 A2. Some murine residues may also be retained within the human variable region framework domains to ensure proper target site binding characteristics. Humanized vascular smooth muscle binding partners will be recognized to have the advantage of decreasing the immunoreactivity of the antibody or polypeptide in the host recipient, which may thereby be useful for increasing the in vivo half-life and reducing the possibility of adverse immune reactions.

Also contemplated as useful binding peptides for restenosis treatment sustained release dosage forms of the present invention are those that localize to intercellular stroma and matrix located between and among vascular smooth muscle cells. Such binding peptides deliver the therapeutic agent to the interstitial space between the target cells. The therapeutic agent is released into such interstitial spaces for subsequent uptake by the vascular smooth muscle cells. Preferred binding peptides of this type are associated with epitopes on collagen, extracellular glycoproteins such as tenascin, reticulum and elastic fibers, cytokeratin and other intercellular matrix components. Minimal peptides, mimetic organic chemical compounds, human or humanized monoclonal antibodies and the like that localize to intracellular stroma and matrix are also useful as binding peptides in this embodiment of the present invention. Such binding peptides may be identified and constructed or isolated in accordance with known techniques. In preferred embodiments of the present invention, the interstitial matrix binding protein binds to a target epitope with an association constant of at least about $10^{-4}$ M.

Useful binding peptides for cancer treatment embodiments of the present invention include those associated with cell membrane and cytoplasmic epitopes of cancer cells and the like. These binding peptides localize to the surface membrane of intact cells and internal epitopes of disrupted cells, respectively, and deliver the therapeutic agent for assimilation into the target cells. Minimal peptides, mimetic organic compounds and human or humanized antibodies that localize to the requisite tumor cell types are also useful as binding peptides of the present invention. Such binding peptides may be identified and constructed or isolated in accordance with known techniques. Preferred binding peptides of these embodiments of the present invention bind to a target epitope with an association constant of at least about $10^{-6}$M.

Binding peptides to membrane and cytoplasmic epitopes and the like that localize to immune system-mediated disease effector cells, e.g., cells of the lymphoreticular system, are also useful to deliver sustained release dosage forms of the present invention. The therapeutic agent is delivered to target cells for internalization therein by such sustained release dosage forms. Minimal peptides, mimetic organic compounds and human or humanized antibodies that localize to the requisite effector cell types are also useful as binding peptides of the present invention. Such binding peptides may be identified and constructed or isolated in accordance with known techniques. Preferred binding peptides of these embodiments of the present invention bind to a target epitope with an association constant of at least about $10^{-6}$ M.

Other preferred binding proteins or peptides useful in the practice of the present invention include moieties capable of localizing to pathologically proliferating normal tissues, such as pericytes of the intraocular vasculature implicated in degenerative eye disease. The therapeutic agent is delivered to target cells for internalization therein by such sustained release dosage forms. Minimal peptides, mimetic organic compounds and human or humanized antibodies that localize to the requisite pathologically proliferating normal cell types are also useful as binding peptides of the present invention. Such binding peptides may be identified and constructed or isolated in accordance with known techniques. Preferred binding peptides of these embodiments of the present invention bind to a target epitope with an association constant of at least about $10^{-6}$M.

Representative "coupling" methods for linking the therapeutic agent through covalent or non-covalent bonds to the vascular smooth muscle binding protein include chemical cross-linkers and heterobifunctional cross-linking compounds (i.e., "linkers") that react to form a bond between reactive groups (such as hydroxyl, amino, amido, or sulfhydryl groups) in a therapeutic agent and other reactive groups (of a similar nature) in the vascular smooth muscle binding protein. This bond may be, for example, a peptide bond, disulfide bond, thioester bond, amide bond, thioether bond, and the like. In one illustrative example, conjugates of monoclonal antibodies with drugs have been summarized by Morgan and Foon (Monoclonal Antibody Therapy to Cancer: Preclinical Models and Investigations, *Basic and Clinical Tumor Immunology*, Vol. 2, Kluwer Academic Publishers, Hingham, Mass.) and by Uhr *J. of Immunol.* 133:i-vii, 1984). In another illustrative example where the conjugate contains a radionuclide cytostatic agent, U.S. Pat. No. 4,897,255, Fritzberg et al., incorporated herein by reference, is instructive of coupling methods that may be useful. In one presently preferred embodiment, the therapeutic conjugate contains a vascular smooth muscle binding protein coupled covalently to a trichothecene drug. In this case, the covalent bond of the linkage may be formed between one or more amino, sulfhydryl, or carboxyl groups of the vascular smooth muscle binding protein and a) the trichothecene itself; b) a trichothecene hemisuccinate carboxylic acid; c) a trichothecene hemisuccinate (HS) N-hydroxy succinimidate ester; or d) trichothecene complexes with poly-L-lysine or any polymeric carrier. Representative examples of coupling methods for preparing therapeutic conjugates containing a trichothecene therapeutic agent are described in U.S. Pat. Nos. 4,906,452 and 4,744,981, incorporated herein by reference. Other examples using a hydrazide for forming a Schiff base linkage between binding proteins and trichothecenes are disclosed in pending U.S. patent application Ser. No. 07/415,154, incorporated herein by reference.

The choice of coupling method will be influenced by the choice of vascular smooth muscle binding protein or peptide, interstitial matrix binding protein or peptide and therapeutic agent, and also by such physical properties as, e.g., shelf life stability, and/or by such biological properties as, e.g., half-life in cells and blood, intracellular compartmentalization route, and the like. For example, in one presently preferred therapeutic conjugate, hemisuccinate conjugates of the Roridin A therapeutic agent have a longer serum half-life than those of Verrucarin A, and this increased stability results in a significantly increased biological activity.

The sustained release embodiment of the present invention includes a therapeutic agent dispersed within a non-biodegradable or biodegradable polymeric structure. Such dispersion is conducted in accordance with the procedure described by Cowsar et al., "Poly(Lactide-Co-Glycolide) Microcapsules for Controlled Release of Steroids," *Methods Enzvmology,* 112:101-116, 1985; Eldridge et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies," *Infection and Immunity,* 59:2978-2986, 1991; Cohen et al., "Controlled Delivery Systems for Proteins Based on Poly(Lactic/Glycolic Acid) Microspheres," *Pharmaceutical Research,* 8(6):713-720, 1991; and Sanders et al., "Controlled Release of a Luteinizing Hormone-Releasing Hormone Analogue from Poly(D,L-Lactide-Co-Glycolide) Microspheres," *J. Pharmaceutical Science,* 73(91:1294-1297, 1984.

The physical and chemical character of the sustained release dosage form of the present invention is amenable to several alternative modes of attachment to binding proteins or peptides. Dosage forms (sustained release-type) of the present invention are capable of binding to binding proteins/peptides through, for example, covalent linkages, intermediate ligand sandwich attachment, or non-covalent adsorption or partial entrapment. When the preferred polylactic/glycolic acid particulates are formed with the therapeutic agent dispersed therein, the uncharged polymer backbone is oriented both inward (with the quasi lipophilic therapeutic agent contained therein) and outward along with a majority of the terminal carboxy groups. These surface carboxy groups may serve as covalent attachment sites when activated by, for example, a carbodiimide) for nucleophilic groups of the binding protein/peptide. Such nucleophilic groups include lysine epsilon amino groups (amide linkage), serine hydroxyl groups (ester linkage) or cysteine mercaptan groups (thioester linkage). Reactions with particular groups depend upon pH and the reduction state of the reaction conditions.

For example, poly-lactic/glycolic acid particulates having terminal carboxylic acid groups are reacted with N-hydroxybenztriazole in the presence of a water soluble carbodiimide of the formula R—N═C═N—R' (wherein R is a 3-dimethylaminopropyl group or the like and R' is an ethyl group or the like). The benztriazole-derivatized particulates (i.e., activated imidate-bearing moieties) are then reacted with a protein/peptide nucleophilic moiety such as an available epsilon amino moiety. Alternatively, p-nitrophenol, tetrafluorophenol, N-hydroxysuccinimide or like molecules are useful to form an active ester with the terminal carboxy groups of poly-lactic/glycolic acid particulates in the presence of carbodiimide. Other binding protein/peptide nucleophilic moieties include hydroxyl groups of serine, endogenous free thiols of cysteine, thiol groups resulting from reduction of binding protein/peptide disulfide bridges using reducing agents commonly employed for that purpose (e.g., cysteine, dithiothreitol, mercaptoethanol and the like) and the like. Additionally, the terminal carboxy groups of the poly lactic/glycolic acid particulates are activatable by reaction with thionyl chloride to form an acyl chloride derivatized moiety. The derivatized particulates are then reacted with binding peptide/protein nucleophilic groups to form targeted dosage forms of the present invention.

Direct sustained release dosage form-binding protein or peptide conjugation may disrupt binding protein/peptide target cell recognition. Ligand sandwich attachment techniques are useful alternatives to achieve sustained release dosage form-binding protein/peptide attachment. Such techniques involve the formation of a primary peptide or protein shell using a protein that does not bind to the target cell population. Binding protein/peptide is then bound to the primary peptide or protein shell to provide the resultant particulate with functional binding protein/peptide. An exemplary ligand sandwich approach involves covalent attachment of avidin or streptavidin to the particulates through functional groups as described above with respect to the "direct" binding approach. The binding protein or peptide is derivatized, preferably minimally, with functionalized biotin (e.g., through active ester, hydrazide, iodoacetal, maleimidyl or like functional groups). Ligand (i.e., binding peptide or protein/functionalized biotin) attachment to the available biotin binding sites of the avidin/streptavidin primary protein shell occurs through the use of a saturating amount of biotinylated protein/peptide.

For example, poly-lactic/glycolic acid particulates having terminal carboxylic acid groups are activated with carbodiimide and subsequently reacted with avidin or streptavidin. The binding protein or peptide is reacted with biotinamidocaproate N-hydroxysuccinimide ester at a 1-3 molar offering of biotin-containing compound to the binding protein/peptide to form a biotinylated binding protein/peptide. A molar excess of the biotinylated binding protein/peptide is incubated with the avidin-derivatized particulates to form a targeted dosage form of the present invention.

Alternatively, the particulate carboxy groups are biotinylated (e.g., through carbodiimide activation of the carboxy group and subsequent reaction with amino alkyl biotinamide). The biotinylated particulates are then incubated with a saturating concentration (i.e., a molar excess) of avidin or streptavidin to form protein coated particulates having free biotin binding sites. Such coated particulates are then capable of reaction with a molar excess of biotinylated binding protein formed as described above. Another option involves avidin or streptavidin bound binding peptide or protein attachment to biotinylated particulates.

In addition, binding protein/peptide-particulate attachment can be achieved by adsorption of the binding peptide to the particulate, resulting from the nonionic character of the partially exposed polymer backbone of the particulate. Under high ionic strength conditions (e.g., 1.0 molar NaCl), hydrogen and hydrophobic particulate-binding protein/peptide binding are favored.

Moreover, binding protein/peptide may be partially entrapped in the particulate polymeric matrix upon formation thereof. Under these circumstances, such entrapped binding protein/peptide provides residual selective binding character to the particulate. Mild particulate formation conditions, such as those employed by Cohen et al., *Pharmaceutical Research,* 8: 713-720 (1991), are preferred for this embodiment of the present invention. Such entrapped binding protein is also useful in target cell reattachment of a partially degraded particulate that has undergone exocytosis. Other polymeric particulate dosage forms (e.g., non-biodegradable dosage forms) having different exposed functional groups can be bound to binding proteins or peptides in accordance with the principles discussed above.

Exemplary non-biodegradable polymers useful in the practice of the present invention are polystyrenes, polypropylenes, styrene acrylic copolymers and the like. Such non-biodegradable polymers incorporate or can be derivatized to incorporate functional groups for attachment of binding protein/peptide, including carboxylic acid groups, aliphatic primary amino groups, aromatic amino groups and hydroxyl groups.

Carboxylic acid functional groups are coupled to binding protein or peptide using, for example, the reaction mechanisms set forth above for poly-lactic/glycolic acid biodegradable polymeric particulate dosage forms. Primary amino functional groups are coupled by, for example, reaction thereof with succinic anhydride to form a terminal carboxy moiety that can be bound to binding peptide/protein as described above. Additionally, primary amino groups can be activated with cyanogen bromide and form guanidine linkages with binding protein/peptide primary amino groups. Aromatic amino functional groups are, for example, diazotized with nitrous acid to form diazonium moieties which react with binding protein/peptide tyrosines, thereby producing a diazo bond between the non-biodegradable particulate and the binding protein/peptide. Hydroxyl functional groups are coupled to binding protein/peptide primary amino groups by, for example, converting the hydroxyl moiety to a terminal carboxylic acid functional group. Such a conversion can be accomplished through reaction with chloroacetic acid followed by reaction with carbodiimide. Sandwich, adsorption and entrapment techniques, discussed above with respect to biodegradable particulates, are analogously applicable to non-biodegradable particulate-binding protein/peptide affixation.

In a preferred embodiment, targeting is specific for potentially proliferating cells that result in increased smooth muscle in the intimal region of a traumatized vascular site, e.g., following angioplasty, e.g., pericytes and vascular smooth muscle cells. Aspects of the invention relate to therapeutic modalities in which the therapeutic conjugate of the invention is used to delay, reduce, or eliminate smooth muscle proliferation after angioplasty, e.g., PTCA, atheroectomy and percutaneous transluminal coronary rotational atheroblation.

In another preferred embodiment, targeting is specific for primary or metastatic tumor foci accessible to local administration, e.g., tumors exposed for infiltration by laparotomy or visible for fluoroscopic or computerized tomography guiding and infusion needle administration to internal tumor foci or tumors confined to a small area or cavity within the mammal, e.g., ovarian cancer located in the abdomen, focal or multifocal liver tumors or the like. Aspects of this embodiment of the invention involve therapeutical modalities wherein the therapeutic agent is cytotoxic to the target cells or metabolically modulates the cells, increasing their sensitivity to chemotherapy and/or radiation therapy.

In another embodiment, targeting is specific for a local administration accessible effector cell population implicated in immune system-mediated diseases, e.g., arthritis, intraocular immune system-mediated disease or sprue. Aspects of this embodiment of the present invention involve therapeutic modalities wherein the therapeutic agent is cytotoxic or modifies the biological response of the target cells to effect a therapeutic objective.

In another embodiment, targeting is specific for a local administration accessible pathologically proliferating or hyperactive normal cell population implicated in, e.g., degenerative eye disease, corneal pannus, hyperactive endocrine glands or the like. Aspects of this embodiment of the present invention involve therapeutic modalities wherein the therapeutic agent reduces or eliminates proliferation or hyperactivity of the target cell population.

For treatment of a traumatized or diseased vascular site, the therapeutic conjugates or dosage forms of the invention may be administered to the host using an infusion catheter, such as produced by C. R. Bard Inc., Billerica, Mass., or that disclosed by Wolinsky (7; U.S. Pat. No. 4,824,436) or Spears (U.S. Pat. No. 4,512,762). In this case, a therapeutically effective dosage of the therapeutic conjugate will be typically reached when the concentration of conjugate in the fluid space between the balloons of the catheter is in the range of about $10^{-3}$ to $10^{-12}$ M. It will be recognized from the Examples provided herewith that therapeutic conjugates of the invention may only need to be delivered in an anti-proliferative therapeutic dosage sufficient to expose the proximal (6 to 9) cell layers of the intimal or tunica media cells lining the lumen to the therapeutic anti-proliferative conjugate, whereas the anti-contractile therapeutic dosage needs to expose the entire tunica media, and further that this dosage can be determined empirically, e.g., by a) infusing vessels from suitable animal model systems and using immunohistochemical methods to detect the conjugate and its effects (e.g., such as exemplified in the EXAMPLES below); and b) conducting suitable in vitro studies such as exemplified in EXAMPLES 3, 4, and 5, below).

In a representative example, this therapeutically effective dosage is achieved by preparing 10 ml of a 200 μg/ml therapeutic conjugate solution, wherein the vascular smooth muscle protein binding protein is NR-AN-01 and the therapeutic agent is Roridin A, a trichothecene drug. For treating vascular trauma, e.g., resulting from surgery or disease (e.g., see below), when the therapeutic conjugate is administered with an infusion catheter, 10 ml will commonly be sufficient volume to fill the catheter and infuse 1 to 1.5 ml into one to three traumatic lesion sites in the vessel wall. It will be recognized by those skilled in the art that desired therapeutically effective dosages of a therapeutic conjugate according to the invention will be dependent on several factors, including, e.g.: a) the binding affinity of the vascular smooth muscle binding protein in the therapeutic conjugate; b) the atmospheric pressure applied during infusion; c) the time over which the therapeutic conjugate administered resides at the vascular site; d) the nature of the therapeutic agent employed; and/or e) the nature of the vascular trauma and therapy desired. Those skilled practitioners trained to deliver drugs at therapeutically effective dosages (e.g., by monitoring drug levels and observing clinical effects in patients) will determine the optimal dosage for an individual patient based on experience and professional judgment. In a preferred embodiment, about 0.3 atm (i.e., 300 mm of Hg) to about 5 atm of pressure applied for 15 seconds to 3 minutes directly to the vascular wall is adequate to achieve infiltration of a therapeutic conjugate containing the NR-AN-01 binding protein into the smooth muscle layers of a mammalian artery wall. Those skilled in the art will recognize that infiltration of the therapeutic conjugate into intimal layers of a diseased human vessel wall will probably be variable and will need to be determined on an individual basis.

Sustained release dosage forms of an embodiment of the invention may only need to be delivered in an anti-proliferative therapeutic dosage sufficient to expose the proximal (6 to 9) cell layers of the tunica media smooth muscle cells lining the lumen to the dosage form. This dosage is determinable empirically, e.g., by a) infusing vessels from suitable animal model systems and using immunohistochemical, fluorescent or electron microscopy methods to detect the dosage form and its effects; and b) conducting suitable in vitro studies.

In a representative example, this therapeutically effective dosage is achieved by determining in smooth muscle cell tissue culture the pericellular agent dosage, which at a continuous exposure results in a therapeutic effect between the toxic and minimal effective doses. This therapeutic level is obtained in vivo by determining the size, number and therapeutic agent concentration and release rate required for particulates infused between the smooth muscle cells of the artery wall to maintain this pericellular therapeutic dosage. The dosage form should release the therapeutic agent at a rate that approximates the pericellular dose of the following exemplary therapeutic agents: from about 0.01 to about 100 micrograms/ml nitroglycerin, from about 1.0 to about 1000 micrograms/ml of suramin, from about 0.001 to about 100 micrograms/ml for cytochalasin, and from about 0.01 to about $10^5$ nanograms/ml of staurosporin as well as from about 0.001 to about 100 micrograms/ml taxol.

For TGF-beta activators or production stimulators, such as tamoxifen, several exemplary dosing regimens are contemplated, depending upon the condition being treated and the stage to which the condition has progressed. For prophylactic purposes with respect to atherosclerosis, for example, a low chronic dose sufficient to elevate in vivo TGF-beta production or activation is contemplated. An exemplary dose of this type is about 0.1 mg/kg/day (ranging between about 0.1 and about 10 mg/kg/day). Another exemplary dose range is from about 0.01 to about 1000 micrograms/ml. Low doses, such as 0.1 ng/Kg/day, are also contemplated for use with respect to ameliorating stenosis following relatively low trauma injury or intervention, such as vein grafts or transplants or organ allografts, for example. No adverse side effects (e.g., nausea as experienced by recipients of higher dose administrations when tamoxifen has been employed in the treatment of breast cancer) are anticipated with respect to these chronic or low dosing regimens.

For prevention of restenosis following angioplasty, an example of a higher trauma injury or intervention resulting in a stronger acute proliferative stimulus to smooth muscle cells, a higher dose would be required. For example, a dosing regimen is contemplated which involves a single "pre-loading" dose (or multiple, smaller pre-loading doses) given before or at the time of the intervention, with a chronic smaller (follow up) dose delivered for two to three weeks or longer following intervention. For example, a single pre-loading dose may be administered about 24 hours prior to intervention, while multiple preloading doses may be administered daily for several days prior to intervention. An exemplary single pre-loading dose is about 50 mg/kg (ranging between about 5 and about 1000 mg/kg), while an exemplary multiple pre-loading individual dose is about 10 mg/kg/day (ranging between about 0.01 and 10 mg/kg/day). Such a dosing regimen may involve a systemic pre-loading dose followed by a sustained release chronic dose, or the sustained release dosage form may be designed to deliver a large dose over a short time interval as well as a smaller chronic dose for the desired time period thereafter. Some nausea may be encountered at the higher dose; however, the use of a sustained release or other targeted dosage form is expected to obviate this side effect, because the recipient will not be subjected to a high systemic dose of the therapeutic agent.

It will be recognized by those skilled in the art that desired therapeutically effective dosages of the catheter administered sustained release dosage forms of the invention will be dependent on several factors, including, e.g.: a) the binding affinity of the binding protein associated with the dosage form, if any; b) the atmospheric pressure and duration of the infusion; c) the time over which the dosage form administered resides at the target site; d) the rate of therapeutic agent release from the particulate dosage form; e) the nature of the therapeutic agent employed; f) the nature of the trauma and/or therapy desired; and/or g) the intercellular and/or intracellular localization of the particulate dosage form. Those skilled practitioners trained to deliver drugs at therapeutically effective dosages, (e.g., by monitoring therapeutic agent levels and observing clinical effects in patients) are capable of determining the optimal dosage for an individual patient based on experience and professional judgment. In a preferred embodiment, about 0.3 atm (i.e., 300 mm of Hg) to about 3 atm of pressure applied for 15 seconds to 3 minutes to the arterial wall is adequate to achieve infiltration of a sustained release dosage form bound to the NR-AN-01 binding protein into the smooth muscle layers of a mammalian artery wall. Wolinsky et al., "Direct Intraarterial Wall Injection of Microparticles Via a Catheter: A Potential Drug Delivery Strategy Following Angioplasty," *Am. Heart Jour.,* 122(4):1136-1140, 1991. Those skilled in the art will recognize that infiltration of a sustained release dosage form into a target cell population will probably be variable and will need to be determined on an individual basis.

It will also be recognized that the selection of a therapeutic agent that exerts its effects intracellularly, e.g., on ribosomes or DNA metabolism, will influence the dosage and time required to achieve a therapeutically effective dosage, and that this process can be modeled in vitro and in animal studies, such as those described in the Examples provided below, to find the range of concentrations over which the therapeutic conjugate or dosage form should be administered to achieve its effects of delaying, reducing or preventing restenosis following angioplasty. For example, therapeutic conjugates radiolabeled with alpha-, beta- or gamma-emitters of known specific activities (e.g., millicuries per millimole or milligram of protein) are useful for determining the therapeutically effective dosage by using them in animal studies and human trials with quantitative imaging or autoradiography of histological tissue sections to determine the concentration of therapeutic conjugate that is required by the therapeutic protocol. A therapeutically effective dosage of the therapeutic conjugate or dosage form will be reached when at least three conditions are met: namely, (1) the therapeutic conjugate or dosage form is distributed in the intimal layers of the traumatically injured vessel; (2) the therapeutic conjugate or dosage form is distributed within the desired intracellular compartment of the smooth muscle cells, i.e., that compartment necessary for the action of the therapeutic agent, or the therapeutic agent released from the dosage form extracellularly is distributed within the relevant intracellular compartment; and (3) the therapeutic agent inhibits the desired cellular activity of the vascular smooth muscle cell, e.g., proliferation, migration, increased cellular volume, matrix synthesis, cell contraction and the like described above.

It will be recognized that where the therapeutic conjugate or dosage form is to be delivered with an infusion catheter, the therapeutic dosage required to achieve the desired inhibitory activity for a therapeutic conjugate or dosage form can also be anticipated through the use of in vitro studies. In a preferred aspect, the infusion catheter may be conveniently a double balloon or quadruple balloon catheter with a permeable membrane. In one representative embodiment, a therapeutically effective dosage of a therapeutic conjugate or dosage form is useful in treating vascular trauma resulting from disease (e.g., atherosclerosis, aneurysm, or the like) or vascular surgical procedures such as angioplasty, atheroectomy, placement of a stent (e.g., in a vessel), thrombectomy, and grafting. Atheroectomy may be performed, for example, by surgical excision, ultrasound or laser treatment, or by high pressure fluid flow. Grafting may be, for example, vascular grafting using natural or synthetic materials or surgical anastomosis of vessels such as, e.g., during organ grafting. Those skilled in the art will recognize that the appropriate therapeutic dosage for a given vascular surgical procedure (above) is determined in in vitro and in vivo animal model studies, and in human preclinical trials. In the EXAMPLES provided below, a therapeutic conjugate containing Roridin A and NR-AN-01 achieved a therapeutically effective dosage in vivo at a concentration which inhibited cellular protein synthesis in test cells in vitro by at least 5 to 50%, as judged by incorporation of radiolabeled amino acids.

In the case of therapeutic agents of conjugates or dosage forms containing anti-migratory or anti-matrix therapeutic agents, cell migration and cell adherence in in vitro assays, respectively, may be used for determining the concentration at which a therapeutically effective dosage will be reached in the fluid space created by the infusion catheter in the vessel wall.

While one representative embodiment of the invention relates to therapeutic methods employing an infusion catheter, it will be recognized that other methods for drug delivery or routes of administration may also be useful, e.g., injection by the intravenous, intralymphatic, intrathecal, intraarterial, local delivery by implanted osmotic pumps or other intracavity routes. Dosage form administration by these routes in accordance with the present invention may be continuous or intermittent, depending, for example, upon the patient's physiological condition, whether the purpose of the administration is therapeutic or prophylactic and other factors known to and evaluable by a skilled practitioner. For intravenous administration, nanoparticulate dosage forms of the present invention are preferred. Intravenous administration of nanoparticulates is useful, for example, where vascular permeability is increased in tumors for leakage, especially in necrotic areas of tumors having damaged vessels which allow the leakage of particles into the interstitial fluid, and where artery walls have been denuded and traumatized allowing the particles to enter the interstitial area of the tunica media.

In the practice of certain embodiments of the present invention, catheter and other administration routes are preferably conducted using dosage forms or therapeutic agents dispersed in a pharmaceutically acceptable carrier that is in liquid phase. Useful pharmaceutically acceptable carriers for these purposes include generally employed carriers, such as phosphate buffered saline solution, water, emulsions (e.g., oil/water and water/oil emulsions) and wetting agents of various types.

Advantageously, non-coupled vascular smooth muscle cell binding protein (e.g., free NR-AN-01 antibody) is administered prior to administration of the therapeutic agent conjugate or dosage form to provide a blocker of non-specific binding to cross-reactive sites. Blocking of such sites is important because vascular smooth muscle cell binding proteins will generally have some low level of cross-reactivity with cells in tissues other than the desired smooth muscle cells. Such blocking can improve localization of the therapeutic conjugate or dosage form at the specific vascular site, e.g., by making more of the therapeutic conjugate available to the cells. As an example, non-coupled vascular smooth muscle binding protein is administered from about 5 minutes to about 48 hours, most preferably from about 5 minutes to about 30 minutes, prior to administration of the therapeutic conjugate or dosage form. In one preferred embodiment of the invention, the unlabeled specific "blocker" is a monovalent or bivalent form of an antibody (e.g., a whole antibody or an $F(ab)'_2$, Fab, Fab', or Fv fragment of an antibody). The monovalent form of the antibody has the advantage of minimizing displacement of the therapeutic conjugate or dosage form while maximizing blocking of the non-specific cross-reactive sites. The non-coupled vascular smooth muscle cell binding protein is administered in an amount effective to blocking binding of a least a portion of the non-specific cross-reactive sites in a patient. The amount may vary according to such factors as the weight of the patient and the nature of the binding protein. In general, about 0.06 mg to 0.20 mg per kg body weight or more of the unlabeled specific blocker is administered to a human.

In addition, a second irrelevant vascular smooth muscle cell binding protein may optionally be administered to a patient prior to administration of the therapeutic conjugate or dosage form to reduce non-specific binding of the therapeutic conjugate or dosage form to tissues. In a preferred embodiment, the irrelevant binding protein may be an antibody which does not bind to sites in the patient through antigen-specific binding, but instead binds in a non-specific manner, e.g., through Fc receptor binding reticuloendothelial cells, asialo-receptor binding, and by binding to ubiquitin-expressing cells. The irrelevant "blocker" decreases non-specific binding of the therapeutic conjugate or dosage form and thus reduces side-effects, e.g., tissue toxicity, associated with the use of the therapeutic conjugate or dosage form. The irrelevant "blocker" is advantageously administered from 5 minutes to 48 hours, most preferably from 15 minutes to one hour, prior to administration of the therapeutic conjugate or dosage form, although the length of time may vary depending upon the therapeutic conjugate and route or method of injection. Representative examples of irrelevant "blockers" include antibodies that are nonreactive with human tissues and receptors or cellular and serum proteins prepared from animal sources that when tested are found not to bind in a specific manner (e.g., with a $Ka<10^3\ M^{-1}$) to human cell membrane targets.

It will be recognized that the conjugates and dosage forms of the invention are not restricted in use for therapy following angioplasty; rather, the usefulness of the therapeutic conjugates and dosage forms will be proscribed by their ability to inhibit cellular activities of smooth muscle cells and pericytes in the vascular wall. Thus, other aspects of the invention include therapeutic conjugates and dosage forms and protocols useful in early therapeutic intervention for reducing, delaying, or eliminating (and even reversing) atherosclerotic plaques and areas of vascular wall hypertrophy and/or hyperplasia. Therapeutic conjugates and dosage forms of the invention also find utility for early intervention in pre-atherosclerotic conditions, e.g., they are useful in patients at a high risk of developing atherosclerosis or with signs of hypertension resulting from atherosclerotic changes in vessels or vessel stenosis due to hypertrophy of the vessel wall.

The therapeutic conjugates and dosage forms of the invention may also be used in therapeutic modalities for enhancing the regrowth of endothelial cells in injured vascular tissues and in many kinds of wound sites including epithelial wounds. In these therapeutic modalities, the therapeutic conjugates and dosage forms of the invention find utility in inhibiting the migration and/or proliferation of smooth muscle cells or pericytes. Smooth muscle cells and pericytes have been implicated in the production of factors in vitro that inhibit endothelial cell proliferation, and their proliferation can also result in a physical barrier to establishing a continuous endothelium. Thus, the therapeutic conjugates and dosage forms of the invention find utility in promoting neo-angiogenesis and increased re-endothelialization, e.g., during wound healing, vessel grafts and following vascular surgery. The dosage forms may also release therapeutic modalities that stimulate or speed up re-endothelialization of the damaged vessel wall. An exemplary therapeutic agent for this purpose is vascular permeability factor.

Still other aspects of the invention relate to therapeutic modalities for enhancing wound healing in a vascular site and improving the structural and elastic properties of healed vascular tissues. In these therapeutic modalities using the therapeutic conjugate or dosage form of the invention, i.e., to inhibit the migration and proliferation of smooth muscle cells or pericytes in a vessel wall, the strength and quality of healing of the vessel wall are improved. Smooth muscle cells in the vascular wound site contribute to the normal process of contraction of the wound site which promotes wound healing. It is presently believed that migration and proliferation of smooth muscle cells and matrix secretion by transformed smooth muscle cells may detract from this normal process and impair the long-term structural and elastic qualities of the healed vessel. Thus, other aspects of the invention provide for therapeutic conjugates and dosage forms that inhibit smooth muscle and pericyte proliferation and migration as well as morphological transformation, and improve the quality of the healed vasculature.

The present invention also provides a combination therapeutic method involving a cytocidal therapeutic conjugate and a cytostatic therapeutic agent. The cytocidal conjugate includes a binding partner (such as a protein or peptide) capable of specifically localizing to vascular smooth muscle cells and an active agent capable of killing such cells. The cytocidal conjugate is administered, preferably intravenously or through any other convenient route therefor, localizes to the target smooth muscle cells, and destroys proliferating cells involved in stenotic or restenotic events. This cellular destruction causes the release of mitogens and other metabolic events, which events generally lead, in turn, to vascular smooth muscle cell proliferation. The sustained release anti-proliferative or anti-contractile dosage forms of the present invention are next administered, preferably through an infusion catheter or any convenient dosage form therefor. The sustained release dosage form retards the vascular smooth muscle cell proliferation and/or migration and contraction, thereby maintaining luminal diameter. This treatment methodology constitutes a biological arteromyectomy useful in stenotic vessels resulting from vascular smooth muscle cell hyperplasia and the like.

Alternatively, a combination protocol can be employed involving a, for example, systemically administered TGF-beta, TGF-beta activator or TGF-beta production stimulator capable of stabilizing or organizing the proliferation occurring at a diseased or traumatized smooth muscle site. The therapeutic or prophylactic agent combined by, for example, local administration in protocols employing the aforementioned stabilizer/organizer may be either a cytotoxic agent (e.g., free cytotoxic agent, a cytotoxic conjugate, or a sustained dosage form incorporating a cytotoxic agent) or a cytostatic agent (e.g., free, targeted or sustained release formulations of an agent capable of generating a biological stenting effect, an anti-migratory agent, a cytoskeletal inhibitor, a metabolic inhibitor, an anti-proliferative agent or the like).

When a cytotoxic agent is employed, the stabilizer or organizer is preferably administered prior to cytotoxic agent administration. A preferred embodiment of this aspect of the present invention for the prevention or treatment of restenosis features the following steps:

1) systemic administration of a large, prophylactically effective dose of tamoxifen;
2) after the passage of from about 0 to about 72 hours (preferably 24 to 72), an effective amount of a, for example, *Pseudomonas* exotoxin-monoclonal antibody conjugate capable of localizing to vascular smooth muscle cells is locally administered (e.g., via a catheter during an angioplasty procedure); and 3) daily system administrations of smaller, follow up doses of tamoxifen.

Optionally, a follow up dose of tamoxifen could also be locally administered in step 2.

Using this protocol offers reduced and more highly organized or more stable proliferation by smooth muscles cells that are susceptible to a cytotoxic agent targeted thereto. The cytotoxic agent acts on the proliferating cells. The follow up doses of tamoxifen facilitate the prevention of proliferation resulting from smooth muscle cell death caused by the action of the cytotoxic agent.

When cytostatic agents are employed, the stabilizer or organizer is preferably administered prior to cytostatic agent administration. A preferred embodiment of this aspect of the present invention for the prevention or treatment of restenosis features the following steps:

1) systemic administration of a large, prophylactically effective dose of tamoxifen;

2) after the passage of from about 0 to about 72 hours (preferably 24-72 hours), an effective amount of cytochalasin B is locally administered (e.g., via a catheter during an angioplasty procedure); and 3) daily system administrations of smaller, follow up doses of tamoxifen.

Optionally, a follow up dose of tamoxifen could also be locally administered in step 2.

Using this protocol offers reduced and more highly organized or more stable proliferation by smooth muscles cells in combination with a biological stenting effect.

The present invention also provides methods for the treatment of cancer and immune system-mediated diseases through local administration of a targeted particulate dosage form. The particulate dosage form is, for example, administered locally into primary and/or metastatic foci of cancerous target cells. Local administration is preferably conducted using an infusion needle or intraluminal administration route, infusing the particulate dosage form in the intercellular region of the tumor tissue or in luminal fluid surrounding the tumor cells.

Primary foci introduction is preferably conducted with respect to target cells that are generally situated in confined areas within a mammal, e.g., ovarian carcinomas located in the abdominal cavity. The dosage form of the present invention binds to the target cell population and, optionally, is internalized therein for release of the therapeutic agent over time. Local administration of dosage forms of the present invention to such primary foci results in a localized effect on such target cells, with limited exposure of other sensitive organs, e.g., the bone marrow and kidneys, to the therapeutic agent.

When metastatic foci constitute the target cell population, the administered microparticles and larger nanoparticles are primarily bound to the target cells situated near the infusion site and are, optionally, internalized for release of the therapeutic agent, thereby generating a marked and localized effect on the target cells immediately surrounding the infusion site. In addition, smaller nanoparticles follow interstitial fluid flow or lymphatic drainage channels and bind to target cells that are distal to the infusion site and undergoing lymphatic metastasis.

The targeted dosage forms of this embodiment of the present invention can be used in combination with more commonly employed immunoconjugate therapy. In this manner, the immunoconjugate achieves a systemic effect within the limits of systemic toxicity, while the dosage form of the present invention delivers a concentrated and sustained dose of therapeutic agent to the primary and metastatic foci, which often receive an inadequate therapeutic dose from such "systemic" immunoconjugate administration alone, and avoids or minimizes systemic toxic effects.

Where the target cell population can be accessed by local administration, the dosage forms of the present invention are utilized to control immune system-mediated diseases. Exemplary of such diseases are arthritis, sprue, uveitis, endophthalmitis, keratitis and the like. The target cell populations implicated in these embodiments of the present invention are confined to a body cavity or space, such as joint capsules, pleural and abdominal cavity, eye and sub-conjunctival space, respectively. Local administration is preferably conducted using an infusion needle for a intrapleural, intraperitoneal, intraocular or sub-conjunctival administration route.

This embodiment of the present invention provides a more intense, localized modulation of immune system cells with minimal effect on the systemic immune system cells. Optionally, the systemic cells of the immune system are simultaneously treatable with a chemotherapeutic agent conjugated to a binding protein or peptide. Such a conjugate preferably penetrates from the vascular lumen into target immune system cells.

The local particulate dosage form administration may also localize to normal tissues that have been stimulated to proliferate, thereby reducing or eliminating such pathological (i.e., hyperactive) conditions. An example of this embodiment of the present invention involves intraocular administration of a particulate dosage form coated with a binding protein or peptide that localizes to pericytes and smooth muscle cells of neovascularizing tissue. Proliferation of these pericytes causes degenerative eye disease. Preferred dosage forms of the present invention release compounds capable of suppressing the pathological proliferation of the target cell population. The preferred dosage forms can also release compounds that increase vessel lumen area and blood flow, reducing the pathological alterations produced by this reduced blood supply.

Still another aspect of the present invention relates to therapeutic modalities for maintaining an expanded luminal volume following angioplasty or other vessel trauma. One embodiment of this aspect of the present invention involves administration of a therapeutic agent capable of inhibiting the ability of vascular smooth muscle cells to contract. Exemplary agents useful in the practice of this aspect of the present invention are those capable of causing a traumatized artery to lose vascular tone, such that normal vascular hydrostatic pressure (i.e., blood pressure) expands the flaccid vessel to or near to its maximal physiological diameter. Loss of vascular tone may be caused by agents that interfere with the formation or function of contractile proteins (e.g., actin, myosin, tropomyosin, caldesmon, calponin or the like). This interference can occur directly or indirectly through, for example, inhibition of calcium modulation, phosphorylation or other metabolic pathways implicated in contraction of vascular smooth muscle cells.

Inhibition of cellular contraction (i.e., loss of vascular tone) may operate through two mechanisms to reduce the degree of vascular stenosis. First, inhibition of cellular contraction for a prolonged period of time limits the number of smooth muscle cells that migrate from the tunica media into the intima, the thickening of which results in vascular luminal stenosis. Second, inhibition of cellular contraction causes the smooth muscle wall to relax and dilate under normal vascular hydrostatic pressure (i.e., blood pressure). Therapeutic agents, such as the cytochalasins, inhibit smooth muscle cell contraction without abolishing the protein synthesis necessary for traumatized, post-angioplasty or other surgically- or disease-damaged, smooth muscle cells to repair themselves. Protein synthesis is also necessary for the smooth muscle cells to secrete matrix, which fixes or retains the lumen in a state near its maximum systolic diameter as the vascular lesion stabilizes (i.e., a biologically-induced stenting effect).

This biological stenting effect not only results in an expanded vessel luminal area and increased blood flow rate through the vessel, but also significantly reduces elastic recoil following angioplasty. Elastic recoil is an acute closure of the vessel associated with vasospasm or early relaxation of the muscular wall, due to trauma shock resulting from vessel over-stretching by a balloon catheter during angioplasty. This spasm of the tunica media which leads to decreases in the luminal area may occur within hours, days or weeks after the balloon dilation, as restoration of vascular muscle wall tone occurs. Recent observations during microscopic examination of atheroectomy specimens suggest that elastic recoil may occur in up to 25% of angioplasty procedures classified as successful, based on the initial post-procedure angiogram. Because the biological stenting procedure relaxes the artery wall following balloon angioplasty, the clinician can eliminate over-inflation and its resultant trauma shock as a means to diminish or delay the vessel spasm or elastic recoil. Reduction or elimination of over-inflation decreases trauma to the muscular wall of the vessel, thereby reducing the determinants of smooth muscle cell proliferation in the intima and, therefore, reducing the incidence or severity of restenosis.

Biological stenting also decreases the incidence of thrombus formation. In pig femoral arteries treated with cytochalasin B, for example, the incidence of mural microthrombi was decreased as compared to the balloon traumatized arteries that were not treated with the therapeutic agent. This phenomenon appears to be a secondary benefit that may result from the increased blood flow through the traumatized vessel, said benefit being obtained through the practice of the present invention.

Cytochalasins are exemplary therapeutic agents capable of generating a biological stenting effect on vascular smooth muscle cells. Cytochalasins are thought to inhibit both migration and contraction of vascular smooth muscle cells by interacting with actin. The cytochalasins interact with the ends of filamentous actin to inhibit the elongation of the actin filaments. Low doses of cytochalasins (e.g., cytochalasin B) also disrupt microfilament networks of actin. In vitro data indicate that after vascular smooth muscle cells clear cytochalasin B, the cells regenerate enough polymerized actin to resume migration within about 24 hours. In vivo assessments reveal that vascular smooth muscle cells regain vascular tone within 2 to 4 days. It is during this recuperative period that the lumen diameter fixation and biological stenting effect occurs.

The therapeutic agent may be targeted, but is preferably administered directly to the traumatized vessel following the angioplasty or other traumatic event. The biological stenting effect of cytochalasin B, for example, is achievable using a single infusion of the therapeutic agent into the traumatized region of the vessel wall at a dose concentration ranging from about 0.1 microgram/ml to about 1.0 micrograms/ml.

Inhibition of vascular smooth muscle cell migration (from the tunica media to the intima) has been demonstrated in the same dose range (Example 11); however, a sustained exposure of the vessel to the therapeutic agent is preferable in order to maximize these anti-migratory effects. If the vascular smooth muscle cells cannot migrate into the intima, they cannot proliferate there. Should vascular smooth muscle cells migrate to the intima, a subsequently administered anti-proliferative sustained release dosage form inhibits the intimal proliferation. As a result, the sustained release dosage form of the present invention, incorporating a cytochalasin or other anti-proliferative therapeutic agent, can be administered in combination with a free cytochalasin therapeutic agent. In this manner, the biological stenting effect, as well as an anti-proliferative or anti-migratory effect, can be achieved in a single administration protocol.

Agents useful in the protocols of the present invention are identifiable, for example, in accordance with the following procedures. A potential agent for free agent (i.e., non-targeted) administration exhibits one or more of the following characteristics:

(i) retains an expanded luminal volume following angioplasty (e.g., PTCA, percutaneous transluminal angioplasty (PTA) or the like) or other trauma, including atheroectomy (e.g., rotoblater, laser and the like), coronary artery bypass procedures or the like; or resulting from vascular disease (e.g., atherosclerosis, eye diseases secondary to vascular stenosis or atrophy, cerebral vascular stenotic diseases or the like);

(ii) the initial increase in luminal area facilitated by the agent does not result in or accentuate chronic stenosis of the lumen;

(iii) inhibits target cell contraction or migration; and (iv) is cytostatic.

Preferably, a therapeutic agent employed herein will have all four properties; however, the first and third are more important than the second and fourth for practice of the present invention. Cytochalasin B, for example, was evaluated to determine suitability for use in free therapeutic agent protocols. The biological stenting effect of cytochalasin B is achievable using a single infusion of the therapeutic agent into the traumatized region of the vessel wall at a dose concentration ranging from about 0.1 microgram/ml to about 1.0 micrograms/ml.

An agent useful in the sustained release embodiments of the present invention exhibits one or more of the following characteristics:

(i) retains an expanded luminal volume following angioplasty (e.g., PTCA, percutaneous transluminal angioplasty (PTA) or the like) or other trauma, including atheroectomy (e.g., rotoblater, laser and the like), coronary artery bypass procedures or the like; or resulting from vascular disease (e.g., atherosclerosis, eye diseases secondary to vascular stenosis or atrophy, cerebral vascular stenotic diseases or the like);

(ii) inhibits target cell proliferation (e.g., following 5 minute and 24 hour exposure to the agent, in vitro vascular smooth muscle tissue cultures demonstrate a level of inhibition of $^3$H-thymidine uptake and, preferably, display relatively less inhibition of $^3$H-leucine uptake);

(iii) at a dose sufficient to inhibit DNA synthesis, produces only mild to moderate (e.g., grade 2 or 3 in the assays described below) morphological cytotoxic effects;

(iv) inhibits target cell contraction; and (v) is cytostatic.

Upon identification of a therapeutic agent exhibiting one or more of the preceding attributes, the agent is subjected to a second testing protocol that involves longer exposure of vascular smooth muscle cells to the therapeutic agent.

An agent useful in the sustained release embodiments of the present invention exhibits the following characteristics:

(i) upon long term (e.g., 5 days) exposure, the agent produces the same or similar in vitro effect on vascular smooth muscle tissue culture DNA synthesis and protein synthesis, as described above for the 5 minute and 24 hour exposures; and (ii) at an effective dose in the long term in vitro assay for DNA synthesis inhibition, the agent exhibits mild to moderate morphological cytotoxic effects over a longer term (e.g., 10 days).

Further evaluation of potential anti-proliferative agents within the present invention is conducted in an in vivo balloon traumatized pig femoral artery model. Preferably, such agents demonstrate a 50% or greater inhibition of cell proliferation in the tunica media vascular smooth muscle cells, as indicated by a 1 hour “BRDU flash labeling” prior to tissue collection and histological evaluation. If an agent is effective for a period of time sufficient to inhibit intimal smooth muscle proliferation 50% or greater with a single exposure, it is an agent within the present invention that does not require administration in a sustained release dosage form. Agents having shorter duration activity are evaluated for sustained release if the systemic toxicity and potential therapeutic index appear to permit intravenous administration to achieve the 50% inhibition, or if the agent is amenable to local delivery to the vascular smooth muscle cells with sustained release at an effective anti-proliferative dose. Sustained release agents are evaluated in a sustained release dosage form for dose optimization and efficacy studies. Preferably, anti-proliferative agents useful in the practice of the present invention decrease vascular stenosis by 50% in balloon traumatized pig femoral arteries and, more preferably, to decrease vascular stenosis to a similar extent in pig coronary arteries. Such agents are then evaluable in human clinical trials.

Cell proliferation (i.e., DNA synthesis) inhibition is the primary characteristic for sustained release of agents. Staurosporin, for example, exhibits a differential between $^3$H-leucine and $^3$H-thymidine uptake such that it is cytostatic at administered doses. Longer duration cytotoxicity studies did not indicate that prolonged exposure to the therapeutic agent would adversely impact the target cells. In addition, BRDU pulsing indicated that staurosporin inhibits target cell proliferation. Any convenient method for evaluating the capability of inhibiting cell proliferation may alternatively be employed, however. Consequently, staurosporin is effective in retaining an expanded luminal volume.

High levels of lipoprotein Lp(a) are known to constitute a major risk factor for atherosclerosis, coronary heart disease and stroke. One symptom associated with such conditions and other problems, such as restenosis following balloon angioplasty and other pathogenic conditions, is the proliferation or the migration of smooth muscle cells. No direct link between Lp(a) and proliferation of vascular smooth muscle cells had been established in the prior art.

Figure 15:
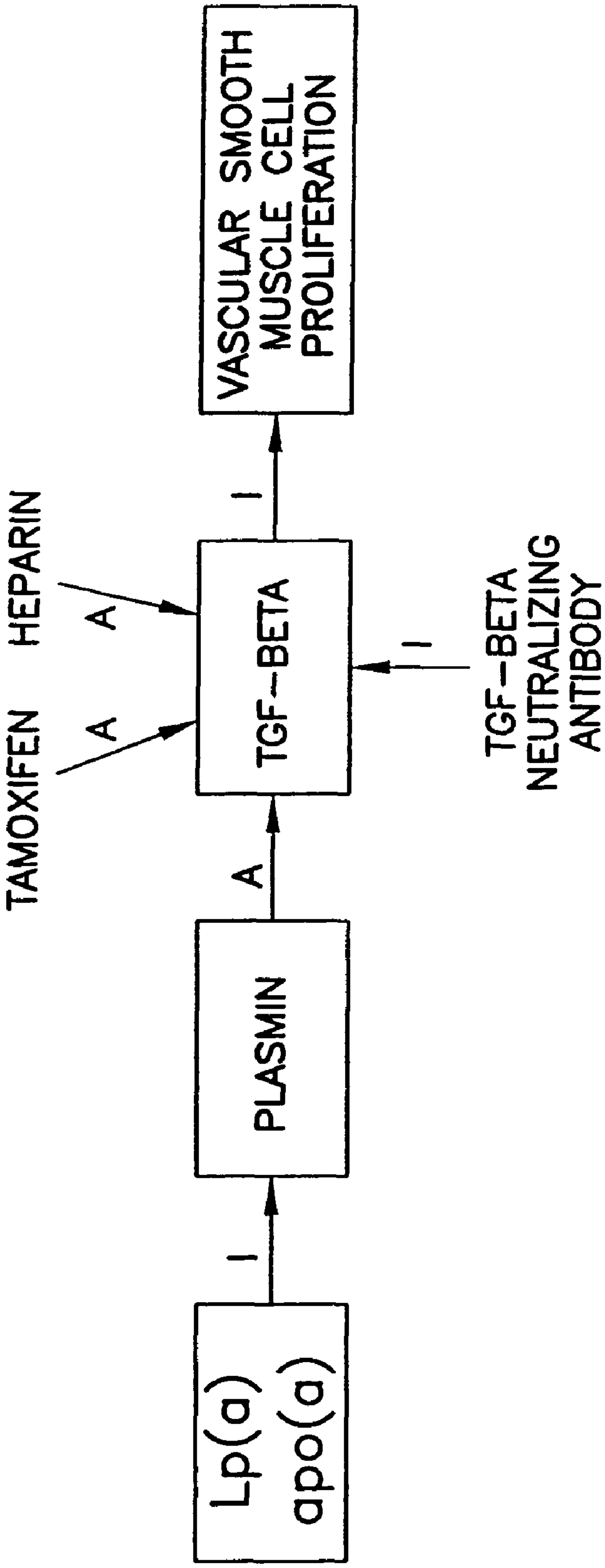
FIGS. 15 and 16 depict pathways for the modulation of vascular smooth muscle cell proliferation in vivo.

An in vivo pathway for the modulation of vascular smooth muscle cell proliferation is shown in FIG. 15. This mechanism is believed to constitute a portion of the mechanism that maintains vascular smooth muscle cells in a non-proliferative state in healthy vessels. The pathway has been elucidated by the inventors of a patent application filed on even date herewith, entitled Prevention and Treatment of Pathologies Associated with Abnormally Proliferative Smooth Muscle Cells.

Vascular smooth muscle cell proliferation is inhibited by an active form of TGF-beta. Tamoxifen has been shown by the experimentation detailed in Example 16 hereof to stimulate both the production and the activation of TGF-beta. Heparin stimulates the activation of TGF-beta by affecting the release of the active form of TGF-beta from inactive complexes present in serum. TGF-beta neutralizing antibodies inhibit the activity of TGF-beta, thereby facilitating the proliferation of vascular smooth muscle cells. The apparent in vivo physiological regulator of the activation of TGF-beta is plasmin. Plasmin is derived from plasminogen through activation by, for example, tPA (tissue plasminogen activator). Plasminogen and, therefore, plasmin activity is inhibited by the lipoprotein Lp(a) or apolipoprotein(a) (apo(a)), thereby decreasing the activation of the latent form of TGF-beta and facilitating proliferation of vascular smooth muscle cells.

Figure 16:
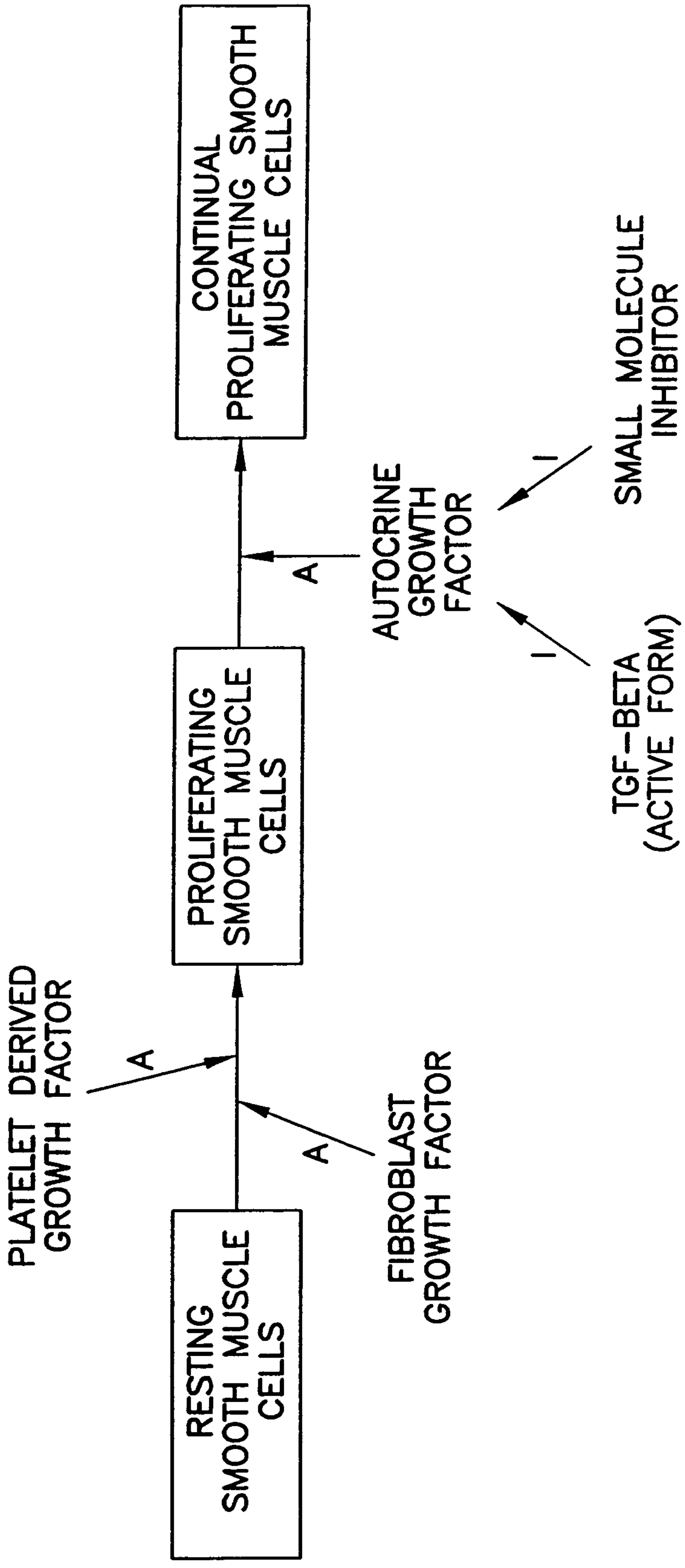

An additional pathway for the modulation of vascular smooth muscle cell proliferation is shown in FIG. 16. Resting smooth muscle cells constitute cells in their normal, quiescent non-proliferative state. Such resting smooth muscle cells may be converted to proliferating smooth muscle cells through activation by platelet derived growth factor (PDGF), fibroblast growth factor (FGF) or other stimulatory moieties. The proliferating smooth muscle cells may be converted to continual proliferating smooth muscle cells (i.e., smooth muscle cells capable of generating a pathological state resulting from over-proliferation thereof) by an autocrine growth factor. This growth factor is believed to be produced by proliferating smooth muscle cells. An increased level of autocrine growth factor, which can be inhibited by the active form of TGF-beta or an appropriately structured (e.g., designed) small molecule inhibitor, is believed to mediate the production of continual proliferating smooth muscle cells.

Lp(a) consists of low density lipoprotein (LDL) and apo (a). Apo(a) shares approximately 80% amino acid identity with plasminogen (see MacLean et al., *Nature,* 330: 132, 1987). Lp(a) has been found to inhibit cell-associated plasminogen activity (see, for example, Harpel et al., *Proc. Natl. Acad. Sci. USA,* 86: 3847, 1989). Experiments conducted on human aortic vascular smooth muscle cells derived from healthy transplant donor tissue, cultured in Dulbecco’s modified Eagles medium (DMEM)+10% fetal calf serum (FCS) as described in Grainger et al., *Biochem. J.,* 283: 403, 1992, indicated the following:

1) Addition of Lp(a) to sub-confluent human vascular smooth muscle cells stimulated their proliferation in a dose dependent manner (addition of 500 nM Lp(a) to human vascular smooth muscle cells caused a reduction in doubling time from 82+/−4 hours to 47+/−4 hours);
2) Addition of apo(a) had a similar effect, although a higher concentration of apo(a) appeared to be required therefor; and
3) Addition of LDL at varying concentrations up to 1 micromolar had no effect on proliferation.

One possible mode of action for Lp(a) and apo(a) is competitive inhibition of surface-associated plasminogen activation and the subsequent activation of TGF-beta by plasmin. TGF-beta is a potent growth inhibitor of a number of anchorage-dependent cells, including smooth muscle cells. TGF-beta is produced as a latent propeptide having a covalently linked homodimer structure in which the active moiety is non-covalently linked to the amino-terminal portion of the propeptide. Latent TGF-beta must be cleaved (e.g., in vitro by acid treatment or in vivo by the serine protease plasmin) in order to become capable of inhibiting the proliferation of vascular smooth muscle cells. Plasmin is therefore a leading candidate to be a physiological regulator of TGF-beta.

The hypothesis that Lp(a) and apo(a) were acting on cultured human vascular smooth muscle cells by interfering with activation of latent TGF-beta was tested. In support of this hypothesis, an observation was made that plasmin activity associated with vascular smooth muscle cells was reduced 7-fold by Lp(a) and 5-fold by apo(a). The plasmin activity in the conditioned medium was also reduced by Lp(a) and apo (a) by about 2-fold, but was much lower than cell-associated plasmin activity in vascular smooth muscle cell cultures. These observations are consistent with previous findings that Lp(a) is a more potent inhibitor of surface-associated, rather than fluid phase, plasminogen activation.

To exclude the possibility that Lp(a) was affecting the synthesis of plasminogen activators rather than plasminogen activation, plasminogen activator levels in human vascular smooth muscle cell cultures were measured in the presence and absence of the lipoproteins and in the presence of a large excess of plasminogen, so that the lipoproteins present would not significantly act as competitive inhibitors. Total plasminogen activator activity was not affected by the presence of any of the lipoproteins in the vascular smooth muscle cell cultures. For example, plasminogen activator activity in the conditioned medium remained at 0.7+/−0.06 mU/ml with Lp(a) additions up to 500 nM.

Lp(a) and apo(a) both reduced the level of active TGF-beta by more than 100-fold compared to control or LDL-treated cultures. The level of total latent plus active TGF-beta measured by ELISA as described in Example 16 was unaffected by the presence of Lp(a) or apo(a), however. These facts lead to the conclusion that Lp(a) stimulates proliferation of human vascular smooth muscle cells by inhibiting plasmin activation of latent TGF-beta to active TGF-beta.

To further test this conclusion and exclude the possibility that Lp(a) was acting by binding active TGF-beta as well as reducing plasmin activity, human vascular smooth muscle cells were cultured in the presence of Lp(a). These cells had a population doubling time of 47+/−3 hours. Addition of plasmin was able to overcome the population doubling time reducing effect of Lp(a) and reduce the cell number to control levels, with the population doubling time increased to 97+/−4 hours.

The role of plasmin in the pathway was confirmed by studies in which inhibitors of plasmin activity were added to human vascular smooth muscle cells. Like Lp(a), these protease inhibitors increased cell number. Aprotinin, for example, decreased the population doubling time from 82+/−4 hours in control cultures to 48+/−5 hours, and alpha2-antiplasmin decreased the population doubling time to 45+/−2 hours. 500 nM Lp(a) and aprotinin addition resulted in only a slight additional stimulation of proliferation, with the population doubling time for cultures of this experiment being 45+/−6 hours. Neutralizing antibodies to TGF-beta similarly decreased population doubling time in vascular smooth muscle cells (see, for example, Example 16). In summary, Lp(a), plasmin inhibitors and neutralizing antibody to TGF-beta stimulate proliferation of vascular smooth muscle cells, while plasmin nullifies the growth stimulation of Lp(a). These results support the theory that the mode of action of Lp(a) and apo(a) is the competitive inhibition of plasminogen activation.

Experimentation conducted to ascertain the impact of tamoxifen on TGF-beta and vascular smooth muscle cell proliferation is set forth in detail in Example 16. The results of those experiments are summarized below.

1) Addition of tamoxifen decreased the rate of proliferation, with maximal inhibition observed at concentrations above 33 micromolar. 50 micromolar tamoxifen concentrations produced an increase in cell number (96 hours following the addition of serum) that was reduced by 66%+/−5.2% (n=3).
2) Tamoxifen did not significantly reduce the proportion of cells completing the cell cycle and dividing. Inhibition of vascular smooth muscle cells caused by tamoxifen therefore appears to be the result of an increase in the cell cycle time of nearly all (>90%) of the proliferating cells.
3) Tamoxifen decreases the rate of proliferation of serum-stimulated vascular smooth muscle cells by increasing the time taken to traverse the $G_2$ to M phase of the cell cycle.
4) Tamoxifen decreased the rate of proliferation of vascular smooth muscle cells by inducing TGF-beta activity.
5) Vascular smooth muscle cells produced TGF-beta in response to tamoxifen. Tamoxifen appears to increase TGF-beta activity in cultures of rat vascular smooth muscle cells by stimulating the production of latent TGF-beta and increasing the proportion of the total TGF-beta which has been activated.
6) Tamoxifen, unlike heparin, does not act by releasing TGF-beta from inactive complexes present in serum.
7) TGF-beta1 mRNA was increased by approximately 10-fold by 24 hours after addition of tamoxifen (10 micromolar). This result suggests that the expression of TGF-beta mRNA by the smooth muscle cells will be increased, thereby facilitating decreased proliferation thereof by activated TGF-beta. This mechanism can be exploited using cells incorporating nucleic acids encoding TGF-beta mRNA, which cells are identifiable by persons skilled in the art employing known techniques.
8) Tamoxifen is a selective inhibitor of vascular smooth muscle proliferation with an $ED_{50}$ at least 10-fold lower for vascular smooth muscle cells than for adventitial fibroblasts.

Additional experimentation has shown that the addition of Lp(a) or apo(a) substantially reduced the vascular smooth muscle cell proliferation inhibitory activity of tamoxifen, with the population doubling time in the presence of tamoxifen and Lp(a) being 42+/−2 hours. Also, the presence of Lp(a) reduced the levels of active TGF-beta produced in response to the addition of tamoxifen by about 50-fold. Addition of plasmin to rat vascular smooth muscle cells treated with tamoxifen and Lp(a) resulted in most of the TGF-beta being activated, and proliferation was again slowed (with the population doubling time being 57+/−3 hours). These observations are consistent with the theory that Lp(a) acts by inhibiting TGF-beta activation.

Identification of therapeutic agents (direct or indirect TGF-beta activators or production stimulators) that act to inhibit vascular smooth muscle cell proliferation by the pathway shown in FIG. 15 can be identified by a practitioner in the art by conducting experiments of the type described above and in Example 16. Such experimental protocols facilitate the identification of therapeutic agents useful in the practice of the present invention and capable of one of the following activities:

1) activation or production of TGF-beta;
2) having TGF-beta activity;
3) activation of plasmin;
4) activation of plasminogen; and
5) reduction of Lp(a) or apo(a) level.

Having TGF-beta activity includes, but is not limited to, disruption of cyclin-dependent protein kinase (CDK) transformation from a slow migrating form to a rapid migrating form, disruption of CDK-cyclin complex formation or activation or the like.

Identification of therapeutic agents (direct or indirect TGF-beta activators or production stimulators) that act to inhibit vascular smooth muscle cell proliferation by the pathway shown in FIG. 16 can be identified by a practitioner in the art by conducting experimentation using known techniques that is designed to identify growth factors made by proliferating smooth muscle cells, pericytes, lymphorecticular cells or the like, which growth factors also act on those cells (i.e., autocrine growth factors). Known techniques for rational drug design are then used to screen small molecules for the ability to inhibit the production or activity of such autocrine growth factors. Such experimental protocols facilitate the identification of therapeutic agents useful in the practice of the present invention and capable of one of the following activities:

1) production or activation of TGF-beta;
2) having TGF-beta activity; and
3) inhibit the activity or production of an autocrine growth factor produced by proliferating smooth muscle cells.

Smooth muscle cell proliferation is a pathological factor in myocardial infarctions, atherosclerosis, thrombosis, restenosis and the like. Therapeutic agents of the present invention, including tamoxifen, TGF-beta and the like, having at least one of the activities recited above and therefore being capable of inhibiting proliferation of vascular smooth muscle cells, are useful in the prevention or treatment of these conditions. Manipulation of the proliferation modulation pathway for vascular smooth muscle cells to prevent or reduce such proliferation removes or reduces a major component of the arterial lesions of atherosclerosis and the restenosed arteries following angioplasty, for example.

More specifically, chronically maintaining an elevated level of activated TGF-beta reduces the probability of atherosclerotic lesions forming as a result of vascular smooth muscle cell proliferation. Consequently, administration of TGF-beta, TGF-beta activators or TGF-beta production stimulators protects against atherosclerosis and subsequent myocardial infarctions that are consequent to coronary artery blockage. Also, substantially increasing the activated TGF-beta level for a short time period allows a recipient to at least partially offset the strong stimulus for vascular smooth muscle cell proliferation caused by highly traumatic injuries or procedures such as angioplasty. Continued lower dose delivery to the traumatized site further protects against restenosis resulting from vascular smooth muscle cell proliferation in the traumatized area.

Other embodiments of the present invention involve the administration of taxol or analogs thereof in soluble or sustained release dosage form. Taxol is believed to stabilize vascular smooth muscle cells against division by binding to microtubules and inhibiting the organization and ordering of the microtubule network. Cell migration may also be inhibited by this mechanism. Taxotere, an exemplary taxol analog, has a different method of action, but also inhibits cell division.

The invention will be better understood by making reference to the following specific examples.

Example 1

Binding to Vascular Smooth Muscle Cells in the Blood Vessel Wall in Vivo

Figure 1B:

FIG. 1 illustrates the binding of NR-AN-01 (a murine IgG2b MAb) to the smooth muscle cells in the vascular wall of an artery in a 24-year old male patient, 4 days after the i.v. administration of NR-AN-01. FIG. 1 is a photomicrograph of a histological section taken through the medial region of an arterial wall of the patient after NR-AN-01 administration, where the section was reacted ex vivo with HRP-conjugated goat anti-mouse IgG. The reaction of the HRP-conjugate with NR-AN-01 MAb was visualized by adding 4-chloro-1-naphthol or 3,3'-diaminobenzidine tetrahydrochloride as a peroxidase substrate (chromogen). The reaction product of the substrate forms an insoluble purple or dark brown precipitate at the reaction site (shown at #2, FIG. 1). A counter stain was used to visualize collagenous extracellular matrix material (shown at #2, FIG. 1) or cell nuclei (#1, FIG. 1). Smooth muscle cells are visualized under microscopic examination as purple stained cells. This photomicrograph demonstrates the ability of the MAb to specifically bind to human vascular smooth muscle in vivo, and to be internalized by the cells and remain in the cells for extended periods.

Example 2

Therapeutic Conjugates Containing Trichothecene Therapeutic Agents

Figure 2:
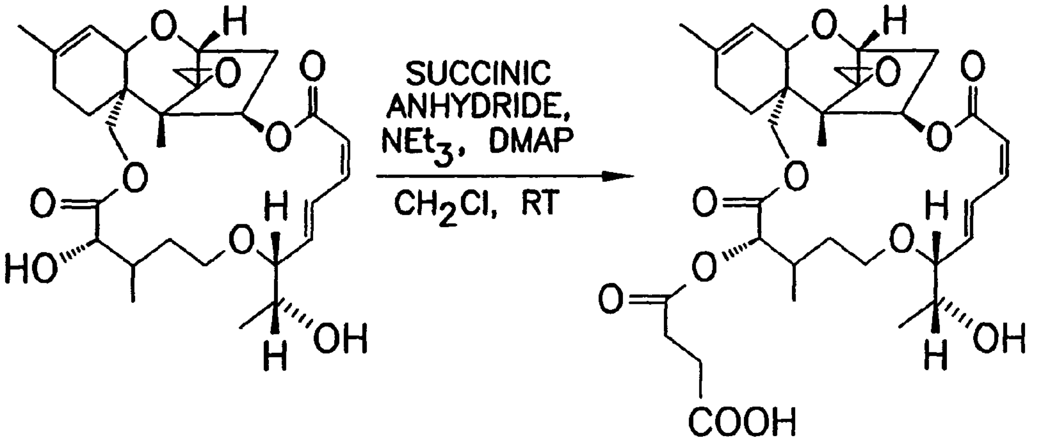
FIG. 2 depicts a first scheme for chemical coupling of a therapeutic agent to a vascular smooth muscle binding protein.
Figure 2:
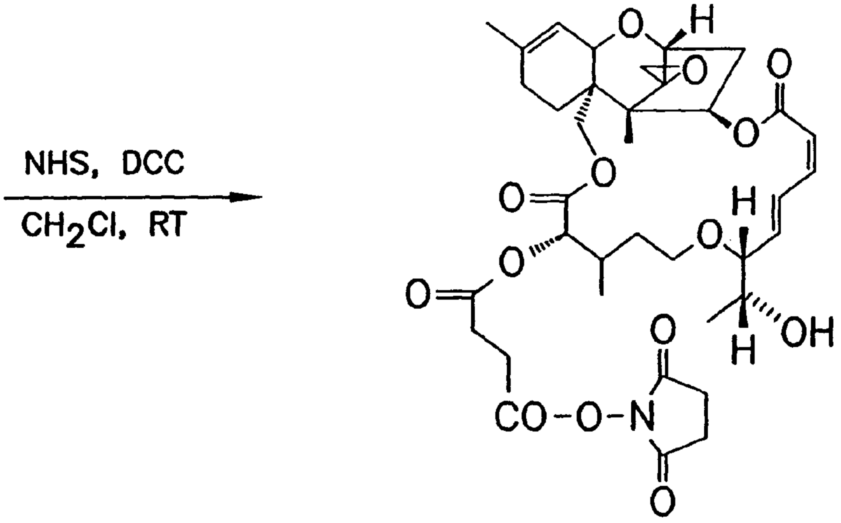
Figure 3:
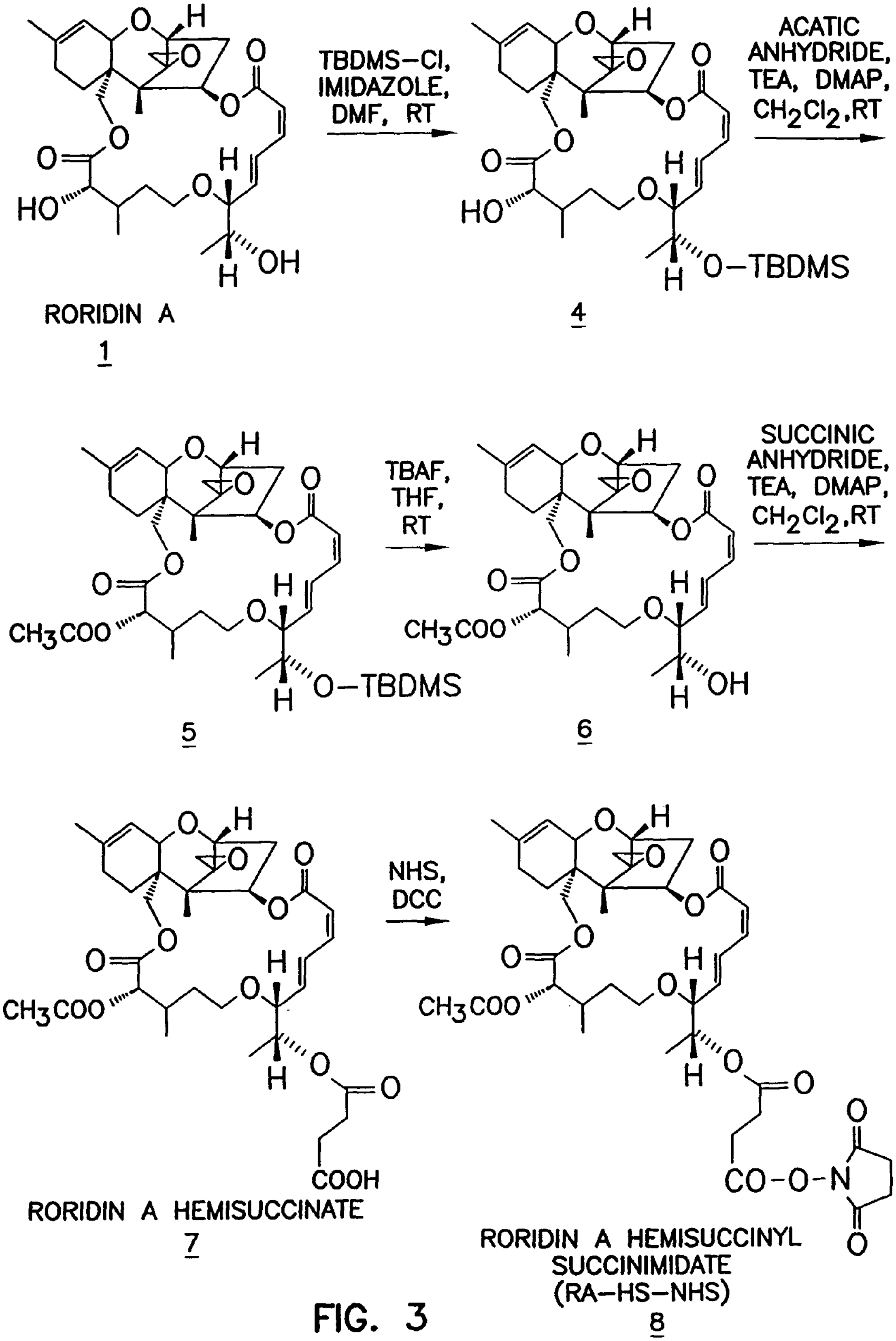
FIG. 3 depicts a second scheme for chemical coupling of a therapeutic agent to a vascular smooth muscle binding protein.

Conjugates of NR-AN-01 and Roridin A were constructed by chemically coupling a hemisuccinate derivative of the trichothecene cytotoxin (as described below) to a monoclonal antibody designated NR-AN-01. Two conjugates were prepared, one coupled at the Roridin A 2' position and one at the 13' position. Two schemes were used in this synthesis, as depicted in FIG. 2 and FIG. 3. The conjugate was then purified from unreacted Roridin A by PD-10 SEPHAROSE® column chromatography (Pharmacia; Piscataway, N.J.), analyzed by size exclusion high pressure liquid chromatography, and the column fractions were characterized by SDS-PAGE and isoelectric focusing (IEF), as described below.

FIG. 2 shows diagrammatically the first reaction scheme for synthesis of Roridin A hemisuccinyl succinimidate (RA-HS-NHS) through a two step process with reagents: succinic anhydride, triethylamine (NEt) and dimethyl amino pyridine (DMAP) present in dichloromethane ($CH_2Cl_2$) at room temperature (RT); and, N-hydroxysuccinimide (NHS) and dicyclohexyl carbodiimide (DCC) reagents also in $CH_2Cl_2$ at RT.

FIG. 3 shows diagrammatically the second reaction scheme for synthesis of Roridin A hemisuccinyl succinimidate (RA-HS-NHS) through a five step process with reagents: t-butyl dimethyl silyl chloride (TBMS-Cl) and imidazole in dimethylformamide (DMF) at room temperature (RT); acetic anhydride, triethylamine (TEA), and diethylaminopyridine in dichloromethane ($CH_2Cl_2$) at RT; succinic anhydride, triethylamine (TEA) and dimethylaminopyridine (DMAP) in ($CH_2Cl_2$) at RT; and, N-hydroxysuccinimide (NHS) and dicyclohexyl carbodiimide (DCC) reagents.

Synthesis of 2' Roridin-A Hemisuccinic Acid (2)

To 0.5 g (0.94 mmol) of Roridin A, 15 ml of dichloromethane was added. To this solution with stirring was added 0.104 g (1.04 mmol) of succinic anhydride. To the reaction mixture, 0.2 ml of triethylamine in 5 ml dichloromethane was added. To the homogeneous reaction mixture, a catalytic amount of dimethylaminopyridine was added and stirred at room temperature for 15 hours. Completion of the reaction was followed by thin layer chromatography ($CH_2Cl_2$:$CH_3OH$=9.7:0.3 with few drops of acetic acid). At the end of the reaction, 0.3 ml of glacial acetic acid was added and the solvent removed under reduced pressure. The dried crude residue was partitioned between water and methylene chloride. The combined methylene chloride extracts (3×50 ml) were dried over anhydrous sodium sulfate, solvent was removed under vacuum and dried to yield 0.575 g (96%) of a crude mixture of three compounds. Preparative C18 HPLC separation of the crude mixture in 50% acetonitrile-water with 2% acetic acid yielded 0.36 g (60%) of 2 as a white solid.

Synthesis of Succinimidyl 2'-Roridin A Hemisuccinate (3)

To 0.3 g (0.476 mmol) of 2' Roridin A hemisuccinic acid in 30 ml dichloromethane, 0.055 g (0.478 mmol) N-hydroxysuccinimide was added. To the clear reaction mixture, 0.108 g (0.524 mmol) dicyclohexylcarbodiimide was added. The reaction mixture was stirred at room temperature for 6 hours. Completion of the reaction was followed by TLC ($CH_2Cl_2$: $CH_3OH$=9.7:0.3 with a few drops of acetic acid) as a developing solvent. A few drops of glacial acetic acid was added to the reaction mixture and the solvent was removed under reduced pressure. To the dried residue dichloromethane was added and the precipitated DCU was filtered. Solvent from the filtrate was removed under reduced pressure to yield a white solid. From the crude product, 0.208 g (60%) of 3 was purified by preparative HPLC in 50% acetonitrile with 2% acetic acid as a mobile phase.

Synthesis of 13'-t-Butyldimethylsilyl Roridin A (4)

To 72.3 mg (0.136 mmol) of Roridin A in 0.5 ml dimethylformamide solution, 0.055 g (0.367 mmol) t-butyldimethylsilyl chloride and 0.025 g (0.368 mmol) of imidazole were added. The reaction mixture was stirred at room temperature for 15 hours. Completion of the reaction was followed by silica gel thin layer chromatography using 1% MeOH—$CHCl_3$ as a developing solvent. Solvent from the reaction mixture was removed in vacuo and dried. The crude product was partitioned between water and methylene chloride. Solvent from the combined methylene chloride extracts was removed under reduced pressure and dried. The crude product was purified by flash chromatography using EtOAc:Hexane (1:3) as an eluting solvent. Solvent from the eluants was removed under reduced pressure to yield 0.66 g (75%) of 4 as a solid.

Synthesis of 13'-t-Butyldimethylsilyl 2' Acetyl Roridin A (5)

To 0.1 g (0.155 mmol) of 13'-t-butyldimethylsilyl Roridin A in 10 ml dichloromethane, 0.3 ml acetic anhydride, 0.2 ml triethylamine and a few crystals of dimethylaminopyridine were added and stored at room temperature for 2 hours. Completion of the reaction was followed by TLC in 1% methanol-methylene chloride as a developing solvent. Solvent was removed under reduced pressure and purified by a silica gel column using 1% methanol-chloroform as an elution solvent. Solvent from the eluants was removed under vacuum to yield 0.085 g (80%) of 5 as a solid.

Synthesis of 2' Acetyl Roridin A (6)

To 0.0 5 g (0.073 mmol) of 2' acetyl 13'-t-butyldimethylsilyl Roridin A in 5 ml tetrahydrofuran, 0.3 ml of 1 M tetrabutyl-ammonium fluoride solution in THF was added. The reaction mixture was stirred at room temperature for 2 hours. Completion of the reaction was followed by silica gel thin layer chromatography using 1% MeOH—$CHCl_3$ as the developing solvent. Solvent from the reaction mixture was removed under reduced pressure and dried. The crude product was purified on a silica gel column using 1% $CH_3OH$—$CHCl_3$ as an eluting solvent. Solvent from the combined eluants were removed under vacuum to yield 0.020 g (48%) of 6 as a solid.

Synthesis of 2'-Acetyl 13'-hemisuccinyl Roridin A (7)

To 0.05 g (0.087 mmol) of 2'-acetyl Roridin A in 1 ml of dichloromethane, 0.025 g (0.25 mmol) succinic anhydride and 35 ml of triethylamine was added. A few crystals of dimethylaminopyridine was added as a catalyst. The reaction mixture was stirred at room temperature for 24 hours. Completion of the reaction was followed by thin layer chromatography using 5% MeOH—$CH_2Cl_2$ as developing solvent. At the end of the reaction 30 ml of glacial acetic acid was added. Solvent from the reaction mixture was removed under reduced pressure and dried. The crude product was partitioned between water and ethyl acetate. Solvent from the combined ethyl acetate fractions was removed under reduced pressure. Crude product was purified by passing through a silica gel column to yield 0.039 g (66%) of 7 as a white solid.

Synthesis of Succinimidyl 2'-Acetyl 13'-Roridin A Hemisuccinate (8)

To 0.036 g (0.0050 mmol) of 2'-acetyl 13'-Roridin A hemisuccinic acid in 2 ml dichloromethane, 0.009 g (0.09 mmol) N-hydroxysuccinimide was added. To a stirred solution, 0.012 g (0.059 mmol) dicyclohexylcarbodiimide was added. The reaction mixture was stirred at room temperature for 8 hours. Completion of the reaction was followed by silica gel thin layer chromatography using 5% MeOH—$CH_2Cl_2$ as a developing solvent. A few drops of glacial acetic acid was added to the reaction mixture. Solvent from the reaction mixture was removed under reduced pressure and dried. The crude product was purified on a silica gel column using 5% MeOH—$CH_2Cl_2$ as an eluting solvent. Solvent from the combined eluants was removed under vacuum to yield 0.025 g (61%) of 8 as a white solid.

Conjugation of Succinimidyl 2'-Roridin A Hemisuccinate (3) and Succinimidyl 2'-Acetyl 13'-Roridin A Hemisuccinate (8) to NR-AN-01 Whole Antibody (MAb)

Conjugation reactions were performed at pH 8.0 in borate buffer in the presence of 25% dimethylsulfoxide (DMSO) solvent at room temperature with gentle mixing for 45 minutes prior to purification by gel permeation chromatography. The molar trichothecene drug precursor to antibody offerings were 25:1 and 40:1 for the 2' and 13' Roridin A analogues (3 and 8), respectively. Antibody concentration was 0.9 to 1.0 mg/ml during the conjugation reaction.

A Typical 2' Analogue (3) Reaction with 25 mg of Antibody was as follows:

To 4.7 ml of 5.3 mg Ab/ml in phosphate buffered saline (i.e., PBS; 150 mM NaCl, 6.7 mM Phosphate, pH 7.3) was added 10 ml PBS and 5 ml of borate buffer (0.5 M, pH 8.0). With stirring gently to the reaction mixture, 6.3 ml of DMSO containing 1.37 mg of succinimidyl 2' Roridin A hemisuccinate (3) was then added dropwise over a 15 second period.

Purification:

To purify, one ml reaction aliquots were applied to Pharmacia PD-10 Sepharose® columns equilibrated in PBS. The eluted conjugate was collected in 2.4 to 4.8 ml fractions. The PD-10 purified conjugate aliquots were then pooled and concentrated on an Amicon PM-10 DiAflo® concentrator to 1.5 to 2.0 mg of Ab/ml; sterile filtered through a 0.2Ξ Gelman Acrodisce and filled into sterile glass vials in 5 ml volume.

The 2' conjugate was quick frozen in liquid nitrogen and then stored at −70° C. until use. The 13' Roridin A NR-AN-01 conjugate was stored frozen or refrigerated (i.e., 5-10° C.).

Characterization of Conjugates:

Protein concentration was determined by BCA assay using the copper reagent method (Pierce Chemical Corp.).

Assessment of degree of antibody derivatization was performed by first hydrolyzing an aliquot of conjugate in 0.2 M carbonate, pH 10.3 for 4 hours (at room temperature for 2' conjugate or at 37° C. for the 13' conjugate) followed by filtration through a PM-30 membrane. The filtrate was then assayed for Roridin A on C-18 reverse phase HPLC using a mobile phase of 50:48:2 ratio $CH_3CN:H_2O:HOAC$, respectively. A 1.32 correction factor was used to correct for parallel macrocyclic ring decomposition that gives polar products during the hydrolysis of the 13' conjugate.

Size exclusion chromatography on DuPont Zorbax® HPLC and isoelectric focusing using Serva® gel plates (pH 3 to 10) were also performed. No indication of aggregation was observed by HPLC.

Immunoassay of the Roridin A-antibody conjugates was performed by either competitive ELISA using biotinylated-Ab with Streptavidin/Peroxidase detection or by a competitive cell binding assay using $^{125}$I-labeled antibody. Alternatively, immunoreactivity was measured under conditions of antigen saturation in a cell binding assay wherein antibody was first trace labeled with I-125 by the chloramine T method and then subsequently derivatized with 2' and 13' Roridin A precursors.

The structural formula of the trichothecene is shown below:

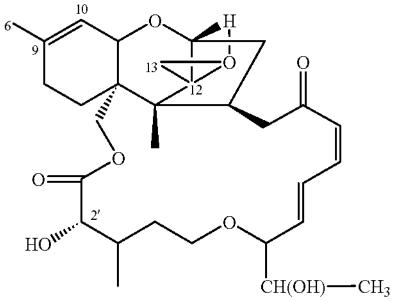

Example 3

Kinetics of Binding to Smooth Muscle Cells

For administration by i.v. catheter, it is desirable that the therapeutic conjugates of the invention be administered in less than 3 to 5 minutes, so that blood flow can be reestablished in the patient. Therefore, studies were conducted to determine the binding kinetics of a smooth muscle binding protein with a Ka of >109 liter/mole. Because human vascular smooth muscle cells grow slowly in culture, and baboon smooth muscle cells were found to express the human CSPG cell surface marker, BO54 baboon artery smooth muscle cells and human A375 M/M (melanoma; ATCC #CRL1619) cells bearing CSPG surface marker were used in many of the studies described in the Examples, below.

For the kinetic binding studies, A375 M/M and BO54 cells were seeded in sterile 96 well microtiter plates at 2500 cells/well. Plates were wrapped in aluminum foil, and incubated at 37° C. overnight in a humidified atmosphere of 5% $CO_2$/95% air. After approximately 18 hr, incubation plates were removed and cells were fixed with 0.05% glutaraldehyde for 5 minutes to prevent membrane turnover. Following fixation, the plates were exhaustively washed with PBS containing 0.5% Tween-200. Serial two-fold dilutions of an NR-AN-01 therapeutic conjugate containing Roridin A were prepared at protein concentrations of 10 mg/ml to 20 ng/ml, and each dilution was aliquoted into two wells. The plates were incubated at 4° C. with the NR-AN-01 for 5, 15, 30, and 60 minutes, after which the unbound protein was removed by aspiration and 100 ml of CS buffer was added (5% chicken serum/0.5% Tween-20® in PBS) to each well. CS buffer was removed and the NR-AN-01 therapeutic conjugate bound to the cells was visualized by adding 100 ml of HRP-conjugated goat anti-mouse IgG (Sigma Chemical Co., St. Louis, Mo.) to each well; incubating at 4° C. for 1 hr.; washing with PBS/0.05% Tween® to remove unbound goat IgG; and, adding 2,2'-azino-bis(3-ethylbenzthiazoline-6-sulfonic acid (ABTS) chromogenic substrate (i.e., for HRP). After incubating for 30 minutes, the amount of NR-AN-01 bound to the cells was quantified by measuring the absorbance at 415 nm and 490 nm using an ELISA plate reader equipped for data acquisition by a Compaq computer.

Figure 4A:
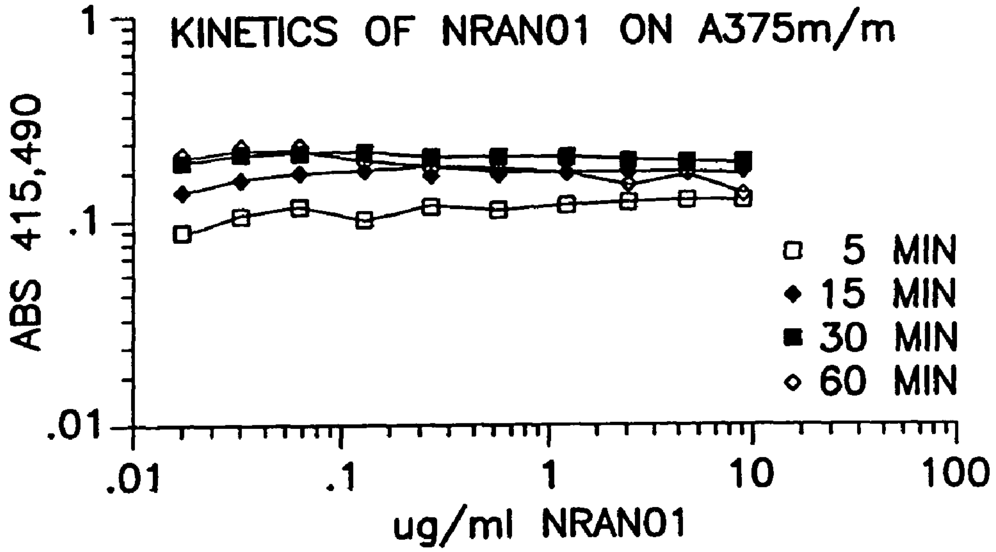
FIG. 4A graphically depicts experimental data showing rapid binding of vascular smooth muscle binding protein to marker-positive test cells in vitro.

FIG. 4A graphically depicts the results of in vitro studies in which A375m/m marker-positive cells were held at 4° C. (i.e., to prevent membrane turnover) for 5 minutes (open squares, FIG. 4A), 15 minutes (closed diamonds, FIG. 4A), 30 minutes (closed squares, FIG. 4A) or 60 minutes (open diamonds, FIG. 4A) with different concentrations of NR-AN-01 (NRAN01 μg/ml). The binding of the NR-AN-01 MAb to the A375 cells was quantified by washing to remove unbound antibody, adding HRP-conjugated goat anti-mouse IgG to react with the cell-bound MAb, washing to remove unbound goat second antibody, and adding 2,2'-azino-bis(3-ethylbenzthiazoline-6-sulfonic acid) (ABTS) substrate for peroxidase. Color development was monitored after 30 minutes at both 415 nm and 490 nm (ABS415,490).

Figure 4B:
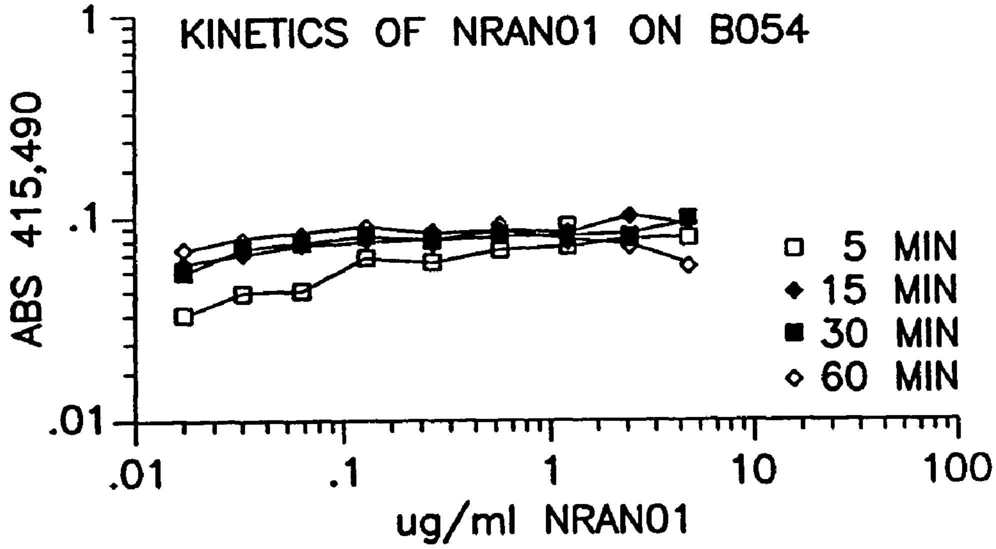
FIG. 4B graphically depicts experimental data showing rapid binding of vascular smooth muscle binding protein to vascular smooth muscle cells in vitro.

FIG. 4B graphically depicts the results of in vitro studies conducted in a manner similar to those described above in regard to FIG. 4A, but using BO54 marker-positive smooth muscle cells, i.e., instead of the A375 m/m cells.

The results presented in FIG. 4A and FIG. 4B show significant binding of NR-AN-01 to A375 and BO54 cells within 5 minutes at 4° C., even at the lowest dose of 20 ng/ml.

Example 4

Effects of Roridin A and RA-NR-AN-01 Conjuqates

The effects of Roridin A (RA) and RA-NR-AN-01 conjugates on cellular protein synthesis (i.e., by $^3$H-leucine incorporation) and metabolic activity (i.e., by mitochondrial MTT assay) were tested in the experiments detailed in EXAMPLE 5 and EXAMPLE 6, below. The studies in EXAMPLE 4 include experiments to determine the effects of long-term (i.e., 24 hour) treatment with the agents. The studies in EXAMPLE 5 include experiments to determine the effects of "pulse" (i.e., 5 minute) treatment on cells. In both studies, the cellular specificity of the effects were evaluated by including "target" cells (i.e., cells bearing the CSPG "marker") and non-target cells. For comparative purposes, free-RA (i.e., uncoupled) was also included in the studies. The effects on cellular protein synthesis or metabolic activity were evaluated either immediately following the treatment, or a "recovery period" was allowed (i.e., involving incubation of the cells overnight at 37° C.) to determine the long-term effects of the agents on the cell populations.

Metabolic Effects After 24 Hours Exposure:

While it is known that monoclonal antibody-drug conjugates may have a degree of specificity for cells bearing marker antigens when employed in vivo, it has proven more difficult in many systems to demonstrate in vitro specificity of action, especially with compounds that are lipophilic. Therefore, the present experiments were conducted in which the inhibitory effects of the NR-AN-01-Roridin A conjugate was tested on target and non-target cells over 24 hours. The results with RA-NR-AN-01 were compared to the effect of free Roridin A over the same 24-hour period. A modified methyl-tetrazolium blue (MTT) assay was utilized with 3-(4,5-dimethylthiazol-2-yl)-2,5-diphenyl tetrazoliumbromide (Sigma) to determine cellular metabolic activity. This assay is thought to measure cellular mitochondrial dehydrogenase activity. For some of these studies, M14 (melanoma) and BO54 (smooth muscle) cell lines were used as marker-positive target cells and HT29 cells (colon carcinoma; ATCC #HTB38) were used as the non-target specificity control. In other studies, A375 was used as a marker-positive cell. The HT29 and M14 cells were seeded in 96-well microtiter plates at a concentration of $5.0\times10^3$ cells/well, and the BO54 cells were seeded at $2.5\times10^3$ cells/well. Serial two-fold dilutions of free Roridin A and 2'RA-HS-NR-AN-01 (i.e., Roridin A coupled through a hemisuccinate (HS) coupling agent at the 2' position to NR-AN-01) were prepared in DMEM over a range of protein concentrations from 20 mg/ml to 40 pg/ml. Test agents were added (in duplicate) to microtiter wells (100 ml/well), and the plates were wrapped in aluminum foil and incubated at 37° C. in a humidified atmosphere consisting of 5% $Co_2$/95% air for 24 hours. After 24 hours, medium was removed (by aspiration), fresh DMEM was added (100 ml/well), and the cells were returned to incubate for an additional overnight (i.e., 16-18 hours) "recovery period". At the end of the "recovery period" cellular metabolic activity was determined by adding 20 ml to each well of a 5 mg/ml MTT solution. The plates were covered and incubated at 37° C. for 4 hours and then the reaction was developed by adding 100 ml/well of 10% SDS/0.1 N HCl. The dark blue solubilized formazan reaction product was developed at room temperature after 16-18 hours and quantified using an ELISA microtiter plate reader at an absorbance of 570 nm.

Figure 5A:
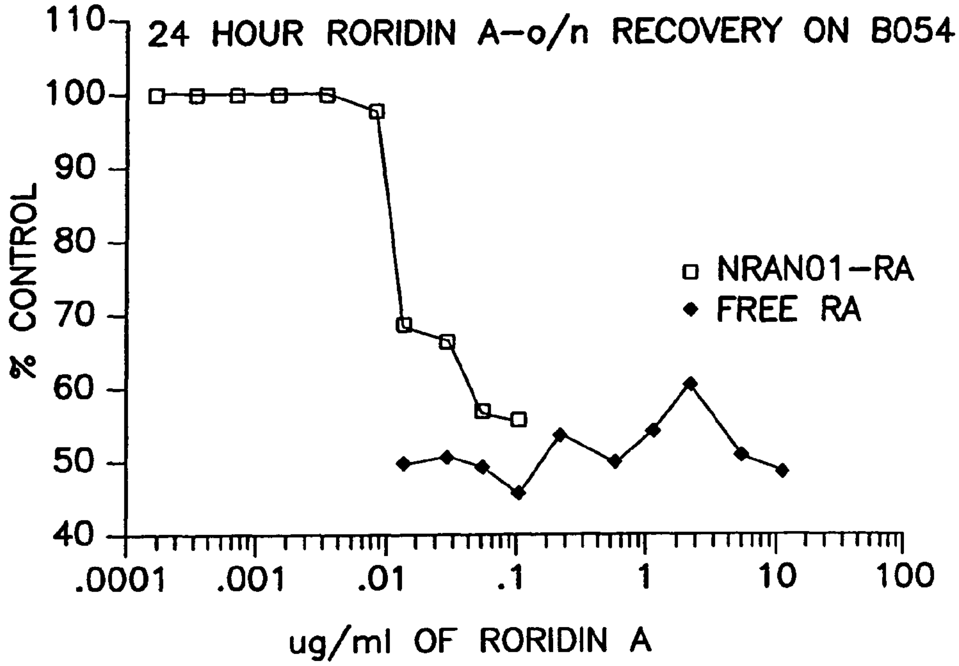
FIG. 5A presents graphically experimental data showing undesirable cytotoxicity of even low levels of therapeutic conjugate (i.e., RA-NR-AN-01), and the free RA therapeutic agent, when vascular smooth muscle cells were treated for 24 hours in vitro.

FIG. 5A graphically depicts the results of in vitro studies in which BO54 marker-positive smooth muscle cells were incubated with different concentrations of RA-NR-AN-01 (NRAN01-RA; open squares, FIG. 5A) or free Roridin A (Free RA; closed diamonds, FIG. 5A) for a period of 24 hours, washed, and then returned to culture for an additional 16-18 hour overnight (o/n) recovery period prior to testing metabolic activity in an MTT assay. The concentrations of Free RA and RA-NR-AN-01 are expressed as the calculated concentration of Roridin A (in mg/ml plotted on a log scale) in the assay (i.e., rather than the total mg/ml of NR-AN-01 protein in the assay), so that direct comparisons could be made. The metabolic activity of the cells in the MTT assay is presented as the percentage of the metabolic activity measured in a control untreated culture of cells (i.e., % control).

Figure 5B:
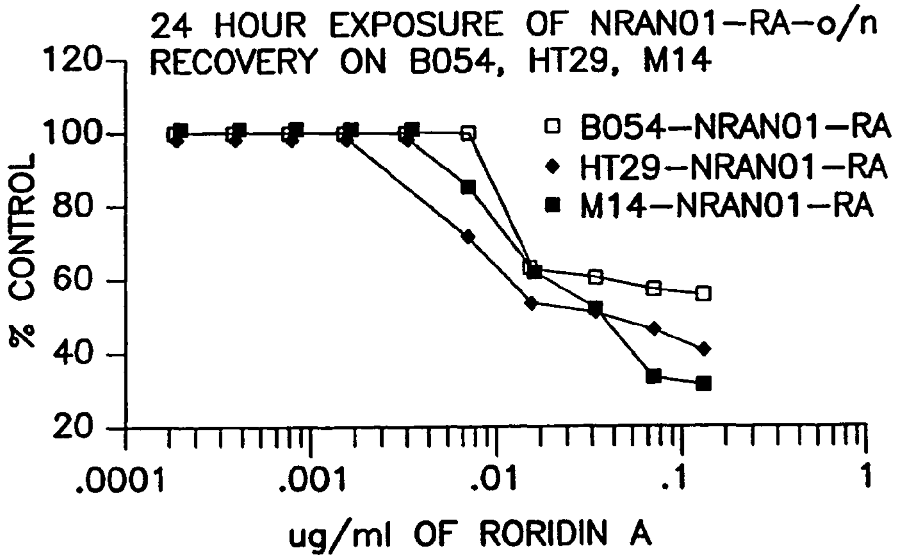
FIG. 5B graphically presents experimental data showing the effects of RA-NR-AN-01 therapeutic conjugate on metabolic activity of marker-positive and -negative cells. The data show undesirable nonspecific cytotoxicity of the conjugate for all these cells in a 24 hour treatment in vitro. The non-specificity results from extracellular hydrolysis of the coupling ligand which exposes the tested cells to free drug.

FIG. 5B graphically depicts the results of in vitro studies conducted in a manner similar to those described above in regard to FIG. 5A, but comparing the effects of only RA-NR-AN-01 (NRAN01-RA) on three different cell types: namely, BO54 marker-positive smooth muscle cells (BO54-NRAN01-RA; open squares, FIG. 5B); HT29 marker-negative control cells (HT29-NRAN01-RA; closed diamonds, FIG. 5B); and, M14 marker-positive cells (M14-NRAN01-RA; closed squares, FIG. 5B). As described above in regard to FIG. 5A, the concentrations in the present experiment are expressed in terms of ug/ml of Roridin A. Metabolic activity of the cells is expressed in a manner similar to that in FIG. 5A, i.e., as the percentage of activity measured in an untreated control culture of cells (% control).

The results presented in FIG. 5A and FIG. 5B show that metabolic activity measured in the MTT assay was significantly decreased in all populations of test cells, even 16-18 hours after a 24-hour incubation in either free Roridin A or the 2' or 13' RA-NR-AN-01 conjugates. The effects of the RA-NR-AN-01-conjugates appeared to be non-specifically inhibitory for both target (BO54 and M14) and non-target (HT29) cells (FIGS. 5A and 5B). The inhibitory effects were observed at a free Roridin A or RA-conjugate concentration of >10 ng/ml.

For comparative purposes, a second study was conducted in which the effects of *Pseudomonas* exotoxin (PE) conjugates on cells were evaluated in a similar protocol. For these studies, target and non-target cells were treated with PE or PE-NR-AN-01 for 24 hours, and then allowed a "recovery period" (as above) before metabolic activity was tested in an MTT assay.

Figure 6A:
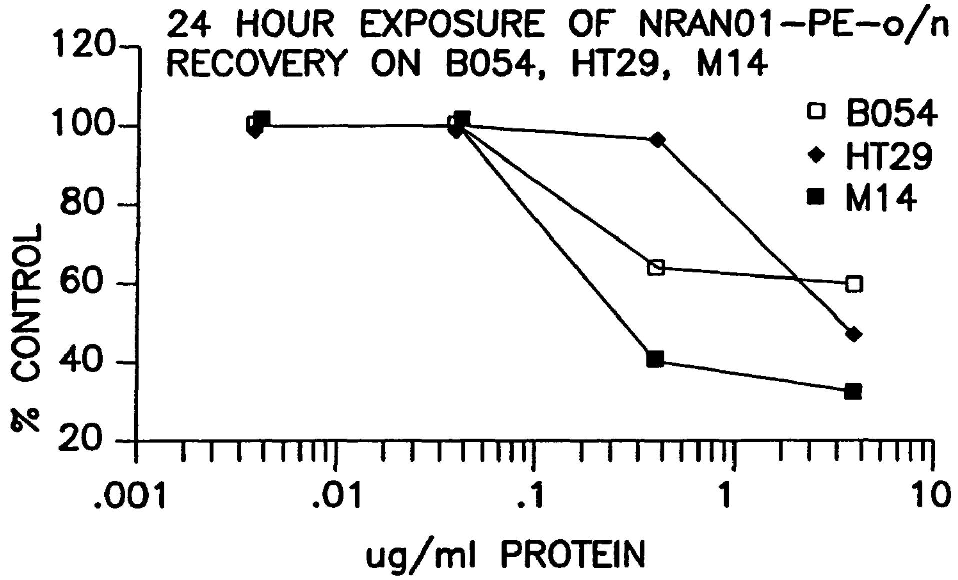
FIG. 6A graphically depicts experimental data showing undesirable nonspecific cytotoxicity of PE-NR-AN-01 therapeutic conjugate for marker-positive and marker-negative test cells after 24 hours of treatment in vitro, even though the 24 hour treatment was followed by an overnight recovery period prior to testing the metabolic activity.

FIG. 6A graphically depicts the results of in vitro studies conducted in a manner similar to those described above in regard to FIG. 5A, but designed to study the metabolic effects of PE-NR-AN-01 (NRAN01-PE) on cells, i.e., rather than RA-NR-AN-01. Three different cell types were utilized: namely, BO54 marker-positive smooth muscle cells (BO54; open squares, FIG. 6A); HT29 marker-negative control cells (HT29; closed diamonds, FIG. 6A); and, M14 maker-positive cells (MT14; closed squares, FIG. 6A). In this study, the concentration of conjugate is expressed in μg/ml NR-AN-01 protein (plotted on a log scale), and the metabolic activity is expressed as the percentage of the MTT activity measured in an untreated control culture (% control).

Figure 6B:
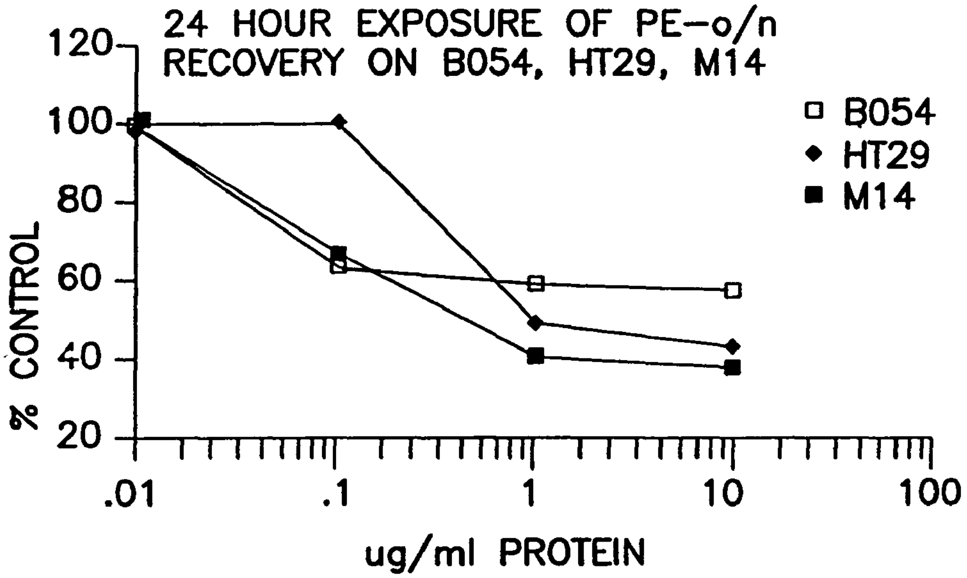
FIG. 6B depicts experimental data showing nonspecific cytotoxicity of the free PE therapeutic agent on marker-positive and -negative test cells after 24 hours of treatment in vitro.

FIG. 6B graphically depicts the results of in vitro studies conducted in manner similar to those discussed above in regard to FIG. 6A, but designed to compare the effects obtained with free PE (PE) to those obtained above, i.e., in FIG. 6A, with PE-NR-AN-01. The cells, culture conditions, calculations, and presentation of the results are the same as in FIG. 6A, above.

The results presented in FIG. 6A and FIG. 6B show that 24 hours exposure to PE-NR-AN-01 or free PE was non-specifically inhibitory to cells at concentrations of >100 ng/ml.

While this type of non-specific inhibition was judged to be of potential value for biological atheroectomy, it was not considered desirable for treatment of restenosis following angioplasty where dead and dying cells may release factors that stimulate smooth muscle proliferation.

Example 5

Effects of Pulse-Treatment on Cellular Activity

Additional studies were conducted to evaluate the effects of a short-term, i.e., 5 minute, exposure to a Roridin A-containing therapeutic conjugate on cells. In these studies, both metabolic activity (measured in MTT assays) and cellular protein synthesis (measured by $^3$H-leucine incorporation) were evaluated.

Effects After 5 Minutes of Exposure: Protein Synthesis

The effects of a 5-minute exposure to free Roridin A (RA) or a therapeutic conjugate were evaluated. Roridin A-NR-AN-01 coupled through a hemisuccinyl (HS) at either the 2' position (2'RA-HS-NR-AN-01) or the 13' position (13'RA-HS-NR-AN-01) were employed. (In the case of 13'RA-HS-NR-AN-01, the 2' position of Roridin A was also acetylated.) The RA, 2' or 13'RA-NR-AN-01 conjugates were diluted two fold in sterile DMEM over a range of concentrations from 400 ng/ml to 780 pg/ml of Roridin A. (The test samples were all normalized to Roridin A, so that direct comparisons could be made of the effects at comparable doses.) Samples were aliquoted (in duplicate) into duplicate microtiter plates at 100 ml/well and incubated at room temperature for five minutes.

Both short-term and long-term effects of the test samples on marker-positive A375 and marker-negative HT29 cells were determined. For studying the short-term effects, 100 ml/well of [$^3$H]-leucine (0.5 mCi/ml) was added immediately after the 5-minute treatment with conjugate (or RA) and protein synthesis was evaluated over a four-hour period. For determining the long-term effects, the cells were treated for 5 minutes, washed, and then returned to culture for a 24-hour "recovery" period in DMEM medium containing either 5% NBS/5% Serum Plus® (i.e., for A375 or HT29 cells) or 10% FBS (i.e., for BO54 cells). At the end of the "recovery" period, the incubation medium was removed (i.e., by aspiration) and $^3$H-leucine was added (as above). In both cases (i.e., whether short-term or long-term), protein synthesis of the cells was evaluated by incubating the cells with the $^3$H-leucine for 4 hours at 37° C. in a humidified chamber (as above), and all results are calculated by comparison with non-treated cells (i.e., 100% control). After 4 hours the $^3$H-leucine was removed, the cells were removed from the substrata by trypsin-treatment, aspirated (using a PHD™ cell harvester (Cambridge Technology, Inc., Cambridge, Mass.)) and collected by filtration on glass fiber filters. The glass fiber filters were dried and radioactivity quantified by liquid scintillation spectroscopy in a Beckman liquid scintillation counter.

Figure 7A:
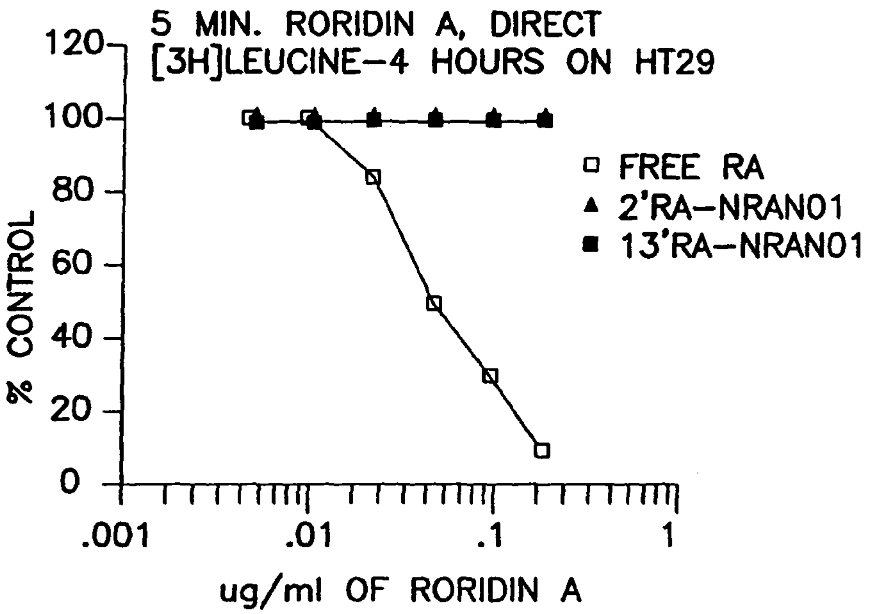
FIG. 7A graphically presents experimental data showing that a short 5 minute "pulse" treatment, i.e., instead of 24 hours, followed by exposure to [3H]leucine, with free RA therapeutic agent being nonspecifically cytotoxic, i.e., for control HT29 marker-negative cells, but, in contrast, the RA-NR-AN-01 therapeutic conjugate is not cytotoxic in this "pulse" treatment.

FIG. 7A graphically depicts the results of in vitro studies conducted to investigate the effects on control HT29 marker-negative cells of a 5 minute exposure to different concentrations of Roridin A (Free RA; open squares, FIG. 7A), or 2'RA-NR-AN-01 (2'RA-NRAN01; closed squares, FIG. 7A), or 13'RA-NR-AN-01 (13'RA-NRAN01; closed triangles, FIG. 7A) conjugates. The concentrations of Free RA, 2'RA-NR-AN-01 or 13'NR-AN-01 are expressed as the calculated concentration of Roridin A in the assay (in μg/ml plotted on a log scale), i.e., rather than the total μg/ml of NR-AN-01 protein, so that direct comparisons of the results can be made. For these studies, the cells were treated for 5 minutes, washed, and then returned to culture for 4 hours, during which time cellular protein synthesis was evaluated by adding 0.5 mCi/ml of $^3$H-leucine to the culture medium. At the end of the 4 hour period, cellular proteins were collected and radioactivity was determined. The results are expressed as the percentage of the radioactivity recorded in a control (non-treated) HT29 cell culture (i.e., % control).

Figure 7B:
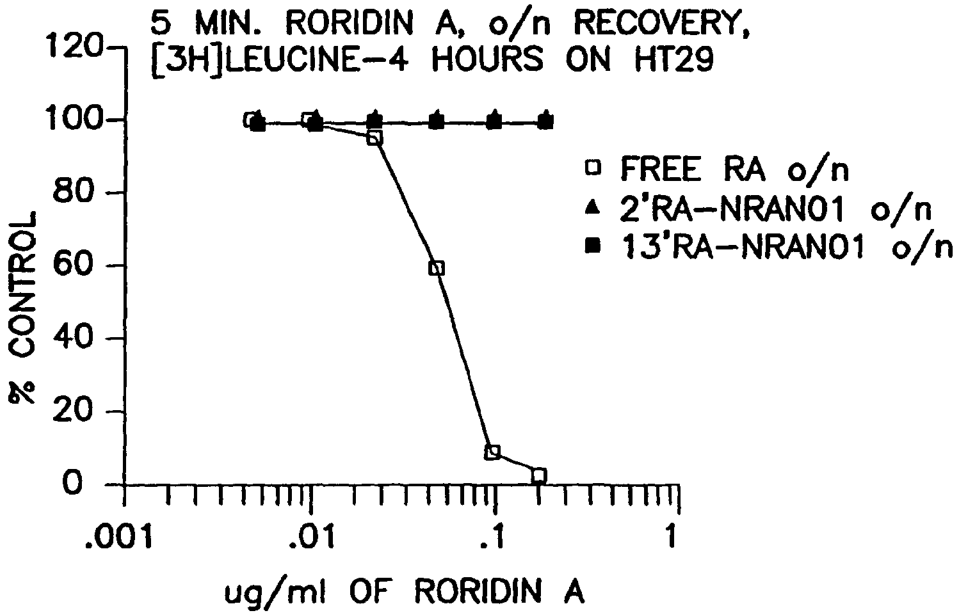
FIG. 7B presents graphically experimental data showing that free RA therapeutic agent is nonspecifically cytotoxic for control HT29 marker-negative cells, even in a 5' "pulse" treatment followed by a 24 hour recovery period prior to [3H]leucine exposure, but, in contrast, the RA-NR-AN-01 therapeutic conjugate is not cytotoxic to cells.

FIG. 7B graphically depicts the results of in vitro studies investigating the effects on control HT29 marker-negative cells of a 5 minute expose to different concentrations of Free RA (open squares, FIG. 7B), 2'RA-NRAN01 (closed squares, FIG. 7B), or 13'RA-NRAN01 (closed triangles, FIG. 7B), as described above in regard to FIG. 7A, but in the present experiments the cells were incubated for a 16-18 hour recovery period (i.e., overnight; o/n) prior to testing protein synthesis in a four hour $^3$H-leucine protein synthesis assay. The results are presented in a manner similar to those above in FIG. 7A.

The results presented in FIG. 7A and FIG. 7B show the short-term and long-term effects, respectively, of RA, 2'RA-HS-NR-AN-01, and 13'RA-HS-NR-AN-01 on protein synthesis by HT29 control cells. The results show a dose-response inhibition of cellular protein synthesis by the free Roridin A, but not by RA-NR-AN-01, in HT29 cells. The inhibition triggered by RA during the 5 minutes of incubation was still manifest after the 16-18 hours recovery period (FIG. 7B). In contrast, treatment of non-target HT29 cells with 2'RA-HS-NR-AN-01 or 13'RA-HS-NR-AN-01 did not result in detectable inhibition of protein synthesis. Thus, these results (in contrast to those obtained above over 24 hours) seem to suggest a surprising degree of specificity to the in vitro action of the NR-AN-01-conjugates when treatment was delivered in a 5-minute "pulse". However, it was also possible that the NR-AN-01-conjugate was inactive, and so additional experiments were conducted to evaluate the effect of the conjugates on target cells.

Figure 7C:
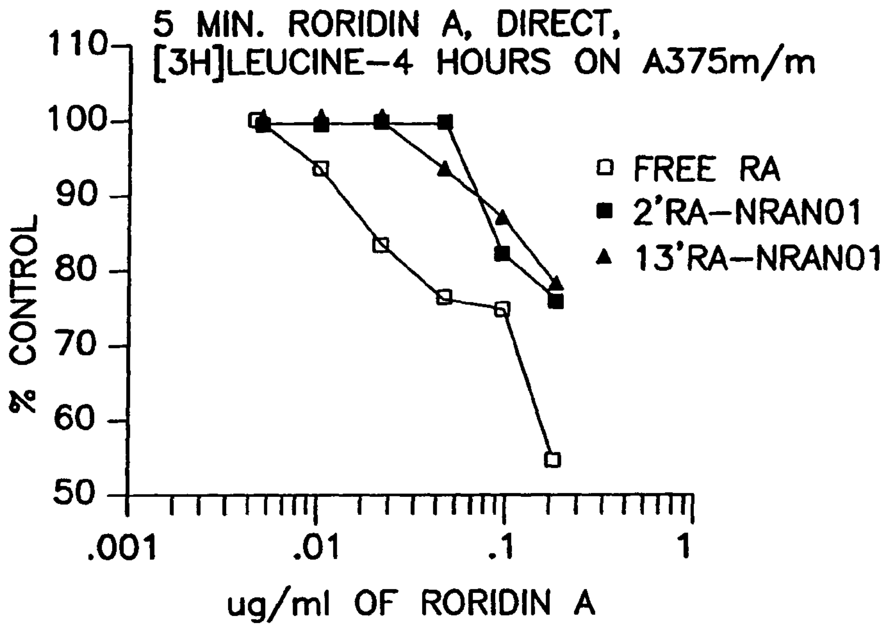
FIG. 7C presents graphically results of experiments showing that "pulse" treatment of cells in vitro with the RA-NR-AN-01 therapeutic conjugate inhibits cellular activity in marker-positive A375 cells, as measured by protein synthesis.

FIG. 7C graphically depicts the results of in vitro studies investigating the effects on A375m/m marker-positive cells of a 5 minute exposure to different concentrations of Free RA (open squares, FIG. 7C), 2'RA-NR-AN-01 (closed squares, FIG. 7C) or 13'RA-NR-AN-01 (closed triangles, FIG. 7C), as described above in regard to FIG. 7A. In the present studies, the A375 cells were incubated for 5 minutes in the test agent, washed, and tested for protein synthesis over the next 4 hours by adding 0.5 mCi/ml $^3$H-leucine to the culture medium. The results of the experiments are plotted in a manner similar to those described, above, in regard to FIG. 7A.

Figure 7D:
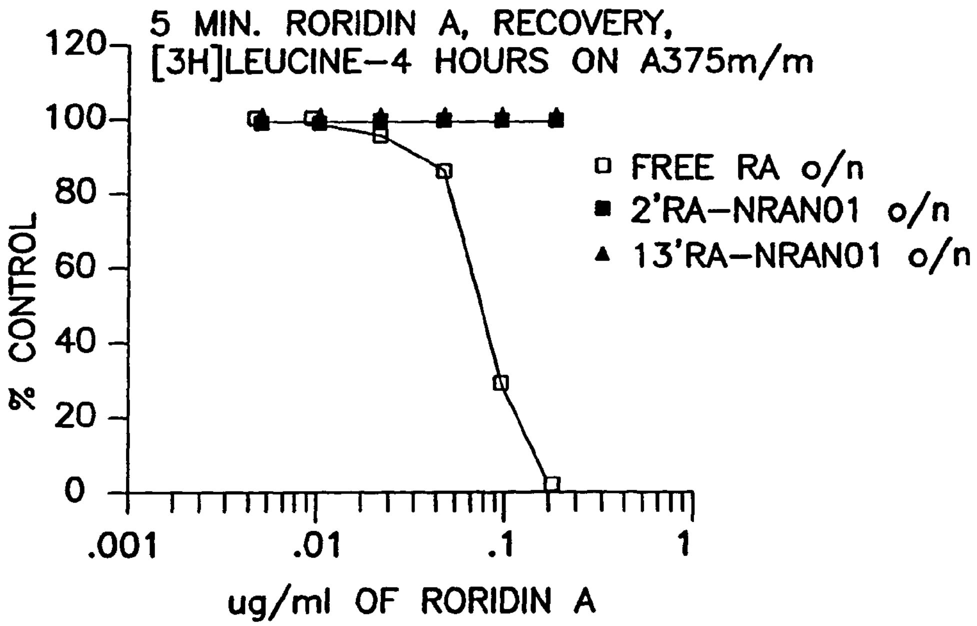
FIG. 7D presents graphically experimental data showing that "pulse" treatment of cells in vitro with the RA-NR-AN-01 therapeutic conjugate did not exert long-lasting inhibitory effects on cellular activity in marker-positive cells, since protein synthesis in A375 cells was not inhibited when the cells were allowed an overnight recovery period prior to testing in vitro.

FIG. 7D graphically depicts the results of in vitro studies investigating the effects on A375 m/ml marker-positive cells of a 5 minute exposure to different concentrations of Free RA (open squares, FIG. 7D), 2'RA-NRAN01 (closed squares, FIG. 7D), 13'RA-NRAN01 (closed triangles, FIG. 7D), as described above in regard to FIG. 7B. In the present studies, the A375 cells were incubated for 5 minutes in the test agent, washed, and then returned to culture for a 16-18 hour recovery period (i.e., overnight; o/n Recovery), after which time protein synthesis was evaluated during a 4 hour $^3$H-leucine protein synthesis assay. The results of the experiments are plotted in a manner similar to those described above in regard to FIG. 7A.

The results presented in FIG. 7C and FIG. 7D show the short-term and long-term effects, respectively, of RA, 2'RA-HS-NR-AN-01 and 13'-RA-HS-NR-AN-01 on protein synthesis by A375 target cells. Treatment of target cells with either the 2' or 13'RA-NR-AN-01 therapeutic conjugate resulted in a short-term inhibition of protein synthesis, i.e., observed immediately after the 5-minute pulse treatment (FIG. 7C). These findings, when combined with the findings in FIG. 7A and FIG. 7B, above, suggest that the RA-NR-AN-01 conjugates were active and that they were specifically inhibitory for target cells but not non-target cells. Interestingly, when "pulse" treated target cells were returned to culture no long-term inhibitory effects were observed (FIG. 7D). The results presented in FIG. 7C and FIG. 7D again show that Roridin A is non-specifically inhibitory to test cells (i.e., in a manner similar to FIG. 7A and FIG. 7B, above) and that its effect on the cells is manifest even after a 16-18 hour recovery period. Thus, the specific effects of the RA-NR-AN-01 conjugates on target cells during a "pulse" treatment appear to be a property of the NR-AN-01 binding protein.

The results obtained with BO54 arterial smooth muscle cells were similar to those obtained with the A375 cells, above, i.e., free Roridin A showed a dose-response inhibition of protein synthesis in the short-term equated to be 60%, 66%, and 90% of control at 200 ng/ml, 100 ng/ml, and 50 ng/ml; and in long-term the effects on protein synthesis were equated to be 27%, 46%, and 98% of control at the same dosages. In contrast, the 2' or 13'RA-NR-AN-01 showed only 10-20% inhibition for short- or long-term effects on protein synthesis (i.e., >80% of control).

Thus, the results show a short-term specific reversible effect of Roridin A-conjugated NR-AN-01 on target cells when delivered as a "pulse" treatment. However, since only protein synthesis was evaluated in these experiments, it was possible that cellular metabolic activity might be affected in the cells as a result of the "pulse" treatment. Therefore, additional studies were conducted in which cellular metabolic activity was evaluated following "pulse" treatment.

Effects After 5 Minutes of Exposure: Metabolic Activity

MTT assays were conducted at 48 hours following a 5-minute exposure of target and non-target cells to RA or RA-NR-AN-01 conjugates. Target cells in these studies included BO54 and A375, and non-target cells included HT29 cells. Sterile 96 well microtiter plates were seeded with 2500 cells/well, wrapped in aluminum foil and incubated in a humidified chamber containing 5% $CO_2$/95% air for 16-18 hours. Serial two-fold dilutions of Roridin A (RA), 2'RA-HS-NR-AN-01 and 13'RA-HS-NR-AN-01 were prepared from 400 ng/ml to 780 pg/ml, and 100 ml aliquots of the dilutions were dispensed into duplicate wells. After 5 minutes exposure to the test samples, the cells were washed to remove the test samples, and fresh medium was added. The cells were allowed 48 hours of recovery prior to testing: i.e., plates were incubated for 48 hours, and then cellular metabolic activity was determined by adding 20 ml/well of a 5 mg/ml MTT solution. The plates were covered and incubated at 37° C. for 4 hours and then the reaction was developed as described above (see EXAMPLE 4, above). The dark blue solubilized formazan reaction product was developed at room temperature after a 16-18 hour incubation. The samples were quantified using an ELISA microtiter plate reader at an absorbance of 570 nm.

Figure 8A:
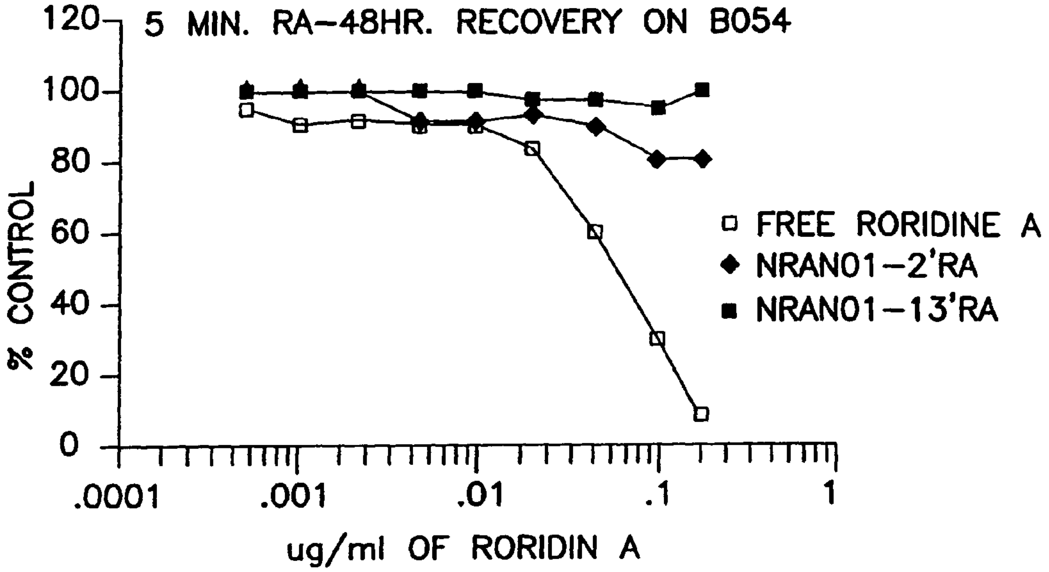
FIG. 8A presents graphically experimental data showing that while a "pulse" treatment of cells in vitro with free RA therapeutic agent was non-specifically cytotoxic, the RA-NR-AN-01 therapeutic conjugate did not exert long-lasting inhibitory effects on cellular activity in vascular smooth muscle cells, as evidenced by metabolic activity in BO54 cells that were allowed a 48 hour recovery period prior to testing.

FIG. 8A graphically depicts the results of in vitro studies investigating the effects on BO54 marker-positive smooth muscle cells of a 5 minute exposure to different concentrations of Roridin A (open squares, FIG. 8A), 2'RA-NR-AN-01 (NRAN01-2'RA; closed diamonds, FIG. 8A), or 13'RA-NR-AN-01 (NRAN01-13'RA; closed squares, FIG. 8A). The experiments were conducted in a manner similar to those described above in regard to FIG. 7B, but metabolic activity was assayed by MTT assay, i.e., rather than protein synthesis as in FIG. 7B, and cells were also given 48 hours to recover (rather than 24 hours, as in FIG. 7B). The results of the experiments are plotted in a manner similar to those described (above) in regard to FIG. 7A.

Figure 8B:
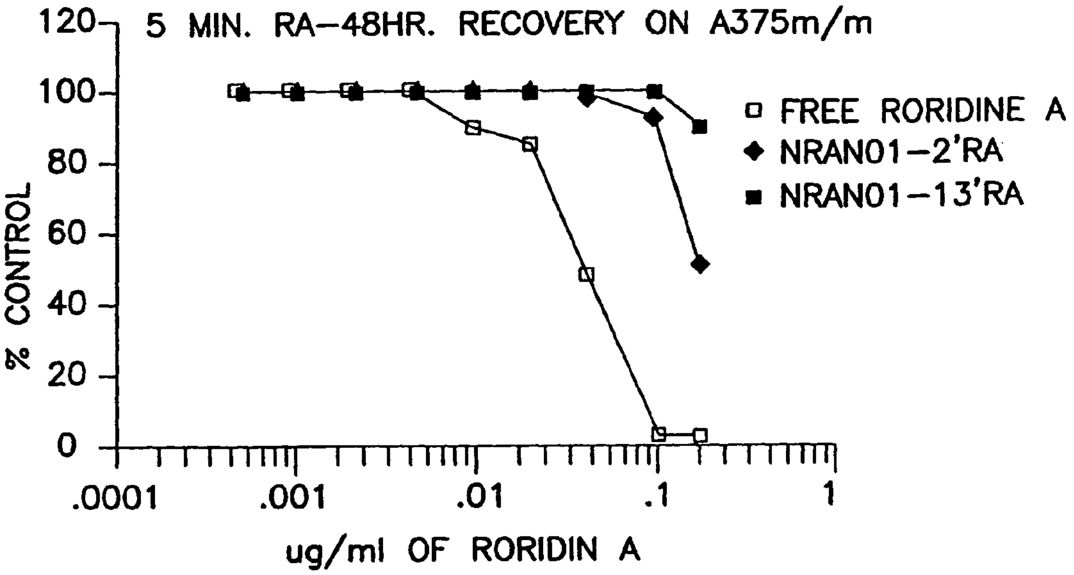
FIG. 8B graphically depicts experimental data similar to those presented in FIG. 8A, above, but using a second marker-positive cell type, namely A375, the data show that "pulse" treatment with the RA-NR-AN-01 therapeutic conjugate did not exert long-lasting inhibitory effects on cellular activity, as measured by metabolic activity in A375 cells that were allowed a 48 hour recovery period prior to testing.

FIG. 8B graphically depicts the results of in vitro studies investigating the effects on A375 m/m marker-positive cells of a 5 minute exposure to different concentrations of Roridin A (open squares, FIG. 5B), 2'RA-NR-AN-01 (NRAN01-2'RA; closed diamonds, FIG. 8B), 13'RA-NR-AN-01 (NRAN01-13'RA; closed squares, FIG. 8B). The experiments were conducted (and the results plotted) in a manner similar to those described above in regard to FIG. 8A.

Figure 8C:
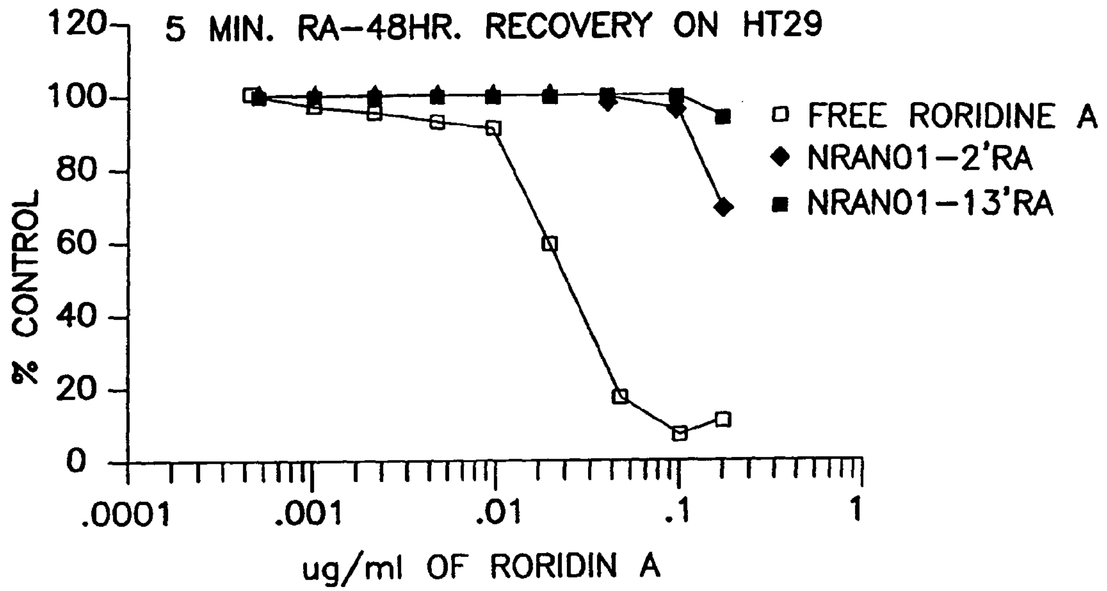
FIG. 8C graphically depicts results similar to those presented in FIG. 8A and FIG. 8B, above, but using a marker-negative control cell type, namely HT29. The results show that the "pulse" treatment with the RA-NR-AN-01 therapeutic conjugate did not exert long-lasting inhibitory effects on the cellular activity of marker-negative control cells, as measured by metabolic activity in HT29 cells that were allowed a 48 hour recovery period prior to testing.

FIG. 8C graphically depicts the results of in vitro studies investigating the effects on HT29 marker-negative cells of a 5 minute exposure to different concentrations of Roridin A (open squares, FIG. 8C), 2'RA-NR-AN-01 (NRAN01-2'RA; closed diamonds, FIG. 8C), 13'RA-NR-AN-01 (NRAN01-13'RA; closed squares, FIG. 8C). The experiments were conducted (and the results plotted) in a manner similar to those described above in regard to FIG. 8A.

The results presented in FIGS. 8A-8C show slight differences between the different RA-NR-AN-01 conjugates at the highest doses, but at the lower doses the 2' and 13'RA-NR-AN-01 did not significantly inhibit target cell (i.e., BO54 and A375) or non-target cell (i.e., HT29) metabolic activity over the long-term (i.e., 48 hours). Thus, the results suggest that the short-term inhibition of target cell protein synthesis (FIGS. 7C-7D, above) does not result in long-term metabolic effects on the cells, as measurable in MTT assays. That these assays were able to detect metabolic alterations in cells resulting from a 5 minute exposure is evidenced by the results obtained with free Roridin A. In this case, free Roridin A was non-specifically inhibitory to target and non-target cell types, even when the cells were exposed to the agent for only 5 minutes and then returned to culture for the 48-hour recovery period (FIGS. 8A-8C).

Thus, the findings with free Roridin A suggest that the MTT assay was capable of detecting metabolic alterations induced during a 5-minute exposure. Taken together these finding suggest that RA-NR-AN-01 conjugates can specifically inhibit target cell activity (i.e., protein synthesis) when administered in a "pulse" treatment, and that these effects were reversible without significant long-term effects on either protein synthesis or cellular metabolic activity (as measured in an MTT assay). These in vitro properties of the RA-NR-AN-01 conjugates were judged to be highly useful for inhibition of smooth muscle cell activity in vivo. Therefore, animal model studies were next conducted to evaluate the effects of these therapeutic conjugates in vivo.

Example 6

Determination of Infusion Conditions in an Animal Model

The therapeutic conjugates of the invention are useful for inhibiting stenosis following vascular trauma or disease. In an illustrative example, vascular trauma that is induced during angioplasty is treated during the surgical procedure by removing the catheter used to perform the angioplasty, and inserting a balloon infusion catheter into the vessel. The infusion catheter is positioned with the instillation port (or, alternatively, a permeable membrane region) in the traumatized area of the vessel, and then pressure is applied to introduce the therapeutic conjugate. For example, an infusion catheter with two balloons may be used, and when one balloon is inflated on either side of the trauma site a fluid space is created that can be filled with a suitable infusion fluid containing the therapeutic conjugate. It has been reported previously that infusion of a horseradish peroxidase (HRP) marker enzyme at a pressure of 300 mm Hg over 45 seconds in dog or human coronary arteries resulted in penetration of the HRP into the vessel wall (6). However, HRP is a smaller molecule than NR-AN-01 and human and dog coronary arteries are also considerably smaller than the carotid or femoral arteries in the present domestic pig model system. Experiments were therefore conducted to determine, in a domestic pig model system, the infusion conditions suitable for delivery of a therapeutic conjugate to the vascular smooth muscle cells in carotid and femoral arteries. Delivery conditions were monitored by evaluating the penetration of the therapeutic conjugate into the vascular wall, and specific binding of the therapeutic conjugate to the vascular smooth muscle cells in the vessel wall.

Using an infusion catheter, the coronary and femoral arteries of domestic pigs or non-human primates were infused with NR-AN-01 for 45 seconds to 3 minutes at multiple pressures in the range of about 0.4 atmospheres (300 mm Hg) to 3 atmospheres. After infusion, the vessels were flushed with sterile saline and prepared for immunohistochemistry using HRP-conjugated goat anti-mouse IgG to detect the NR-AN-01 mouse IgG in the vessel wall. It was determined that full penetration was achieved of NR-AN-01 into these vessel walls at a pressure of 3 atmospheres after 3 minutes.

Immunohistology was also used to determine which animal model systems expressed the target antigen for NR-AN-01. Vascular tissue sections from readily available experimental animal species were exposed to NR-AN-01, washed, and reacted with HRP-conjugated goat anti-mouse IgG. Only non-human primates and swine were found to share the 250 kD NR-AN-01 target antigen with man.

To determine whether NR-AN-01 could bind in a specific manner to its target antigen in vivo, the coronary and femoral arteries of domestic pigs were infused with therapeutic conjugates using an infusion catheter, the infusion sites were flushed with sterile saline, the surgical sites were then closed, and the animals were maintained for an additional 3-5 days. At the end of this time, the vascular infusion sites were excised and prepared for immunohistology, once again using goat anti-mouse IgG to identify NR-AN-01. NR-AN-01 was identified in the vessel wall of swine coronary and femoral arteries 3-5 days after surgery, and the NR-AN-01 appeared to be associated only with vascular smooth muscle cells. These findings suggest that NR-AN-01 is capable of specifically binding to its target antigen in vivo.

Example 7

Inhibition of Vascular Smooth Muscle Cells in Vivo

Intimal smooth muscle proliferation that follows balloon catheter-induced trauma is a good model to evaluate the therapeutic efficacy of conjugates for inhibiting smooth muscle cell activity in vivo in response to vascular trauma, including restenosis following angioplasty. Domestic pigs were used to study the effects of NR-AN-01 (i.e., termed vascular smooth muscle binding protein or simply VSMBP in these studies; and therapeutic conjugates with Roridin A are termed VSMBP-RA). The events which normally follow balloon angioplasty in the porcine artery have been described previously (12). In these studies, dilation of the carotid artery using an oversized balloon (balloon: artery ratio approximately 1.5:1) resulted in complete endothelial denudation over an area of 1.5-2 cm in length. Although this length of traumatic injury was selected in an attempt to minimize thrombosis, there was still marked platelet deposition and thrombus formation. The procedure also resulted in dissection through the internal elastic lamina into the arterial media and necrosis of medial smooth muscle cells. Intimal thickening due to smooth muscle proliferation was apparent 7 days after injury and reached a mean maximum thickness of 85 mm at 14 days. The histological appearance of this neointima is very similar to the proliferative neointimal tissue of human restenosis (13).

A single dose test protocol was conducted in domestic pigs with NR-AN-01-Roridin A conjugates. Localized administration of the test conjugates, i.e., through a catheter into a region of traumatized vessel confined by temporary slip ligatures, was designed to reduce systemic toxicity while providing a high level of exposure for the target smooth muscle cells. This intra-artery route of administration in animal model studies simulates the proposed route in human coronary arteries. The test protocol was designed as an initial in vivo screening of intra-arteriolar, site specific, catheter administered, vascular smooth muscle binding protein (VSMBP) conjugates. Toxicity of free drug was also evaluated, i.e., for pathobiological effects on arteriolar smooth muscle cells. The therapeutically effective dosage of the Roridin A-NR-AN-01 conjugate was determined by in vitro studies, and the proper intra-arteriolar administration pressure was determined by administering free MAb and MAb conjugates to animals, as described above in Example 7.

Six domestic crossbred swine (Duroc X), weanling feeder pigs of approximately 30 pounds body weight, were used in the experiment. The animals were randomly assigned to the following treatment regimen where each pig has four different treatments divided between the right and left carotid and femoral arteries, one of which is a PBS control (Tables 1-3, below).

TABLE 1

| GROUP NO. | TREATMENT GROUP | MATERIAL DESCRIPTION |
|---|---|---|
| 1 | CONTROL, VSMBP | VSMBP, 200 μg/ml in PBS, pH 6.5 |
| 2 | CONTROL, PBS | PBS, pH 6.5, in injection sterile water |
| 3 | CONTROL, DRUG | Roridin A, 2.5 μg/ml in PBS, pH 6.5 |
| 4 | TEST, CONJUGATE | VSMBP-RA2' (200 μg/ml VSMBP & 2.5 μg/ml RA) |
| 5 | TEST, CONJUGATE | VSMBP-RA13' (200 μg/ml VSMBP & 3.1 μg/ml RA) |
| 6 | TEST, CONJ + RA | VSMBP-RA2' (200 μg/ml VSMBP & 2.5 μg/ml RA) PLUS free Roridin A (2.5 μg/ml) |
| 7 | TEST, CONJ + RA | VSMBP-RA13' (200 μg/ml VSMBP & 3.1 μg/ml RA) PLUS free Roridin A (2.5 μg/ml) |

Surgical Procedure:

Test conjugates and control compounds were administered as a single intra-artery infusion at the site of endothelial denuding and trauma induced by a balloon catheter. Both the carotid and femoral arteries were abraded over 1 cm to 2 cm of endothelium by intraluminal passage of a 23 cm, size 3 (femoral) and size 4 (carotid) Uresil Vascu-Flo® silicone occlusion balloon catheter (Uresil Technology Center, Skokie, Ill.), sufficiently distended with saline to generate slight resistance. This technique produced slight distension of the artery. Following this treatment, proximal and distal slip ligatures, 3-0 silk, were placed near the ends of the abraded region, and a size 8 French, Infant Feeding Catheter (Cutter-Resiflex, Berkeley, Calif.) attached to an Inflation Pros (USCI, C.R. Bard, Inc., Billerica, Mass.) pressure syringe was used to administer the test conjugates and control compounds directly to the denuded segment at a pressure of three atmospheres for three minutes. The slip ligatures were removed after the three minute exposure period and arterial blood flow was re-established. In these studies, branches of the femoral or carotid arteries were ligated with 00 silk suture as required to attain pressurized infusion in the treated region. The largest distal branch of the femoral artery (the saphenous artery) was incised and used as an entry site for the catheters which were then passed into the main femoral artery. Following this catheterization procedure in the main femoral artery, the secondary branch was ligated. In these cases, ligation or incision was used to allow entry of the catheters and the opening was then closed with 3 to 4 sutures of 5-0 monosilamen polybutester (Novafil, D & G Monofil Inc., Monati, PR).

Follow-up Procedures:

Following surgery, the pigs were kept in 3×5 foot indoor runs with cement floors during the quarantine and surgical recovery periods. They were then transferred to indoor/outdoor pens for the remainder of the five week healing period prior to collection of tissues for histology.

The animals recovered normally from surgery with no evidence of hemorrhage or inflammation at the surgical sites. All six animals were examined 5 to 6 days after treatment with a doppler stethoscope, and all arteries in each of the animals were patent. Post treatment all animals had normal appetite, activity and weight gain.

Gross Pathology and Histological Evaluation:

Five weeks following the traumatization and treatment of the arteries, the animals were sedated with 0.6 ml Telazol®

(tiletamine hydrochloride; A.H. Robins Co., Richmond, Va.) and 0.5 ml xylazine (Lloyd Laboratories, Shenandoah, Iowa) per 30 lb body weight by intramuscular injection, heparinized (i.v. 2 ml sodium heparin, 1000 units/ml), and euthanized by i.v. pentobarbital. Both the right and left carotid and femoral arteries were removed with normal vessel included both proximal and distal to the treated segment. The arteries were measured and the location of ligatures and gross abnormalities noted. The arteries were transected at 2 mm intervals and arranged in order in cryomolds with O.C.T. (optimum cutting temperature) compound (Tissue Tek®, Miles Laboratories Inc., Elkhart, Ind.) and frozen in liquid nitrogen. The blocks were sectioned at 5 microns and stained with H&E, Massons Trichrome and Movats Pentachrome for morphological studies. Sections were also used for immunohistological staining of vascular smooth muscle.

Histological examination of the step sections of the arteries revealed marked inhibition of intimal smooth muscle proliferation in the regions traumatized and treated with RA-NR-AN-01 conjugates (Table 2). This inhibition was evident even at sub-gross evaluation of the vessels. The inhibition of intimal smooth muscle cell proliferation was produced with minimal or no histological evidence of smooth muscle cell death in the artery wall. A cross-sections of one such traumatized artery is provided in FIGS. 9A and 9B.

TABLE 2

INTIMAL SMOOTH MUSCLE PROLIFERATION IN TRAUMATIZED AND TREATED PORCINE ARTERIES

| TREATMENT | NO. ARTERIES EVALUATED | INTIMAL SMC HYPERTROPHY* ave. (range) |
|---|---|---|
| Control, MAB | 4 | 3.75 (3-4) |
| Control, PBS | 4 | 4 (4) |
| Control, RA | 2 | 4 (4) |
| Test, 2'RA | | |
| (High pressure) | 1 | 1 (1) |
| (Low pressure) | 1 | 3 (3) |
| Test, 13'RA | | |
| (High pressure) | 1 | 1 (1) |
| (Low pressure) | 1 | 1 (1) |

*Intimal SMC Hypertrophy: intimal smooth muscle cell hypertrophy scored on a scale from 1+ (minimal) to 4+ (maximal).

Figure 9A:
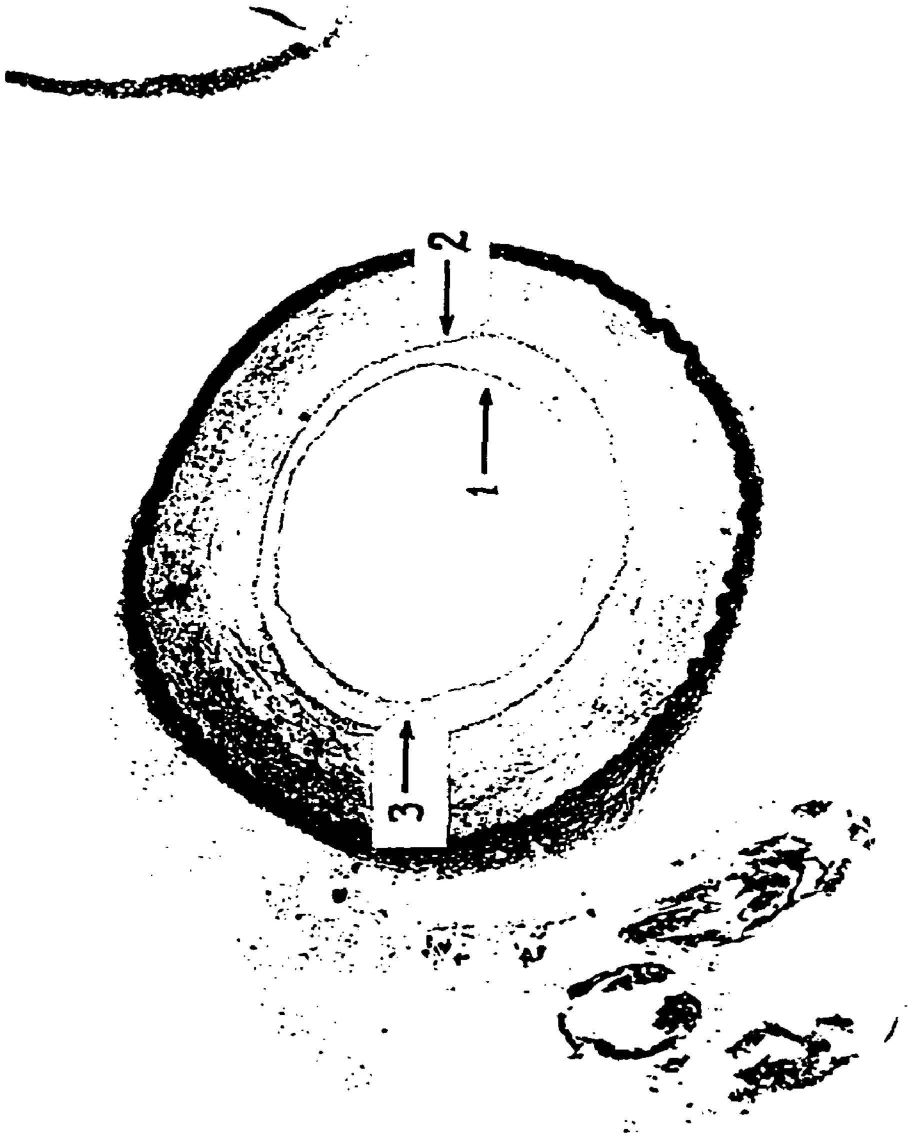
FIG. 9A shows stenosis due to intimal smooth muscle cell proliferation in a histological section of an untreated artery 5 weeks after angioplasty in an animal model.

The results presented in FIG. 9A show (at 160× magnification) a cross-sectional of an untreated artery 5 weeks after angioplasty. Dominant histological features of the artery include displacement of the endothelium (see #1 in FIG. 9A) away from the internal elastic lamina (see #2, FIG. 9A), apparently due to intimal smooth muscle proliferation (see #3, FIG. 9A).

Figure 9B:
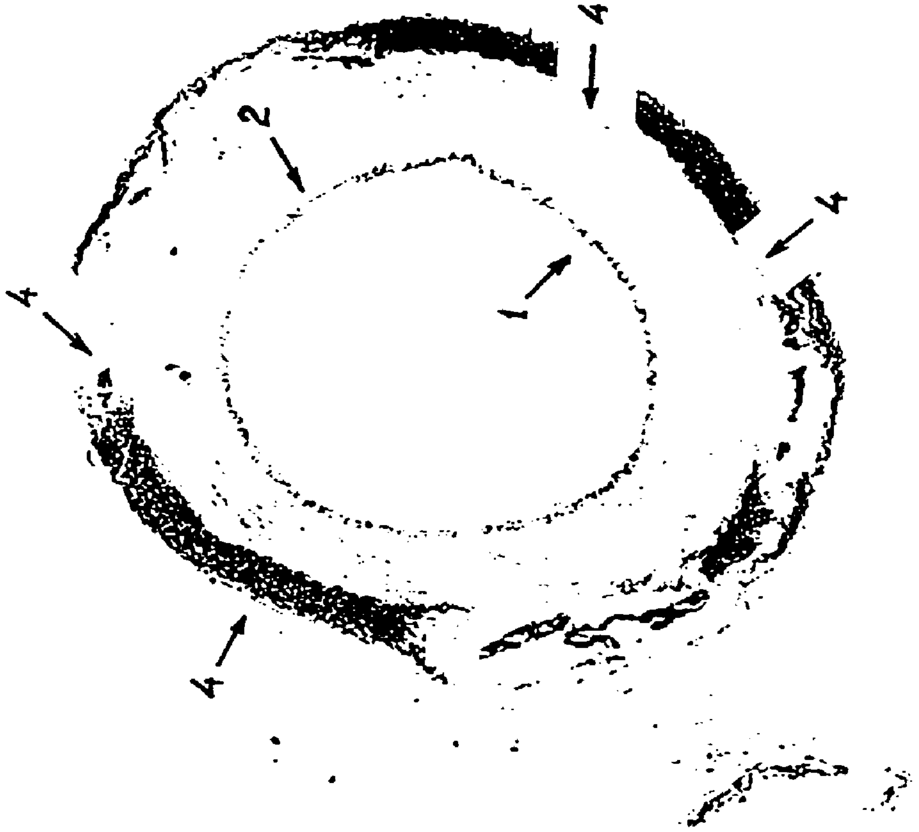
FIG. 9B shows inhibition of stenosis in a histological section of an artery treated with therapeutic conjugate at 5 weeks after angioplasty in an animal model.
Figure 10A:
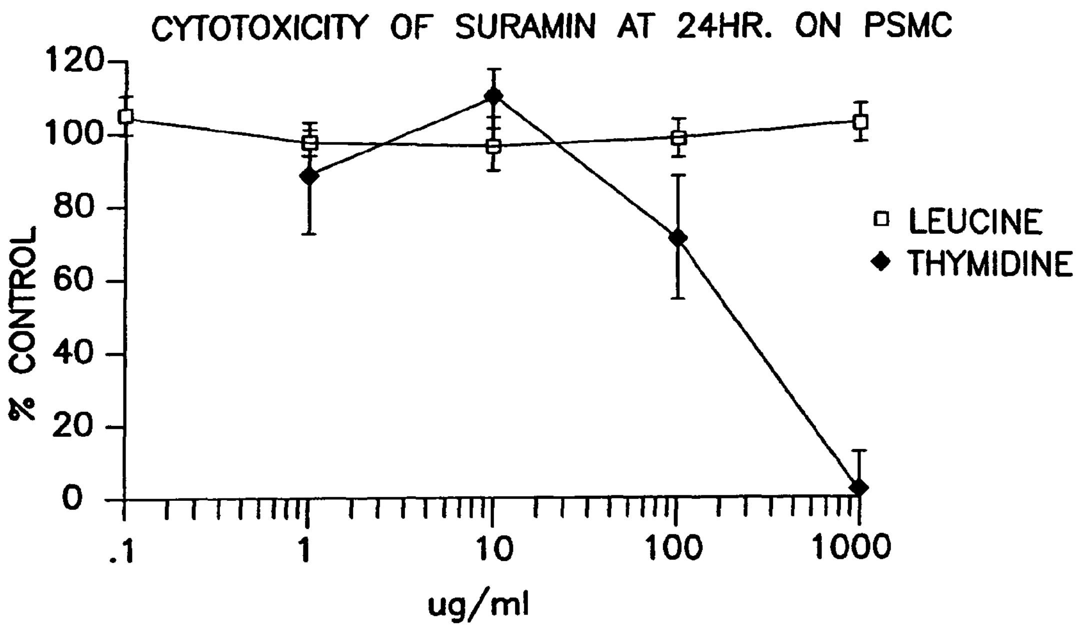
FIG. 10A graphically depicts experimental data comparing protein synthesis and DNA synthesis inhibition capability of suramin with respect to vascular smooth muscle cells.
Figure 10B:
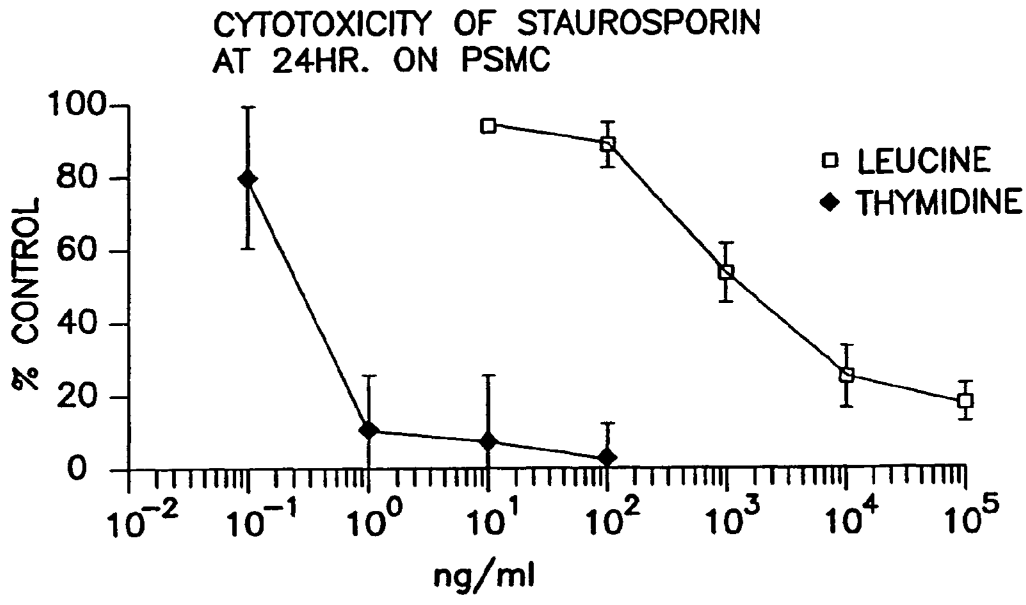
FIG. 10B graphically depicts experimental data comparing protein synthesis and DNA synthesis inhibition capability of staurosporin with respect to vascular smooth muscle cells.
Figure 10C:
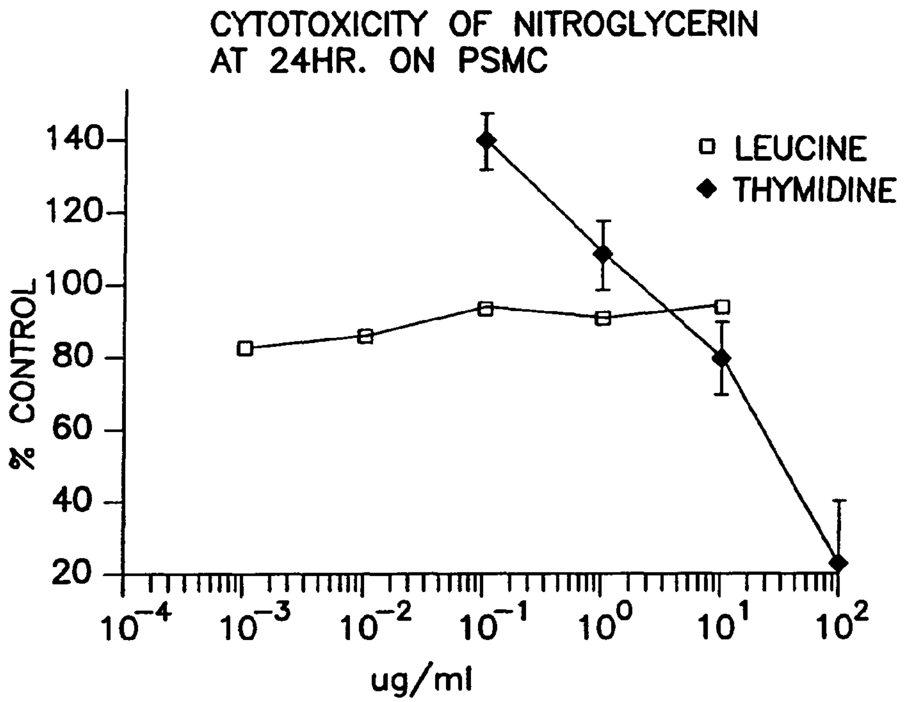
FIG. 10C graphically depicts experimental data comparing protein synthesis and DNA synthesis inhibition capability of nitroglycerin with respect to vascular smooth muscle cells.
Figure 10D:
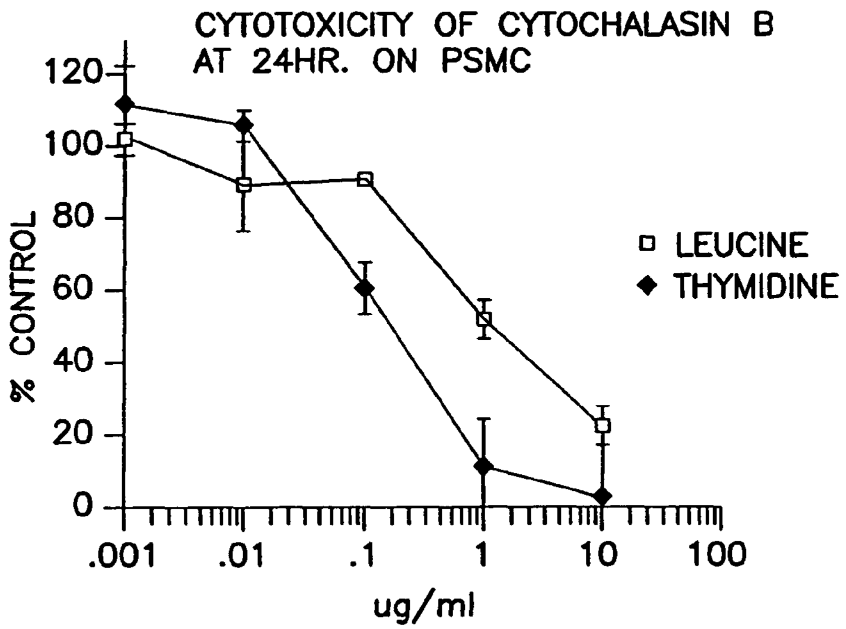
FIG. 10D graphically depicts experimental data comparing protein synthesis and DNA synthesis inhibition capability of cytochalasin with respect to vascular smooth muscle cells.

The results presented in FIG. 9B show (at 160× magnification) a cross-section of a treated artery 5 weeks after angioplasty and infusion of the RA-NR-AN-01 therapeutic conjugate. The vessel in this section was subjected to greater mechanical stresses than the vessel shown in FIG. 9A, with multiple sites where the external elastic membrane was ruptured and associated proliferation of smooth muscle cells in the outer layers of the media was observed (i.e., see #4 in FIG. 9B). Treatment with therapeutic conjugate inhibited intimal hypertrophy, as evidenced by the lack of displacement of the endothelium (see #1, FIG. 9B) from the internal elastic lamina (see #2, FIG. 9B). Surprisingly, this inhibitory effect on intimal smooth muscle cells was accomplished without inhibiting hypertrophy of medial smooth muscle cells in the areas where the external elastic membrane was ruptured (see #4, FIG. 9B).

This is a highly fortunate result because wound healing proceeds in the treated vessel without the adverse consequences of intimal hyperplasia and stenosis, or necrosis of smooth muscle cells in the media.

In these histological studies, comparisons were also made of the effectiveness of both the 2' and the 13'-Roridin A conjugate with the finding that the 13' conjugate (i.e., 13'RA-HS-NR-AN-01) appeared to be more active in inhibiting intimal hyperplasia of smooth muscle cells than the 2' conjugate (i.e., 2' RA-HS-NR-AN-01). In this study, low pressure infusion of the 13' conjugate appeared to inhibit smooth muscle proliferation more effectively than high pressure and the 13' conjugate also appeared to be more effective than the 2' conjugate.

In FIG. 9B, therapeutic conjugate administered at the site following angioplasty resulted in approximately 95% inhibition of the smooth muscle hypertrophy that restricted the lumen of the untreated vessel (FIG. 9A). Significantly, the therapeutic conjugate exerted its effects on the smooth muscle cells migrating from the medial smooth muscle layers into the intima, without affecting either endothelium, or producing any signs of necrosis (i.e., cell death) in the smooth muscle cells in the medial layers of the arterial wall. Studies also failed to show any histological signs of mononuclear infiltration or fibrosis such as might result from toxic effects on the vessel wall. Also, visible signs of healing were observed in the intimal layers of treated vessels and with re-growth of endothelium observed, i.e., endothelial cells growing over the thin layer of smooth muscle cells in the intima that lie between the endothelium and internal elastic lamina (i.e., #1 and #2, FIG. 9B). These combined histological observations suggest the highly desirable features of wound healing, re-growth of endothelium and improved vascular strength following treatment with a therapeutic conjugate that inhibits smooth muscle hyperplasia in the intimal layers of the vessel.

Example 8

Vascular Smooth Muscle Cell in Vitro DNA and Protein Synthesis Inhibition

The ability of various therapeutic agents to inhibit DNA synthesis and protein synthesis in vascular smooth muscle cells was tested. $^3$H-leucine and $^3$H-thymidine uptake and cytotoxicity assays were conducted in accordance with the following protocols.

5 minute exposure; $^3$H-leucine uptake: Vascular smooth muscle cells at 40,000 cells/ml were seeded in sterile 24 well plates at 1 ml/well. The plates were incubated overnight at 37° C., 5% $CO_2$, 95% air in a humidified atmosphere (saturation). Log dilutions of the therapeutic agent of interest were incubated with the vascular smooth muscle cells for 5 minutes or 24 hours. Samples of the therapeutic agents were diluted in DMEM:F-12 medium (Whittaker Bioproducts, Walkersville, Md.) with 5% fetal bovine serum (FBS, Gibco BRL, Gaithersburg, Md.) and 5% Serum Plus® (JRH Biosciences, Lenexa, Kans.). Following therapeutic agent incubation, the solution was aspirated, and 1 ml/well of 0.5 microcurie/ml $^3$H-leucine in leucine-free DMEM (Dulbecco's Modified Eagle's Medium) with 5% Serum Plus® was added. The plates were re-incubated overnight at 37° C., 5% $CO_2$ in a humidified atmosphere. The cells were visually graded using an inverted microscope using a scoring scale to determine viability and cell number. The 1 to 3 grade is based upon percent of cell viability and number compared to control wells, with 3=100%, 2=70%-100% and 1=0%-70%. A record of this scoring assisted in determining the immediate cytotoxic effect of the therapeutic agents. The medium was then aspirated, and the cells were washed twice with cold 5% TCA. 400 microliters of 0.2M NaOH was added per well, and the plates were incubated for two hours at room temperature on a rotating platform. 200 microliters per well of the cell solution was transferred into plastic scintillation vials (Bio-Rad Laboratories), and 4 milliliters of Bio-Safe® II liquid scintillation fluid (Research Products InterCorp., Mount Prospect, Ill.) was added prior to vortexing. Vials were counted on a Beckman LS2800 liquid scintillation counter interfaced with Beckman "Data Capture" software for conversion to a Lotus 1-2-3® file and analysis using Lotus 1-2-3®.

5 minute exposure; $^3$H-thymidine uptake: Vascular smooth muscle cells were incubated in complete medium with 5% FBS (Gibco) overnight at 37° C. in a humidified, 5% $Co_2$ environment in sterile 24 well plates. The medium was aspirated from the wells and serum free medium supplemented with growth factors (DMEM: F-12 basal medium supplemented with growth factor cocktail, catalog number 11884, which contains insulin (5 micrograms/ml), transferrin (5 micrograms/ml) and sodium selenite (5 nanograms/ml), available from Sigma Chemical, St. Louis, Mo.) was added. Cells were incubated in this medium for 24 hours. For a 5 minute therapeutic agent exposure, log dilutions of the therapeutic agent were incubated with the cells in complete medium. After 5 minutes and medium aspiration, 1 ml/well of 1.0 microcurie/ml $^3$H-thymidine dispersed in complete medium was added. The 24 hour exposure involved incubation of the cells with 1 ml/well of 1.0 microcurie/ml of $^3$H-thymidine dispersed in complete medium and log dilutions of the therapeutic agent being tested. In both exposure trials, the cells were then incubated overnight at 37° C. in a humidified, 5% $CO_2$ environment. The cells were visually scored for viability and cell number. Cells were washed and prepared for transfer into plastic scintillation vials as described for the $^3$H-leucine protocol. Vials were counted on a Beckman LS2800 liquid scintillation counter interfaced with Beckman "Data Capture" software for conversion to a Lotus 1-2-3® file and analysis using Lotus 1-2-3®.

These protocols are amenable to use with other target cell populations, especially adherent monolayer cell types.

Morphological Cytotoxicity Evaluation-Pulsed Exposure: Vascular smooth muscle cells were seeded at $4.0 \times 10^4$ cells/ml medium/well on a commercially prepared four well slide (Nunc, Inc., Naperville, Ill.). Enough slides were seeded to accommodate two pulsed exposure lengths (5 minutes and 24 hours) and prescribed increment evaluation points (24 hours to 128 hours). All slides were run in duplicate to reveal any assay anomalies. The therapeutic agent was diluted in the same medium used in the $^3$H-leucine and $^3$H-thymidine assays. Each four well slide was concentration bracketed to one log greater concentration (well "B"), one log lower concentration (well "D") of the minimal effective concentration (well "C"), as determined by the 3H-leucine and 3H-thymidine assays described above. As a control for normal morphology, one well (well "A") was left untreated (medium only). Incubation took place in a 37° C., 5% $CO_2$ humidified incubator. After each of the two (5 minutes and 24 hours) exposure points, the therapeutic agent medium was aspirated from each well, including the untreated well. One milliliter of fresh medium was then added to replace the aspirated medium. Re-incubation followed until each of the incremented evaluation points were achieved. At those points, the medium was aspirated and subsequently replaced with 1 ml of 10% neutral buffered formalin for one hour to allow for proper fixation. These fixed slides were stained by hematoxylin (nuclear) and eosin (cytoplasmic) for morphologic evaluation and grading.

Results: The results of the 24 hour $^3$H-leucine protein inhibition assay and the 24 hour $^3$H-thymidine DNA synthesis inhibition assay are shown in FIGS. 10A-10D for suramin, staurosporin, nitroglycerin and cytochalasin B, respectively. All of the tested compounds showed an available therapeutic range (area under the curve of $^3$H-leucine assay is greater than that resulting from the $^3$H-thymidine assay), indicating usefulness in the practice of sustained release dosage form embodiments of the present invention. More specifically, the compounds inhibited the ability of vascular smooth muscle cells to undergo DNA synthesis in the presence of 5% FBS to a greater extent than they inhibited protein synthesis of vascular smooth muscle cells. The protein and DNA synthesis inhibitory effects of suramin, staurosporin, nitroglycerin and cytochalasin B during a 5 minute and 24 hour pulsed exposure are shown in FIG. 10 A-D, respectively.

Example 9

Specific Binding and Internalization of Targeted Particles by Vascular Smooth Muscle Cells The ability of vascular smooth muscle cells to bind and internalize particles coated with binding protein or peptide was demonstrated with monoclonal antibody (NR-AN-01) coated gold beads both in vitro and in vivo. The vascular smooth muscle cell tissue cultures (BO54), an antigen positive control cell line (A375) and an antigen negative control cell line (HT29) were incubated with 10 nm gold beads, with one group coated with NR-AN-01 and a second, uncoated control group. The cells were exposed to the beads as monolayer and cell suspension cultures, and were examined at six time points (i.e., 1 minute, 5 minutes, 15 minutes, 30 minutes, 60 minutes and 24 hours) for binding and internalization by electron microscopy.

Table 3 shows the results of the experimentation, indicating that the binding to the cell surface is specific. The relative grading system used throughout Table 3 represents a subjective assessment of particle binding, wherein 0=none; 1=minimal; 2=mild; 3=moderate; and 4=marked. If aggregates of particles settled on the monolayer surface of both the smooth muscle cells and the control cells, the particles were nonspecifically internalized by macro and micro phagocytosis. When the cells were maintained in a cell suspension, non-specific internalization was minimal or absent. Non-specific adherence of gold beads devoid of NR-AN-01 to surface mucin produced by HT29 cells was observed, resulting in modest non-specific internalization thereof. Vascular smooth muscle cell uptake of NR-AN-01 targeted gold beads was highly specific in cell suspension cultures.

TABLE 3

| Time | Grid | Product | Cell Line | Cell Surface | Primary vessicle micro/macro phagostatis pinocytosis | coated pit | secondary vessicle | lysosome | golgi | endoplasmic reticulum |
|---|---|---|---|---|---|---|---|---|---|---|
| | | | | Cell Monolayer | | | | | | |
| 1 min | Aa | 05(G) | A375 | 2 | 0 | 0 | 0 | 0 | 0 | 0 |
| | Ba | 05(G) | HT29 | 0 | 0 | 0 | 0 | 0 | 0 | 0 |
| | C | 05(G) | B054 | 2 | 1 | 0 | 0 | 0 | 0 | 0 |
| | Da | (G) | A375 | 0 | 0 | 0 | 0 | 0 | 0 | 0 |
| | Eb | (G) | HT29 | 0 | 0 | 0 | 0 | 0 | 0 | 0 |
| | F | (G) | B054 | 0 | 0 | 0 | 0 | 0 | 0 | 0 |
| 5 min | Ac | 05(G) | A375 | 4 | 1 | 0 | 0 | 0 | 0 | 0 |
| | Bb | 05(G) | HT29 | 0 | 0 | 0 | 0 | 0 | 0 | 0 |
| | Ca | 05(G) | B054 | 3 | 0 | 0 | 0 | 0 | 0 | 0 |
| | Dc | (G) | A375 | 0 | 0 | 0 | 0 | 0 | 0 | 0 |
| | Ea | (G) | HT29 | 0 | 0 | 0 | 0 | 0 | 0 | 0 |
| | Fa | (G) | B054 | 0 | 0 | 0 | 0 | 0 | 0 | 0 |
| 15 min | Aa | 05(G) | A375 | 3 | 1 | 0 | 0 | 0 | 0 | 0 |
| | Bb | 05(G) | HT29 | 0 | 0 | 0 | 0 | 0 | 0 | 0 |
| | Ca | 05(G) | B054 | 2 | 1 | 0 | 0 | 0 | 0 | 0 |
| | Da | (G) | A375 | 0 | 0 | 0 | 0 | 0 | 0 | 0 |
| | Ea | (G) | HT29 | 0 | 0 | 0 | 0 | 0 | 0 | 0 |
| | Fa | (G) | B054 | 0 | 0 | 0 | 0 | 0 | 0 | 0 |
| 30 min | A | 05(G) | A375 | 4 | 3 | 0 | 2 | 0 | 0 | 0 |
| | B | 05(G) | HT29 | 0 | 0 | 0 | 0 | 0 | 0 | 0 |
| | C | 05(G) | B054 | 3 | 2 | 0 | 1 | 0 | 0 | 0 |
| | D | (G) | A375 | 0 | 0 | 0 | 0 | 0 | 0 | 0 |
| | E | (G) | HT29 | 0 | 1 | 0 | 0 | 0 | 0 | 0 |
| | F | (G) | B054 | 1 | 1 | 0 | 0 | 0 | 0 | 0 |
| 60 | Aa | 05(G) | A375 | 4 | 3 | 2 | 3 | 2 | 0 | 1 |
| | Ba | 05(G) | HT29 | 0 | 0 | 0 | 0 | 0 | 0 | 0 |
| | Cc | 05(G) | B054 | 3 | 2 | 0 | 2 | 0 | 0 | 1 |
| | Da | (G) | A375 | 0 | 1 | 0 | 0 | 0 | 0 | 1 |
| | Ec | (G) | HT29 | 1 | 1 | 0 | 1 | 0 | 0 | 0 |
| | Fa | (G) | B054 | 1 | 2 | 0 | 1 | 0 | 0 | 0 |
| 24 hrs | Ab | 05(G) | A375 | 2 | 1 | 1 | 2 | 4 | 0 | 2 |
| | Ba | 05(G) | HT29 | 0 | 1 | 1 | 2 | 3 | 0 | 0 |
| | Cc | 05(G) | B054 | 3 | 3 | 1 | 3 | 4 | 1 | 1 |
| | Da | (G) | A375 | 0 | 3 | 0 | 2 | 3 | 0 | 0 |
| | Eb | (G) | HT29 | 0 | 3 | 0 | 3 | 1 | 0 | 0 |
| | Fb | (G) | B054 | 0 | 2 | 0 | 2 | 3 | 0 | 0 |
| | | | | Cell Pellets | | | | | | |
| 1 min | 1A | 05(G) | A375 | 2 | 0 | 0 | 0 | 0 | 0 | 0 |
| | 7A | 05(G) | HT29 | 0 | 0 | 0 | 0 | 0 | 0 | 0 |
| | 13A | 05(G) | B054 | 3 | 0 | 1 | 0 | 0 | 0 | 0 |
| | 1B | (G) | A375 | 0 | 0 | 0 | 0 | 0 | 0 | 0 |
| | 7B | (G) | HT29 | 0 | 0 | 0 | 0 | 0 | 0 | 0 |
| | 13B | (G) | B054 | 0 | 0 | 0 | 0 | 0 | 0 | 0 |
| 5 min | 2A | 05(G) | A375 | 3 | 1 | 0 | 0 | 0 | 0 | 0 |
| | 8A | 05(G) | HT29 | 0 | 0 | 0 | 0 | 0 | 0 | 0 |
| | 14A | 05(G) | B054 | 2 | 1 | 0 | 0 | 0 | 0 | 0 |
| | 2B | (G) | A375 | 0 | 0 | 0 | 0 | 0 | 0 | 0 |
| | 8B | (G) | HT29 | 0 | 0 | 0 | 0 | 0 | 0 | 0 |
| | 15B | (G) | B054 | 0 | 0 | 0 | 0 | 0 | 0 | 0 |
| 15 min | 3A | 05(G) | A375 | 4 | 1 | 0 | 1 | 0 | 0 | 0 |
| | 9A | 05(G) | HT29 | 0 | 0 | 0 | 0 | 0 | 0 | 0 |
| | 15A | 05(G) | B054 | 1 | 1 | 0 | 0 | 0 | 0 | 0 |
| | 3B | (G) | A375 | 0 | 0 | 0 | 0 | 0 | 0 | 0 |
| | 9B | (G) | HT29 | 0 | 0 | 0 | 0 | 0 | 0 | 0 |
| | 15B | (G) | B054 | 0 | 0 | 0 | 0 | 0 | 0 | 0 |
| 30 min | 4A | 05(G) | A375 | 4 | 2 | 0 | 0 | 0 | 0 | 0 |
| | 10A | 05(G) | HT29 | 0 | 0 | 0 | 0 | 0 | 0 | 0 |
| | 16A | 05(G) | B054 | 2 | 1 | 0 | 0 | 0 | 0 | 0 |
| | 4B | (G) | A375 | 0 | 0 | 0 | 0 | 0 | 0 | 0 |
| | 10B | (G) | HT29 | 0 | 0 | 0 | 0 | 0 | 0 | 0 |
| | 16G | (G) | B054 | 0 | 0 | 0 | 0 | 0 | 0 | 0 |
| 60 min | 5A | 05(G) | A375 | 3 | 3 | 0 | 2 | 1 | 0 | 0 |
| | 11A | 05(G) | HT29 | 0 | 0 | 0 | 0 | 0 | 0 | 0 |
| | 17A | 05(G) | B054 | 2 | 2 | 0 | 2 | 0 | 0 | 0 |
| | 5B | (G) | A375 | 0 | 0 | 0 | 0 | 0 | 0 | 0 |
| | 11B | (G) | HT29 | 0 | 0 | 0 | 0 | 0 | 0 | 0 |
| | 17B | (G) | B054 | 0 | 0 | 0 | 0 | 0 | 0 | 0 |
| 24 hrs | 6A | 05(G) | A375 | 3 | 1 | 0 | 3 | 3 | 0 | 0 |
| | 12A | 05(G) | HT29 | 0 | 0 | 0 | 0 | 0 | 0 | 0 |
| | 18A | 05(G) | B054 | 2 | 1 | 0 | 1 | 3 | 0 | 0 |
| | 6B | (G) | A375 | 0 | 0 | 0 | 0 | 0 | 0 | 0 |

TABLE 3-continued

| Time | Grid | Product | Cell Line | Cell Surface | Primary vessicle micro/macro phagostatis pinocytosis | coated pit | secondary vessicle | lysosome | golgi | endoplasmic reticulum |
|---|---|---|---|---|---|---|---|---|---|---|
| | 12B | (G) | HT29 | 1 | 2 | 0 | 2 | 2 | 0 | 0 |
| | 18B | (G) | B054 | 0 | 0 | 0 | 0 | 0 | 0 | 0 |

Figure 11:
FIG. 11 shows a tangential section parallel to the inner surface of a smooth muscle cell which is magnified 62,500 times and is characterized by numerous endocytic vesicles, several of which contain antibody coated gold beads in the process of being internalized by the cell in vitro.
Figure 12:
FIG. 12 shows a smooth muscle cell which is magnified 62,500 times and is characterized by a marked accumulation of gold beads in lysosomes at 24 hours following exposure of the cell to the beads in vitro.

FIG. 11 shows a tangential section parallel to the inner surface of a smooth muscle cell characterized by numerous endocytic vesicles, several of which contain antibody coated gold beads in the process of being internalized by the cell. These endocytic vesicles with particles attached to cell surface antigens were stimulated to fuse with lysosomes at a higher than expected rate for normal cell surface membrane recycling. The resultant marked accumulation of internalized particles was observed at the 24 hour time point and is shown in FIG. 12.

Figure 13:
FIG. 13 shows a smooth muscle cell which is magnified 62,500 times and is characterized by accumulation of gold beads in lysosomes in vivo.

The targeted gold bead vascular smooth muscle cell surface binding, internalization and lysosome concentration was observed in vivo as well. NR-AN-01 coated gold beads were infused via intravascular catheter, open ended with treated area occluded proximally and distally with slip ligatures, at 3 atm pressure applied for 3 minutes into the wall of a pig femoral artery immediately following balloon trauma. The bead internalization rate varied with the degree of damage sustained by the vascular smooth muscle cell during the balloon trauma. Cells with minimal or no damage rapidly internalized the particles by endocytosis and phagocytosis, concentrating the internalized particles in lysosomes. Cells that were killed by the trauma exhibited surface bead binding. Cells that were damaged by the trauma but survived were characterized by bead surface binding with delayed internalization and lysosome concentration. FIG. 13 shows particulate concentration in the lysosomes in vivo at one week following bead administration.

Example 10

Vascular Smooth Muscle in Vitro DNA and Protein Synthesis Inhibition BV Staurosporin and Cytochalasin The ability of staurosporin and cytochalasin to inhibit in vitro DNA and protein synthesis in vascular smooth muscle cells was tested. $^3$H-leucine and $^3$H-thymidine uptake and cytotoxicity assays were conducted in accordance with the following protocols.

Cultured Cells:

BO54 cells (baboon smooth muscle cells) were derived from explants of aortic baboon smooth muscle cells. Cells were expanded in DMEM (Dulbecco's Modified Eagle's Medium):F-12 medium (Whittaker Bioproducts, Walkersville, Md.) with 5% fetal bovine serum (FBS, Gibco) and 5% Serum Plus® (JRH Biologicals) ("complete medium"), and a seed lot of cells was frozen in liquid nitrogen for future use at passage seven.

5 Minute Exposure; Protein Synthesis Assay:

Vascular smooth muscle cells at 40,000-50,000 cells/ml were seeded and processed as described in Example 8, "5 minute exposure; $^3$H-leucine uptake." Log dilutions of staurosporin (200 ng/ml, 20 ng/ml, 2 ng/ml 0.2 ng/ml and 0.02 ng/ml) were dispersed in complete medium. For cytochalasin B, log dilutions at 20 μg/ml, 2.0 μg/ml, 0.2 μg/ml, 0.02 μg/ml and 0.002 μg/ml were dispersed in complete medium. Complete medium was then added to the control wells. One ml/well of each therapeutic agent dilution was added in quadruplicate wells, and the agent of interest was incubated with the vascular smooth muscle cells for 5 min at room temperature in a sterile ventilated hood. Following therapeutic agent incubation, the wells were subsequently treated as described in Example 8, "5 minute exposure; $^3$H-leucine uptake."

5 Minute Exposure; DNA Synthesis Assay: Vascular smooth muscle (BO54) cells were seeded and processed in 24 well plates, as described above under "5 Minute Exposure: Protein Synthesis Assay." After 5 min incubation with the test therapeutic agent, the medium was aspirated and 1 ml/well of 1.0 μCi/ml $^3$H-thymidine (rather than $^3$H-leucine) dispersed in complete medium was added. The cells were then incubated overnight at 37° C. in a humidified, 5% COZ environment. The toxic effect of the therapeutic agent was then determined, as described in the Protein Synthesis Assay, above.

24 and 120 Hour Exposure; Protein Synthesis Assay: Vascular smooth muscle (BO54) cells at 20,000 cells/ml were seeded in sterile 24 well plates and incubated in complete medium (1 ml/well) overnight at 37° C., 5% $CO_2$, 95% air in a humidified atmosphere (saturation). Log dilutions of staurosporin (100 ng/ml, 10 ng/ml, 1 ng/ml, 0.1 ng/ml and 0.01 ng/ml) were dispersed sequentially in the two media, as described below. For cytochalasin B, log dilutions at 10 μg/ml, 1.0 μg/ml, 0.1 μg/ml, 0.01 μg/ml and 0.001 μg/ml were dispersed sequentially in the two media, as described below:

Medium (1)=Complete medium; and

Medium (2)=DMEM (leucine-free) with 0.5 μCi/ml $^3$H-leucine. Medium (2) is used for the final 24 hour incubation period of the experiment.

More specifically, in the 24 hour assay, each therapeutic agent was diluted in Medium (2), as noted above. Medium (1) was aspirated from the wells, and aliquots of therapeutic agent dilutions in Medium (2) were added in quadruplicate to the appropriate wells. Medium (2) was then added to the control wells.

In the 120 hour assay, each therapeutic agent was diluted in Medium (1), as noted above. Medium (1) was aspirated from the wells, and aliquots of therapeutic agent dilutions in Medium (1) were added in quadruplicate to the appropriate wells. Medium (1) was then added to the control wells. The medium was changed every 24 hours, and fresh therapeutic agent was added to the test wells. At 96 hr, (i.e., the fourth day), each therapeutic agent was diluted in Medium (2), as noted above. Medium (1) was aspirated from the wells, and aliquots of therapeutic agent dilutions in Medium (2) were added in quadruplicate to the appropriate wells. Medium (2) was then added to the control wells.

The test agents in $^3$H-leucine (and controls) were incubated overnight at 37° C., 5% $Co_2$ in a humidified atmosphere. The toxic effect of the therapeutic agents was then determined, as described in the 5 Minute Exposure: Protein Synthesis Assay, described above. In addition, the changes in cells at each dilution were photographed using a Zeiss microscope (Zeiss, West Germany) at 320X. The medium was then aspirated, and the cells were processed with TCA, as described above.

24 and 120 Hour Exposure; DNA Synthesis Assay: This assay was performed according to the procedure described for "24 and 120 Hour Exposure; Protein Synthesis Assay", except Medium (2) in this 24 & 120 hr DNA Synthesis Assay is:

Medium (2)=Complete Medium with 1.0 μCi/ml $^3$H-thymidine.

Medium (2) is used in the final 24 hour incubation of the experiment.

These protein and DNA synthesis assays are amenable for use with other target cell populations, especially adherent monolayer cell types.

Results: The minimum effective dose (MED) of each agent was determined as a percentage of the control that was treated with medium only; 50% of control values was chosen as the cytotoxicity benchmark. At a 5 min exposure, staurosporin demonstrated an MED of 100 ng/ml in the protein synthesis assay and 1 ng/ml in the DNA assay. The 24 hour MED for staurosporin was 10 ng/ml in the protein synthesis assay and 1 ng/ml in the DNA synthesis assay. Both assays gave an MED of 1 ng/ml for a 120 hour exposure of staurosporin.

At a 5 minute exposure, cytochalasin B demonstrated an MED of 10 μg/ml in the protein synthesis assay as well as in the DNA assay. The 24 hour MED for cytochalasin B was 1.0 μg/ml in the protein synthesis assay and 0.1 μg/ml in the DNA synthesis assay. Both assays gave an MED of approximately 0.1 μg/ml for a 120 hour exposure of staurosporin.

Cytochalasin C and cytochalasin D therapeutic agents were tested at 24 and 48 hour exposures using the same dilutions as described for cytochalasin B, above. At 24 hours, cytochalasin C demonstrated an MED of 1.0 μg/ml in the protein synthesis assay and an MED of 0.01 μg/ml in the DNA synthesis assay. At 48 hours, cytochalasin C demonstrated an MED of 0.1 μg/ml in the protein synthesis assay and 0.01 μg/ml in the DNA synthesis assay. Cytochalasin D demonstrated an MED of 1.0 μg/ml in the 24 hour protein synthesis assay and an MED of 0.1 μg/ml in the 24 hr DNA synthesis assay. A 48 hour exposure to cytochalasin D gave an MED ranging between 0.1 and 0.01 μg/ml in both the protein synthesis and DNA synthesis assays.

Example 11

Vascular Smooth Muscle Cell Migration Inhibition

Scratch assays to determine the extent of smooth muscle cell migration inhibition by cytochalasin B were performed in accordance with the following protocol:

Vascular smooth muscle cells (BO54) were derived from explants of baboon aortic smooth muscle, as described in Example 10. The cells were grown in flat bottom, six well tissue culture plates, which hold about 5 ml of medium. The vascular smooth muscle cells were plated at 200,000 cells/well and placed at 37° C. in a humidified 5% $CO_2$ incubator for 18 hours. The wells were then scratched with a sterile portion of a single edge razor blade that was held by clamp or pliers and was brought aseptically into contact with the bottom of the well at a 90° angle. The cells from a small area along the scratch were removed by a sterile cotton tipped applicator while the blade was in contact with the bottom of the well. After incubation, the presence of cells in the "scratched" area is indicative of cell migration across the scratch line. A control incubation showed significant cellular migration, and serves as the standard against which the migration of cells exposed to the therapeutic agent is compared.

Briefly, a stock solution of cytochalasin B (Sigma Chemical Co.) in dimethyl sulfoxide (DMSO) at 1 mg/ml was prepared. Test dilutions of cytochalasin B or control medium were added. Each experiment included two sets of plates:

A set: Test agent exposure for 1, 3, 6, 8 and 10 days only; and

B set: Test agent exposure for 1, 3, 6, 8 and 10 days, followed by a seven day recovery time with control medium.

Both sets of plates were fixed (10% formalin in PBS) and stained (0.02% crystal violet) at the end of the timed exposures. Test concentrations for cytochalasin B were 1, 0.1 and 0.01 μg/ml, and a negative medium control was included. Fresh medium and drug were supplied 3 times per week.

Table 4 shows the results of these experiments. In this Table, "M" indicates Migration Grade, wherein −=no migration; +1 minimal; +2=mild; +3=moderate; and +4=marked (maximum density; limit of cell contact inhibition) migration of vascular smooth muscle cells into the cleared area adjacent to the scratch. In this Table, "T" denotes a morphological Toxicity Grade, wherein −=no toxicity; +1=minimal; +2=mild; +3=moderate; and +4=marked toxicity. The migration results are expressed as "Grade in the Cleared Area of the Well/Grade in an Undisturbed Region of the Well." The toxicity values represent a grade for all cells in each well.

The data indicate that cytochalasin B inhibits the migration (+1 to +2) of vascular smooth muscle cells into the cleared area adjacent to the scratch at a dose of 0.1 μg/ml with only minimal (− to +1) morphological toxicity. The data also show that the treated cells (0.1 μg/ml) regain the ability to migrate (+3 to +4) following removal of the therapeutic agent, even after 10 days of continuous exposure to the therapeutic agent.

TABLE 4

SCRATCH-MIGRATION ASSAY: INHIBITION OF VASCULAR SMOOTH MUSCLE CELL MIGRATION BY CYTOCHALASIN B

| | Continuous Exposure Dosage μg/mL | | | | 7-day Recovery Post Exposure Dosage μg/mL | | | |
|---|---|---|---|---|---|---|---|---|
| Day | Control 0.0 | 0.01 | 0.1 | 1.0 | Control 0.0 | 0.01 | 0.1 | 1.0 |
| 1 M | +1/+3 | +1/+3 | +1/+3 | —/+2 | +3/+4 | +3/+4 | +3/+4 | +2/+3 |
| T | — | — | — | +3 | — | — | — | +2 |
| 3 H | +3/+4 | +3/+4 | +1/+4 | —/+2 | +3/+4 | +3/+4 | +3/+4 | +2/+3 |
| T | — | — | +1 | +3 | — | — | — | +1 |
| 6 M | +3/+4 | +3/+4 | +2/+4 | —/+2 | +4/+4 | +4/+4 | +3/+4 | +2/+3 |
| T | — | — | +1 | +4 | — | — | — | +3 |
| 8 M | +3/+4 | +3/+4 | +2/+4 | —/+2 | +4/+4 | +41+4 | +3/+4 | +2/+3 |
| T | — | — | +1 | +4 | — | — | — | +3 |
| 10 M | +3/+4 | +3/+4 | +2+4 | —/+2 | +4/+4 | +4/+4 | +4/+4 | +2/+3 |
| T | — | — | +1 | +4 | — | — | — | +3 |

Example 12

Therapeutic Agent Cytotoxic Effects on Vascular Smooth Muscle Cells—Pulse and Continuous Exposure Vascular smooth muscle cells were exposed to a therapeutic agent in one of two exposure formats:

Pulse exposure: The pulse exposure protocol is described in Example 8 above (see "Morphological Cytotoxicity Evaluation—Pulsed Exposure").

Continuous exposure: The same methodology is used for continuous exposure morphological cytotoxicity evaluation as for the pulse exposure, except that the test wells were continuously exposed to therapeutic agent in medium during the exposure period. The medium and therapeutic agent were aspirated from each well daily, including from the untreated control well, and were replaced with 1 ml of fresh medium and therapeutic agent (or medium alone for control wells). Re-incubation followed, until each of the incremental evaluation points of the long term continuous exposure protocol was achieved. These incremental evaluation time points were at 6, 24, 48, 72, 96, 120, 168, 216 and 264 hours. At the designated time period, the appropriate cells were fixed, stained and evaluated as in the pulse exposure protocol. The results of a continuous exposure experiment are shown in Table 5 for suramin, staurosporin and cytochalasin B. The 5 min and 24 hr data presented in Table 5 are correlates of the data contained in FIGS. 10A, 10B and 10C.

TABLE 5

MORPHOLOGICAL CYTOTOXICITY ASSAY
Drug & Dose

| | Cytochalasin B | | | | Suramin | | | | Staurosporine | | | |
|---|---|---|---|---|---|---|---|---|---|---|---|---|
| Exposure Protocol | 10 ug | 1 ug | 0.1 ug | 0.01 ug | 10 mg | 1 mg | 0.1 mg | 0.01 mg | 100 ng | 10 ng | 1 ng | 0.1 ng |
| 5 min + 2 hrs | 0.5 | 0 | 0 | — | 0 | 0 | 0 | — | 0 | 0 | 0 | — |
| 5 min + 6 hrs | 4 | 1 | 0 | — | 1 | 0 | 0 | — | 0 | 0 | 0 | — |
| 5 min + 24 hrs | 4 | 0.5 | 0 | — | 1 | 0 | 0 | — | 0 | 0 | 0 | — |
| 5 min + 48 hrs | 4 | 1 | 0 | — | 2 | 0 | 0 | — | 2 | 1 | 0 | — |
| 5 min + 72 hrs | 4.5 | 1 | 0 | — | 3 | 1 | 0 | — | 3 | 1.5 | 0 | — |
| 5 min + 96 hrs | 5 | 1 | 0 | — | 3 | 1 | 0 | — | 3.5 | 1.5 | 0 | — |
| 5 min + 120 hrs | 5 | 1 | 0 | — | 3 | 1 | 0 | — | 4 | 1.5 | 0 | — |
| Continuous 6 hrs | — | 3 | 0 | 0 | 3 | 1 | 0 | — | 0 | 0 | 0 | 0 |
| Continuous 24 hrs | — | 3 | 1 | 0 | 3 | 2 | 0 | — | — | 0 | 0 | 0 |
| 24 hrs + 24 hrs | — | 3 | 0.5 | 0 | 4 | 3 | 0 | — | — | 0.5 | 0 | 0 |
| 24 hrs + 48 hrs | — | 4 | 1 | 0 | 4 | 3 | 0 | — | — | 2 | 0 | 0 |
| 24 hrs + 72 hrs | — | 4 | 0.5 | 0 | 4 | 3 | 0.5 | — | — | 1 | 0 | 0 |
| 24 hrs + 96 hrs | — | 4 | 0 | 0 | 4 | 3.5 | 1 | — | — | 1.5 | 0 | 0 |
| 24 hrs + 120 hrs | — | 4 | 0 | 0 | — | — | — | — | — | 1.5 | 0 | 0 |
| Continuous 24 hrs | — | 3 | 0 | 0 | — | 1 | 1 | 0 | — | 3 | 1 | 0 |
| Continuous 48 hrs | — | 3 | 1 | 0 | — | 3 | 2 | 0 | — | 3 | 2 | 0 |
| Continuous 72 hrs | — | 3 | 1 | 0 | — | 4 | 3 | 0 | — | 3 | 2 | 0 |
| Continuous 96 hrs | — | 3 | 2 | 0 | — | 4 | 3 | 0 | — | 3 | 2 | 1 |
| Continuous 120 hrs | — | 3 | 1 | 0 | — | 5 | 4 | 0 | — | 3 | 2 | 1 |
| Continuous 168 hrs | — | 4 | 1 | 0 | — | 5 | 4 | 0 | — | 3 | 2 | 1 |
| Continuous 216 hrs | — | 4 | 1 | 0 | — | 5 | 4 | 0 | — | 3 | 2 | 1 |
| Continuous 264 hrs | — | 4 | 1 | 0 | — | 5 | 4 | 0 | — | 4 | 2 | 1 |

At an in vitro effective dosage, cytochalasin B (1 μg/ml; an anti-migration/contraction effective dose) and staurosporin (1 ng/ml; an anti-proliferative effective dose) exhibited a cytotoxicity grade of 1 (minimal) and 2 (mild), respectively. Independent studies have indicated that a grade of 3 (moderate) or less is preferred for a cytostatic, anti-proliferative agent of the present invention.

Example 13

In Vivo BRDU Assay

Inhibition of Vascular Smooth Muscle Cell Proliferation

BRDU assay: In vivo vascular smooth muscle proliferation was quantitated by measuring incorporation of the base analog 5-bromo-2'-deoxyuridine (BRDU, available from Sigma Chemical Co.) into DNA during cellular DNA synthesis and proliferation. BRDU incorporation was demonstrated histochemically using commercially available anti-BRDU monoclonal antibodies. The 1 hour pulse labeling permits assessment of the number of cells undergoing division during the pulse period.

The BRDU pulse labeling protocol described above is used as a standard evaluation technique with in vivo pig vascular studies. Following surgical and treatment procedures (discussed, for example, in Examples 7 and 11 herein) and a post-surgical recovery period, pigs were sedated and pulsed with BRDU 1 hour prior to tissue collection.

Briefly, the pigs were sedated with tiletamine hydrochloride and xylazine (as in Example 7, "Gross Pathology and Histological Evaluation") by intramuscular injection. BRDU was then administered intravenously via the lateral ear vein. Two ml of BRDU at a concentration of 50 mg/ml was administered to each 30-40 lb pig. One hour later, the pigs were sacrificed by intravenously administered pentobarbital. Test artery segments were then removed (a segment included normal vessel located proximally and, if possible, distally with respect to the treated artery segment). The artery segments were transected at 2 mm intervals; arranged in order in cryomolds with O.C.T. (optimum cutting temperature) compound (Tissue Tek®, Miles Laboratories, Inc., Elkhart, Ind.); and frozen in liquid nitrogen. The blocks were sectioned at 5 microns and immunohistologically stained to detect BRDU using the following procedure.

BRDU-labeled cell detection: After BRDU (1 g BRDU diluted in 17 ml sterile water and 3 ml 1 N NaOH) pulse labeling and test artery segment removal and sectioning (as above), immunohistochemical staining with anti-BRDU monoclonal antibody provides a visual means of determining a mitotic index over a specified time period. The immunohistochemical staining method was performed as follows:

1) 5 μm sections of test artery were dehydrated in cold acetone (−20° C.) for 10 minutes;
2) Sections were mounted on glass microscope slides, and the slides were dried in a 37° C. oven for 10 minutes;
3) Slides were rehydrated in PBS for 10 minutes;
4) Slides were subjected to Feulgen's acid hydrolysis using 1 N HCl, wherein two aliquots of 1 N HCl are preheated to 37° C. and 60° C. prior to proceeding;

5) Slides were rinsed with 1 ml of 1 N HCl at 37° C. for 1 min;
6) Slides were transferred to 60° C. 1 N HCL for 15 min;
7) Slides were rinsed with 1 ml of 1 N HCl at 37° C. for 1 min;
8) Slides were washed with room temperature PBS, using 3 changes of PBS at 5 min intervals;
9) Endogenous, cross-reactive sites on the sections were blocked with normal goat serum (1:25 in PBS) for 20 min;
10) Slides were washed with PBS, as in step 8;
11) Sections were incubated with mouse anti-BRDU antibody (DAKO Corporation, Carpinteria, Calif.) at 10 μg/ml for 30 min;
12) Slides were washed with PBS, as in step 8;
13) Sections were incubated with horseradish peroxidase-labeled (HRPO) goat anti-mouse $IgG_1$ (Jackson Immunoresearch Laboratories, Inc., West Grove, Pa.; diluted 1:20 in PBS) and 4% human AB serum for 30 min;
14) Slides were washed with PBS, as in step 8;
15) Sections were incubated with chromogen (3,3'-diaminobenzidine (DAB; Sigma) at 5 mg/ml in 200 ml PBS) and 200 μl of 30% $H_2O_2$ for 10 min;
16) Slides were washed with PBS, as in step 8;
17) Samples were counterstained with Gill I hematoxylin (Gill I Lerner Laboratories, Pittsburgh, Pa.; 30 dips);
18) Slides were washed with PBS, as in step 8; rinsed with a bluing solution (1 gm lithium carbonate in 500 ml $dH_2O$); washed with deionized water; and
19) Test samples were then dehydrated, cleared and coverslipped.

At the conclusion of this procedure, a positive immunohistological stain exhibits a brown color at the site(s) of reactivity.

Cytocidal agents inhibited BRDU uptake relative to a PBS control; however, cytochalasin B and staurosporin inhibited BRDU uptake (i.e., cell proliferation) without killing the vascular smooth muscle cells. The number of vascular smooth muscle cells labeled with BRDU was assigned a grade at 400× magnification as follows:

1=≦1/high power field (HPF);
2=2 to 5/HPF;
3=>5 to ≦10/HPF; and
4=>10/HPF.

Both cytochalasin B and staurosporin inhibited proliferation for 24 hours following balloon trauma (grade 1), yielding a BRDU labeling grade equivalent to that of a pre-trauma baseline (grade 1). PBS and monoclonal antibody controls exhibited grade 2.5 to 4 BRDU labeling during the same time period. At 4 days post-trauma, arteries treated with cytochalasin B or staurosporin, as well as PBS and monoclonal antibody controls, exhibited a BRDU labeling grade of 4. The anti-proliferative, non-cytocidal properties of cytochalasin B and staurosporin suggest that these agents are amenable to sustained release dosage formulations for reduction of vascular stenosis.

Example 14

Biological Stenting of Balloon Traumatized Pig Arteries Using Cytochalasin B Balloon traumatized pig arteries that had been treated with cytochalasin B displayed a larger luminal area at the 4 day and 3 week post-treatment time points, as compared to arteries treated with other test agents or controls. Ten femoral arteries (two arteries obtained from each of the 5 pigs that were treated according to the single dose protocol described in Example 7) were evaluated histologically. The maximal luminal area of each artery was measured and calculated from digitized microscopic images by a BQ System IV computerized morphometric analysis system (R & M Biometrics, Inc., Nashville, Tenn.). This experiment was repeated with 5 additional pigs (two arteries per pig; cytochalasin B dose=0.1 μg/ml, applied for 3 min at 1 atm pressure; same time points). The data obtained from the two experiments were combined. An increase in lumen area at the 3 week post-cytochalasin B treatment time point was observed.

The luminal area of the traumatized and cytochalasin B-treated segments of the arteries were also compared to the luminal area of the normal, untreated region of the femoral artery proximal to the test area. The results showed that the lumen area in the test region was approximately two times as large as the area of the normal control segment of the same artery. The negative control agents, PBS and monoclonal antibody NR-AN-01, showed no increase or a slight decrease in lumen area as compared to the normal control segment of the same artery.

Figure 14:
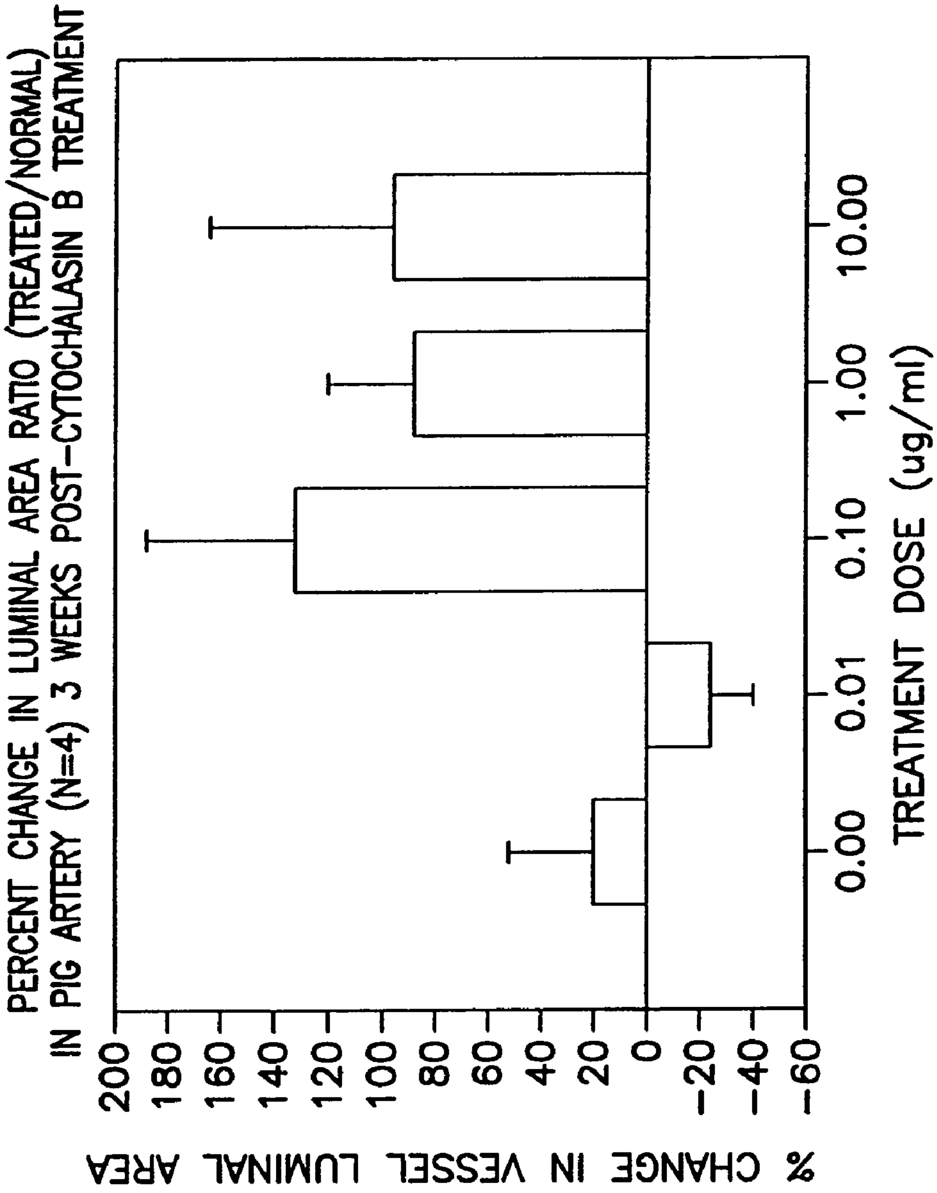
FIG. 14 depicts an in vivo dose response study of the effect of cytochalasin B on the luminal area of pig femoral arteries.

A cytochalasin B dose response study was then conducted on 10 pigs, following the experimental protocol described in Example 7. Briefly, both arteries in each of 2 pigs were treated with one of the following doses of cytochalasin B: 0.0 μg/ml (i.e., PBS negative control); 0.01 μg/ml; 0.10 μg/ml; 1.0 μg/ml; and 10.0 μg/ml. The agent was delivered by intraluminal catheter at 1 atm pressure for 3 min, and the arteries were evaluated 3 weeks later by the morphometric analysis system described above. The ratio of treated artery luminal area to proximal normal artery luminal area was determined as a percent change in treated vs. normal area. A significant threshold effect was observed at doses from 0.1 μg/ml (≈140% increase) to 1.0 μg/ml (FIG. 14). The 10 μg/ml dose appeared to be toxic to the vascular smooth muscle cells (data not shown). The subthreshold dose (0.01 μg/ml) and negative control (PBS) exhibited a ±≈20% change in luminal area. These data suggest that cytochalasin B acts as a "biological stent" when delivered to traumatized arteries.

Example 15

Direct Conjugation of NR-AN-01 Antibody to Carboxylic Functional Groups of a Latex Particle Antibody-coated latex particles (a model of an antibody-coated, sustained release dosage form) may be obtained using the following aseptic technique:

Conjugation:

To 4 ml 0.05 M sodium borate, pH 8.5, containing 0.01% Tween-20® (polyoxyethylene sorbitan monolaurate, Sigma) is added 0.5 ml PBS containing 5 mg NR-AN-01 monoclonal antibody. To this solution at room temperature is added, with vortexing, 2.5 ml of an aqueous suspension containing 50 mg of 1 μm diameter carboxylated latex particles. Immediately thereafter, 0.50 ml of water containing 100 mg of freshly dissolved 1(3-dimethyl-aminopropyl)3-ethyl carbodiimide HCl is added with vortexing. The solution is then incubated with shaking for 1-2 hr at room temperature. The reaction mixture is then diluted with 50 ml of 50 mM phosphate buffer, pH 6.6, containing 0.2% gelatin stabilizer (phosphate/gelatin buffer). The mixture is centrifuged at 40,000×g for 2 hr at 4-10° C. The supernatant is decanted, and the pellet is resuspended in 50 ml phosphate/gelatin buffer using low level sonication for 10 sec. Centrifugation is repeated, and the pellet is resuspended two times, followed by resuspension in the phosphate/gelatin buffer. The conjugated particles are then lyophilized using standard protocols and sorbitol excipients.

Characterization:

(a) Sizing: Particle size homogeneity is assessed by laser anisotropy or, for particles larger than 1 μm, by microscopic examination.

(b) Specific Binding Assessment: Specific binding to smooth muscle cells is determined by histological examination of tissue or cell pellet microtome slices after incubation of protein/peptide conjugates with conjugated particles, with or without blocker protein/peptide included in the incubation mixture. Preferred detection techniques include second antibody assays (i.e., anti-mouse Ig) or competition assays (i.e., radioscintigraphic detection in conjunction with radioisotopically labeled protein/peptide conjugates).

(c) Assessment of the extent of protein/peptide derivitization: This determination is performed by coating the latex particles with radioisotopically labeled antibody, followed by detection of radioactivity associated with the coated particles.

The characterization of antibody-coated particles is described in Table 6.

TABLE 6

Characterization of NR-AN-01-Coated Latex Particles

| Particle Diameter | Offering of Ab/Particle | μg Ab Bound/ 5 mg Latex | Ab Molecules Per Particle |
|---|---|---|---|
| 1.2 μm | 40,000 | 42 | 3520 |
| 1.2 μm | 84,000 | 66 | 5470 |
| 0.4 μm | 32,000 | 99 | 3160 |
| 0.4 μm | 64,000 | 140 | 4550 |
| 0.1 μm | 932 | 140 | 65 |

The particle aggregation effect of pH during antibody conjugation is presented in Table 7.

TABLE 7

Effect of PH During Antibody Conjugation - Particle Aggregation

| Particle | pH* During | Particle Aggregation** | |
|---|---|---|---|
| Diameter | Conjugation | +Tween 20 ® | −Tween 20 ® |
| 1.2 μm | 8.5 | <5% | <2.5% |
| 1.2 μm | 7.0 | ≈20% | ≈10% |
| 1.2 μm | 5.5 | 10% | 100% |
| 0.4 μm | 8.5 | <10% | <5% |
| 0.4 μm | 7.0 | ≈30% | ≈20% |
| 0.4 μm | 5.5 | 100% | 100% |
| 0.1 μm | 8.5 | <20% | <10% |
| 0.1 μm | 7.0 | ≈50% | ≈40% |
| 0.1 μm | 5.5 | 100% | 100% |

*Using 50 mM MES (pH 5.5); phosphate (pH 7.0); or borate (pH 8.5) buffer, as described.
**As assessed by microscopic examination, on a scale of 0-100%.

These data suggest that proteins or peptides may be directly conjugated with sustained release dosage forms of the present invention. More specifically, poly-lactic/glycolic acid particulates having terminal carboxylic acid groups will be conjugated according to the procedure described herein or the alternative procedures described in the specification hereof.

Example 16

Impact of Tamoxifen on Vascular Smooth Muscle Cells and the Relationship thereof to TGF-Beta Production and Activation Cell Culture, DNA Synthesis Assay and Cell Counting. Rat vascular smooth muscle cells were cultured after enzymatic dispersion of the aortic media from 12-17 week old Wistar rats as described in Grainger et al., *Biochem. J.,* 277: 145-151, 1991. When the cells reached confluence (after about 6 days) the cells were released with trypsin/EDTA (available from Gibco) and diluted 1:2 in Dulbecco's modification of Eagle's medium (DMEM; available from ICN/Flow) supplemented with 100 U/ml penicillin and 10% fetal calf serum (FCS). The cells were then replated on tissue culture plastic (available from ICN/Flow) at approximately $1\times10^4$ cells/$cm^2$. The cells were subcultured repeatedly in this way when confluence was attained (about every 4 days), and the cells were used between passages 6 and 12.

Rat adventitial fibroblasts were cultured as described in Grainger et al., *Biochem. J.,* 283: 403-408, 1992. Briefly, the aortae were treated with collagenase (3 mg/ml) for 30 minutes at 37° C. The tunica adventitia was stripped away from the media. The adventitia was dispersed for 2 hours in elastase (1 mg/ml) and collagenase (3 mg/ml) dissolved in medium M199 (available from ICN/Flow). The cells were then spun out (900×g, 3 minutes), resuspended in DMEM+10% FCS and plated out at $8\times10^4$ cells/$cm^2$ on tissue culture plastic. When the cells reached confluence (after about 10 days), they were subcultured as described for vascular smooth muscle cells. Adventitial fibroblasts were subcultured every 3 days at 1:3 dilution and used between passages 3 and 9.

DNA synthesis was assayed by [$^3$H]-thymidine incorporation as described in Grainger et al., *Biochem. J.,* 277:145-151, 1991. Vascular smooth muscle cells were subcultured, grown in DMEM+10% FCS for 24 hours, made quiescent in serum-free DMEM for 48 hours and restimulated with 10% FCS at "0" hours. [$^3$H]-thymidine (5 microcuries/ml; available from Amersham International) was added 12 hours after restimulation and the cells were harvested after 24 hours. DNA synthesis by adventitial fibroblasts was determined similarly, except that the cells were made quiescent in serum-free DMEM for 24 hours.

Cells were prepared for counting by hemocytometer from triplicate culture dishes as described in Grainger et al., *Biochem. J.,* 277:145-151, 1991. Cells were also counted by direct microscopic observation of gridded culture dishes. The grids were scored into the plastic on the inner surface, so that the cells could not migrate into or out of the area being counted during the experiment. Cells in each of four squares in two separate wells were counted at each time point. All cell counting experiments were repeated on at least three separate cultures.

A stock solution of tamoxifen (5 mM; available from ICI Pharmaceuticals) was made up in 10% ethanol (EtOH) and diluted in DMEM and 10% FCS to give the final concentration. The effects of each tamoxifen concentration were compared with the effects observed in control wells containing the same final concentration of the ethanol vehicle. Recombinant TGF-beta (available from Amersham International) was dissolved in 25 mM Tris/Cl to give a 5 microgram/ml stock solution and sterile filtered through a Spinnex Tube (such as a Centrex Disposable Microfilter Unit available from Rainin Instrument Company, Inc., Woburn, Mass.). Neutralizing antiserum to TGF-beta (BDA19; available from R & D Systems) was reconstituted in sterile MilliQ water (available from Millipore Corporation, Bedford, Mass.). At 10 micrograms/ml, this antibody completely abolished the activity of 10 ng/ml recombinant TGF-beta on subcultured (8th passage) vascular smooth muscle cells.

Assays for TGF-beta. The TGF-beta activity present in medium conditioned on various cells was determined by DNA synthesis assay on mink lung endothelial (MvLu) cells; a modification of the assay described in Danielpour et al., *J. Cell. Physiol.,* 138: 79-83, 1989. MvLu cells were subcultured at 1:5 dilution in DMEM+10% FCS. After 24 hours, the medium was replaced with the conditioned medium to be tested in the absence or presence of the neutralizing antiserum to TGF-beta at 10 micrograms/ml. DNA synthesis during a 1 hour pulse of [$^3$H]-thymidine (5 microcuries/ml) was determined 23 hours after addition of the test medium. TGF-beta activity was calculated as the proportion of the inhibition of DNA synthesis which was reversed in the presence of neutralizing antibody, using a standard curve to convert the inhibition values into quantities of TGF-beta. The TGF-beta1 standards and conditioned media both contained 10% FCS in DMEM.

The total latent and active TGF-beta present was determined by a sandwich ELISA. Maxisorb 96-well ELISA plates (available from Gibco) were coated with neutralizing antiserum against TGF-beta (BDA19; available from R & D Systems) at 2 micrograms/cm$^2$ in phosphate buffered saline (PBS) overnight at room temperature. The plates were washed between each step with tris-buffered saline containing 0.1% Triton X-100 (available from Sigma Chemical Company). The plates were incubated with samples for 2 hours, with a second antibody to TGF-beta (BDA5; available from R & D Systems) at 0.1 micrograms/ml for 2 hours, anti-rabbit IgG peroxidase conjugated to antibody (available from Sigma Chemical Co.), made up according to manufacturer's instructions, for 15 minutes. Absorbances at 492 nm were converted into quantities of TGF-beta protein using a standard curve. Both conditioned media and standards were assayed in the presence of 10% FCS in DMEM. This assay was linear for TGF-beta concentrations in the range from 0.1 ng/ml to 20 ng/ml in the presence of 10% FCS in DMEM.

RNA Preparation and Northern Analysis. Total cytoplasmic RNA was isolated from cultured vascular smooth muscle cells as described in Kemp et al., *Biochem. J.,* 277: 285-288, 1991. Northern analysis was performed by electrophoresis of total cytoplasmic RNA in 1.5% agarose gels in a buffer containing 2.2 M formaldehyde, 20 mM 3-(N-morpholino)propanesulfonic acid, 1 mM EDTA, 5 mM sodium acetate and 0.5 micrograms/ml ethidium bromide. The integrity of the RNA was checked by visualizing the gel under UV illumination prior to transfer onto Hybond N (available from Pharmacia LKB) as specified by the manufacturer. Filters were hybridized as described in Kemp et al., *Biochem. J.,* 277: 285-288, 1991, using a [$^{32}$P] oligolabeled mouse TGF-beta1 probe corresponding to amino acids 68-228 in the precursor region of the TGF-beta1 polypeptide as set forth in Millan et al., *Development,* 111: 131-144.

Results. Vascular smooth muscle cells from the aorta of adult rats proliferate with a cell cycle time of approximately 35 hours in DMEM+10% FCS (see, for example, Grainger et al., *Biochem. J.,* 277: 145-151, 1991). Addition of tamoxifen decreased the rate of proliferation with maximal inhibition at concentrations above 33 micromolar. 50 micromolar tamoxifen concentrations produced an increase in cell number (96 hours following the addition of serum) that was reduced by 66%+/−5.2% (n=3). The slower rate of proliferation was hypothesized to stem from a complete blockage of proliferation for a proportion of the vascular smooth muscle cells or from an increase in the cell cycle time of all of the cells. To distinguish between these possibilities, the proportion of the cells passing through M phase and the time course of entry into cell division were determined.

Quiescent vascular smooth muscle cells were stimulated with DMEM+10% FCS in the absence or presence of 33 micromolar tamoxifen, with the cell number being determined at 8 hour intervals by time lapse photomicroscopy. In the presence of ethanol vehicle alone, more than 95% of the vascular smooth muscle cells had divided by 40 hours, whereas there was no significant increase in cell number in the presence of tamoxifen until after 48 hours. By 64 hours, however, more than 90% of the cells had divided in the presence of tamoxifen. The time taken for 50% of the cells to divide after stimulation by serum was increased from 35+/−3 hours (n=7) to 54+/−2 hours (n=3) by 33 micromolar tamoxifen. Since tamoxifen did not significantly reduce the proportion of cells completing the cell cycle and dividing, inhibition of vascular smooth muscle cells caused by tamoxifen appears to be the result of an increase in the cell cycle time of nearly all (>90%) of the proliferating cells.

To determine whether tamoxifen increased the duration of the cell cycle of vascular smooth muscle cells by increasing the duration of the $G_0$ to S phase, the effect of tamoxifen on entry into DNA synthesis was analyzed. Tamoxifen at concentrations up to 50 micromolar did not significantly affect the time course or the proportion of cells entering DNA synthesis following serum stimulation of quiescent vascular smooth muscle cells (DNA synthesis between 12 hours and 24 hours after stimulation was measured by [$^3$H]-thymidine incorporation: control at 17614+/−1714 cpm; 10 micromolar tamoxifen at 16898+/−3417 cpm; and 50 micromolar tamoxifen at 18002+/−4167 cpm). Since the duration of S phase is approximately 12 hours (unpublished data), tamoxifen does not appear to have significantly impacted the time course of entry into DNA synthesis. These results therefore imply that tamoxifen decreases the rate of proliferation of serum-stimulated vascular smooth muscle cells by increasing the time taken to traverse the $G_2$ to M phase of the cell cycle.

Based upon these results, it appeared that tamoxifen exhibited effects similar to those previously described for TGF-beta (see, for example, Assoian et al., *J. Cell. Biol.,* 109: 441-448, 1986) with respect to proliferation of subcultured vascular smooth muscle cells in the presence of serum. Tamoxifen is known to induce TGF-beta activity in cultures of breast carcinoma cell lines as described, for example, in Knabbe, et al., *Cell,* 48: 417-425, 1987. Consequently, experimentation was conducted to determine whether tamoxifen decreased the rate of proliferation of vascular smooth muscle cells by inducing TGF-beta activity. When quiescent vascular smooth muscle cells were stimulated with 10% FCS in the presence of 50 micromolar tamoxifen and 10 micrograms/ml neutralizing antiserum against TGF-beta, the cells proliferated at the same rate as control cells in the presence of ethanol vehicle alone.

To confirm that the vascular smooth muscle cells produced TGF-beta in response to tamoxifen, such cells were treated with tamoxifen for 96 hours in the presence of 10% FCS. The conditioned medium was then collected and TGF-beta activity was determined by the modified mink lung epithelial (MvLu) cell assay described above. Tamoxifen increased the TGF-beta activity in the medium by >50-fold. Addition of tamoxifen (50 micromolar) in fresh DMEM+10% FCS to the MvLu cells had no effect on DNA synthesis, demonstrating that tamoxifen did not induce production of active TGF-beta by the MvLu cells.

TGF-beta is produced as a latent propeptide which can be activated outside the cell by proteases such as plasmin. To determine whether tamoxifen increased TGF-beta activity by promoting the activation of latent TGF-beta or by stimulating the production of the latent propeptide which was subsequently activated, the total latent plus active TGF-beta present in the conditioned medium was determined by sandwich ELISA as described above. After 96 hours in the presence of tamoxifen (50 micromolar), the total TGF-beta protein present was increased by approximately 4-fold. Furthermore, the proportion of the TGF-beta present in active form was increased from <5% in the medium conditioned on vascular smooth muscle cells in the presence of ethanol vehicle alone to approximately 35% in the medium conditioned on cells treated with tamoxifen. Thus, tamoxifen appears to increase TGF-beta activity in cultures of rat vascular smooth muscle cells by stimulating the production of latent TGF-beta and increasing the proportion of the total TGF-beta which has been activated.

Heparin increases TGF-beta activity in medium conditioned on vascular smooth muscle cells (unpublished data). The mechanism of action of heparin in this regard appears to involve the release of TGF-beta from inactive complexes present in serum, because pretreatment of serum with heparin immobilized on agarose beads is as effective as direct addition of free heparin to the cells. To determine whether tamoxifen acts to release TGF-beta from sequestered complexes in serum which are not immunoreactive in the ELISA assay, 10% FCS+DMEM was treated with 50 micromolar tamoxifen for 96 hours at 37° C. in the absence of cells. Medium treated in this way contained similar levels of TGF-beta protein and activity to untreated medium. It appears, therefore, that tamoxifen, unlike heparin, does not act by releasing TGF-beta from inactive complexes present in serum.

The content of TGF-beta1 MRNA was also analyzed by Northern analysis at various time points after addition of tamoxifen. Subcultured rat vascular smooth muscle cells (6th passage in exponential growth) in the absence or presence of ethanol vehicle alone contain very little mRNA for TGF-beta1. By 24 hours after addition of tamoxifen (10 micromolar), TGF-beta1 mRNA was increased approximately 10-fold.

Although TGF-beta decreases the rate of proliferation of vascular smooth muscle cells, it does not affect the rate of proliferation of fibroblasts. Tamoxifen at concentrations of up to 50 micromolar did not reduce the rate of proliferation of subcultured adventitial fibroblasts. Tamoxifen is therefore a selective inhibitor of vascular smooth muscle proliferation with an $ED_{50}$ at least 10-fold lower for vascular smooth muscle cells than for adventitial fibroblasts.

CITATIONS

1. Popma, J. J. et al. 1990. Factors influencing restenosis after coronary angioplasty. Amer. J. Med. 88: 16N-24N.
2. Fanelli, C. et al. 1990. Restenosis following coronary angioplasty. Amer. Heart Jour. 119: 357-368.
3. Johnson, D. E. et al. 1988. Coronary atherectomy: Light microscopic and immunochemical study of excised tissue (abstract). Circulation 78 (Suppl. II): II-82.
4. Liu, M. W. et al. 1989. Restenosis after coronary angioplasty; Potential biologic determinants and role of intimal hyperplasia. Circulation 79: 1374-1387.
5. Clowes, A. W. et al. 1985. Significance of quiescent smooth muscle migration in the injured rat carotid artery. Circ. Res. 56: 139-145.
6. Goldman, B. et al. 1987. Influence of pressure on permeability of normal and diseased muscular arteries to horseradish peroxidase; A new catheter approach. Atherosclerosis 65: 215-225.
7. Wolinsky, H. et al. 1990. Use of a perforated balloon catheter to deliver concentrated heparin into the wall of the normal canine artery. JACC 15 (2): 475-481.
8. Nabel, E. G. et al. 1989. Recombinant gene expression in vivo within endothelial cells of the arterial wall. Science 244: 1342-1344.
9. Middlebrook, J. L. et al. 1989. Binding of T-2 toxin to eukaryotic cell ribosomes. Biochem. Pharm. 38 (18): 3101-3110.
10. Barbacid, M. et al. 1974. Binding of [acetyl-$^{14}$C] trichodermin to the peptidyl transferase center of eukaryotic ribosomes. Eur. J. Biochem. 44: 437-444.
11. Sclingemann et al. 1990. Am. J. Pathol. 136: 1393-1405.
12. Steele P. M., Chesebro J. H., Stanson A. W., et al. 1985. Balloon angioplasty: natural history of the pathophysiological response to injury in a pig model. Circ. Res. 57:105-112.
13. Schwartz, R. S., Murphy J. G., Edwards W. D., Camrud A. R., Vliestra R. E., Holmes D. R. Restenosis after balloon angioplasty. A practical proliferative model in porcine coronary arteries. Circulation 1990; 82:2190-2200.
14. Bumol, T. F. and R. A. Reisfeld. 1982. Unique glycoprotein-proteoglycan complex defined by monoclonal antibody on human melanoma cells. Proc. Natl. Acad. Sci. USA 79:1245-1249.

While the preferred embodiment of the invention has been illustrated and described, it will be appreciated that various changes can be made therein without departing from the spirit and scope of the invention.

What is claimed is:

1. A method for reducing restenosis following a vascular surgical procedure, the method comprising: locally administering to a human a biocompatible, non-biodegradable sustained release dosage form comprising a cytostatic amount of a therapeutic agent dispersed in a polymer matrix, wherein said cytostatic amount of said therapeutic agent inhibits a vascular smooth muscle cell activity without killing the cell, and wherein said therapeutic agent is a TGF-beta production or activation stimulator, TGF-beta, tamoxifen, a nuclear enzyme DNA topoisomerase II inhibitor, a DNA polymerase inhibitor, an RNA polymerase inhibitor, an adenyl guanyl cyclase inhibitor, a superoxide dismutase inhibitor, a terminal deoxynucleotidyl-transferase, a reverse transcriptase, lovastatin, vinblastin, cytochalasins, taxol, taxotere, trichothecene, *Pseudomonas* exotoxin, a chemotactic factor inhibitor, a chemotactic factor receptor inhibitor, an intracellular cytoskeletal protein inhibitor, a caffeic acid derivative, nilvadipine, a steroid hormone, sphingosine, somatostatin, or N-ethylmaleimide.

2. The method of claim 1, wherein the vascular surgical procedure comprises placement of a stent.

3. The method of claim 1, wherein the vascular surgical procedure comprises angioplasty.

4. The method of claim 1, wherein the locally administering comprises administering the cytostatic amount of the therapeutic agent directly to vascular smooth muscle tissue.

5. The method of claim 1, wherein the release of the cytostatic amount of the therapeutic agent from the dosage form occurs during or after the vascular surgical procedure.

6. The method of claim 1, wherein the therapeutic agent comprises taxol or taxotere.

7. The method of claim 1, wherein the sustained release dosage form is a microparticulate.

8. The method of claim 1, wherein locally administering comprises administering the biocompatible, non-biodegradable sustained release dosage form intraluminally.

9. The method of claim 1, wherein locally administering comprises delivering a cytostatic amount of the biocompatible, non-biodegradable sustained release dosage form to the proximal 6 to 9 cell layers of the tunica media smooth muscle cells lining the lumen of a vessel.

* * * * *

UNITED STATES PATENT AND TRADEMARK OFFICE

CERTIFICATE OF CORRECTION

PATENT NO. : 8,067,022 B2
APPLICATION NO. : 09/910388
DATED : November 29, 2011
INVENTOR(S) : Kunz et al.

It is certified that error appears in the above-identified patent and that said Letters Patent is hereby corrected as shown below:

1.) Column 1, Line 9: after "6,268,390" insert --,--.

2.) Column 74, Line 48, Claim 1: delete "vinblastin," and insert --vinblastine,--.

Signed and Sealed this
Thirty-first Day of January, 2012

David J. Kappos
*Director of the United States Patent and Trademark Office*